US012667570B2

(12) United States Patent　　　　(10) Patent No.:　US 12,667,570 B2
　　　Dar et al.　　　　　　　　　　　　(45) Date of Patent:　　Jun. 30, 2026

(54) SMALL MOLECULE MODULATORS OF KSR-BOUND MEK

(71) Applicant: Icahn School of Medicine at Mount Sinai, New York, NY (US)

(72) Inventors: Arvin Dar, New York, NY (US); Alexander P. Scopton, New York, NY (US); Jayasudhan Reddy Yerabolu, New York, NY (US); Zaigham M. Khan, New York, NY (US); Alexander Michael Real, Newton, MA (US); William Michael Marsiglia, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 689 days.

(21) Appl. No.: 17/791,364

(22) PCT Filed: Jan. 8, 2021

(86) PCT No.: PCT/US2021/012808
　　　§ 371 (c)(1),
　　　(2) Date: Jul. 7, 2022

(87) PCT Pub. No.: WO2021/142345
　　　PCT Pub. Date: Jul. 15, 2021

(65) Prior Publication Data
　　　US 2023/0381180 A1　　Nov. 30, 2023

Related U.S. Application Data

(60) Provisional application No. 63/044,338, filed on Jun. 25, 2020, provisional application No. 62/958,626, filed on Jan. 8, 2020.

(51) Int. Cl.
　　　*A61K 31/519*　　　(2006.01)

(52) U.S. Cl.
　　　CPC ................................. *A61K 31/519* (2013.01)

(58) Field of Classification Search
　　　None
　　　See application file for complete search history.

(56) References Cited

U.S. PATENT DOCUMENTS

| | | | |
|---|---|---|---|
| 3,654,090 A | 4/1972 | Schuurs et al. | |
| 3,850,752 A | 11/1974 | Schuurs et al. | |
| | (Continued) | | |

FOREIGN PATENT DOCUMENTS

| | | |
|---|---|---|
| CN | 103819471 A | 5/2014 |
| EP | 0154734 A1 | 9/1985 |
| | (Continued) | |

OTHER PUBLICATIONS

Garuti, et al. "Non-ATP competitive protein kinase inhibitors" Curr Med Chem 2010, 17, 25, 2804-21. DOI: 10.2174/092986710791859333. (Year: 2010).*

(Continued)

*Primary Examiner* — Jennifer A Berrios
*Assistant Examiner* — Sophia Reilly
(74) *Attorney, Agent, or Firm* — Fish & Richardson P.C.

(57)　　　　　　ABSTRACT

An ATP non-competitive inhibitor of mitogen-activated protein kinase (MEK), inter alia, human MEK (MEK1 or MEK2) having the properties: (i) allosterically binds an inhibitor pocket formed at an interaction interface between human MEK (MEK1 or MEK2) and human Kinase Suppressor of Ras (KSR1 or KSR2 or BRAF) adjacent to ATP in a physiological complex between MEK and KSR (or BRAF), forming an inhibitor-inhibitor pocket complex; (ii) is an ATP non-competitive kinase inhibitor; (iii) a structure such that when bound to the inhibitor-inhibitor pocket complex, the complex comprises the structural elements: (a) at least one moiety of the inhibitor engaging A825 of KSR1, (Continued)

or P878 of KSR2; or R662 of BRAF (b) at least one moiety engaging R234 of MEK, wherein where R234 is within 5 Å from any atoms of KSR1 or KSR2 or BRAF is disclosed.

3 Claims, 102 Drawing Sheets

Specification includes a Sequence Listing.

(56) References Cited

U.S. PATENT DOCUMENTS

| | | | |
|---|---|---|---|
| 3,996,345 | A | 12/1976 | Ullman et al. |
| 4,351,760 | A | 9/1982 | Khanna et al. |
| 4,568,649 | A | 2/1986 | Burtoglio-Matte et al. |
| 4,626,513 | A | 12/1986 | Burton et al. |
| 2010/0004234 | A1 | 1/2010 | Santi et al. |
| 2016/0237064 | A1 | 8/2016 | Murphy et al. |
| 2018/0256577 | A1 | 9/2018 | Dar et al. |
| 2020/0109139 | A1 | 4/2020 | Kawasaki et al. |
| 2023/0266321 | A1* | 8/2023 | Dar .................... G01N 33/5011 |
| | | | 435/7.4 |

FOREIGN PATENT DOCUMENTS

| | | | |
|---|---|---|---|
| WO | WO 2005/121142 A1 | 12/2005 | |
| WO | WO 2016/115376 A1 | 7/2016 | |
| WO | WO 2018/107183 A1 | 6/2018 | |
| WO | WO 2019/103998 A1 | 5/2019 | |
| WO | WO 2021/142345 A1 | 7/2021 | |

OTHER PUBLICATIONS

Abe et al. "Discovery of a Highly Potent and Selective MEK Inhibitor: GSK1120212 (JTP-74057 DMSO Solvate)" ACS Med Chem Lett 2011, 2, 4, 320-324. DOI: 10.1021/ml200004g (Year: 2011).*

Abe et al. Supplementary Information "Discovery of a Highly Potent and Selective MEK Inhibitor: GSK1120212 (JTP-74057 DMSO Solvate)" ACS Med Chem Lett 2011, 2, 4, 320-324. DOI: 10.1021/ml200004g (Year: 2011).*

Afonine et al., "Towards automated crystallographic structure refinement with phenix.refine," Acta Crystallogr D Biol Crystallogr, Apr. 2012, available online Mar. 16, 2012, 68(Pt 4):352-367.

Alfthan, "Surface plasmon resonance biosensors as a tool in antibody engineering," Biosens Bioelectron, Sep. 15, 1998, 13(6):653-663.

Baldwin et al., "Cloning and expression of the luxY gene from Vibrio fischeri strain Y-1 in Escherichia coli and complete amino acid sequence of the yellow fluorescent protein," Biochemistry, Jun. 12, 1990, 29(23):5509-5515.

Baud et al., "A bump-and-hole approach to engineer controlled selectivity of BET bromodomain chemical probes," Science, Oct. 31, 2014, published online Oct. 16, 2014, 346(6209):638-641 (Author Manuscript, 9 pages).

Berge, "Pharmaceutical Salts," J Pharm Sci, Jan. 1977, 66(1):1-19.

Bishop et al., "A chemical switch for inhibitor-sensitive alleles of any protein kinase," Nature, Sep. 21, 2000, 407(6802)395-401.

Blasco et al., "c-Raf, but not B-Raf, is essential for development of K-Ras oncogene-driven non-small cell lung carcinoma," Cancer Cell, May 17, 2011, available online Apr. 21, 2011, 19(5):652-663.

Brennan et al., "A Raf-induced allosteric transition of KSR stimulates phosphorylation of MEK," Nature, Apr. 21, 2011, available online Mar. 27, 2011, 472(7343):366-369 (6 pages including the supplemental material).

Bundgaard, "(C) Means to enhance penetration: (1) Prodrugs as a means to improve the delivery of peptide drugs," Advanced Drug Delivery Reviews, Jan.-Feb. 1992, 8(1):1-38.

cambridgemedchemconsulting.com [online], "Bioisosteric Replacements," 2019, retrieved on Oct. 1, 2024, retrieved from URL<https://www.cambridgemedchemconsulting.com/resources/bioisoteres/>, 11 pages.

Canon et al., "The clinical KRAS(G12C) inhibitor AMG 510 drives anti-tumour immunity," Nature, Nov. 2019, Oct. 30, 2019, 575(7781):217-223 (26 pages including the supplemental material).

Cardullo et al., "Detection of nucleic acid hybridization by nonradiative fluorescence resonance energy transfer," Proc Natl Acad Sci U S A, Dec. 1988, 85(23):8790-8794.

Carver et al., "Reciprocal feedback regulation of PI3K and androgen receptor signaling in PTEN-deficient prostate cancer," Cancer Cell, May 17, 2011, 19(5):575-586.

Caunt et al., "MEK1 and MEK2 inhibitors and cancer therapy: the long and winding road, " Nat Rev Cancer, Oct. 2015, 15(10):577-592.

Chang et al., "Targeting pan-essential genes in cancer: Challenges and opportunities," Cancer Cell, Apr. 12, 2021, available online Jan. 14, 2021, 39(4):466-479.

Chapman et al., "Combination of RAF and MEK Inhibition for the Treatment of BRAF-Mutated Melanoma: Feedback Is Not Encouraged," Cancer Cell, Nov. 10, 2014, 26(5):603-604.

Chen et al., "Investigation of atomic level patterns in protein—small ligand interactions," PLoS One, 2009, available online Feb. 16, 2009, 4(2):e4473, 14 pages.

Copeland, "The drug-target residence time model: a 10-year retrospective," Nat Rev Drug Discov, Feb. 2016, available online Dec. 18, 2015, 15(2):87-97 (Advance Online Publication, 9 pages).

Costanzo-Garvey et al., "KSR2 is an essential regulator of AMP kinase, energy expenditure, and insulin sensitivity," Cell Metab, Nov. 2009, 10(5):366-378.

Dar, "A pickup in pseudokinase activity," Biochem Soc Trans, Aug. 2013, 41(4):987-994.

Davies et al., "Mutations of the BRAF gene in human cancer," Nature, Jun. 27, 2002, 417(6892):949-954.

De Freitas et al., "A systematic analysis of atomic protein-ligand interactions in the PDB," MedChemComm, Oct. 2017, available online Sep. 26, 2017, 8(10):1970-1981.

Dexter et al., "A Theory of Sensitized Luminescence in Solids," J of Chemical Physics, May 1953, 21(5):836-850.

Dhawan et al., "Small molecule stabilization of the KSR inactive state antagonizes oncogenic Ras signalling, " Nature, Sep. 1, 2016, available online Aug. 24, 2016, 537(7618):112-116 (Author Manuscript, 39 pages).

Downward, "KSR: a novel player in the RAS pathway," Cell, Dec. 15, 1995, 83(6):831-834.

Ebert, et al., "MAP Kinase Inhibition Promotes T Cell and Anti-tumor Activity in Combination with PD-L1 Checkpoint Blockade," Immunity, Mar. 15, 2016, available online Mar. 2, 2016, 44(3):609-621.

Emery et al., "MEK1 mutations confer resistance to MEK and B-RAF inhibition," Proc Natl Acad Sci U S A, Dec. 1, 2009, available online Nov. 13, 2009, 106(48):20411-20416.

Emsley et al., "Features and development of Coot," Acta Crystallogr D Biol Crystallogr, Apr. 2010, 66(Pt 4):486-501.

Extended European Search Report in European Appln. No. 21738143.3, mailed on Feb. 21, 2024, 7 pages.

Falchook et al., "Activity of the oral MEK inhibitor trametinib in patients with advanced melanoma: a phase 1 dose-escalation trial," Lancet Oncol, Aug. 2012, 13(8):782-789 (Author Manuscript, 22 pages).

Fernandez et al., "Kinase Suppressor of Ras 2 (KSR2) Regulates Tumor Cell Transformation via AMPK," Mol Cell Biol, Sep. 2012, 32(18):3718-3731.

Fischmann et al., "Crystal structures of MEKI binary and ternary complexes with nucleotides and inhibitors," Biochemistry, Jan. 22, 2009, 48(12):2661-2674.

Fivash et al., "BIAcore for macromolecular interaction," Curr Opin Biotechnol, Feb. 1998, 9(1):97-101.

Flaherty et al., "Improved survival with MEK inhibition in BRAF-mutated melanoma," N Engl J Med, Jul. 12, 2012, 367(2):107-114.

Gao et al., "V211D Mutation in MEK1 Causes Resistance to MEK Inhibitors in Colon Cancer," Cancer Discov, Sep. 2019, Jun. 21, 2019, 9(9):1182-1191.

GenBank Accession No. JQ437370.1, "Nanoluc luciferase reporter vector pNL1.1[Nluc], complete sequence," Jun. 19, 2012, 2 pages.

(56)        References Cited

OTHER PUBLICATIONS

Gerry et al., "Unifying principles of bifunctional, proximity-inducing small molecules," Nat Chem Biol, Apr. 2020, available online Mar. 20, 2020, 16(4):369-378 (Author Manuscript, 24 pages).

Gilmartin et al., "GSKI 120212 (JTP-74057) is an inhibitor of\1EK activity and activation with favorable pharmacokinetic properties for sustained in vivo pathway inhibition," Clin Cancer Res, Mar. 1, 2011, available online Jan. 18, 2011, 17(5):989-1000.

Glickman et al., "Converting cancer therapies into cures: lessons from infectious diseases, " Cell, Mar. 16, 2012, 148(6):1089-1098.

Haling et al., "Structure of the BRAF-MEK complex reveals a kinase activity independent role for BRAF in MAPK signaling," Cancer Cell, Sep. 8, 2014, available online Aug. 21, 2014, 26(3):402-413.

Hanselman et al., "A cDNA-dependent scintillation proximity assay for quantifying apolipoprotein A-I," J Lipid Res, Nov. 1997, 38(11):2365-2373.

Hatzivassiliou et al., "Mechanism of MEK inhibition determines efficacy in mutant KRAS-versus BRAF-driven cancers," Nature, Sep. 12, 2013, available online Aug. 11, 2013, 501(7466):232-236 (5 pages).

Hatzivassiliou et al., "RAF inhibitors prime , wild-type RAF to activate the MAPK pathway and enhance growth," Nature, Mar. 18, 2010, available online Feb. 3, 2010, 464(7287):431-435 (6 pages including the supplemental material).

Heim et al., "Engineering green fluorescent protein for improved brightness, longer wavelengths and fluorescence resonance energy transfer," Curr Biol, Feb. 1996, 6(2):178-182.

Ho et a., "Trametinib, a first-in-class oral MEK inhibitor mass balance study with limited enrollment of two male subjects with advanced cancers," Xenobiotica, Apr. 2014, available online Aug. 23, 2013, 44(4):352-368.

Hochstrasser et al., "Distance distribution in a dye-linked oligo-nucleotide determined by time-resolved fluorescence energy transfer," Biophys Chem, Dec. 1992, 45(2):133-141.

Huang et al., "PD0325901, a mitogen-activated protein kinase kinase inhibitor, produces ocular toxicity in a rabbit animal model of retinal vein occlusion," J Ocul Pharmacol Ther, Dec. 2009, 25(6):519-530.

Infante et al., "Safety and efficacy results from the first-in-human study of the oral MEK 1/2 inhibitor GSK1 120212," J Clin Oncol, May 20, 2010, 28(15 suppl):2503.

International Preliminary Report in Patentability in International Appln. No. PCT/US2021/012808, mailed on Jul. 21, 2022, 5 pages.

International Preliminary Report in Patentability in International Appln. No. PCT/US2021/039221, mailed on Jan. 5, 2023, 9 pages.

International Search Report and Written Opinion in International Appln. No. PCT/US2021/012808, mailed on Apr. 1, 2021, 6 pages.

International Search Report and Written Opinion in International Appln. No. PCT/US2021/039221, mailed on Nov. 26, 2021, 12 pages.

Ishii et al., "Enhanced Inhibition of ERK Signaling by a Novel Allosteric MEK Inhibitor, CH5126766, That Suppresses Feedback Reactivation of RAF Activity," Cancer Res, Jul. 1, 2013, available online May 10, 2013, 73(13):4050-4060.

Johannessen et al., "COT drives resistance to RAF inhibition through MAP kinase pathway reactivation," Nature, Dec. 16, 2010, available online Nov. 24, 2010, 468(7326): 968-972 (Author Manuscript, 18 pages).

Kabsch, "XDS," Acta Crystallogr D Biol Crystallogr, Feb. 1, 2010, available online Jan. 22, 2010, 66(Pt 2):125-132.

Kahl et al., "A Multiple-Approach Scintillation Proximity Assay to Measure the Association Between Ras and Raf," Anal Biochem, Dec. 15, 1996, 243(2):282-283.

Kahn et al., "Structural insights into how the pseudokinase KSR modulates the activity of clinical MEK inhibitors," New York Academy of Sciences meeting on Structural Biology, Jan. 2019, 1 page.

Khan et al., "Structural basis for the action of the drug trametinib at KSR-bound MEK," Nature, Dec. 2020, available online Sep. 14, 2020, 588(7838):509-514 (Author Manuscript, 40 pages).

Kinsey et al., "Protective autophagy elicited by RAF→MEK→ERK inhibition suggests a treatment strategy for RAS-driven cancers," Nat Med, Apr. 2019, available online Mar. 4, 2019, 25(4):620-627 (Author Manuscript, 27 pages).

Kondo et al., "Cryo-EM structure of a dimeric B-Raf: 14-3-3 complex reveals asymmetry in the active sites of B-Raf kinases," Science, Oct. 4, 2019, available online Sep. 19, 2019, 366(6461):109-115.

Kornev et al., "Defining the conserved internal architecture of a protein kinase," Biochim Biophys Acta, Mar. 2010, available online Oct. 29, 2009, 1804(3):440-444.

Kornfeld et al., "The ksr-1 gene encodes a novel protein kinase involved in Ras-mediated signaling in C. elegans," Cell, Dec. 15, 1995, 83(6):903-913.

Kung et al., "Prospects for pharmacological targeting of pseudokinases," Nat Rev Drug Discov, Jul. 2019, 18(7):501-526 (26 pages).

Laurent et al., "Active site-directed thrombin inhibitors-II. Studies related to arginine/guanidine bioisosteres," Biorg Med Chem, Aug. 1995, 3(8): 1145-1156.

Lavoie et al., "MEK drives BRAF activation through allosteric control of KSR proteins," Nature, Feb. 22, 2018, available online Feb. 12, 2018, 554(7693):549-553 (Author Manuscript, 40 pages).

Lavoie et al., "Regulation of RAF protein kinases in ERK signalling," Nat Rev Mol Cell Biol, May 2015, 16(5):281-298.

Leslie, "'Dead' enzymes show signs of life," Science, Apr. 5, 2013, 340(6128):25-27.

Levine et al., "Isolation and characterization of a photoprotein, "phialidin", and a spectrally unique green-fluorescent protein from the bioluminescent jellyfish phialidium gregarium," Comp Biochem Physiol. Part B: Comperative Biochemistry, 1982, 72(1):77-85.

Liau et al., "Dimerization Induced by C-Terminal 14-3-3 Binding Is Sufficient for BRAF Kinase Activation," Biochemistry, Oct. 20, 2020, available online Oct. 2, 2020, 59(41):3982-3992.

Liau et al., "Negative regulation of RAF kinase activity by ATP is overcome by 14-3-3-induced dimerization," Nat Struct Mol Biol, Feb. 2020, available online Jan. 27, 2020, 27(2):134-141 (20 pages including the supplemental material).

Liparoto et al., "Biosensor analysis of the interleukin-2 receptor complex," J Mol Recognit, Sep.-Oct. 1999, 12(5):316-321.

Lipschultz et al., "Experimental design for analysis of complex kinetics using surface plasmon resonance," Methods, Mar. 2000, 20(3):310-318.

Lito et al., "Disruption of CRAF-mediated MEK activation is required for effective MEK inhibition in KRAS mutant tumors," Cancer Cell, May 12, 2014, available online Apr. 17, 2014, 25(5):697-710.

Lito et al., "Tumor adaptation and resistance to RAF inhibitors," Nat Med, Nov. 2013, 19(11):1401-1409.

Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res, Apr. 1, 2015, available online Jan. 14, 2015, 21(7):1639-1651.

Long et al., "Dabrafenib and trametinib versus dabrafenib and placebo for Val600 BRAF-mutant melanoma: a multicentre, double-blind, phase 3 randomised controlled trial," Lancet, Aug. 1, 2015, available online May 31, 2015, 386(9992):444-451 (Online Publication, 8 pages).

LoRusso et al., "Phase I pharmacokinetic and pharmacodynamic study of the oral MAPK/ERK kinase inhibitor PD-0325901 in patients with advanced cancers," Clin Cancer Res, Mar. 2010, available online Mar. 9, 2010, 16(6):1924-1937.

Lozano et al., "Deficiency of kinase suppressor of Ras1 prevents oncogenic ras signaling in mice," Cancer Res, Jul. 15, 2003, 63(14):4232-4238.

Malmborg et al., "BIAcore as a tool in antibody engineering," J Immunol Methods, Jun. 14, 1995, 183(1):7-13.

Malmqvist et al, "Biomolecular interaction analysis: affinity biosensor technologies for functional analysis of proteins," Curr Opin Chem Biol, Oct. 1997, 1(3):378-383.

(56) References Cited

OTHER PUBLICATIONS

Malmqvist, "BIACORE: an affinity biosensor system for characterization ofbiomolecular interactions," Biochem Soc Trans, Feb. 1999, 27(2):335-340.

McCoy et al., "Phaser crystallographic software," J Appl Crystallogr, Aug. 1, 2007, available online Jul. 13, 2007, 40(Pt 4):658-674.

McKay et al., "Signaling dynamics of the KSR1 scaffold complex," Proc Natl Acad Sci U S A, Jul. 7, 2009, available online Jun. 18, 2009, 106(27):11022-11027.

Meanwell, "Synopsis of some recent tactical application of bioisosteres in drug design," J Med Chem, Apr. 2011, available online Mar. 17, 2011, 54(8):2529-2591.

Mitra et al., "Fluorescence resonance energy transfer between blue-emitting and red-shifted excitation derivatives of the green fluorescent protein," Gene, 1996, 173(1 Spec No.):13-17.

Mohamed et al., "Composition of Overlapping Protein-Protein and Protein-Ligand Interfaces," PLoS One, Oct. 30, 2015, 10(10):e0140965, 18 pages.

Moore et al., "RAS-targeted therapies: is the undruggable drugged?," Nat Rev Drug Discov, Aug. 2020, available online Jun. 11, 2020, 19(8):533-552 (Author Manuscript, 43 pages).

Moriarty et al., "electronic Ligand Builder and Optimization Workbench ( eLBOW): a tool for ligand coordinate and restraint generation," Acta Crystallogr D Biol. Crystallogr, Oct. 2009, available online Sep. 16, 2009, 65(Pt 10):1074-1080.

Nguyen et al., "Kinase suppressor of Ras (KSR) is a scaffold which facilitates mitogen-activated protein kinase activation in vivo," Mol Cell Biol, May 2002, 22(9):3035-3045.

Norris et al., "Nucleotide sequence of a cDNA clone encoding the precursor of the peridinin-chlorophyll a-binding protein from the dinoflagellate *Symbiodinium* sp," Plant Mol Biol, Feb. 1994, 24(4):673-677.

Ohren et al., "Structures of human MAP kinase kinase 1 (MEK1) and MEK2 describe novel noncompetitive kinase inhibition," Nat Struct Mol Biol, Dec. 2004, available online Nov. 14, 2004, 11(12):1192-1197.

O'Shannessy et al., "Interpretation of deviations from pseudo-first-order kinetic behavior in the characterization of ligand binding by biosensor technology, " Anal Biochem, May 1, 1996, 236(2):275-283.

O'Shannessy, "Determination of kinetic rate and equilibrium binding constants for macromolecular interactions: a critique of the surface plasmon resonance literature," Curr Opin Biotechnol, Feb. 1994, 5(1):65-71.

Park et al., "Architecture of autoinhibited and active BRAF-MEK1-14-3-3 complexes," Nature, Nov. 2019, available online Oct. 3, 2019, 575(7783):545-550 (Author Manuscript, 38 pages).

Partridge et al., "Facing up to the global challenges of ageing," Nature, Sep. 2018, available online Sep. 5, 2018, 561(7721):45-56.

Pearson et al., "Mitogen-activated protein (MAP) kinase pathways: regulation and physiological functions," Endocr Rev, Apr. 2001, 22(2):153-183.

Poulikakos et al., RAF inhibitor resistance is mediated by dimerization of aberrantly spliced BRAF (V600E), Nature, Nov. 23, 2011, 480(7377):387-390 (Author Manuscript, 11 pages).

Poulikakos et al., "RAF inhibitors transactivate RAF dimers and ERK signalling in cells with wild-type BRAF," Nature, Mar. 18, 2010, 464(7287):427-430 (5 pages including the supplemental material).

Price et al., "Summary report on the ISOBM TD-4 Workshop: analysis of 56 monoclonal antibodies against the MUCI mucin: San Diego, Calif., Nov. 17-23, 1996, " Tumour Biol, 1998, 19 Suppl 1:1-20.

Protein Data Bank, 3VVH, "X-ray structure of the human mitogen-activated protein kinase kinase 1 (MEK1) in complex with an inhibitor and MgATP," Released on Aug. 28, 2013, https://www.rcsb.org/structure/3VVH.

Protein Data Bank, 6Q0J, "Structure of a MAPK pathway complex," Released on Oct. 9, 2019, 5 pages https://www.rcsb.org/structure/6q0j.

PubChem SID 238183997, "SCHEMBL13184515," National Library of Medicine, modified on Feb. 13, 2015, retrieved on Oct. 4, 2024, retrieved from URL<https://pubchem.ncbi.nlm.nih.gov/substance/238183997>, 5 pages.

Qu et al., "The Ras Superfarnily of Small GTPases in Non-neoplastic Cerebral Diseases," Front Mol Neurosci, May 21, 2019, vol. 12, Article 121.

Rajakulendran et al., "A dimerization-dependent mechanism drives RAF catalytic activation," Nature, Sep. 24, 2009, available online Sep. 2, 2009, 461(7263):542-545.

Ribas et al., "Phase I study combining anti-PD-LI (MEDI4736) with BRAF ( dabrafenib) and/or MEK (trametinib) inhibitors in advanced melanoma," J Clin. Oncol, May 20, 2015, 3003, 3 pages.

Ritt et al, "Impact of Feedback Phosphorylation and Raf Heterodimerization on Normal and Mutant B-Raf Signaling," Mol Cell Biol, Feb. 2010, available online Nov. 23, 2009, 30(3):806-819.

Ritt et al., "KSR Regulation of the Raf-MEK-ERK Cascade," Methods Enzymol, 2006, 407:224-237.

Robers et al., "Quantitative, Real-Time Measurements of Intracellular Target Engagement Using Energy Transfer," Methods Mol Biol, 2019, 1888:45-71.

Robers et al., "Target engagement and drug residence time can be observed in living cells with BRET," Nat Commun, Dec. 3, 2015, 6:10091, 10 pages.

Roberts et al, "Targeting the Raf-MEK-ERK mitogen-activated protein kinase cascade for the treatment of cancer," Oncogene, May 14, 2007, 26(22):3291-3310.

Roy et al., "KSR is a scaffold required for activation of the ERK/MAPK module," Genes Dev, Feb. 15, 2002, 16(4):427-438.

Samatar et al., "Targeting RAS-ERK signalling in cancer: promises and challenges," Nat Rev Drug Discov, Dec. 2014, 13(12):928-942.

Sanchez-Vega et al., "Oncogenic Signaling Pathways in The Cancer Genome Atlas," Cell, Apr. 5, 2018, 173(2):321-337.e10.

Selvin et al., "Fluorescence resonance energy transfer," Methods Enzymol, 1995, 246:300-334.

Simanshu et al., "RAS Proteins and Their Regulators in Human Disease," Cell, Jun. 29, 2017, 170(1):17-33.

Slack et al., "The Ras-Erk-ETS-Signaling Pathway Is a Drug Target for Longevity," Cell, Jul. 2, 2015, available online Jun. 25, 2015, 162(1):72-83.

Sos et al., "Oncogene mimicry as a mechanism of primary resistance to BRAF inhibitors," Cell Rep, Aug. 21, 2014, available online Aug. 7, 2014, 8(4):1037-1048.

Stanton et al., "Chemically induced proximity in biology and medicine," Mar. 9, 2018, 359(6380):eaao5902, 10 pages.

Steinberg, "Long-range nonradiative transfer of electronic excitation energy in proteins and polypeptides, " Annu Rev Biochem, Jul. 1971, 40:83-114.

Strub et al., "SIRT6 haploinsufficiency induces BRAFV600E melanoma cell resistance to MAPK inhibitors via IGF signalling," Nat Commun, Aug. 24, 2018, 9(1), 3440, 13 pages.

Stryer, "Fluorescence energy transfer as a spectroscopic ruler," Annu Rev Biochem, Jul. 1978, 47:819-846.

Sundaram et al., "The C. elegans ksr-1 gene encodes a novel Raf-related kinase involved in Ras-mediated signal transduction," Cell, Dec. 15, 1995, 83(6):889-901.

Svensson et al., "The design and bioactivation of presystemically stable prodrugs," Drug Metab Rev, 1988, 19(2):165-194.

Therrien et al., "KSR, a novel protein kinase required for RAS signal transduction," Cell, Dec. 15, 1995, 83(6):879-888.

Undenfriend et al., "Scintillation proximity assay: a sensitive and continuous isotopic method for monitoring ligand/receptor and antigen/antibody interactions," Anal Biochem, Mar. 1987, 161(2):494-500.

UniProt Accession No. P04049, "RAF proto-oncogene serine/threonine-protein kinase, " Dec. 5, 2018, 21 pages.

UniProt Accession No. P07949, "Proto-oncogene tyrosine-protein kinase receptor Ret," Dec. 5, 2018, 33 pages.

UniProt Accession No. P10398, "Serine/threonine-protein kinase A-Raf," Dec. 5, 2018, 9 pages.

UniProt Accession No. P12931, "Proto-oncogene tyrosine-protein kinase Src," Dec. 5, 2018, 25 pages.

(56)     References Cited

OTHER PUBLICATIONS

UniProt Accession No. P15056, "Serine/threonine-protein kinase B-raf," Dec. 5, 2018, 21 pages.
UniProt Accession No. P29678, "Dual specificity mitogen-activated protein kinase kinase 1," Dec. 5, 2018, 5 pages.
UniProt Accession No. P36507, "Dual specificity mitogen-activated protein kinase kinase 2," Dec. 5, 2018, 9 pages.
UniProt Accession No. P63104, "14-3-3 protein zeta/delta," Jun. 5, 2019, 15 pages.
UniProt Accession No. Q02750, "Dual specificity mitogen-activated protein kinase kinase 1," Dec. 5, 2018, 14 pages.
UniProt Accession No. Q61097, "Kinase suppressor of Ras 1," Dec. 5, 2018, 7 pages.
UniProt Accession No. Q6VAB6, "Kinase suppressor of Ras 2," Dec. 5, 2018, 7 pages.
UniProt Accession No. Q8IVT5, "Kinase suppressor of Ras 1," Dec. 5, 2018, 8 pages.
Van Regenmortel, "Use of biosensors to characterize recombinant proteins," Dev Biol Stand, 1994, 83:143-151.
Vasta et al., "Quantitative, Wide-Spectrum Kinase Profiling in Live Cells for Assessing the Effect of Cellular ATP on Target Engagement," Cell Chem Biol, Feb. 15, 2018, available online Nov. 22, 2017, 25(2):206-214.e11.
Vauquelin et al., "Long-lasting target binding and rebinding as mechanisms to prolong in vivo drug action," Br J Pharmacol, Oct. 2010, 161(3):488-508.
Vely et al., "BIAcore® analysis to test phosphopeptide-SH2 domain interactions," Methods Mol Biol, 2000, 121:313-321.
Viswanatha et al., "Pooled genome-wide CRISPR screening for basal and context-specific fitness gene essentiality in *Drosophila* cells," Elife, Jul. 27, 2018, 7:e36333, 20 pages.
Vora et al., "CDK 4/6 inhibitors sensitize PIK3CA mutant breast cancer to PI3K inhibitors, " Cancer Cell, Jul. 14, 2014, 26(1):136-149.
Wagle et al., "MAP kinase pathway alterations in BRAF-mutant melanoma patients with acquired resistance to combined RAF/MEK inhibition," Cancer Discov, Jan. 2014, available online Nov. 21, 2013, 4(1):61-68.

Wang et al., "Design and synthesis of new fluorogenic HIV protease substrates based on resonance energy transfer," Tetrahedron Letters, 1990, 31(45):6493-6496.
Wang et al., "Rapid sizing of short tandem repeat alleles using capillary array electrophoresis and energy-transfer fluorescent primers," Anal Chem, Apr. 1995, 67(7):1197-1203.
Ward et al., "Spectral perturbations of the Aequorea green-fluorescent protein," Photochem. Photobiol, Jun. 1982, 35(6):803-808.
Wells et al., "Quantifying CDK inhibitor selectivity in live cells," Nat Commun, Jun. 2, 2020, 11(1):2743, 11 pages.
Westbrook et al., "How Structural Biologists and the Protein Data Bank Contributed to Recent FDA New Drug Approvals," Structure, Feb. 5, 2019, available online Dec. 27, 2018, 27(2):211-217.
Wilbanks et al., "Rod structure of a phycoerythrin II-containing phycobilisome. I. Organization and sequence of the gene cluster encoding the major phycobiliprotein rod components in the genome of marine *Synechococcus* sp. WH8020," J Biol Chem, Jan. 15, 1993, 268(2):1226-1235.
Yaeger et al., "Targeting Alterations in the RAF-MEK Pathway," Cancer Discov, Mar. 2019, available online Feb. 15, 2019, 9(3):329-341.
Yamaguchi et al., "Identification ofJTP-70902, a p15(INK4b)-inductive compound, as a novel MEK1/2 inhibitor," Cancer Sci, Nov. 2007, available online Sep. 2, 2007, 98(11):1809-1816.
Yoshida et al. "Identification and characterization of a novel chemotype MEK inhibitor able to alter the phosphorylation state ofMEK 1/2.," Oncotarget, Dec. 2012, 3(12):1533-1545.
Zhao et al., "The clinical development ofMEK inhibitors," Nat Rev Clin Oncol, Jul. 2014, available online May 20, 2014, 11(7):385-400.
U.S. Appl. No. 18/002,812, filed Dec. 21, 2022, Arvin Dar.
Mikula et al., "Design and Development of Fluorescent Vemurafenib Analogs for In Vivo Imaging", Theranostics, Mar. 2017, 7(5):1257-1265.

\* cited by examiner

| | KSR2:MEK1 :ADP | KSR2:MEK1 in complex with AMP-PNP and following MEK1 | | | | | KSR1:MEK1 AMP-PNP | KSR1:MEK1 in complex with AMP-PNP and following MEK1 | | | | |
|---|---|---|---|---|---|---|---|---|---|---|---|---|
| | | Trametinib | Cobimetinib | Selumetinib | PD0325901 | Trametinib | AMP-PNP | Trametinib | Cobimetinib | Selumetinib | PD0325901 | Trametinib |
| PDB code | 7JUQ | 7JUR | 7JUS | 7JUT | 7JUU | 7JUV | 7JUW | 7JUX | 7JUY | 7JUZ | 7JV0 | 7JV1 |
| Res*(Å) | 3.22 Å | 2.82 Å | 2.99 Å | 3.09 Å | 3.19 Å | 3.35 Å | 2.88 Å | 3.34 Å | 3.10 Å | 3.21 Å | 3.63 Å | 3.62 Å |
| Unique* | 21,247 | 31,247 | 28,127 | 23,585 | 21,548 | 18,480 | 28,300 | 18,630 | 22,406 | 20,359 | 14,589 | 13,697 |
| KSR1/2 pocket | | | | | | | | | | | | |
| MEK1 pocket | | | | | | | | | | | | |
| MEK1 pocket | None | | | | | | None | | | | | |

Res*(Å): Resolution (Å)        Unique*: Number of unique reflections

Figure: 1

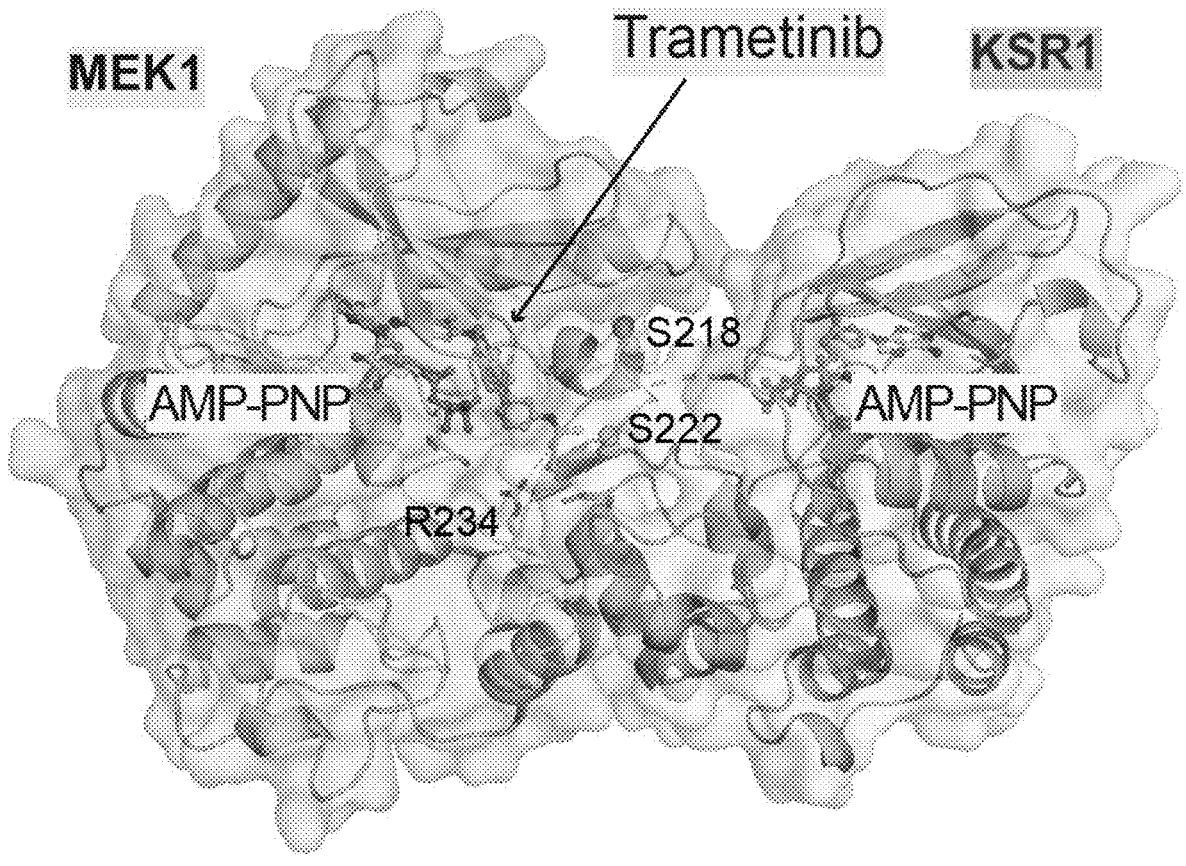
Figure: 2

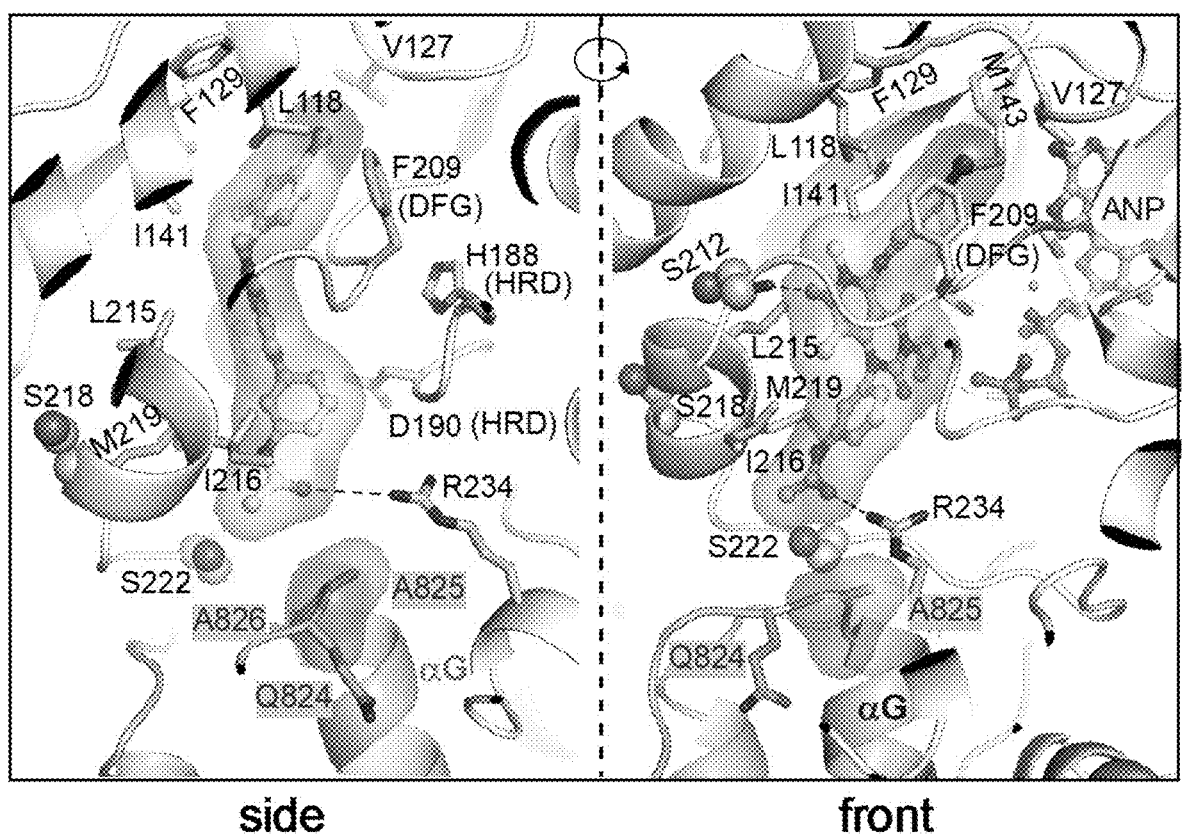
side                                    front
Figure: 3

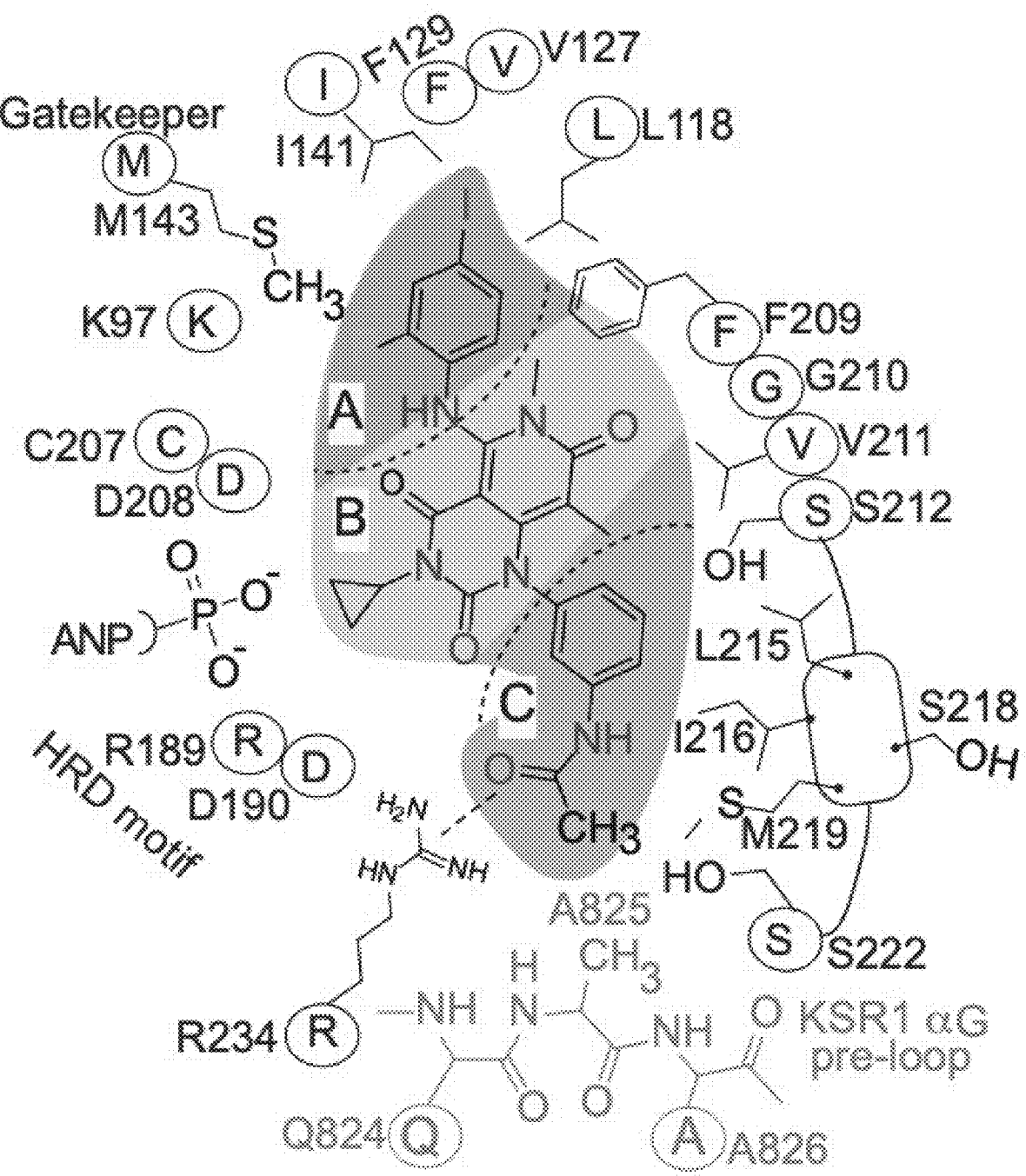
Figure: 4

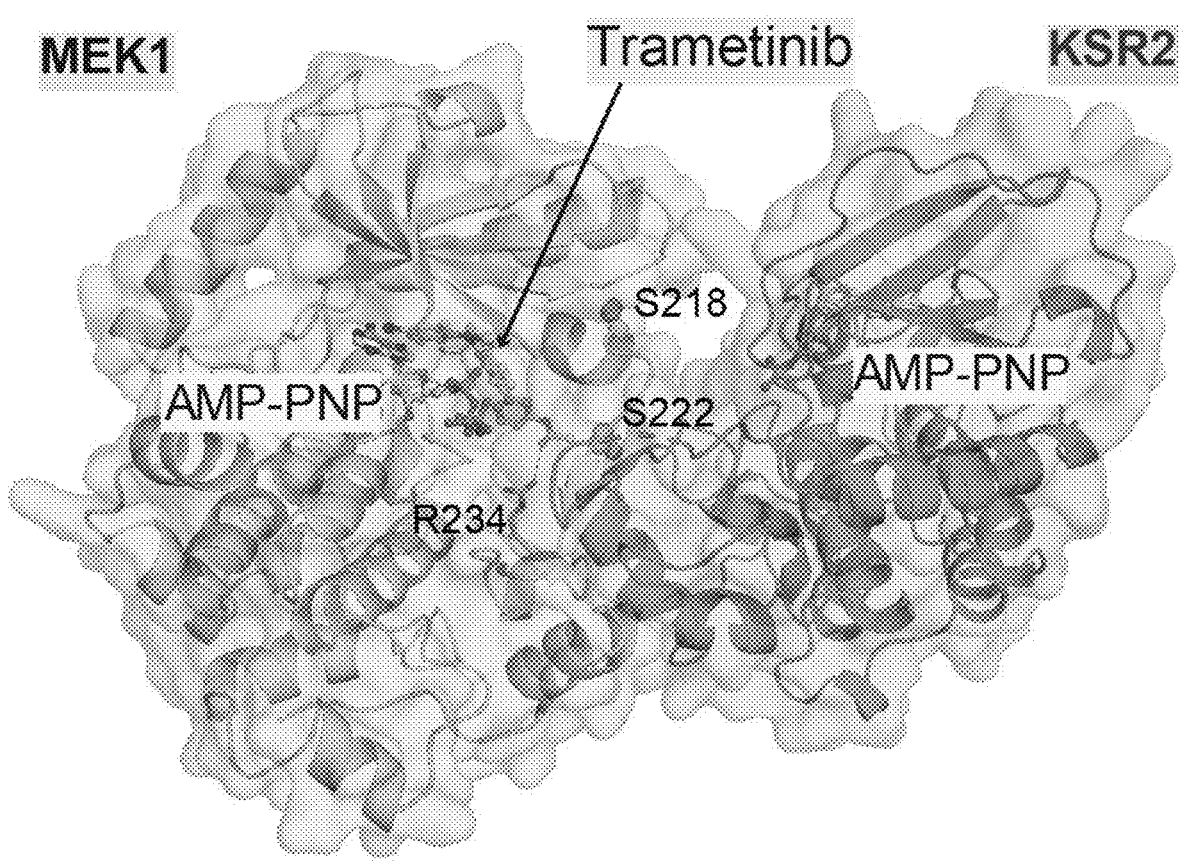
Figure: 5

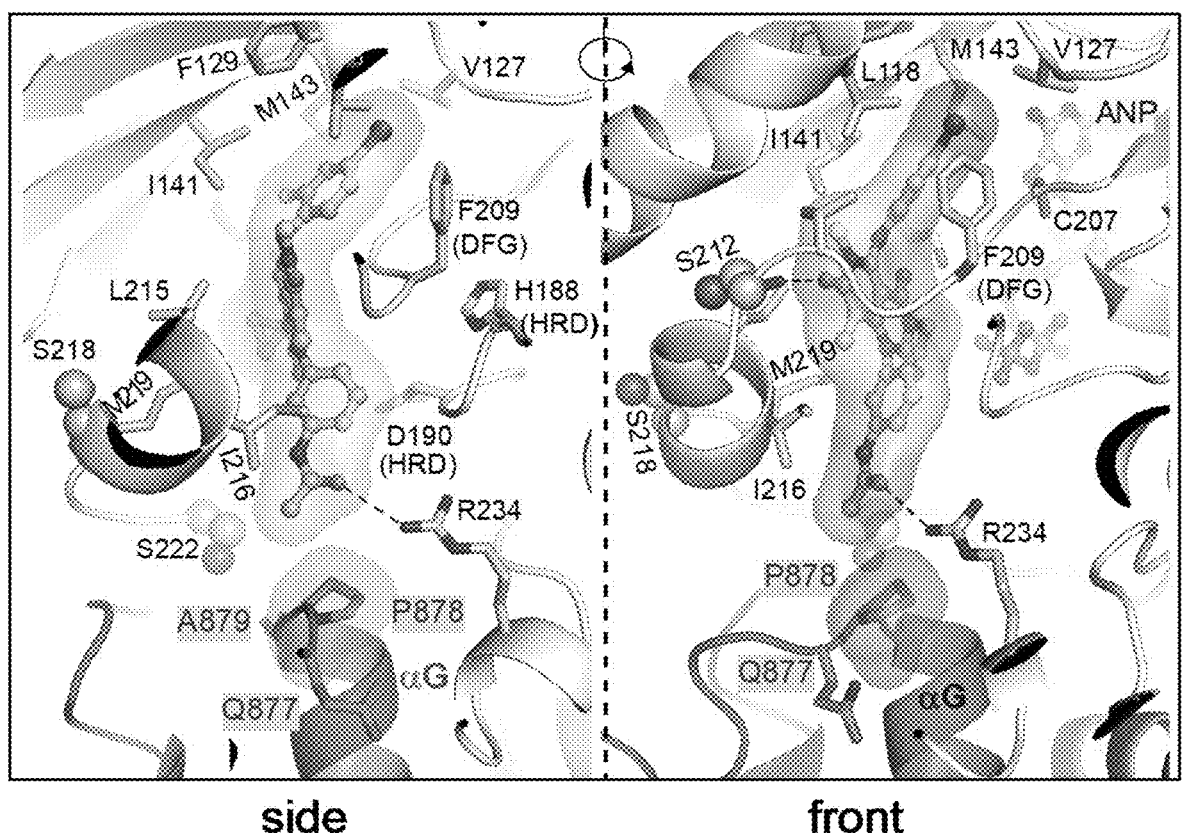
Figure: 6

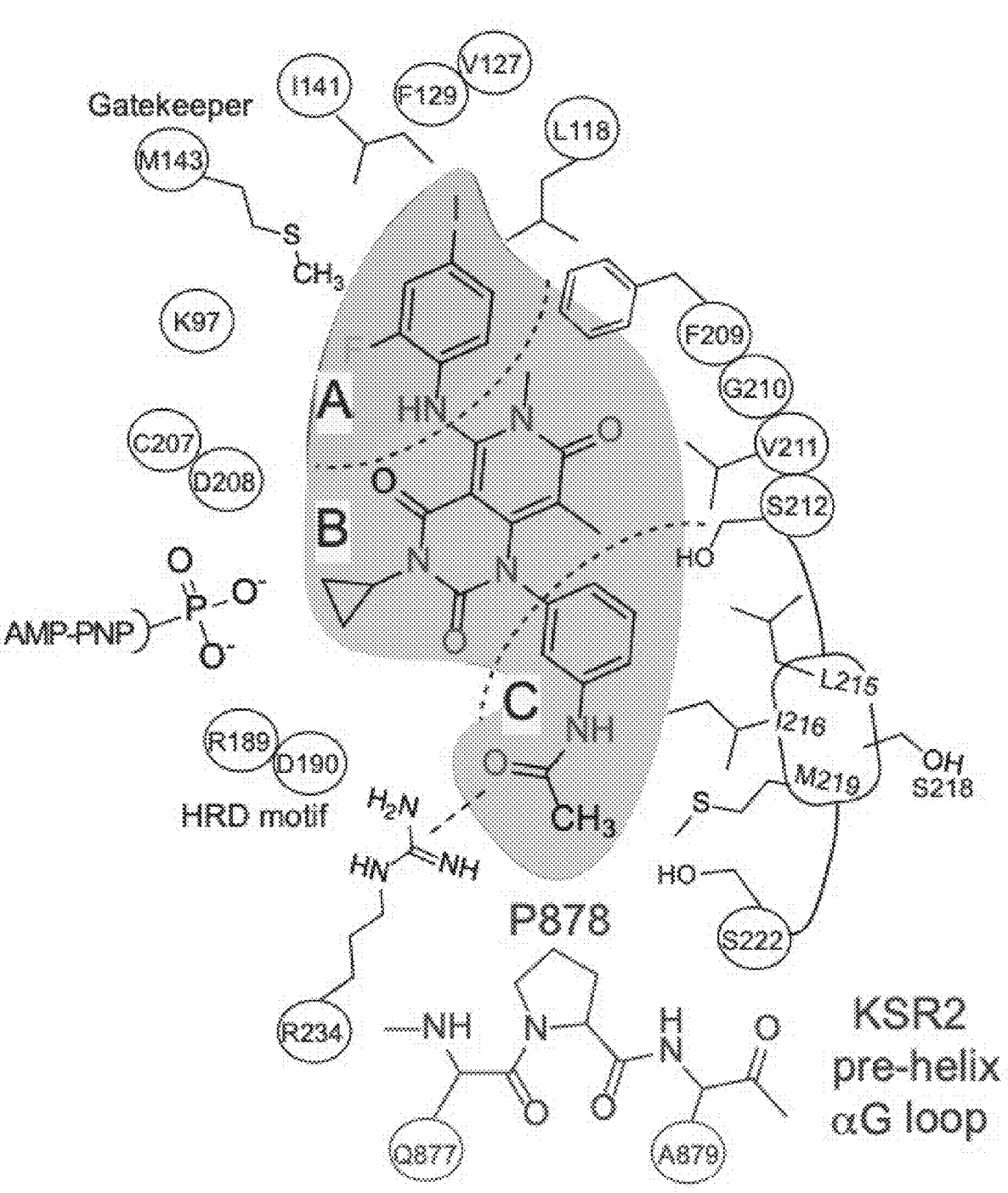
Figure: 7

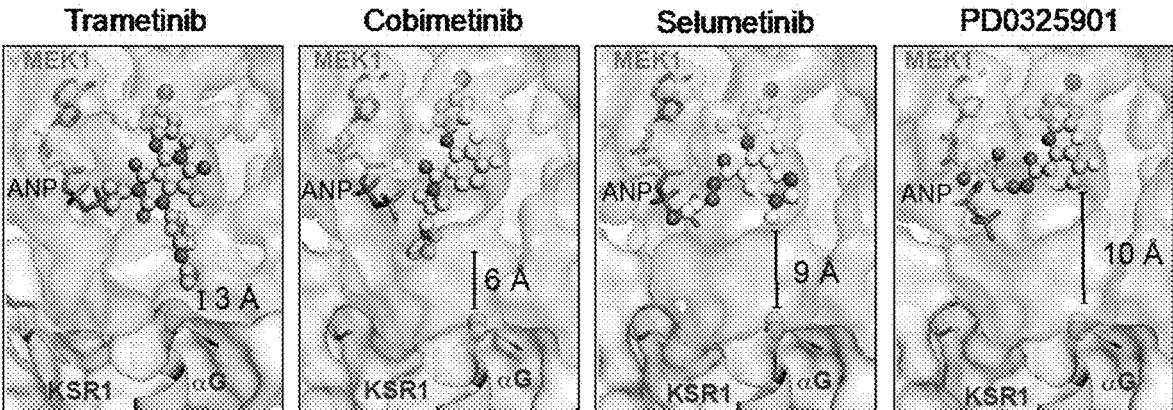
Figure: 8

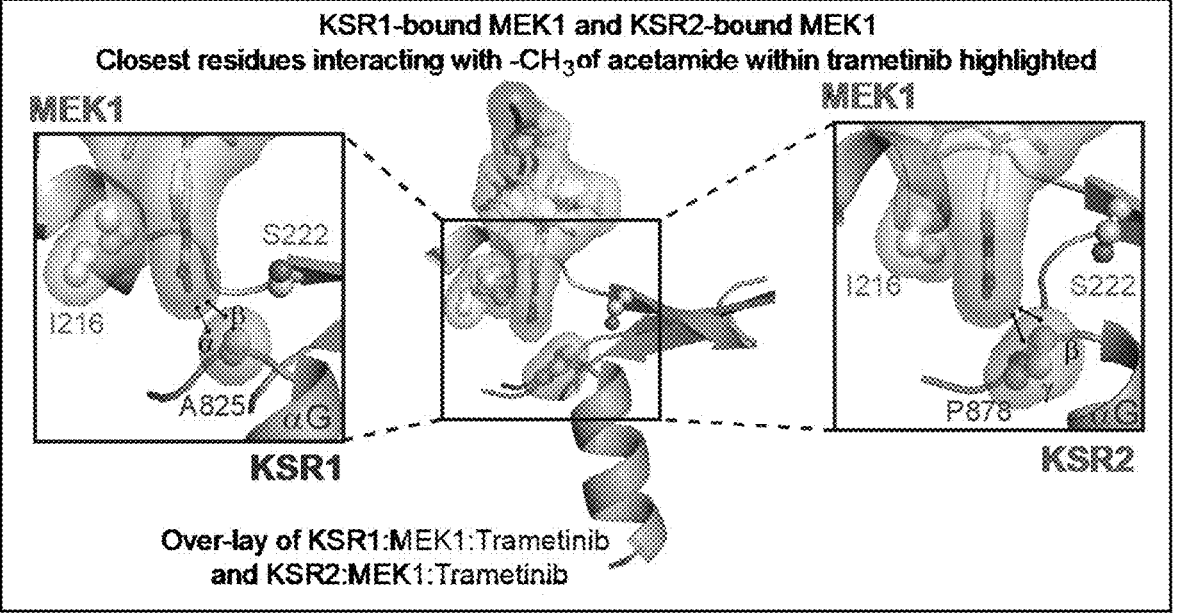
Figure: 9

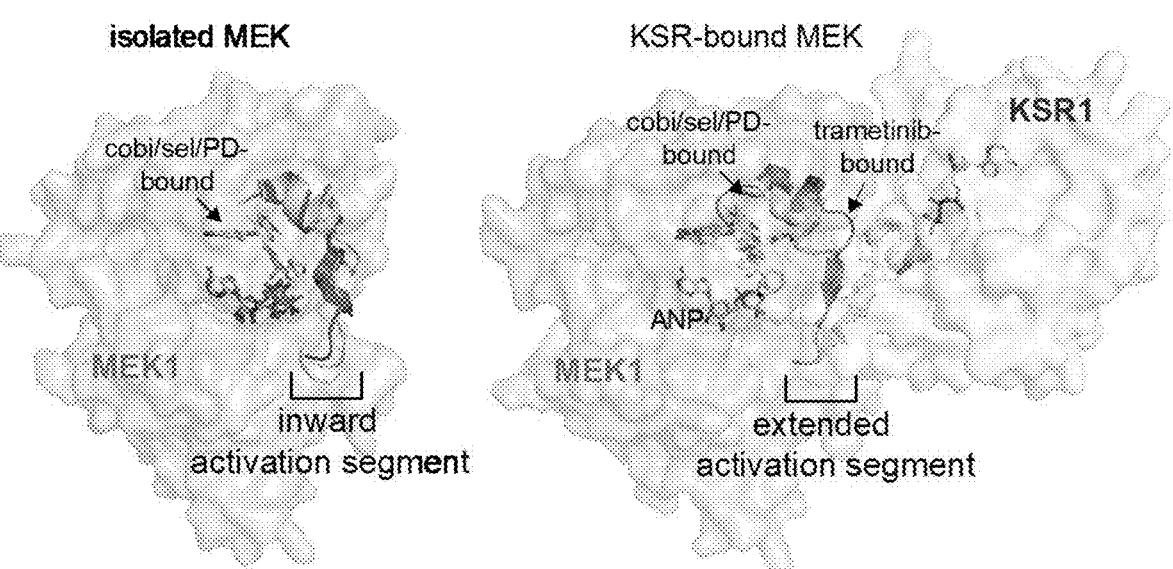
Figure: 10

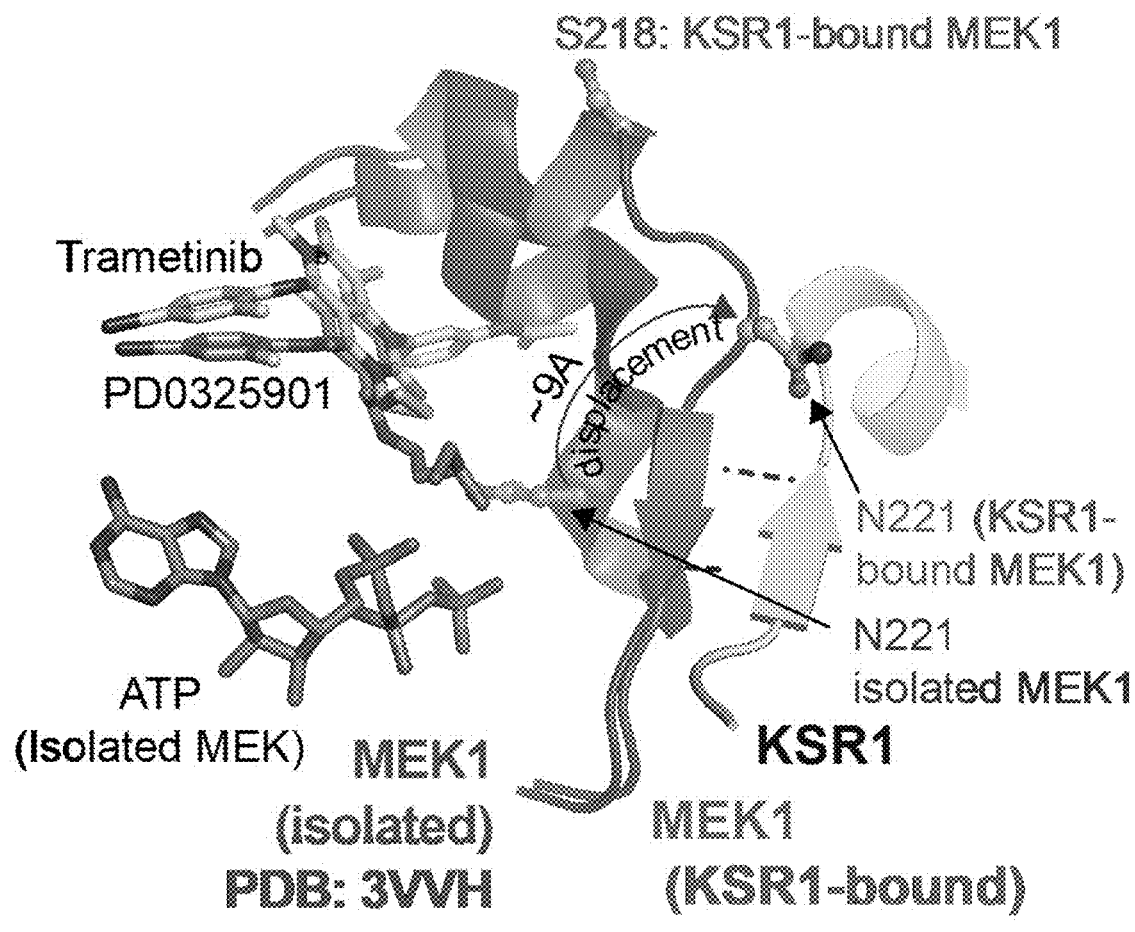
Figure: 11

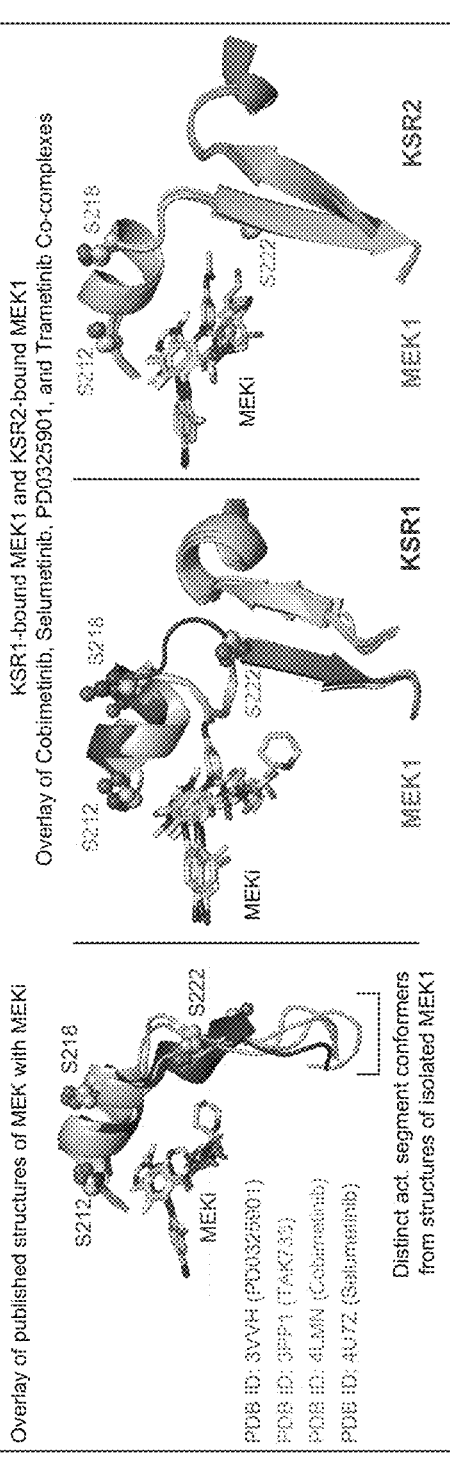
Figure: 12

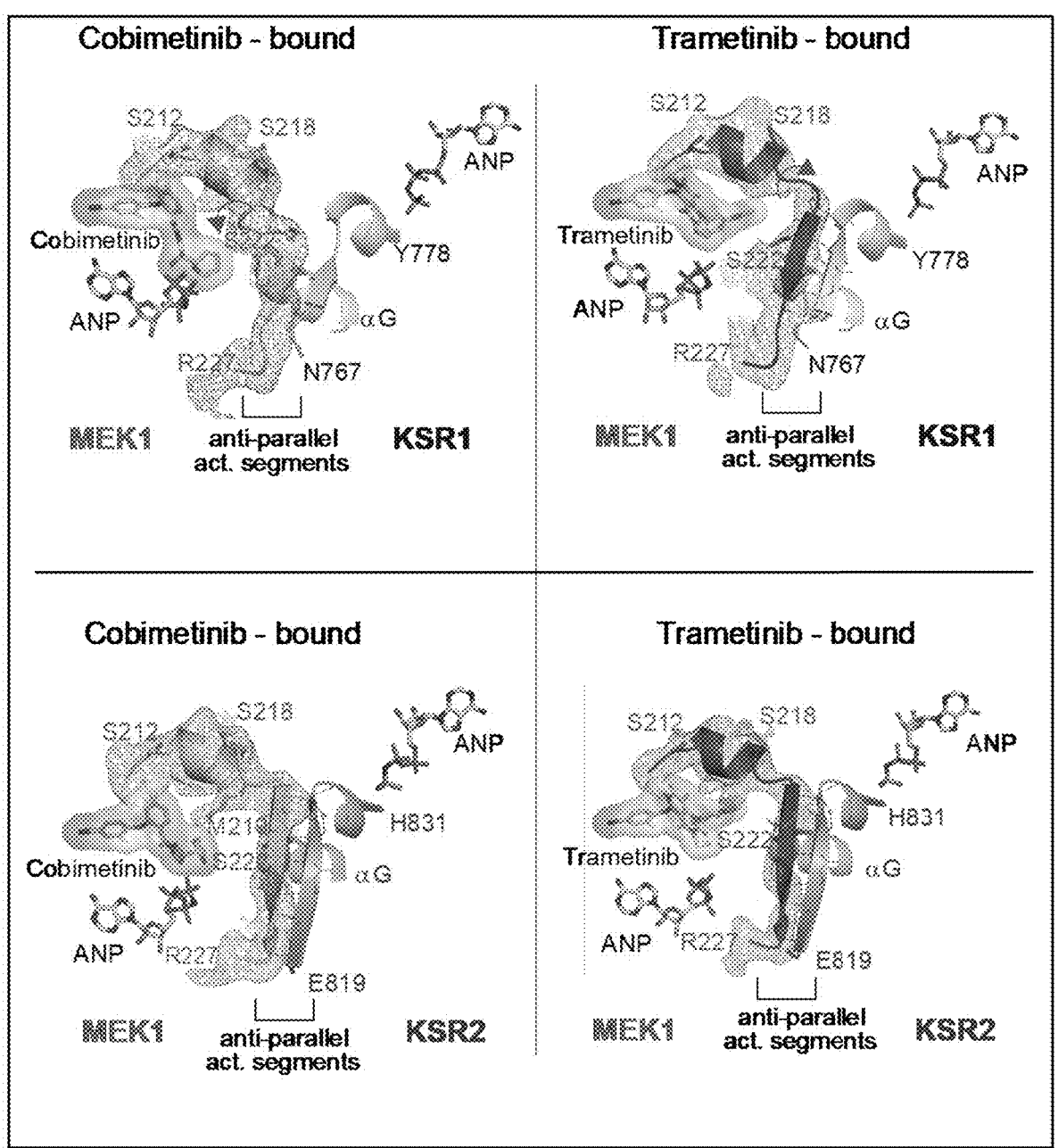
Figure: 13

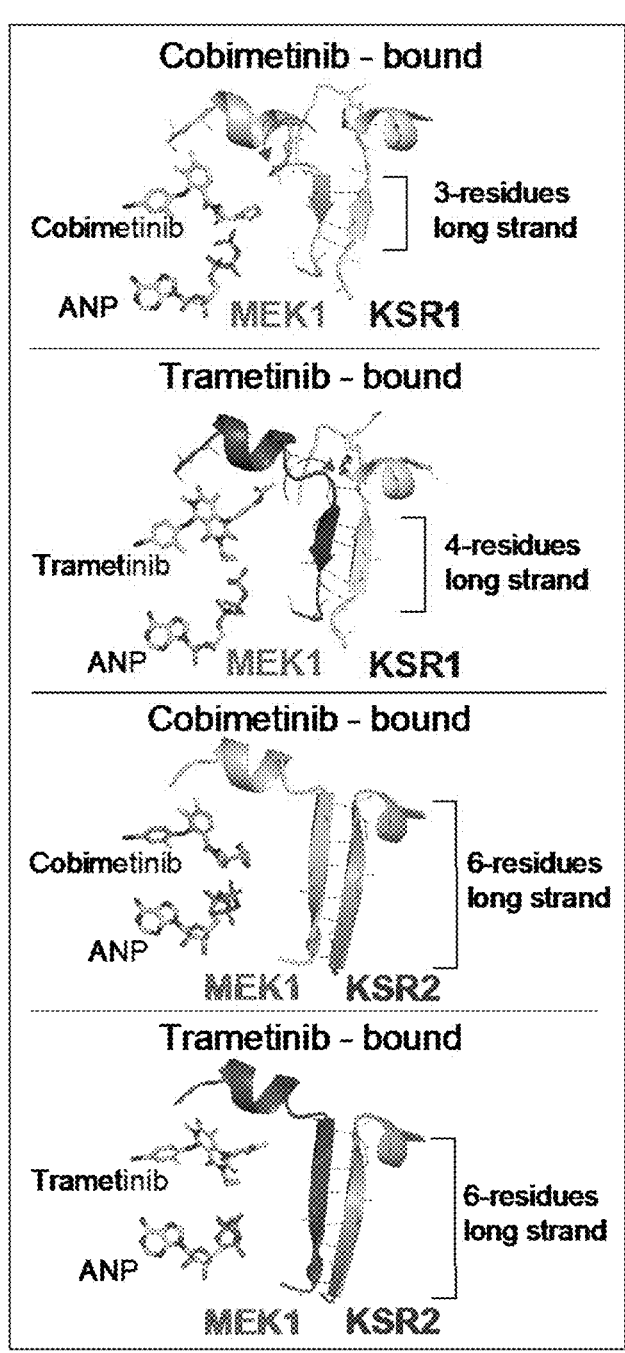
Figure: 14

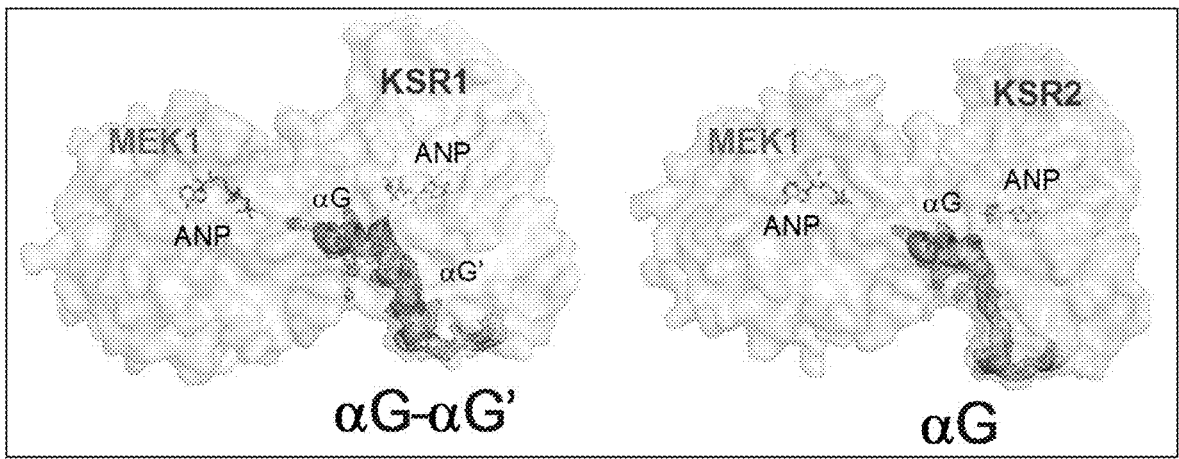
Figure: 15

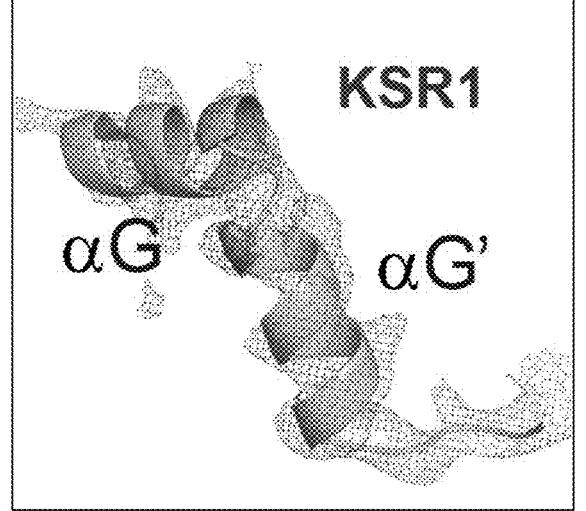 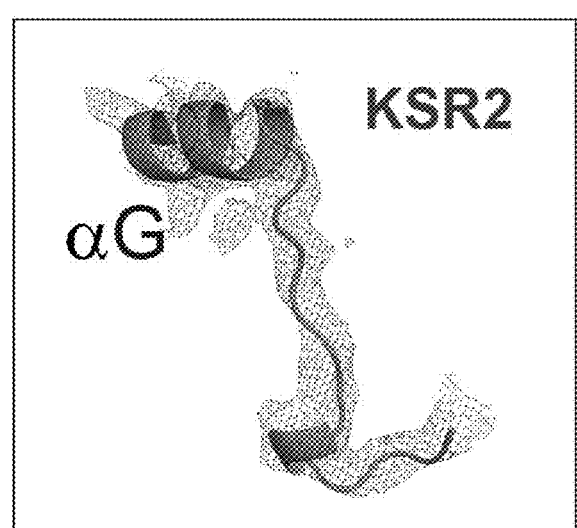
Figure: 16

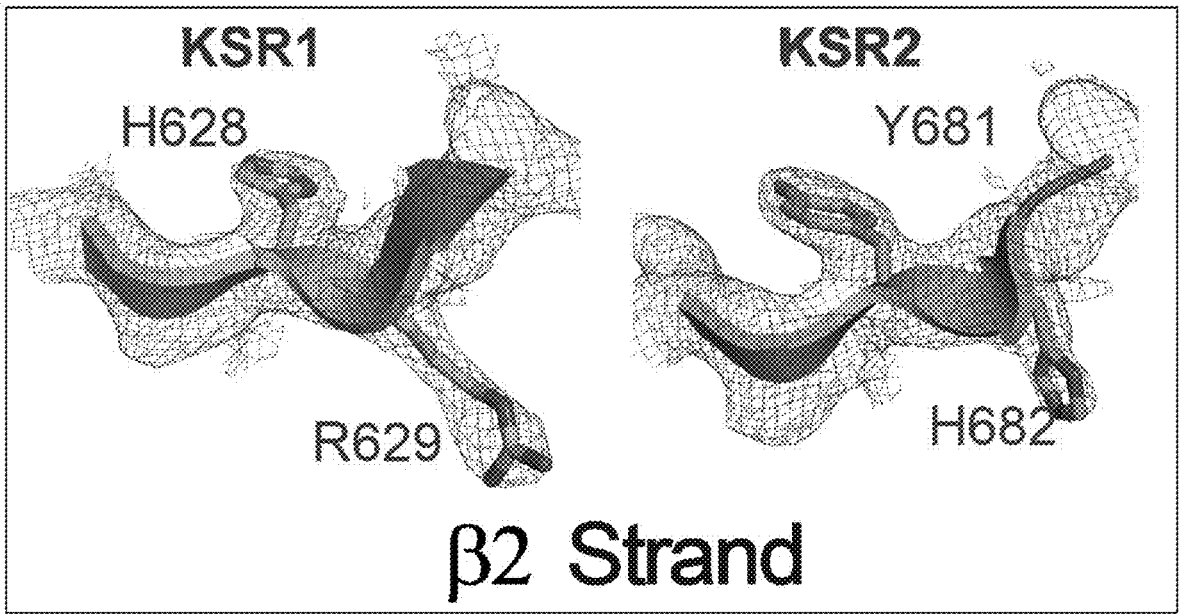
Figure: 17

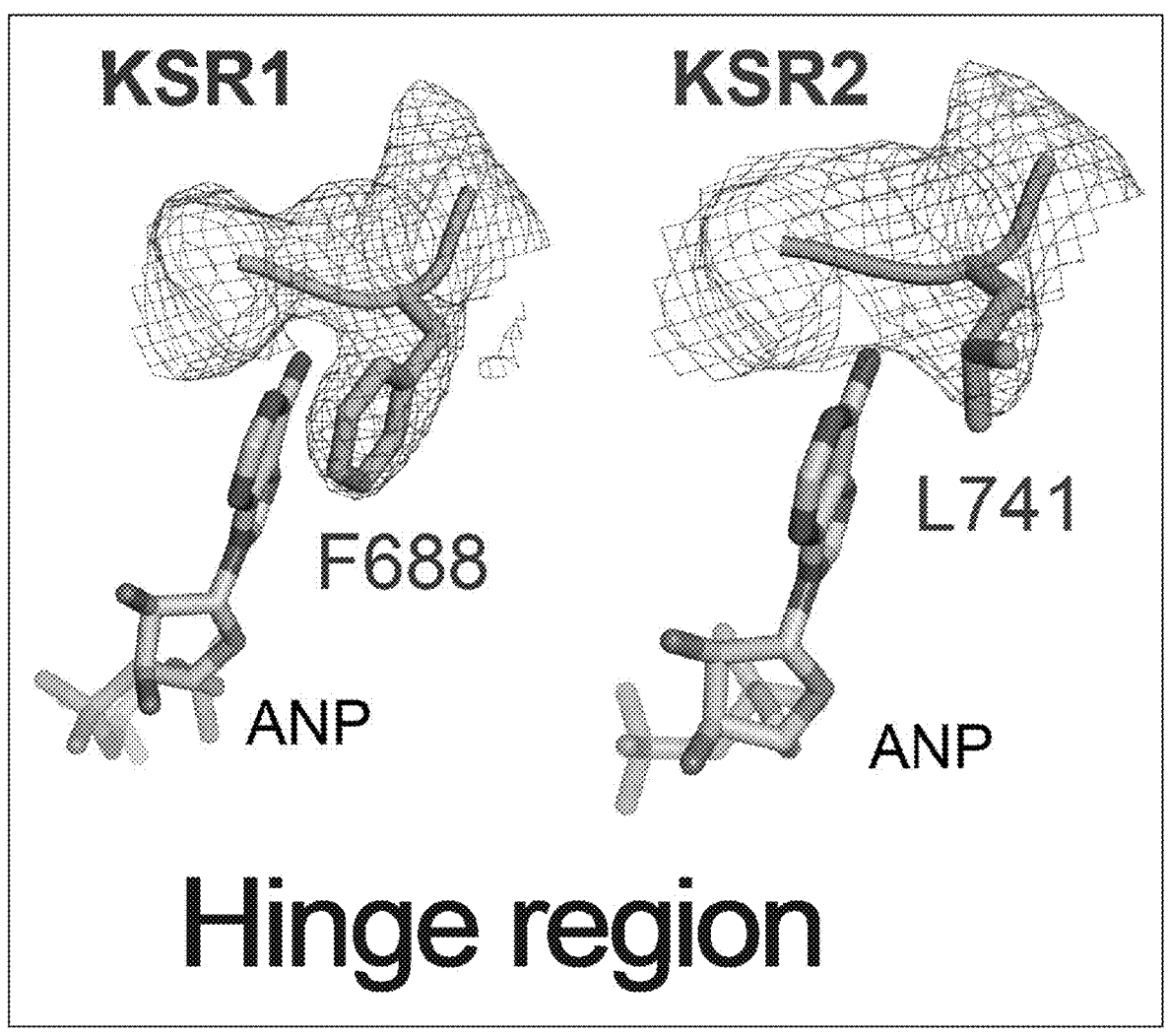
Figure: 18

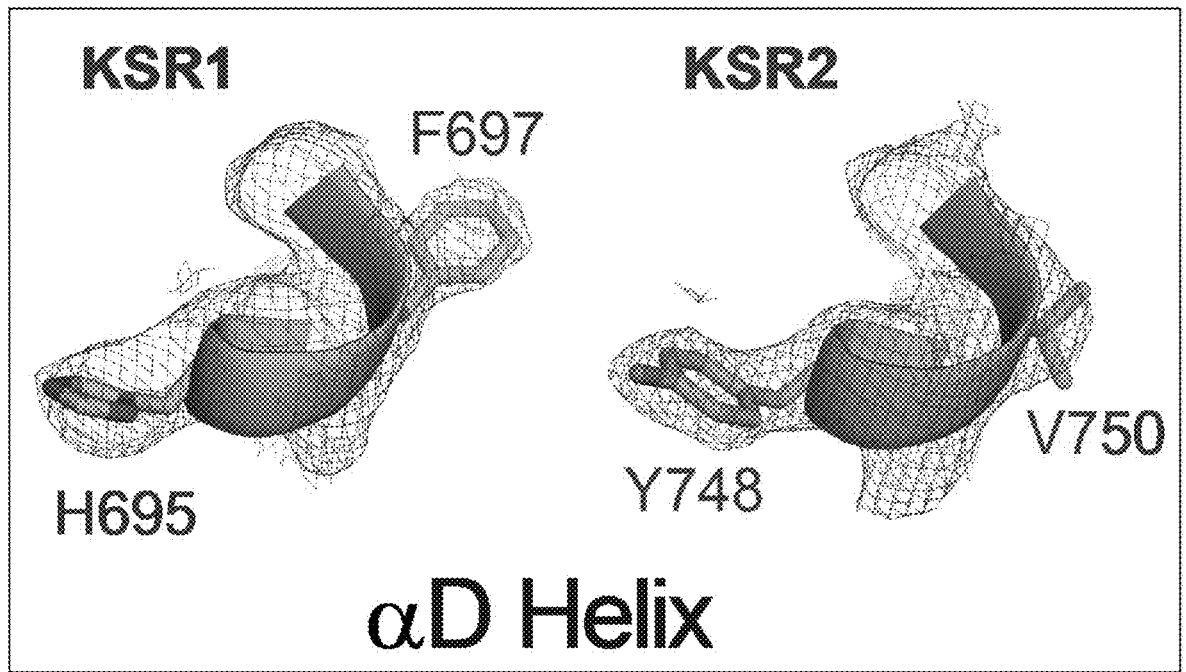
Figure: 19

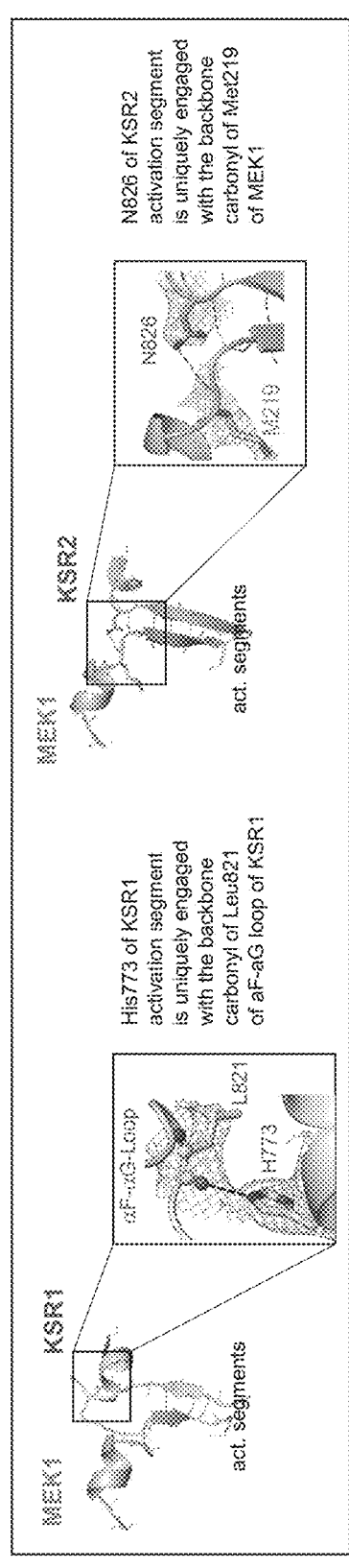
Figure: 20

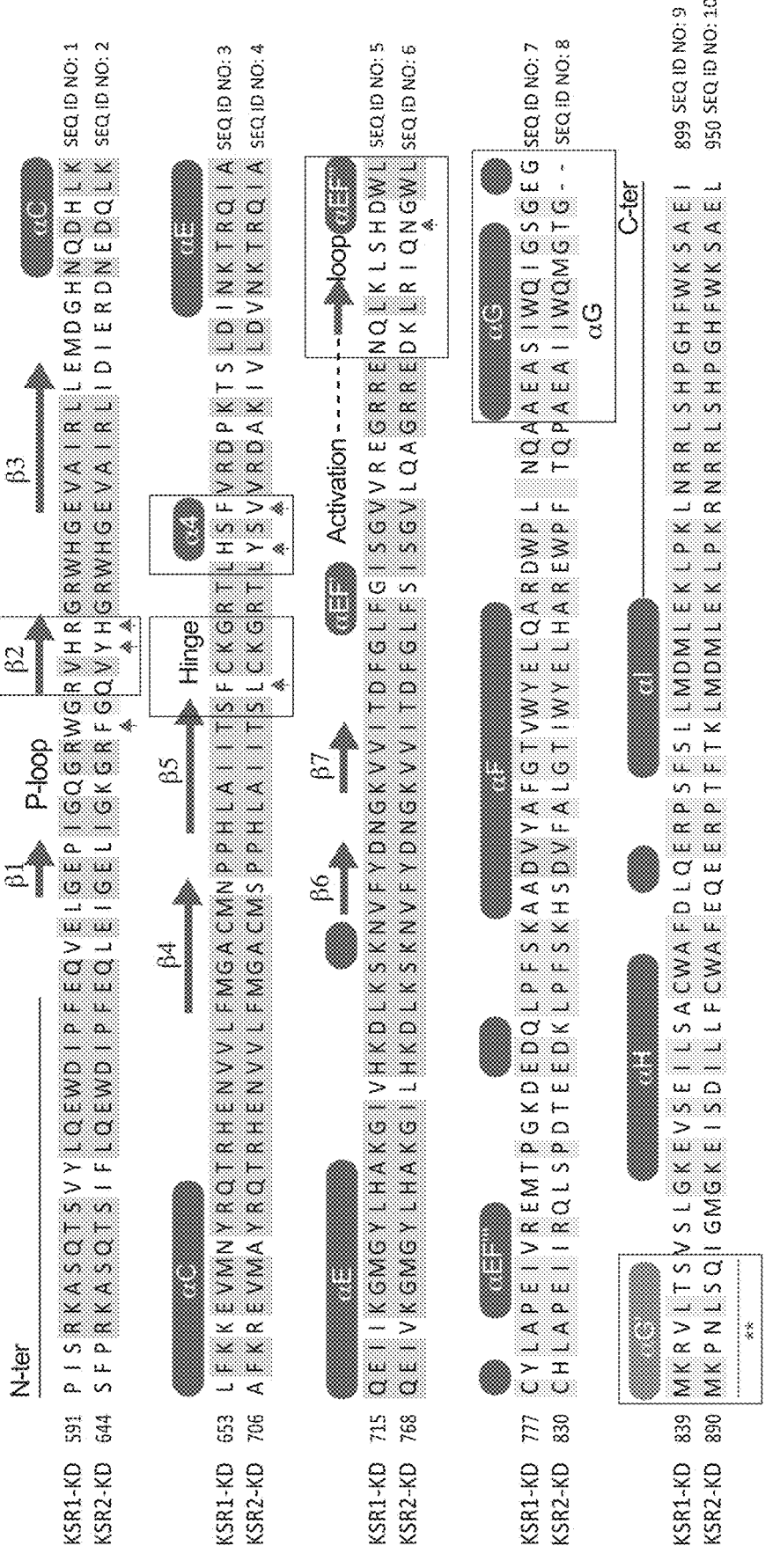
Figure: 21

Figure: 22

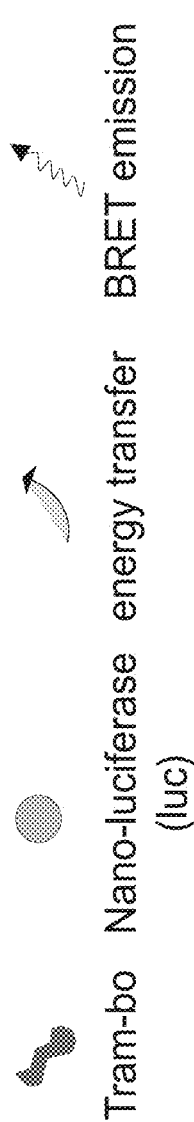
Figure: 23

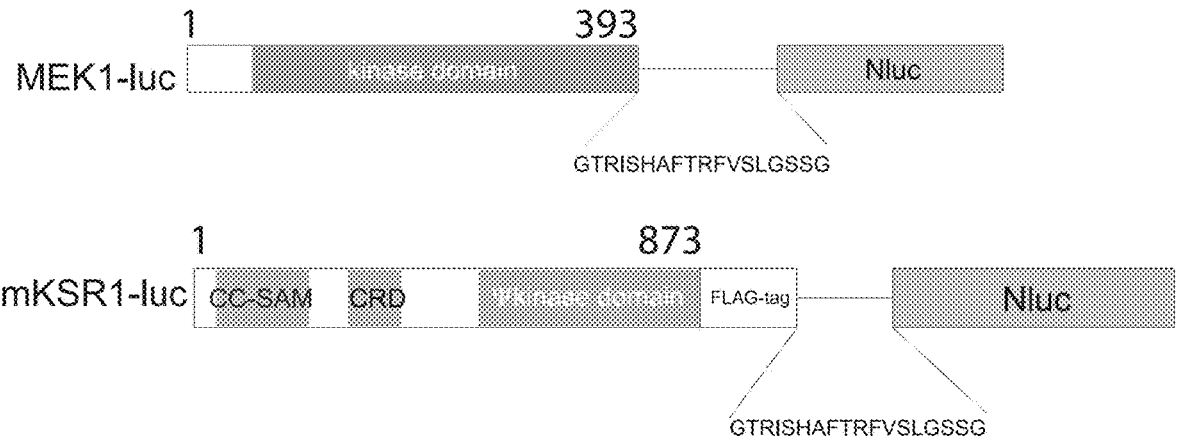
Figure: 24

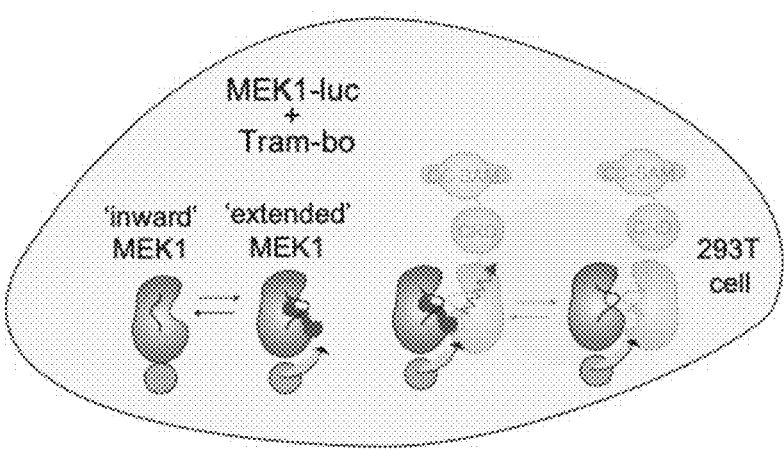
Figure: 25

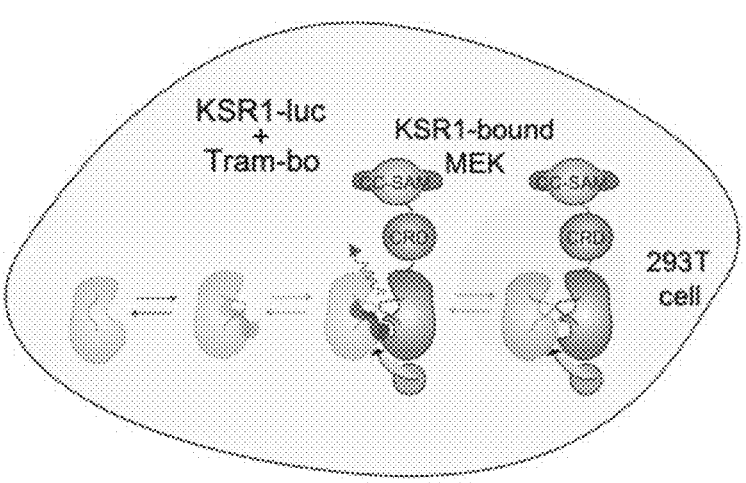
Figure: 26

Steady-state competition
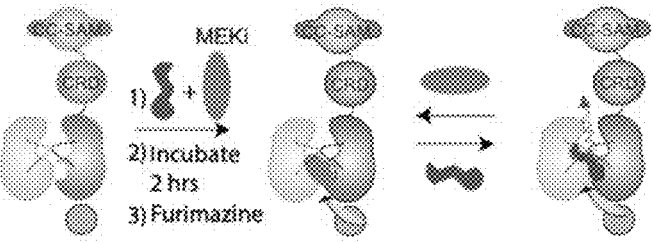
Figure: 27

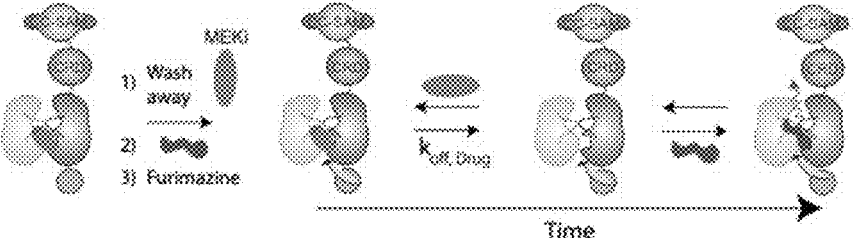
Figure: 28

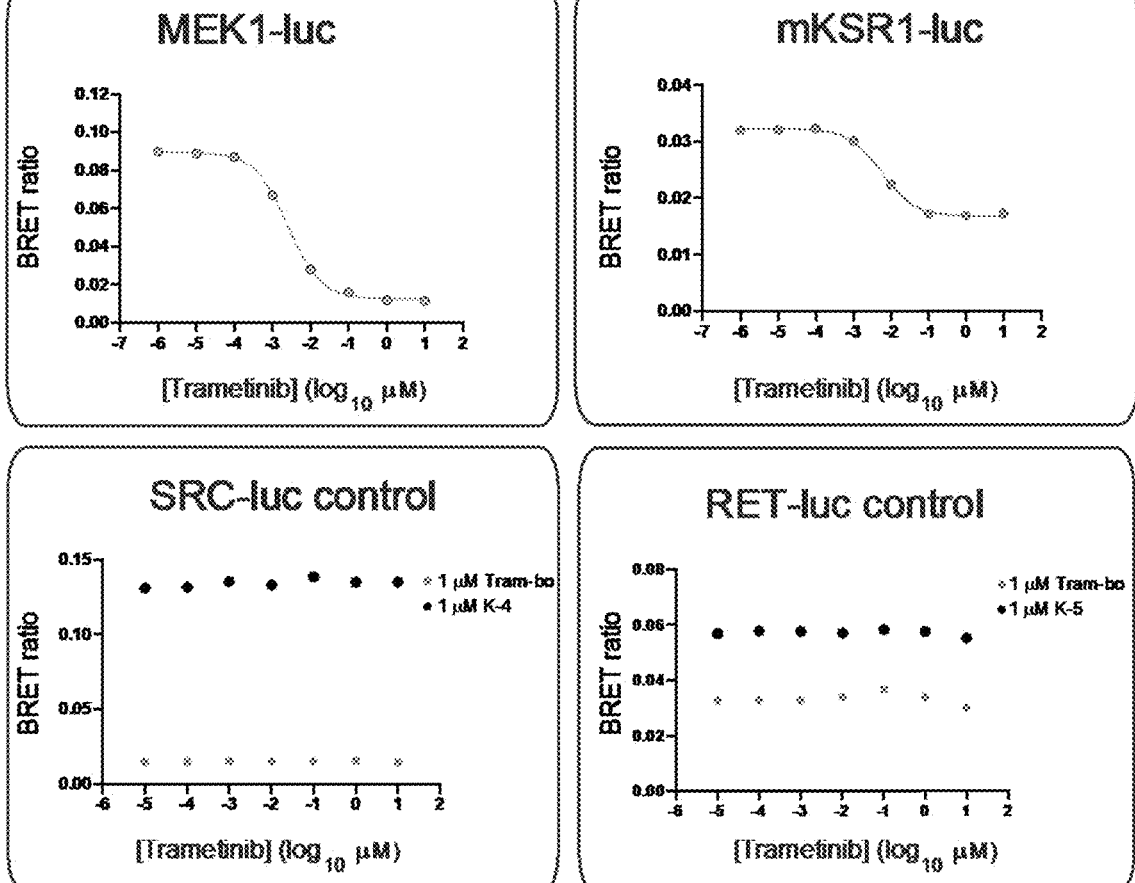
Figure: 29

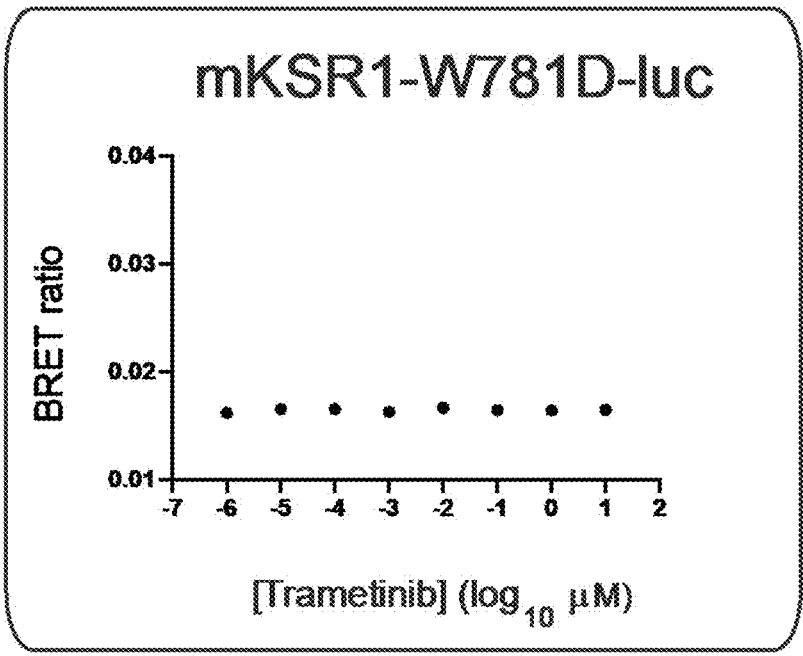
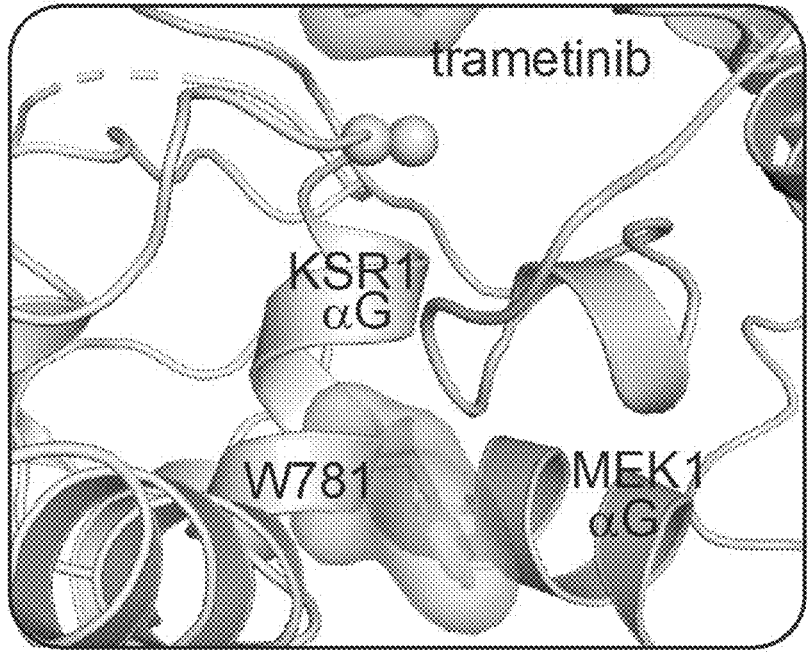
Figure: 30

| Trametinib (aM) | Independent replicate 1 | | | | Independent replicate 2 | | | | Independent replicate 3 | | | | |
|---|---|---|---|---|---|---|---|---|---|---|---|---|---|
| | plate 1 | plate 2 | plate 3 | plate 4 | plate 1 | plate 2 | plate 3 | plate 4 | plate 1 | plate 2 | plate 3 | plate 4 | plate 5 |
| KSR1-luc | 0.007069 | 0.007545 | 0.005778 | 0.00464 | 0.00771 | 0.00725 | 0.006874 | 0.01 | 0.005647 | 0.005176 | 0.005979 | 0.004772 | 0.008716 |
| MEK1-luc | 0.005249 | 0.006208 | 0.006681 | 0.01084 | 0.005434 | 0.005319 | 0.01058 | 0.01844 | 0.003834 | 0.004926 | 0.00738 | 0.00731 | 0.006859 |

| KSR1 (aM) | Ind. Rep 1 | Ind. Rep 2 | Ind. Rep 3 | Average | S.E.M. |
|---|---|---|---|---|---|
| Trametiglue | 0.0441 | 0.0463 | 0.0312 | 0.0405 | 0.0047 |
| CHS5126766 | 15.5500 | 4.5570 | 10.4500 | 10.1875 | 3.1762 |
| PD0325901 | 0.0337 | 0.0226 | 0.0236 | 0.0266 | 0.0035 |
| Cobimetinib | 0.0038 | 0.0056 | 0.0060 | 0.0051 | 0.0007 |
| Selumetinib | 1.0340 | 0.9685 | 0.5851 | 0.8625 | 0.1400 |

| MEK1 (aM) | Ind. Rep 1 | Ind. Rep 2 | Ind. Rep 3 | Average | S.E.M. |
|---|---|---|---|---|---|
| Trametiglue | 0.0352 | 0.0296 | 0.0300 | 0.0316 | 0.0018 |
| CHS5126766 | 6.1620 | 2.8820 | 3.8050 | 4.2830 | 0.9766 |
| PD0325901 | 0.0748 | 0.0588 | 0.0746 | 0.0694 | 0.0053 |
| Cobimetinib | 0.0987 | 0.0961 | 0.1137 | 0.1028 | 0.0055 |
| Selumetinib | 4.9150 | 3.6600 | 7.3450 | 5.3067 | 1.0816 |

| MEK1-luc + KSR1-WT (aM) | ind. rep 1 | ind. rep 2 | ind. rep 3 | Average | SEM |
|---|---|---|---|---|---|
| Trametinib | 0.00429 | 0.01003 | 0.01455 | 0.00962333 | 0.00296878 |
| Trametiglue | 0.004731 | 0.009799 | 0.01782 | 0.01078333 | 0.00381039 |
| CHS5126766 | 4.167 | 8.029 | 12.25 | 8.1486667 | 2.33412813 |
| PD0325901 | 0.0224 | 0.03817 | 0.06024 | 0.04027 | 0.01097382 |
| Cobimetinib | 0.004868 | 0.01346 | 0.01183 | 0.01005267 | 0.00263469 |
| Selumetinib | 0.6553 | 1.162 | 1.357 | 1.0581 | 0.20911889 |

| MEK1-luc + KSR1-W78ID (aM) | ind. rep 1 | ind. rep 2 | ind. rep 3 | Average | SEM |
|---|---|---|---|---|---|
| Trametinib | 0.01149 | 0.01246 | 0.006539 | 0.010163 | 0.00183351 |
| Trametiglue | 0.01574 | 0.02021 | 0.0114 | 0.01578333 | 0.00254332 |
| CHS5126766 | 6.207 | 3.123 | N/A | 4.665 | 1.25903773 |
| PD0325901 | 0.05739 | 0.1017 | 0.05819 | 0.07242667 | 0.01463849 |
| Cobimetinib | 0.07962 | 0.1551 | 0.08446 | 0.10639333 | 0.02439338 |
| Selumetinib | 2.738 | 9.274 | 4.336 | 5.4933333 | 1.96718558 |

Figure: 31

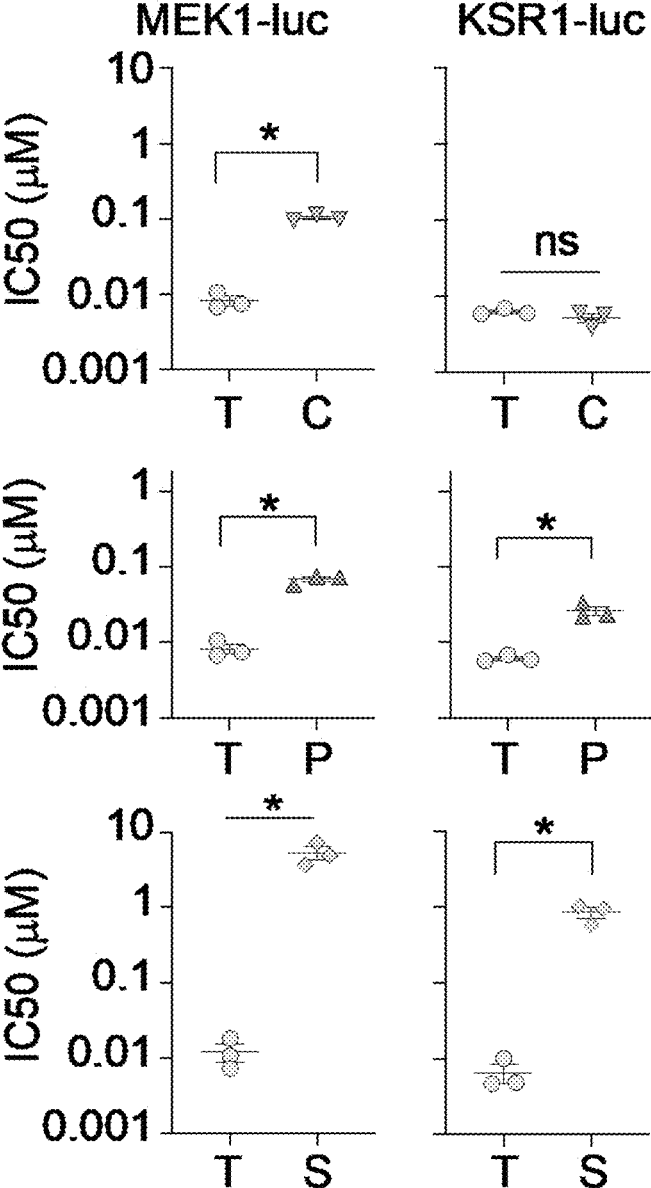
Figure: 32

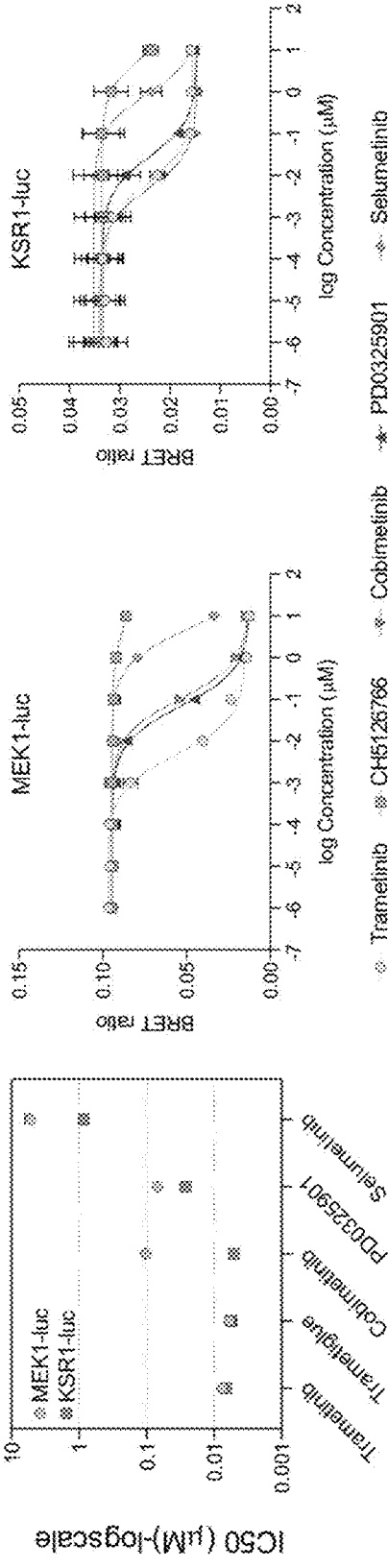
Figure: 33

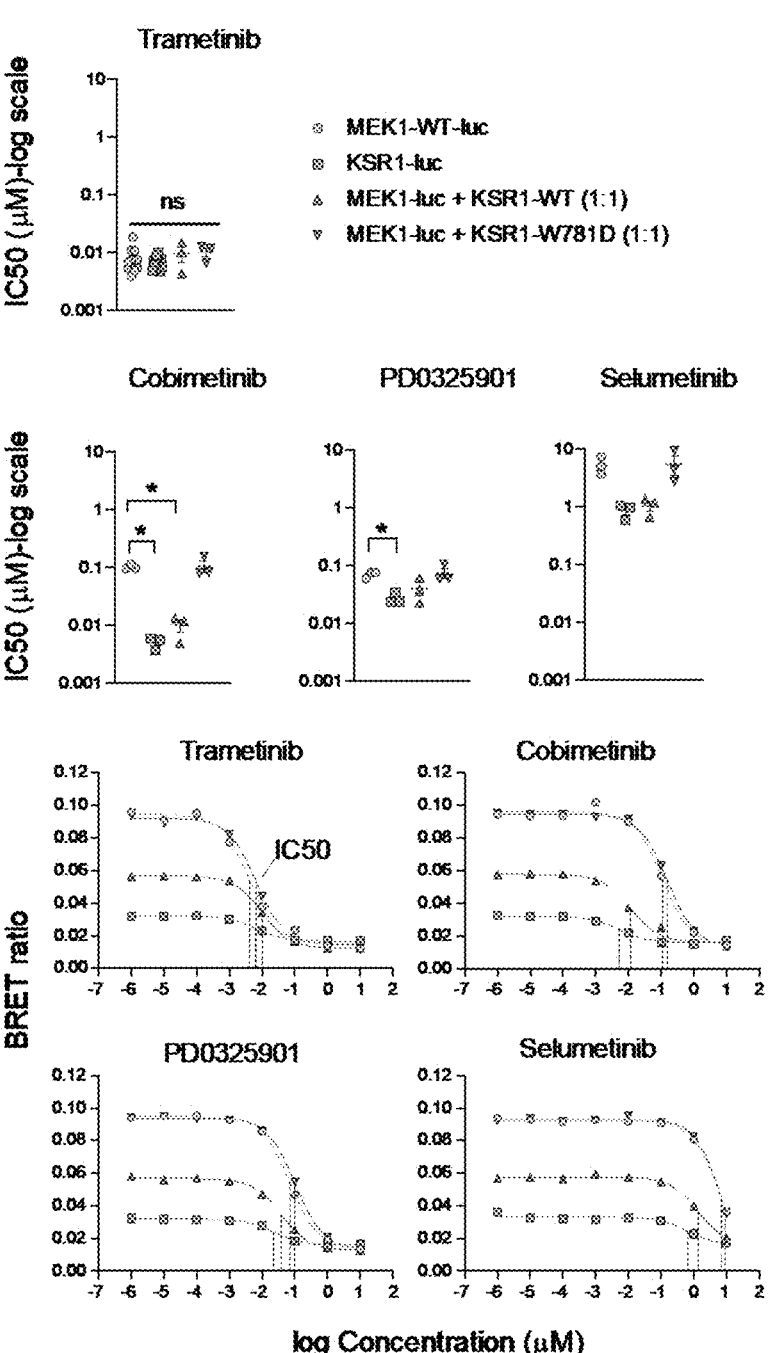
Figure: 34

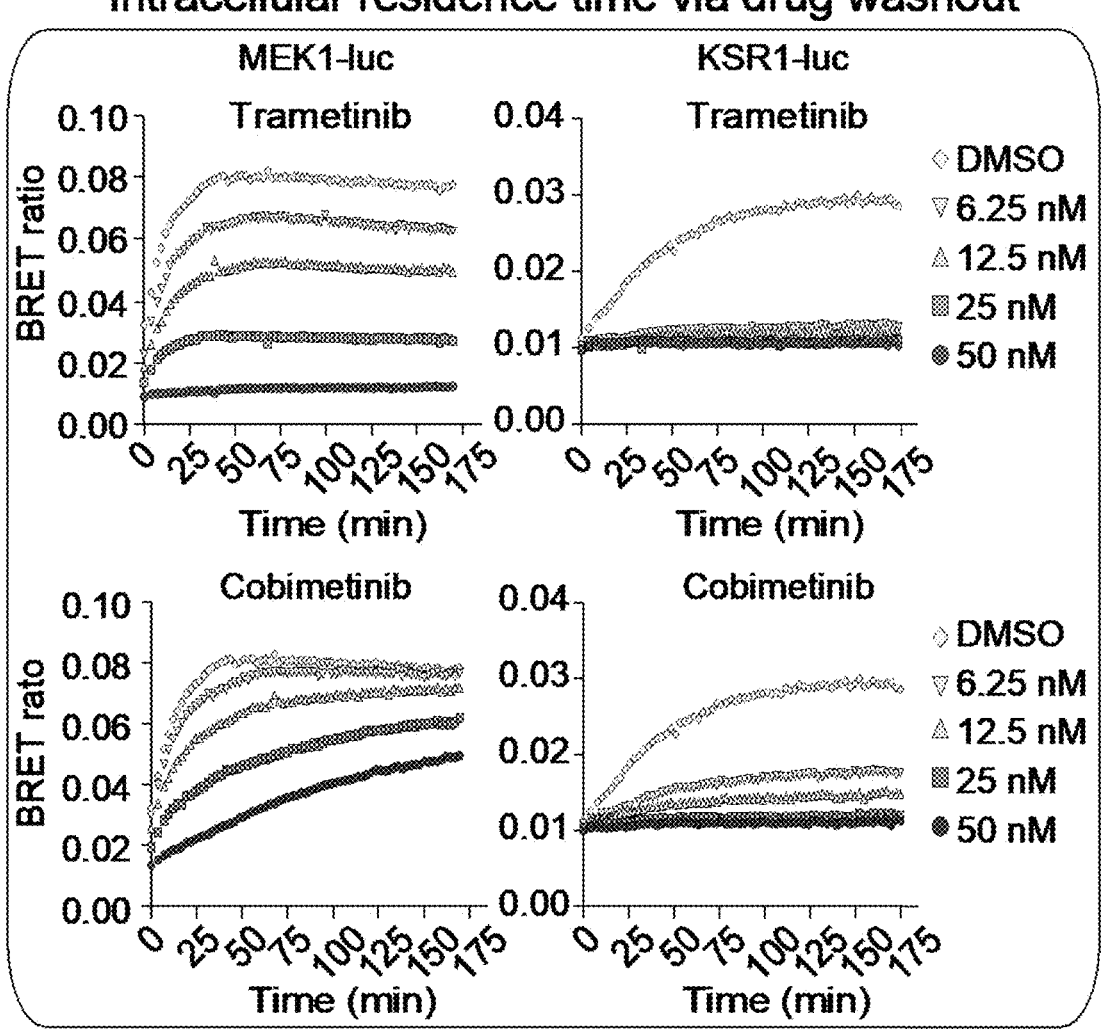
Figure: 35

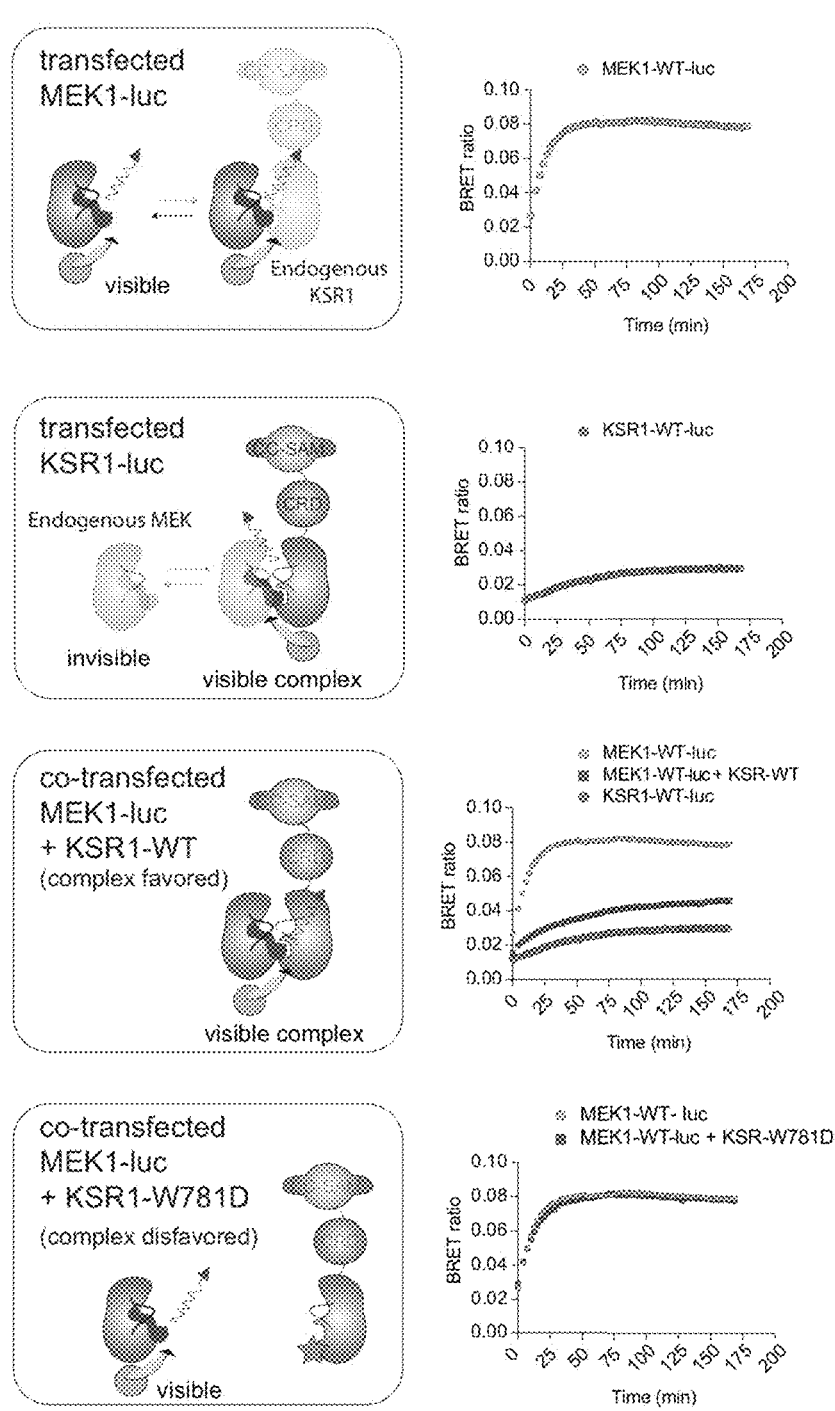
Figure: 36

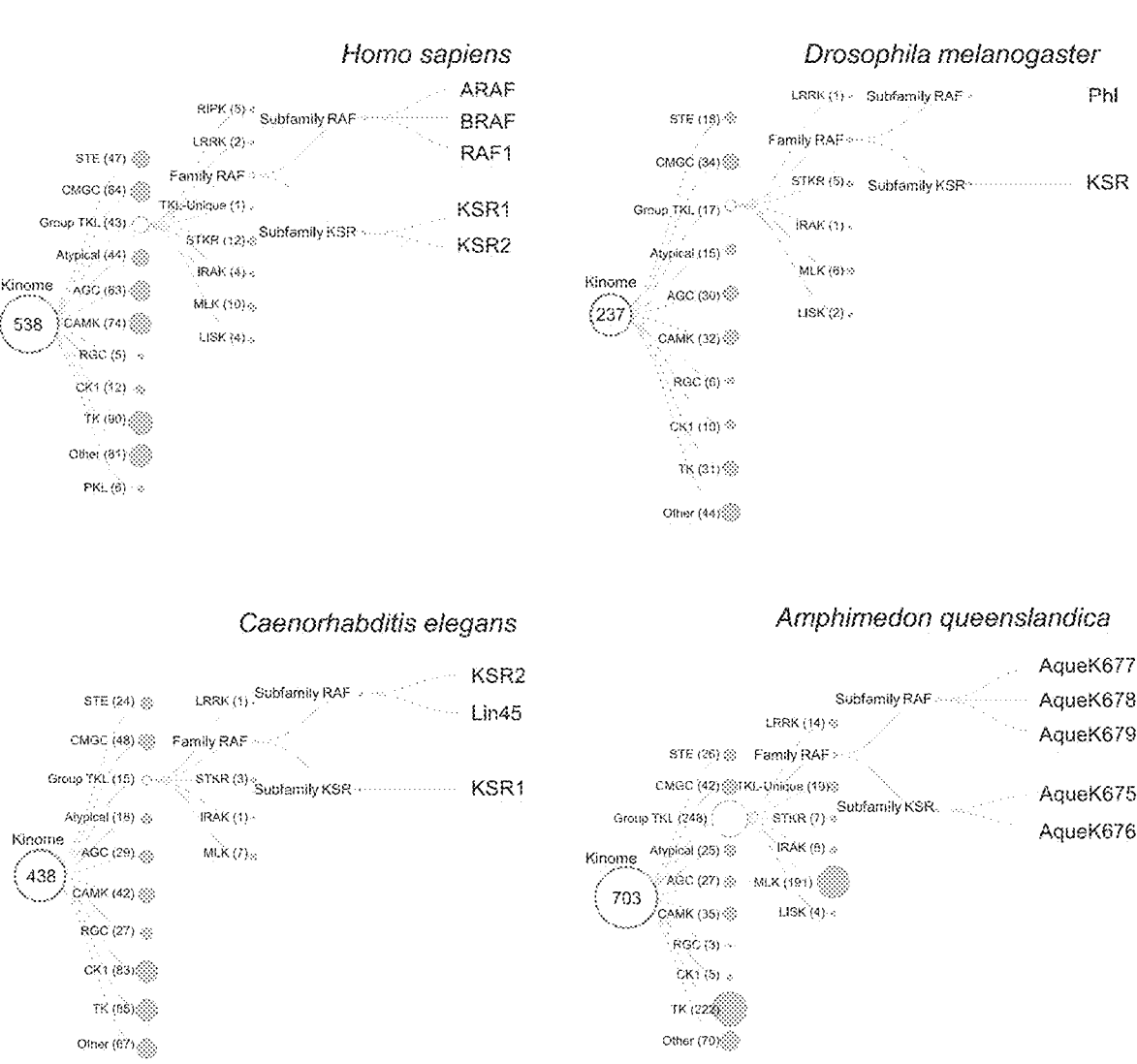
Figure: 37

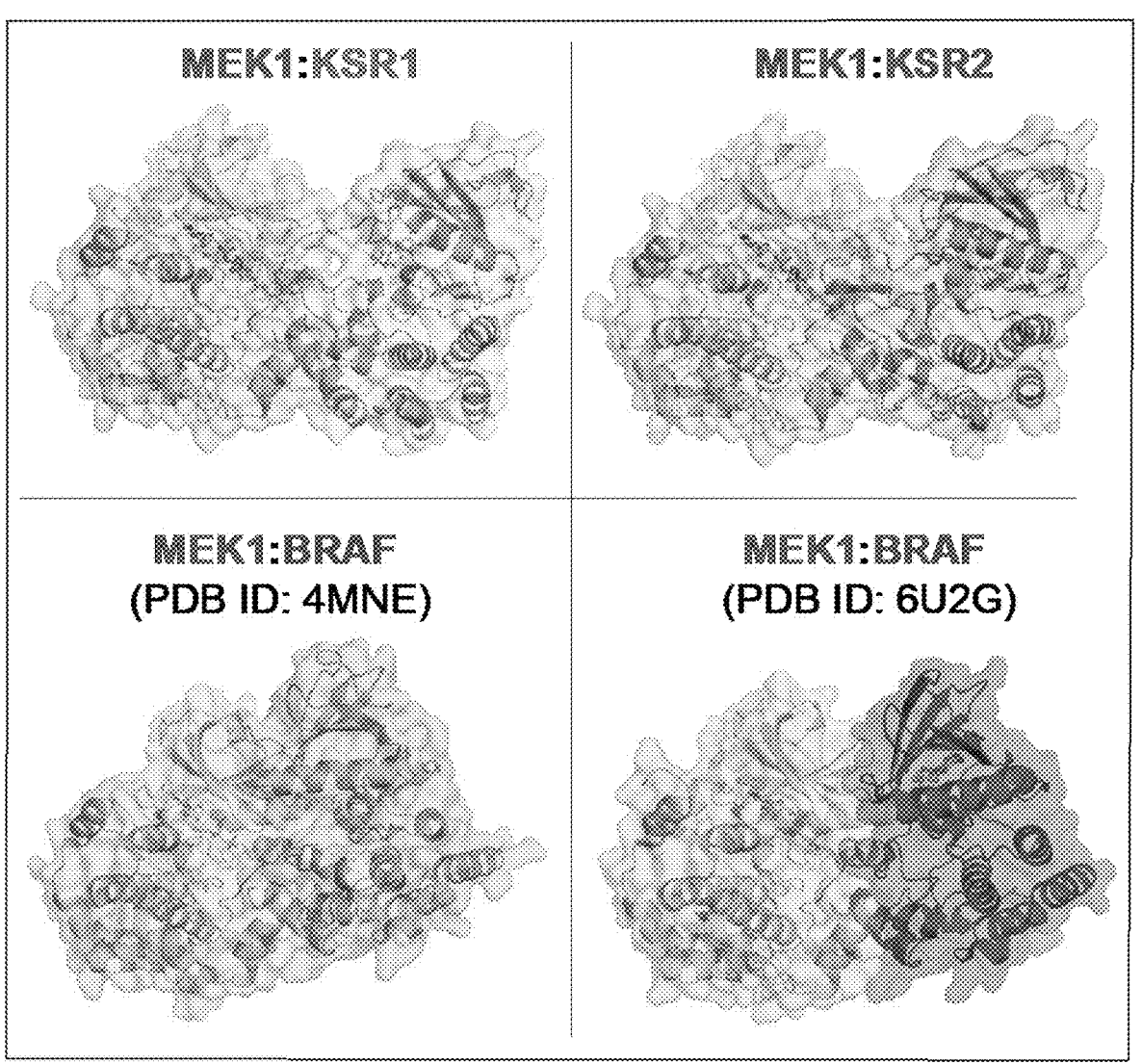
Figure: 38

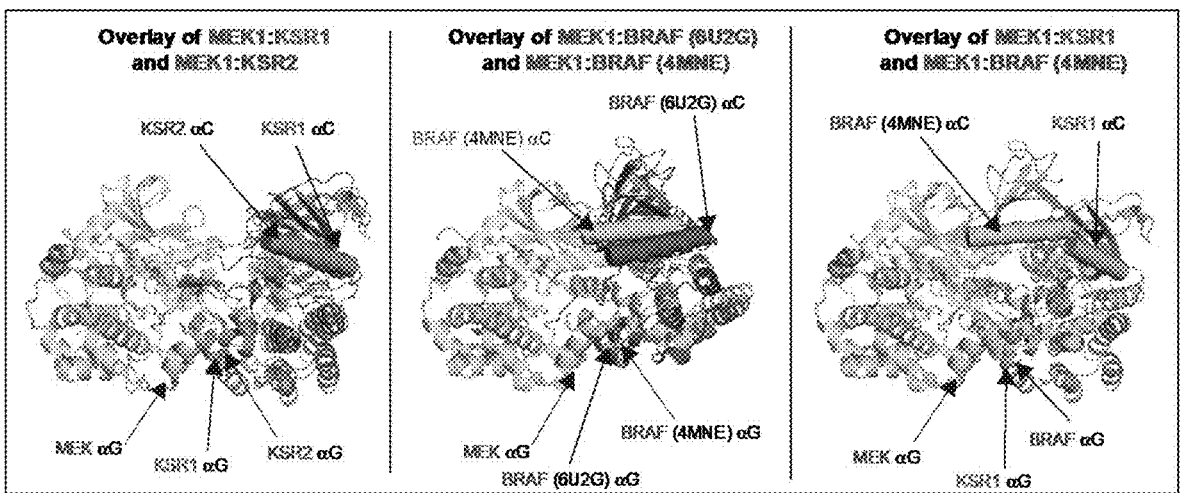
Figure: 39

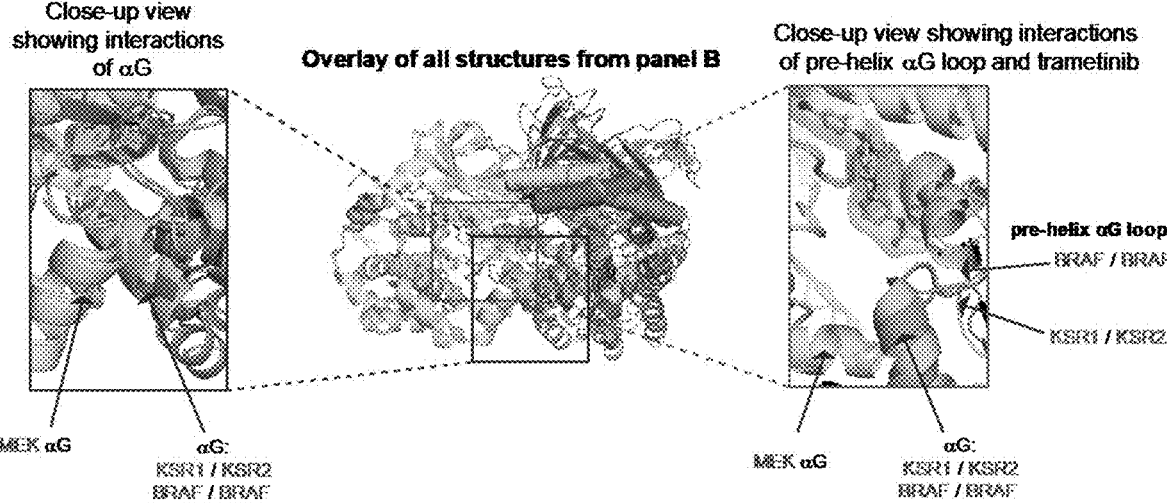
Figure: 40

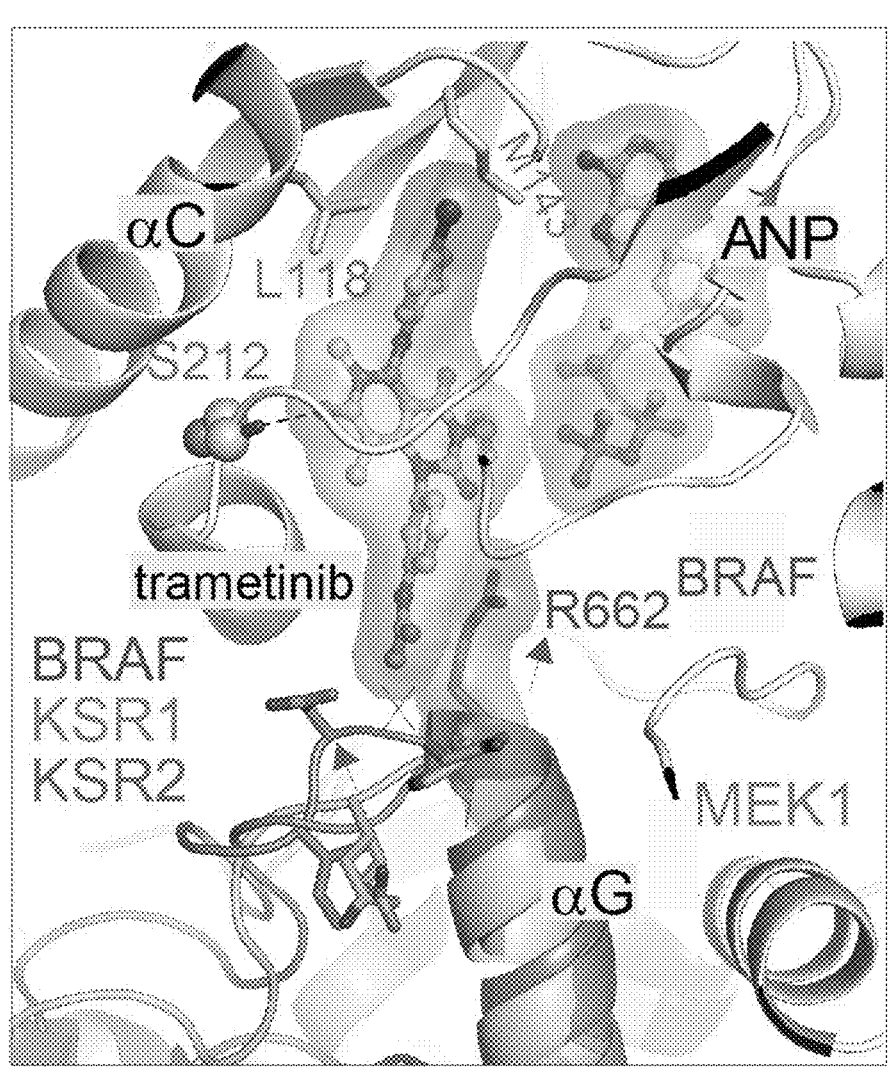
Figure: 41

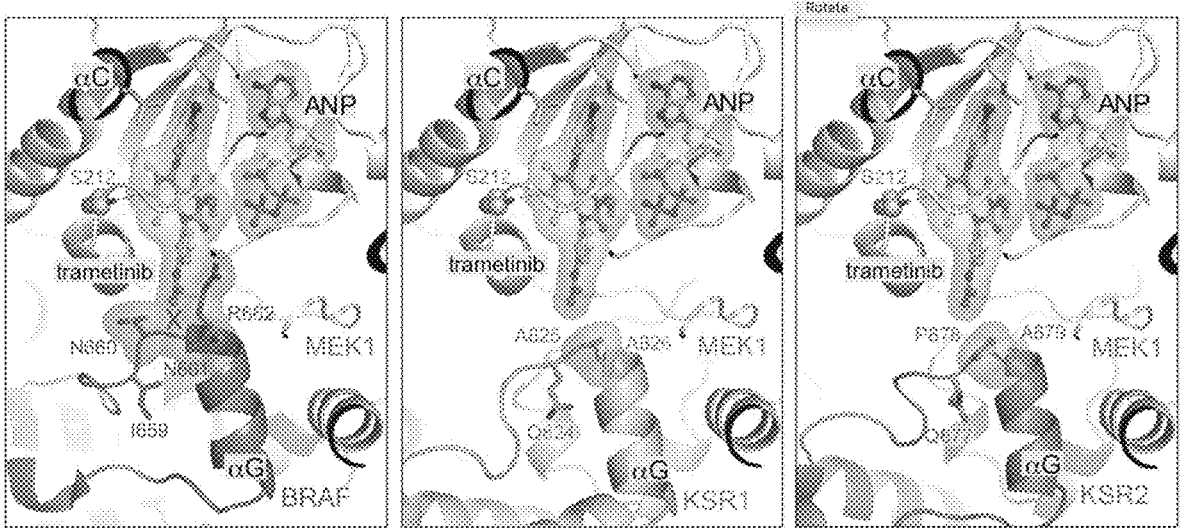
Figure: 42

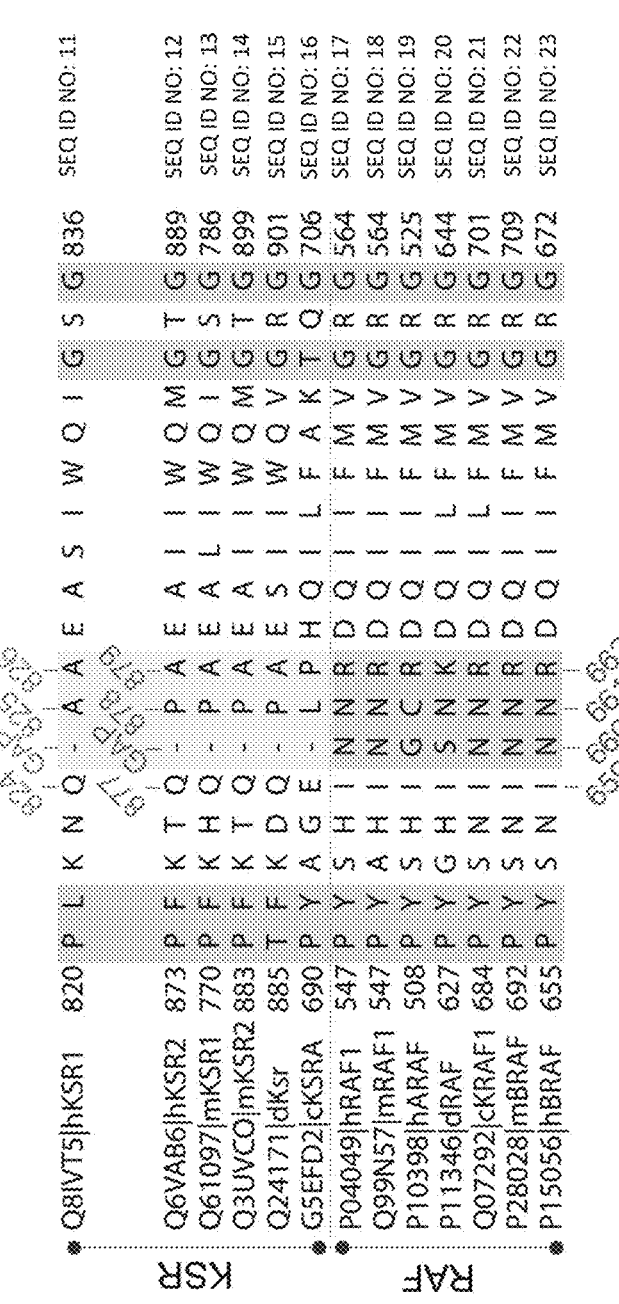
Figure: 43

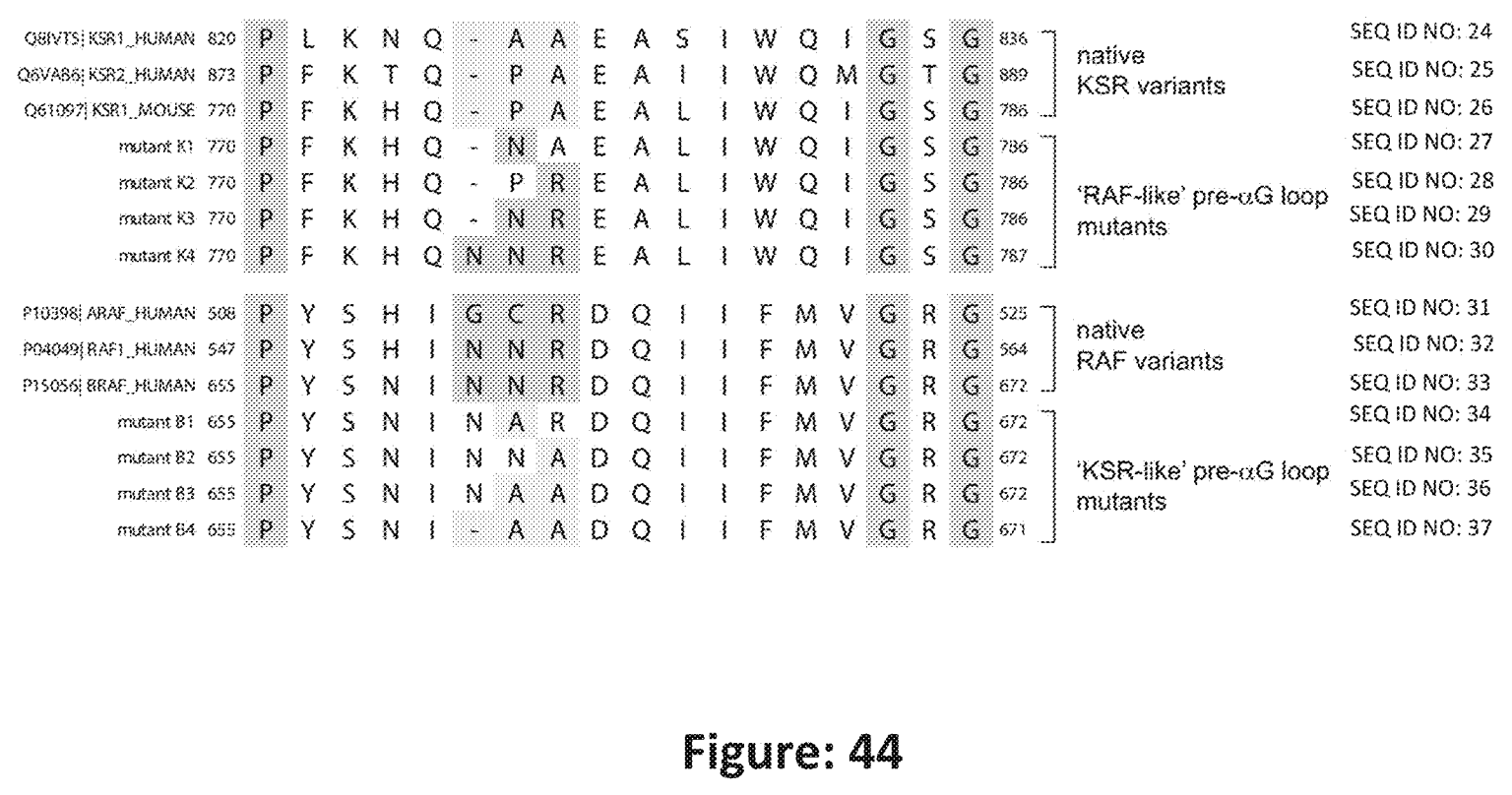

Q8VTS; KSR1_HUMAN 820 ... SEQ ID NO: 24
Q6VAB6; KSR2_HUMAN 873 ... SEQ ID NO: 25
Q61097; KSR1_MOUSE 770 ... SEQ ID NO: 26
mutant K1 770 ... SEQ ID NO: 27
mutant K2 770 ... SEQ ID NO: 28
mutant K3 770 ... SEQ ID NO: 29
mutant K4 770 ... SEQ ID NO: 30

P10398; ARAF_HUMAN 508 ... SEQ ID NO: 31
P04049; RAF1_HUMAN 547 ... SEQ ID NO: 32
P15056; BRAF_HUMAN 655 ... SEQ ID NO: 33
mutant B1 655 ... SEQ ID NO: 34
mutant B2 655 ... SEQ ID NO: 35
mutant B3 655 ... SEQ ID NO: 36
mutant B4 655 ... SEQ ID NO: 37 native KSR variants

'RAF-like' pre-αG loop mutants native RAF variants

'KSR-like' pre-αG loop mutants

Figure: 44

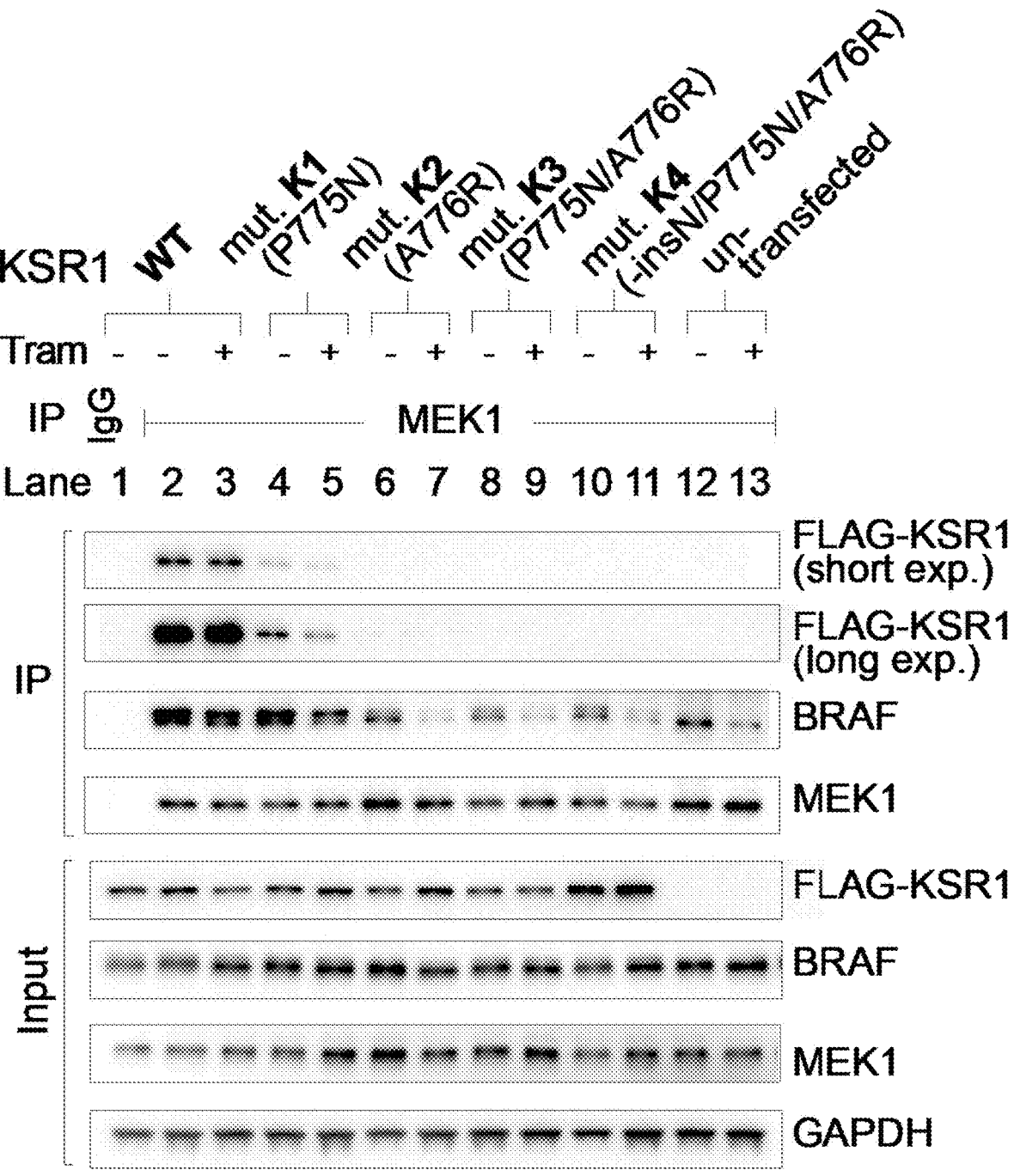
Figure: 45

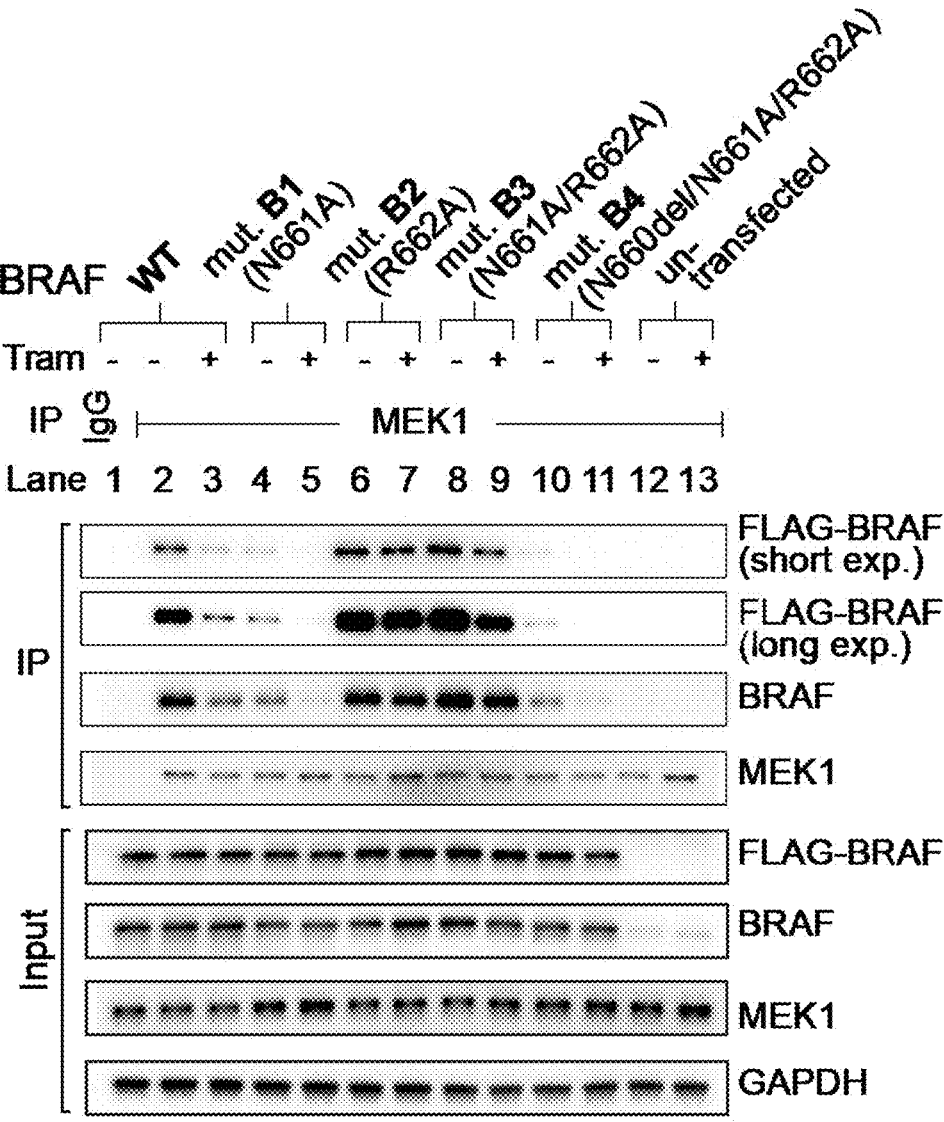
Figure: 46

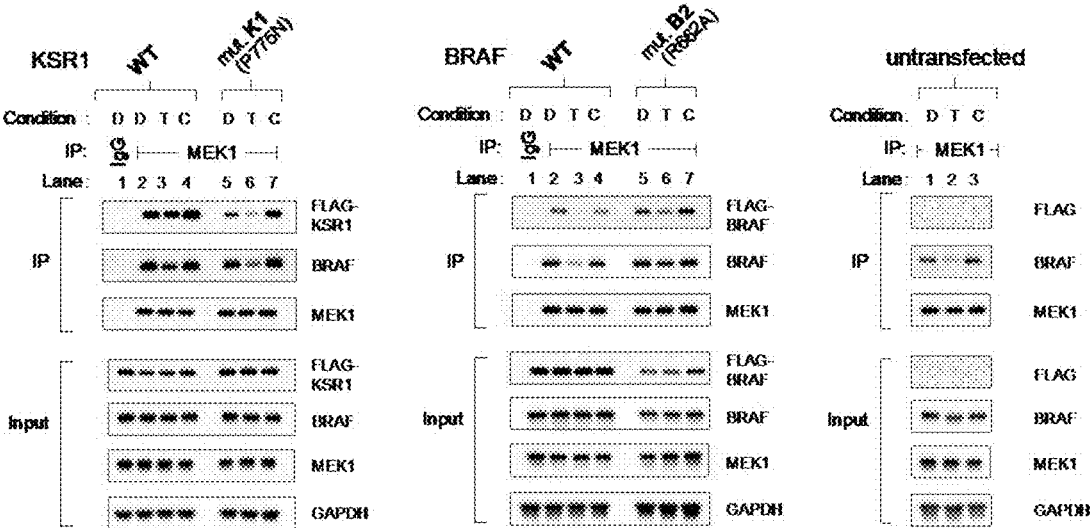
Figure: 47

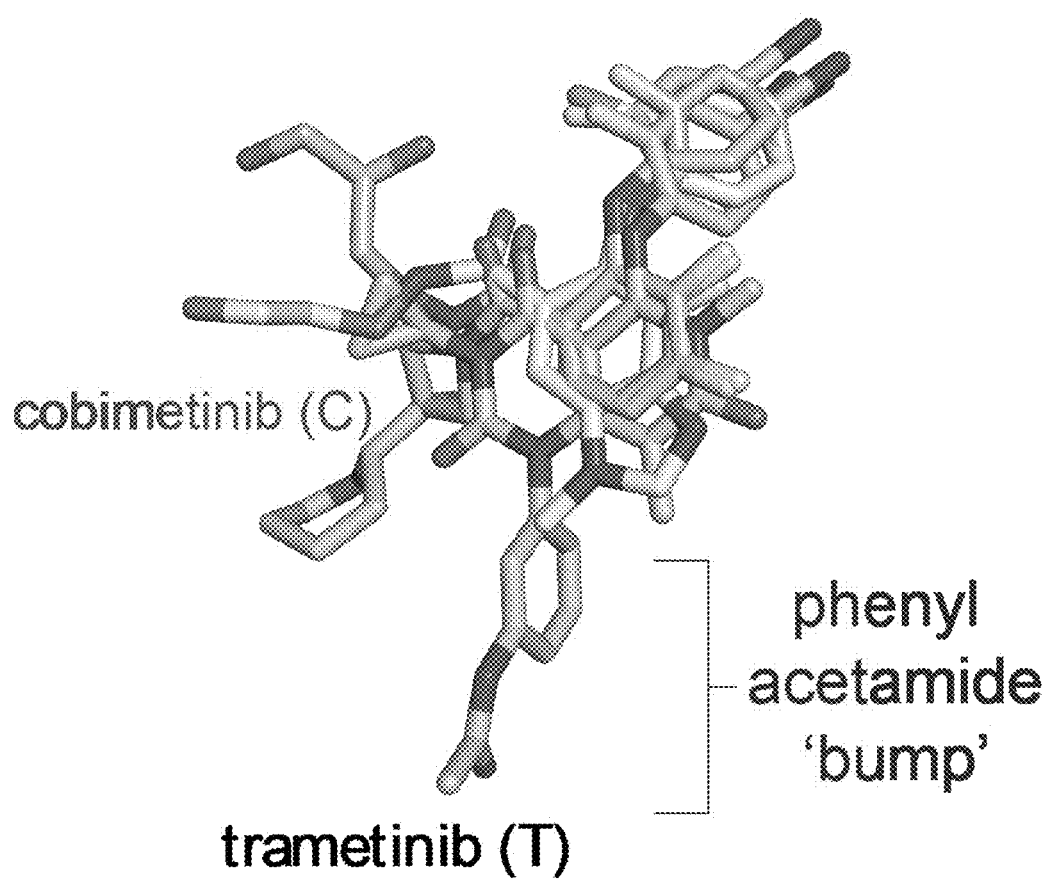
Figure: 48

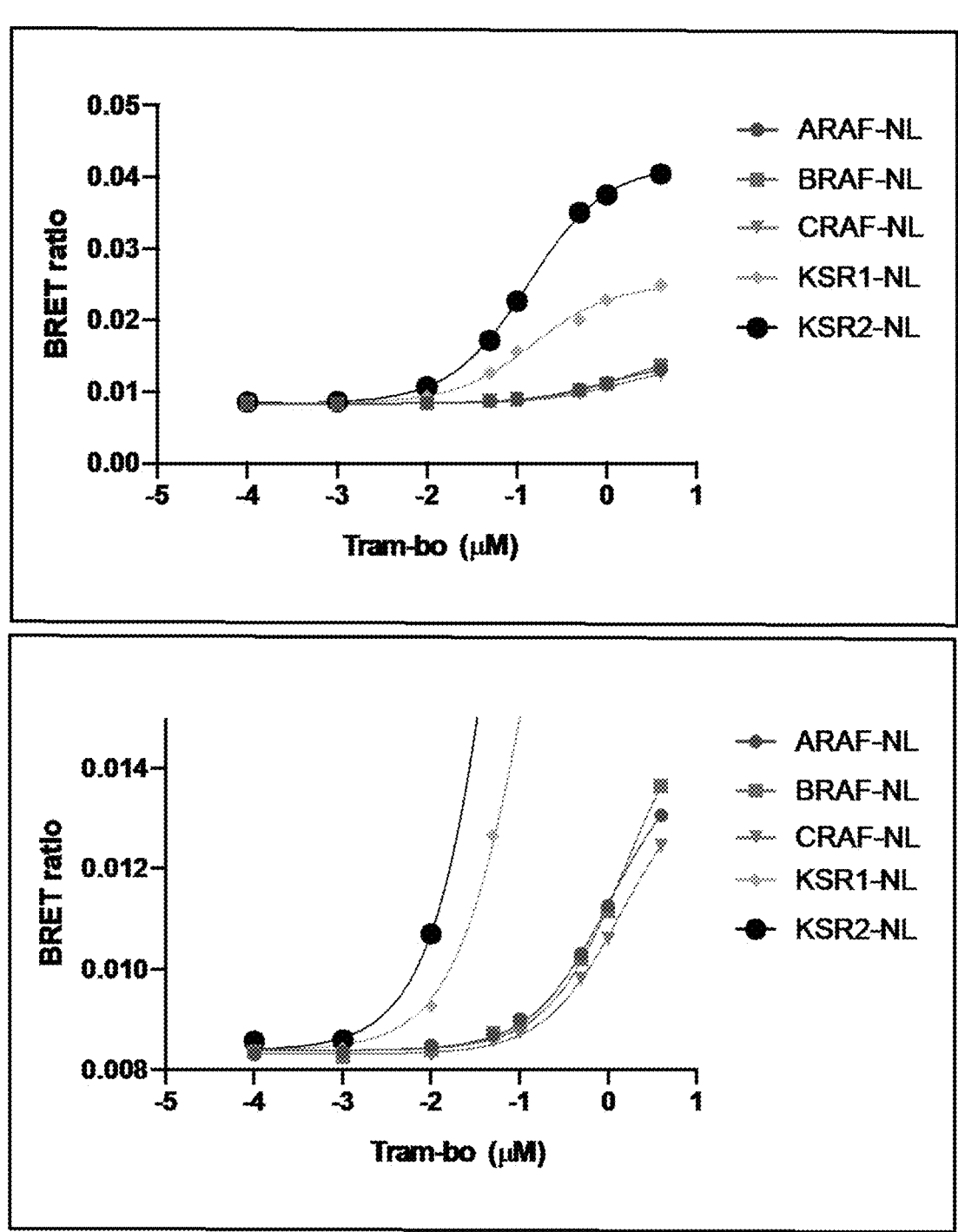
Figure: 49

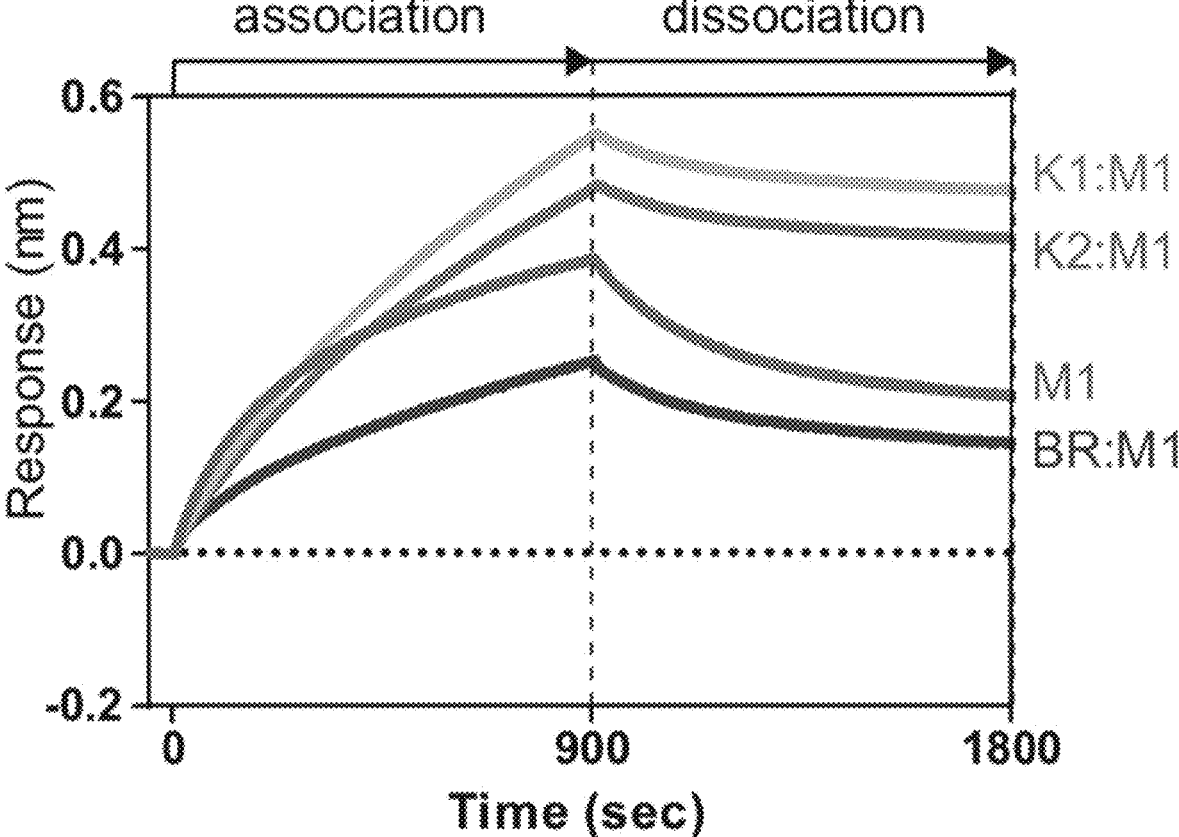
Figure: 50

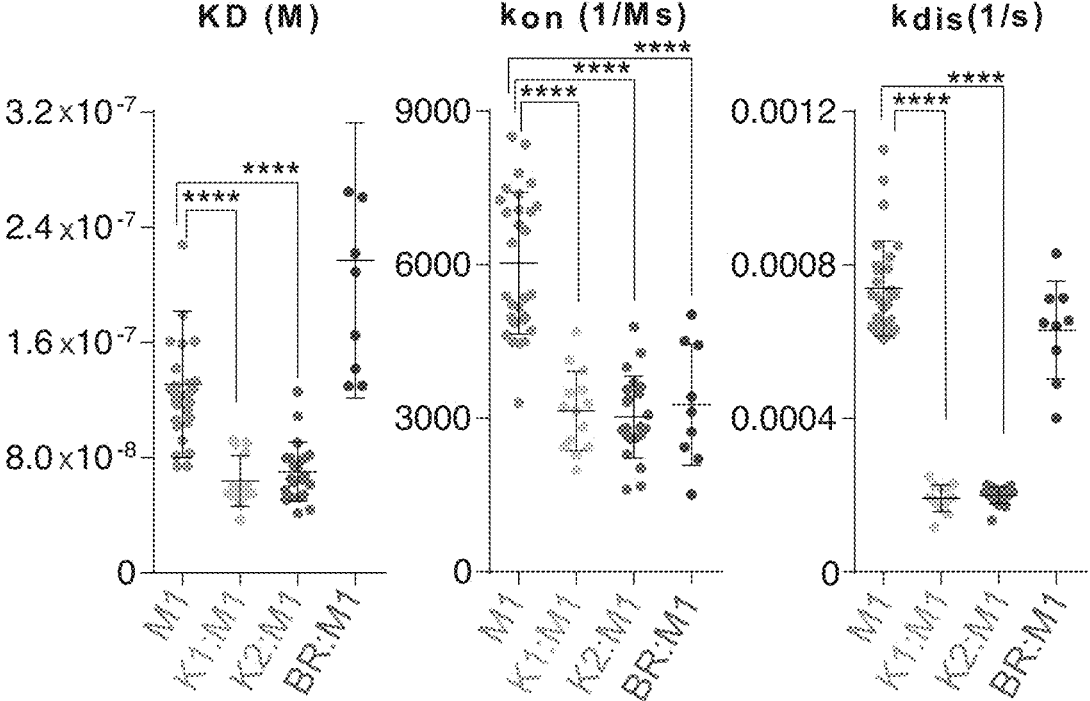
Figure: 51

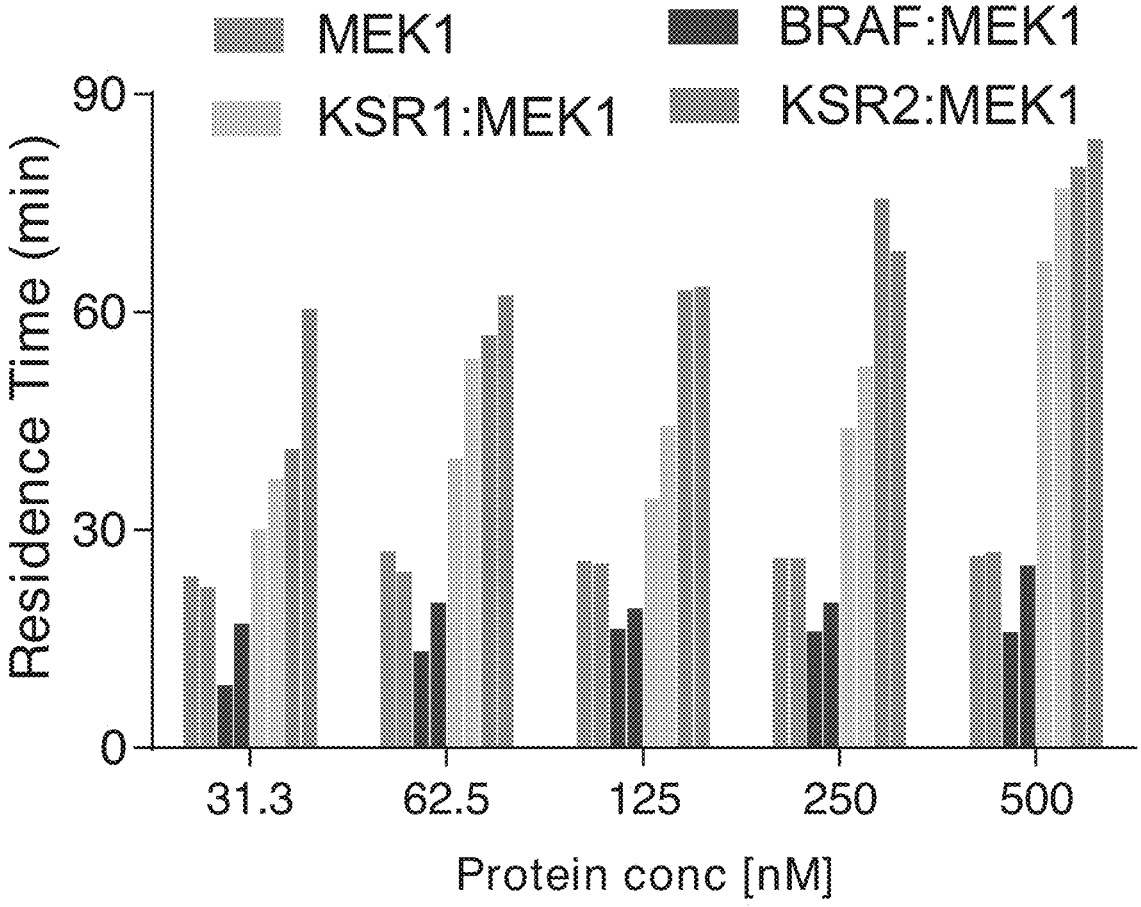
Figure: 52

Entire Sensogram

Figure: 53

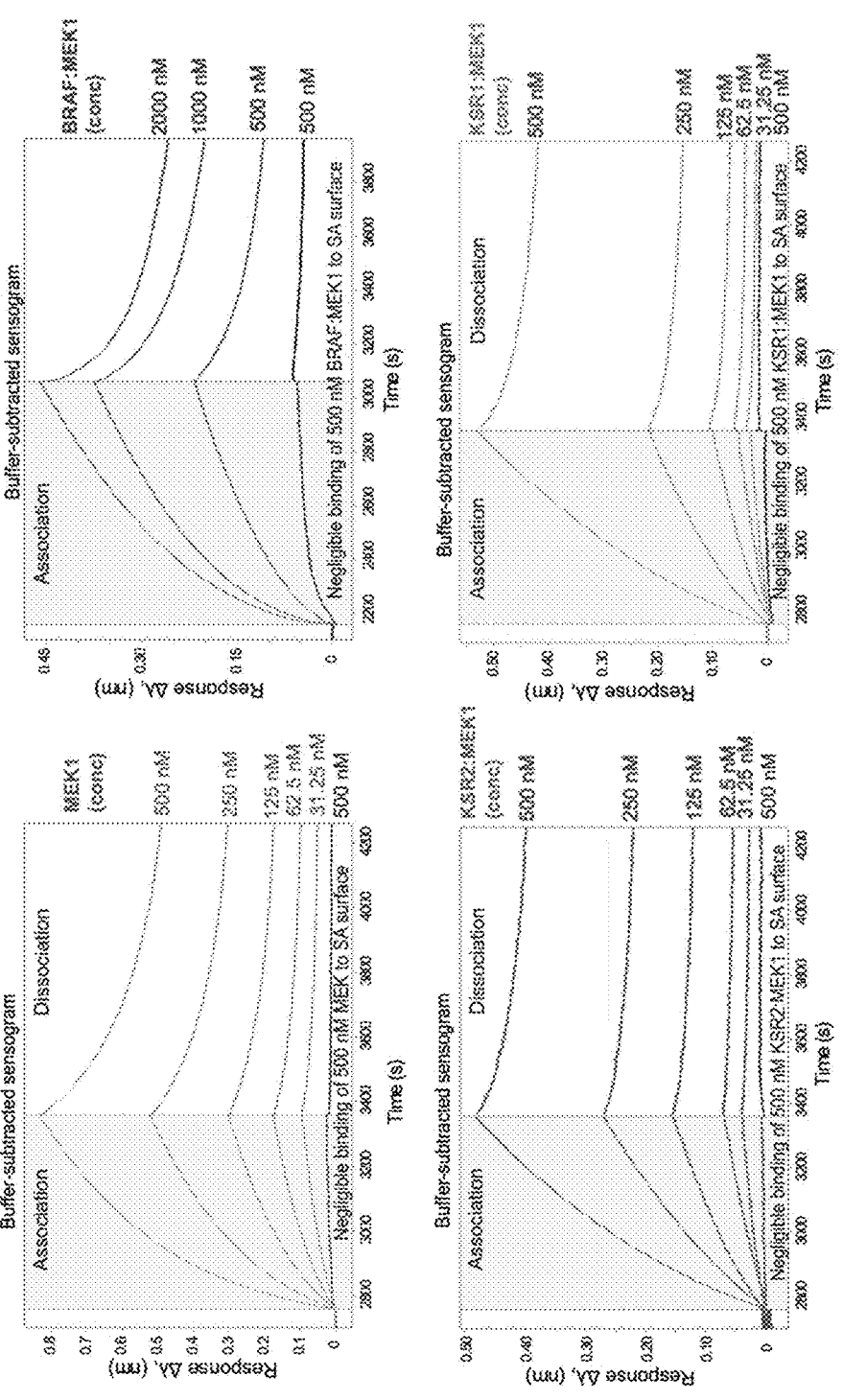
FIGURE: 54

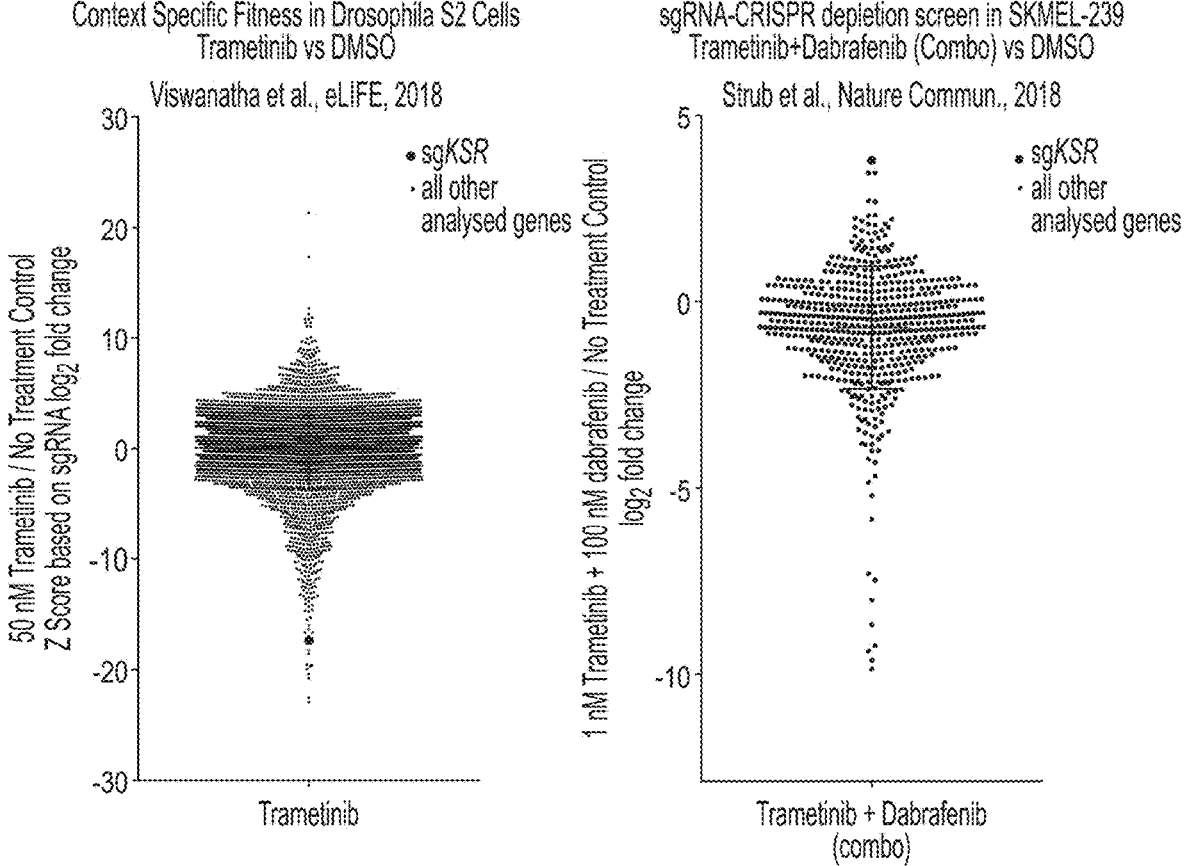
Figure: 55

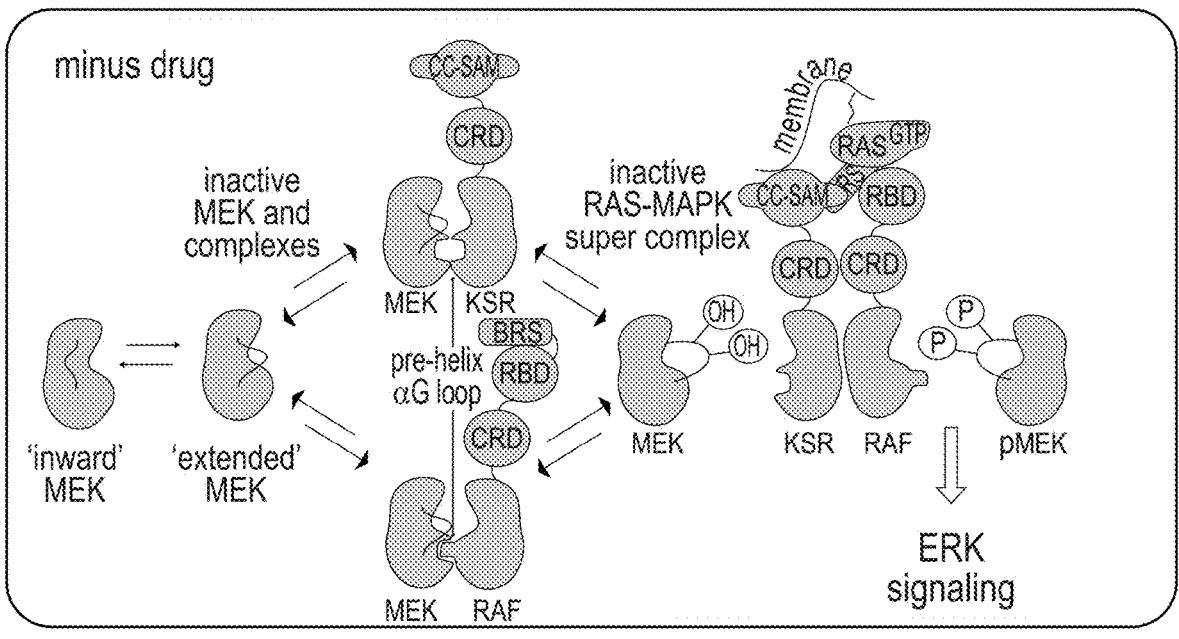
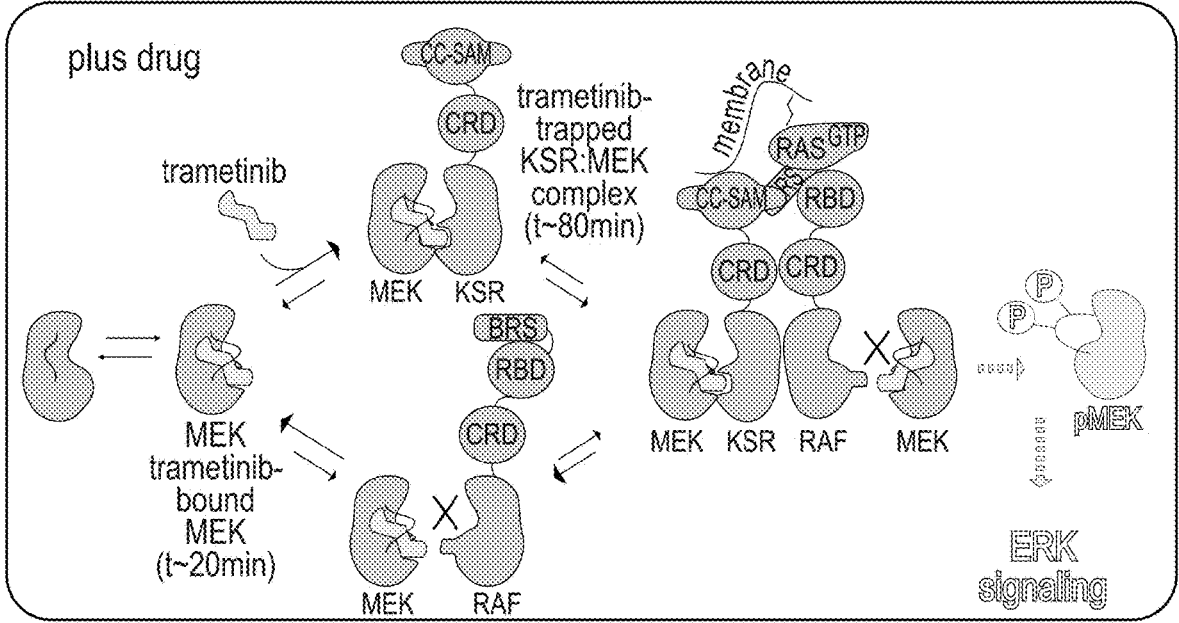
Figure: 56

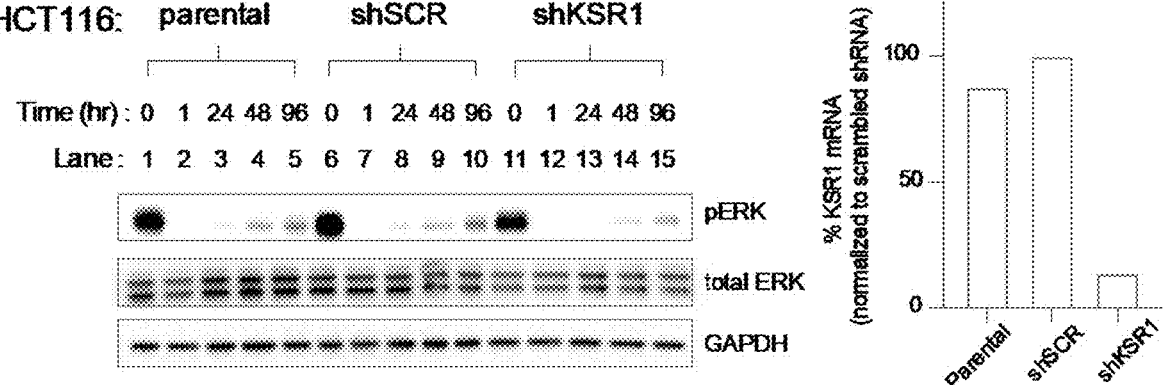
Figure: 57

| Compound | SK-MEL-239 | | HCT116 | | A549 | | A375 | |
|---|---|---|---|---|---|---|---|---|
| | IC50 nM | STDEV | IC50 nM | STDEV | IC50 nM | STDEV | IC50 nM | STDEV |
| Trametiglue | 0.47 | 0.39 | 0.07 | 0.04 | 0.12 | 0.04 | 0.07 | 0.06 |
| Trametinib | 2.52 | 1.52 | 0.51 | 0.29 | 1.13 | 0.87 | 0.45 | 0.31 |
| CH5126766 | 180.30 | 60.36 | 14.82 | 5.44 | 20.52 | 2.83 | 21.73 | 10.88 |
| Cobimetinib | 34.42 | 10.22 | 28.47 | 15.43 | 42.41 | 19.93 | 2.63 | 2.05 |
| PD0325901 | 6.91 | 1.44 | 1.10 | 0.92 | 2.26 | 1.65 | 1.34 | 1.16 |
| Selumetinib | 263.67 | 152.01 | 39.53 | 22.89 | 29.73 | 5.91 | 21.72 | 13.52 |

*IC50s and STDEV determined from 3 independent experiments, each setup in triplicate Figure: 58 trametinib trametiglue

Figure: 59

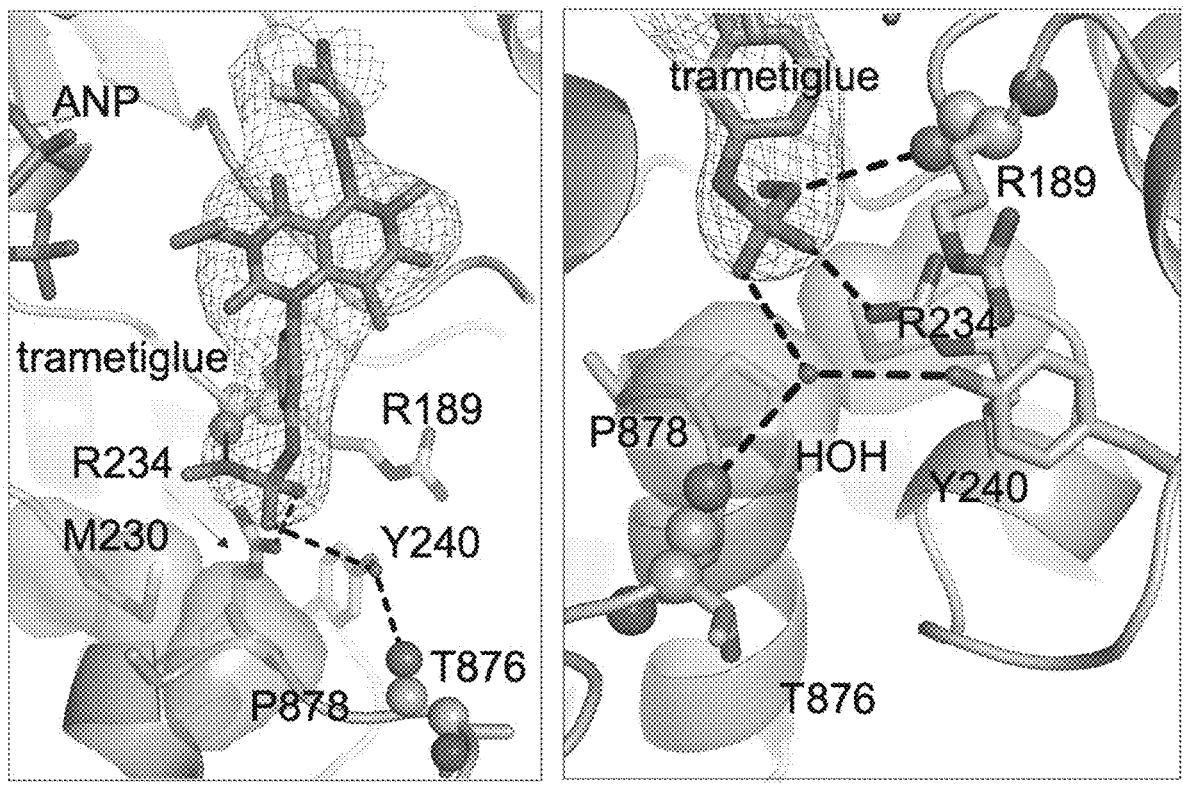
Figure: 60

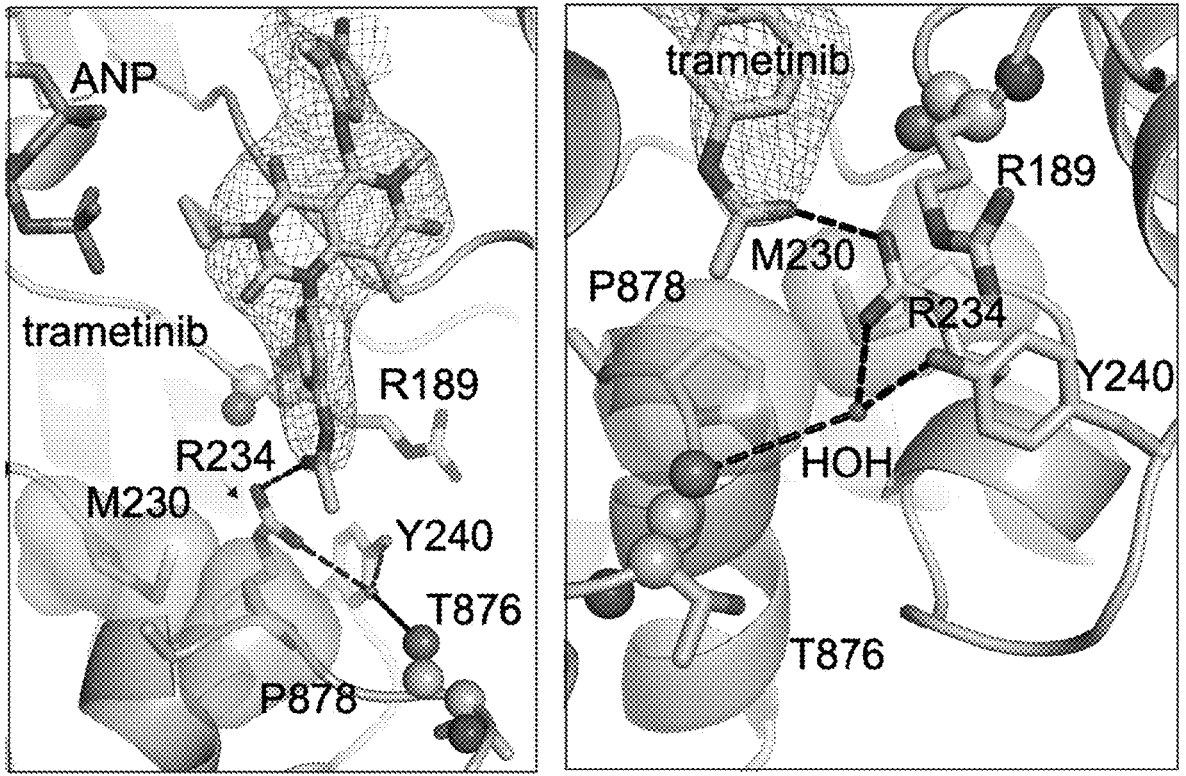
Figure: 61

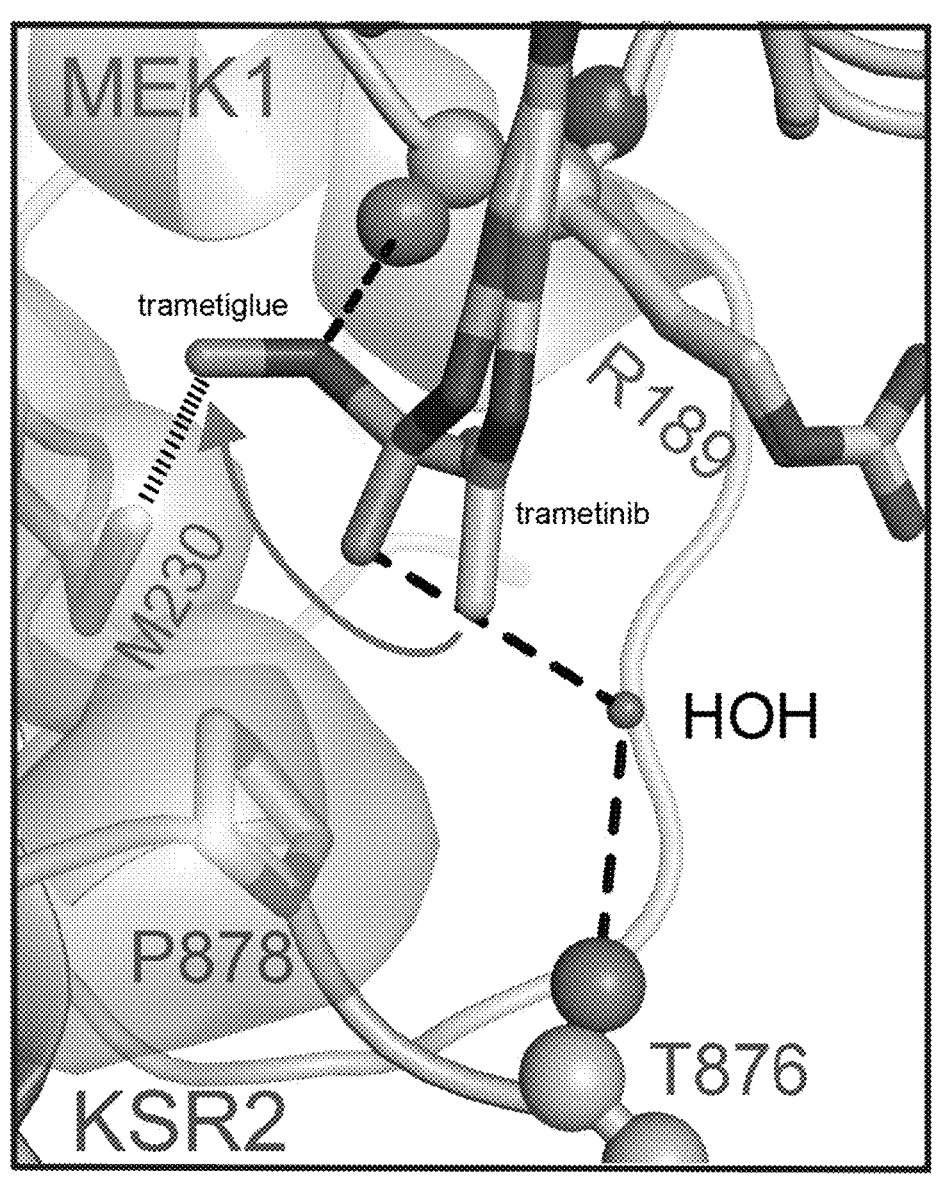
Figure: 62

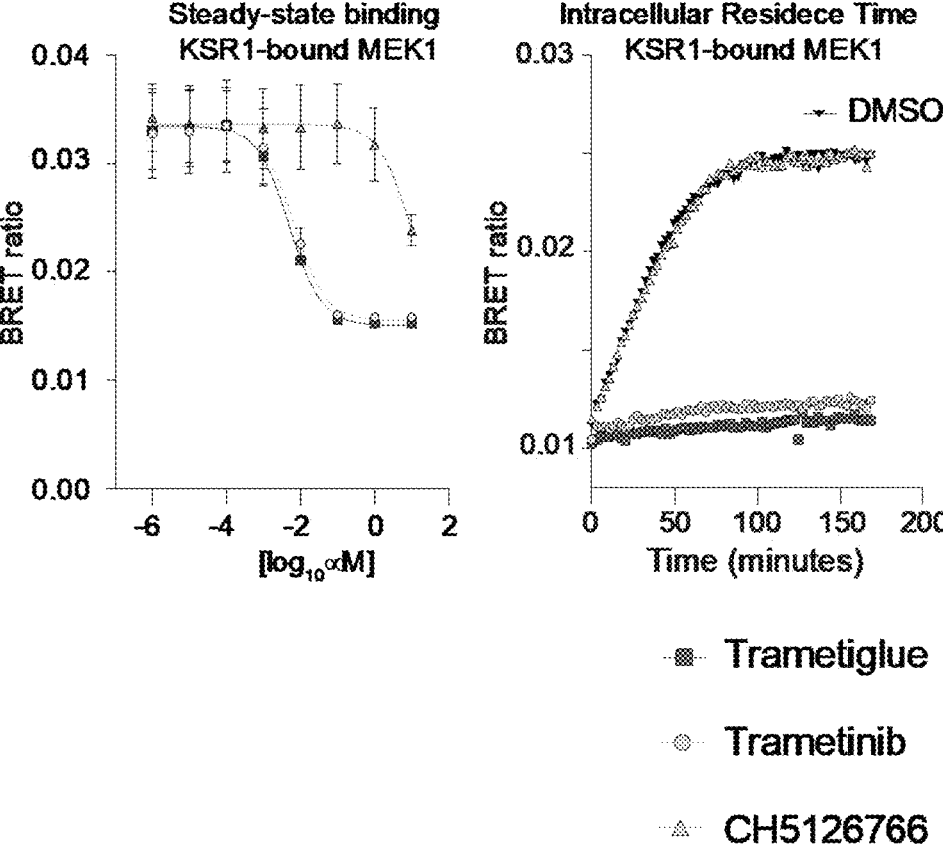
Figure: 63

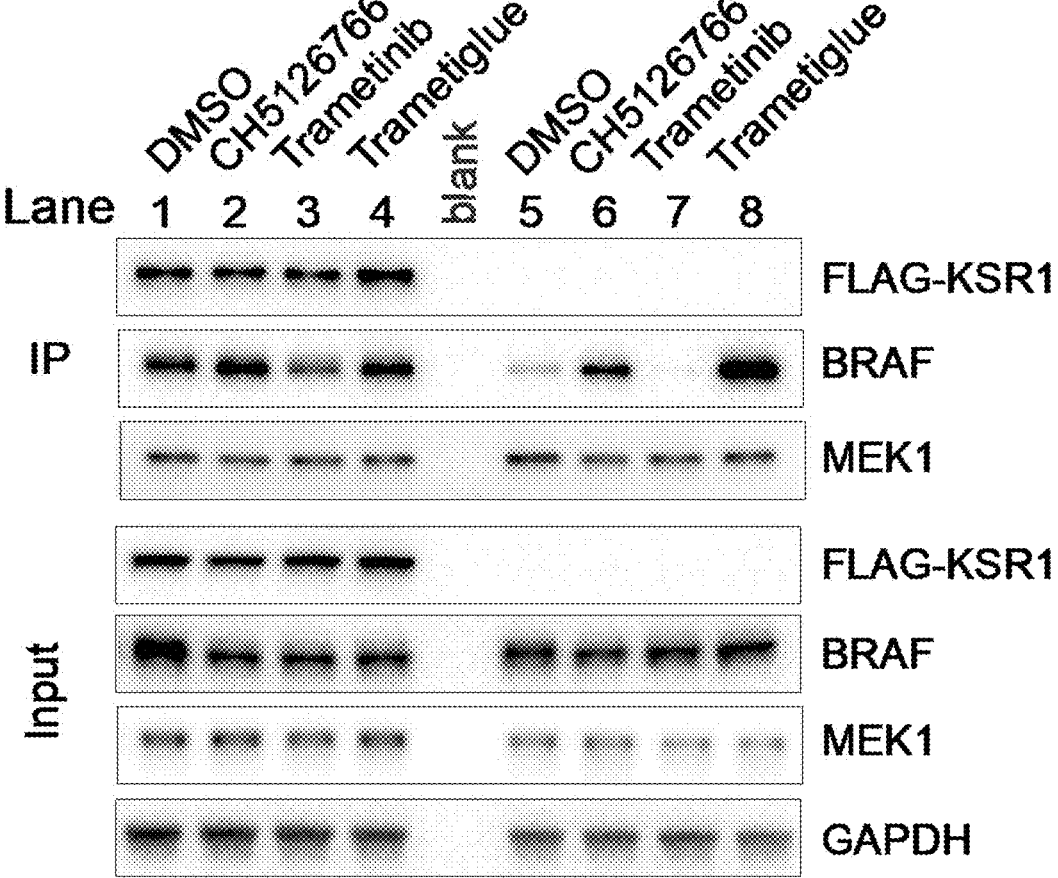
Figure: 64

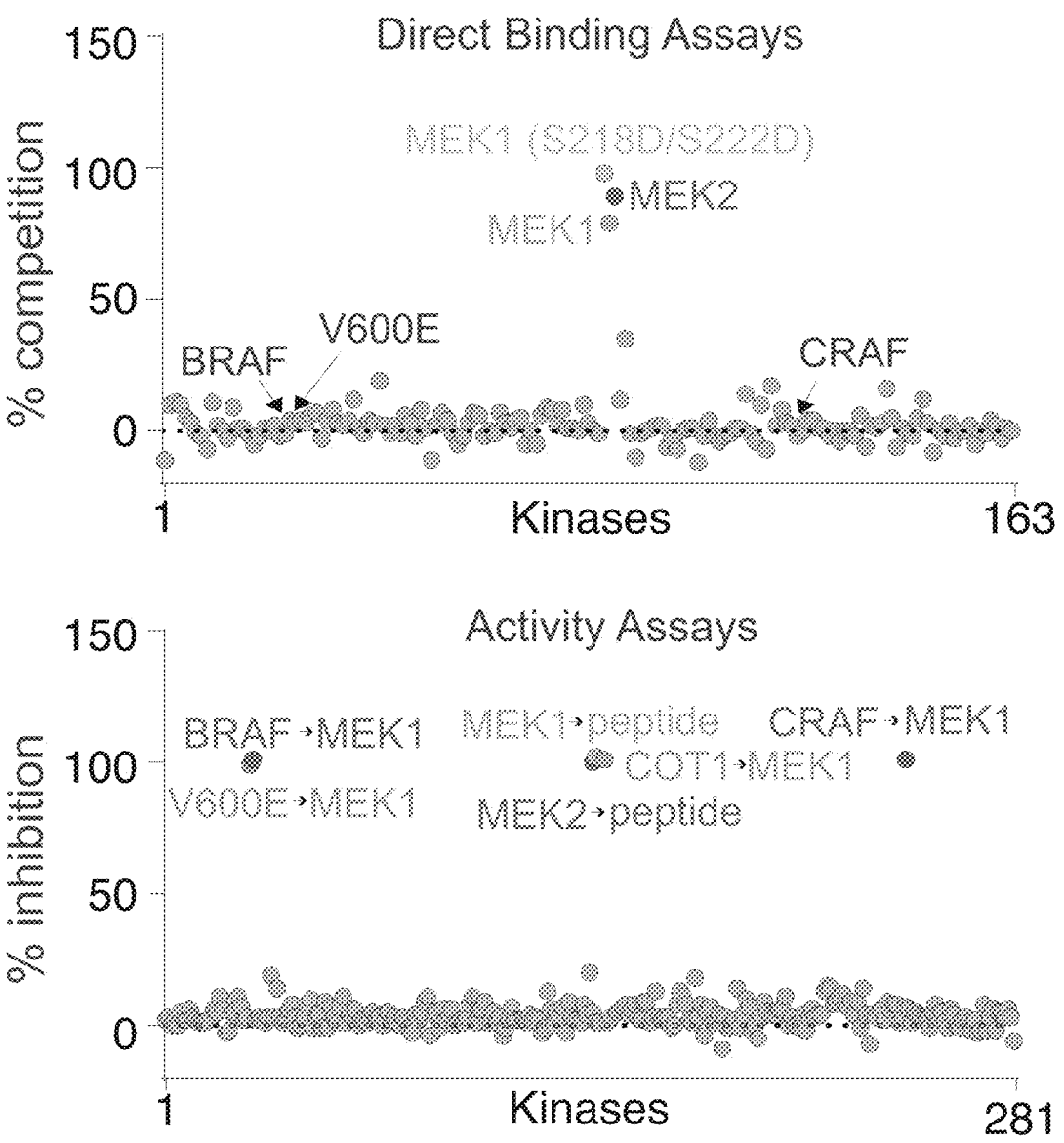
Figure: 65

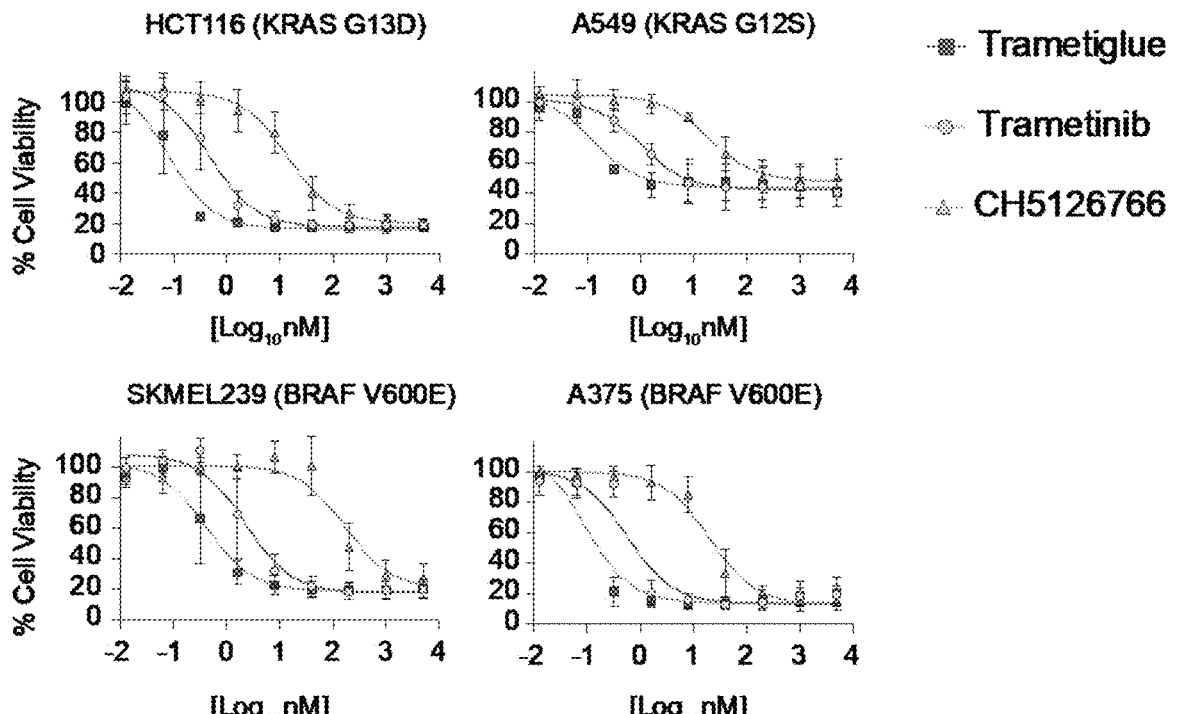
Figure: 66

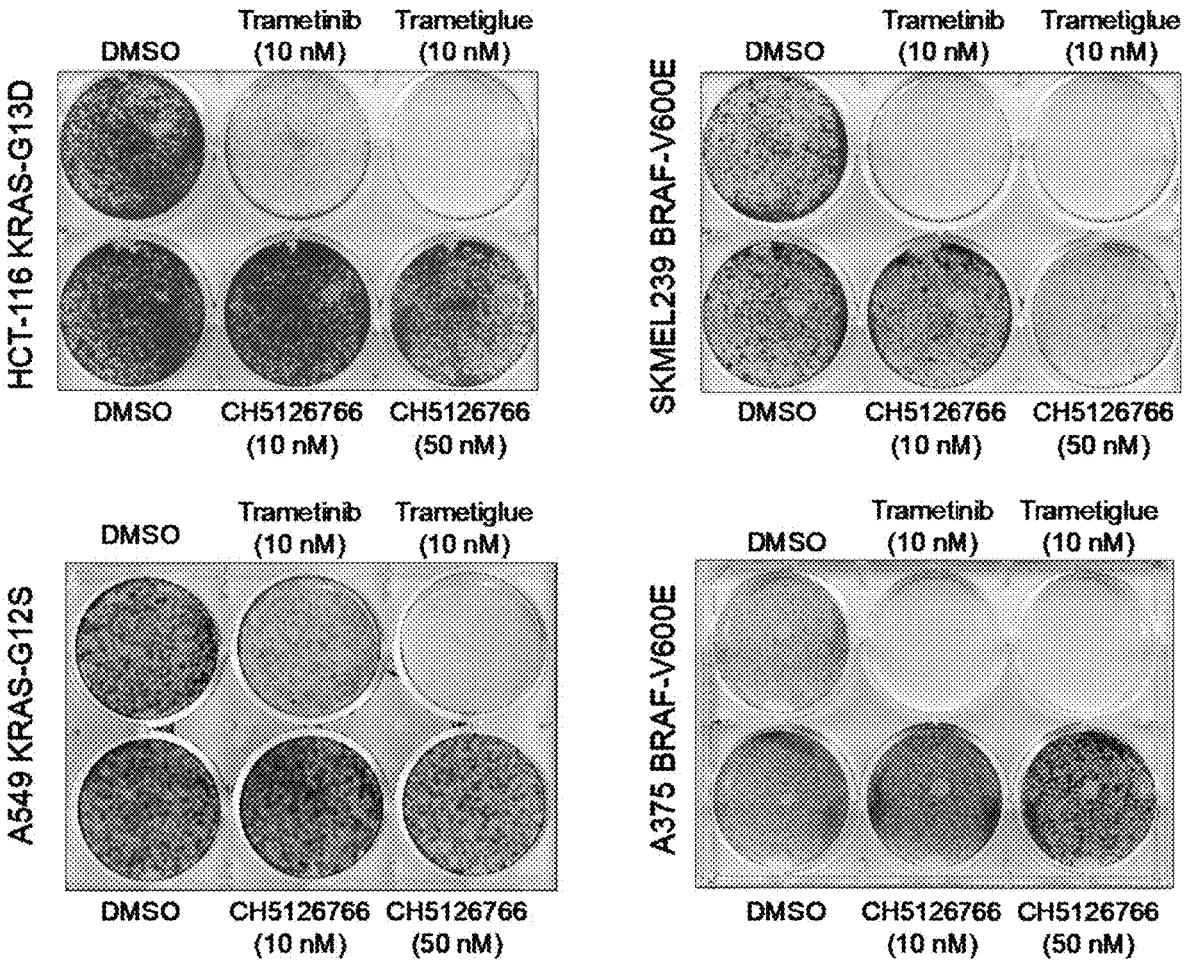
Figure: 67

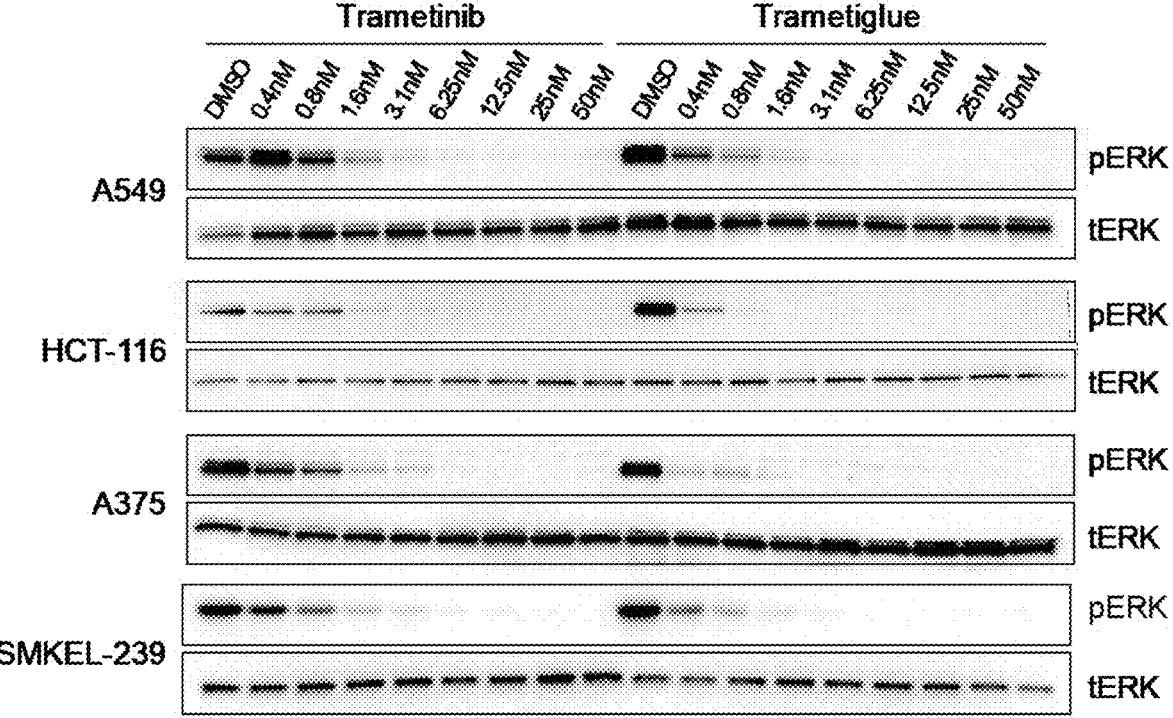
Figure: 68

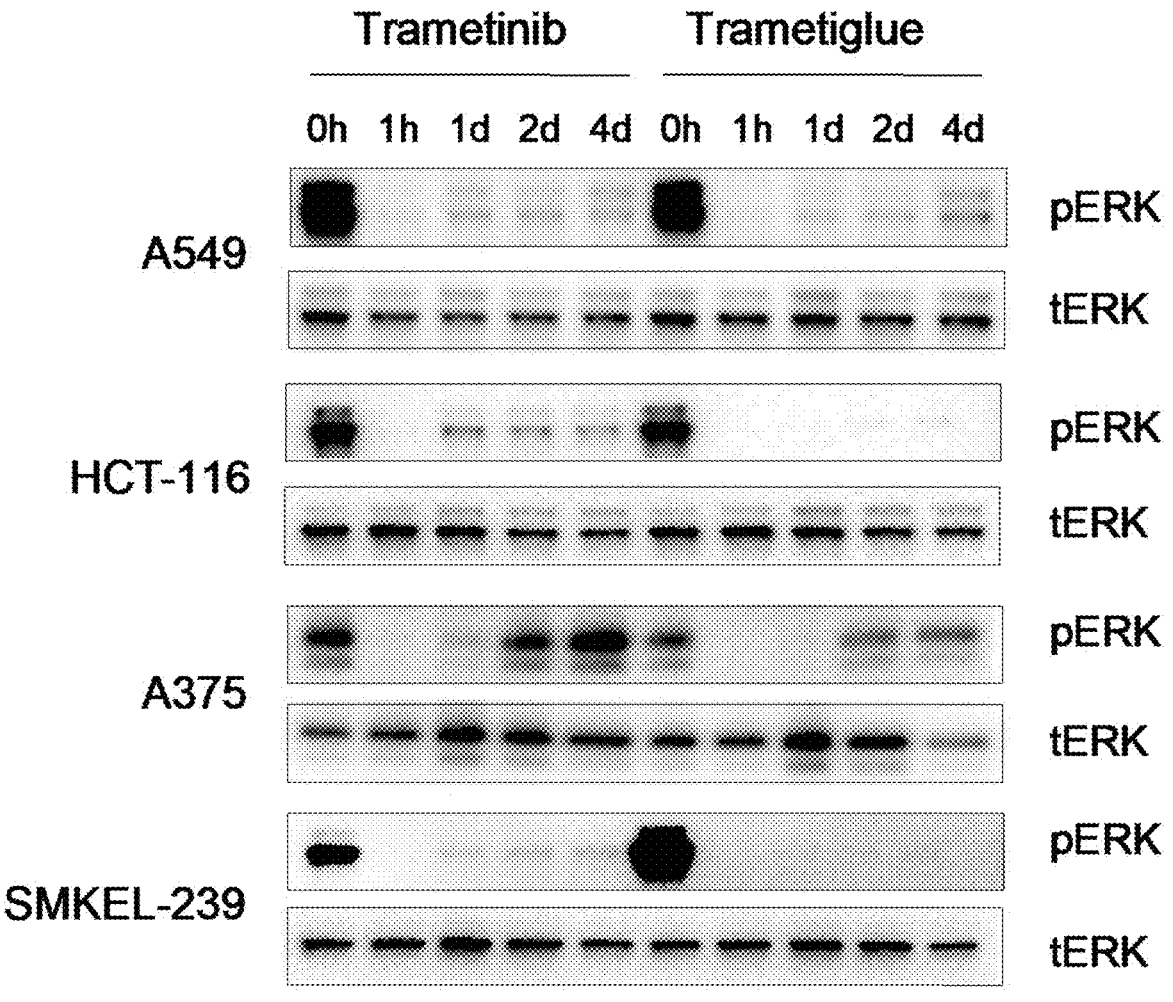
Figure: 69

Supplementary Data Table 1: X-ray Crystal Structure Data collection and Refinement Statistics (molecular replacement)

| Data name | KSR2:MEK1: ADP | KSR2:MEK1: ANP, Trametinib | KSR2:MEK1: ANP, Cobimetinib | KSR2:MEK1: ANP, Selumetinib | KSR2:MEK1: ANP, PD0325901 | KSR2:MEK1: ANP, APS-9-85-1 | KSR1:MEK1: ANP | KSR1:MEK1: ANP, Trametinib | KSR1:MEK1: ANP, Cobimetinib | KSR1:MEK1: ANP, Selumetinib | KSR1:MEK1: ANP, PD0325901 | KSR1:MEK1: ANP, APS-9-85-1 |
|---|---|---|---|---|---|---|---|---|---|---|---|---|
| PDB code | 7JUQ | 7JUR | 7JUS | 7JUT | 7JUU | 7JUV | 7JUW | 7JUX | 7JUY | 7JUZ | 7JV0 | 7JV1 |
| Data collection | | | | | | | | | | | | |
| Space group | $P6_122$ | $P6_122$ | $P6_122$ | $P6_122$ | $P6_122$ | $P6_122$ | $P6_122$ | $P6_122$ | $P6_122$ | $P6_122$ | $P6_122$ | $P6_122$ |
| Cell dimensions | | | | | | | | | | | | |
| $a, b, c$ (Å) | 139.03, 139.03, 222.41 | 139.82, 139.82, 221.58 | 140.04, 140.04, 220.60 | 139.10, 139.10, 218.98 | 138.95, 138.95, 222.10 | 138.74, 138.74, 221.83 | 137.71, 137.71, 218.91 | 137.47, 137.47, 221.80 | 136.20, 136.20, 218.57 | 137.37, 137.37, 216.55 | 137.66, 137.66, 220.89 | 137.05, 137.05, 221.28 |
| $\alpha, \beta, \gamma$ (°) | 90 90 120 | 90 90 120 | 90 90 120 | 90 90 120 | 90 90 120 | 90 90 120 | 90 90 120 | 90 90 120 | 90 90 120 | 90 90 120 | 90 90 120 | 90 90 120 |
| Resolution (Å) | 50 - 3.22 | 50 - 2.82 | 50 - 2.99 | 50 - 3.09 | 50 - 3.19 | 50 - 3.35 | 50 - 2.88 | 50 - 3.34 | 50 - 3.1 | 50 - 3.21 | 50 - 3.63 | 50 - 3.62 |
| $R_{meas}$ (%) | 9.9 (213.1) | 13.7 (197.1) | 8.0 (247.7) | 10.2 (224.8) | 10.2 (222.1) | 9.3 (194.1) | 10.7 (268.3) | 9.0 (227.5) | 9.3 (221.2) | 7.9 (225.4) | 12.3 (187.2) | 8.6 (190.7) |
| $I / \sigma I$ | 20.86 (1.33) | 15.87 (1.30) | 22.26 (1.18) | 20.90 (1.27) | 17.70 (1.20) | 11.90 (1.27) | 18.75 (1.02) | 17.57 (1.24) | 20.4 (1.17) | 20.99 (1.09) | 15.10 (1.30) | 16.46 (1.36) |
| $CC_{1/2}$ | 0.99 (0.51) | 0.99 (0.52) | 1.0 (0.51) | 1.0 (0.51) | 0.99 (0.48) | 0.99 (0.59) | 0.99 (0.51) | 0.99 (0.48) | 1.0 (0.51) | 1.0 (0.54) | 0.99 (0.54) | 1.00 (0.49) |
| Completeness (%) | 99.9 (100) | 100 (100) | 99.9 (100) | 99.9 (99.9) | 99.8 (100) | 99.7 (100) | 99.4 (100) | 99.9 (100) | 99.9 (100) | 99.8 (99.9) | 99.9 (100) | 93.7 (95.3) |
| Redundancy | 11.98 (12.37) | 12.05 (12.42) | 11.98 (12.43) | 11.76 (11.15) | 10.95 (11.38) | 11.02 (11.58) | 14.83 (15.52) | 11.66 (12.35) | 11.95 (12.41) | 10.59 (11.01) | 11.74 (12.28) | 12.55 (12.98) |
| Refinement | | | | | | | | | | | | |
| Resolution (Å) | 3.22 | 2.82 | 2.99 | 3.09 | 3.19 | 3.35 | 2.88 | 3.34 | 3.1 | 3.21 | 3.63 | 3.62 |
| No. reflections | 21247 | 31247 | 28127 | 23585 | 21348 | 18480 | 28300 | 18630 | 22406 | 20359 | 14589 | 13697 |
| Rwork / Rfree (%) | 25.4 / 28.8 | 23.7 / 27.7 | 24.7 / 26.4 | 25.6 / 30.0 | 24.1 / 25.7 | 23.2 / 24.8 | 23.6 / 27.8 | 26.4 / 28.3 | 24.7 / 25.7 | 25.3 / 27.1 | 24.5 / 25.9 | 27.7 / 30.3 |
| No. atoms | | | | | | | | | | | | |
| Protein | 4670 | 4662 | 4651 | 4654 | 4645 | 4662 | 4679 | 4667 | 4668 | 4628 | 4652 | 4639 |
| Ligand/ion | 55 | 101 | 94 | 89 | 90 | 103 | 64 | 100 | 94 | 89 | 89 | 102 |
| Water | 2 | 7 | 11 | 7 | 3 | 12 | 8 | 1 | 1 | 0 | 0 | 0 |
| B-factors | | | | | | | | | | | | |
| Protein | 118.88 | 87.97 | 110.59 | 112.14 | 123.65 | 107.46 | 106.34 | 147.59 | 117.73 | 139.16 | 161.22 | 164.32 |
| Ligand/ion | 108.17 | 83.89 | 110.08 | 110.7 | 118.76 | 106.73 | 104.18 | 136.83 | 124.17 | 146.06 | 173.31 | 184.11 |
| Water | 78.87 | 56.69 | 86.6 | 71.98 | 71.06 | 62.91 | 84.52 | 109.46 | 91.64 | - | - | - |
| R.m.s. deviations | | | | | | | | | | | | |
| Bond lengths (Å) | 0.004 | 0.007 | 0.013 | 0.003 | 0.003 | 0.005 | 0.01 | 0.003 | 0.006 | 0.004 | 0.004 | 0.003 |
| Bond angles (°) | 0.994 | 1.085 | 1.813 | 0.605 | 0.574 | 0.965 | 1.242 | 0.86 | 1.089 | 0.67 | 0.882 | 0.88 |

* Values in parentheses are for highest-resolution shell.

Figure: 70

Bio-Layer Interferometry: Statistical analysis, including mean and s.d. determination, for KD, kon(1/Ms), kdis(1/s), and τ (min)

| Parameter Analyzed | KD (nM) | | | Kon (1/Ms) | | | Koff (1/s) | | | Residence time (min) | | |
|---|---|---|---|---|---|---|---|---|---|---|---|---|
| Column B | KSR1:MEK1 | KSR2:MEK1 | BRAF:MEK1 | KSR1:MEK1 | KSR2:MEK1 | BRAF:MEK1 | KSR1:MEK1 | KSR2:MEK1 | BRAF:MEK1 | KSR1:MEK1 | KSR2:MEK1 | BRAF:MEK1 |
| vs. | vs. | vs. | vs. | vs. | vs. | vs. | vs. | vs. | vs. | vs. | vs. | vs. |
| Column A | MEK1 | MEK1 | MEK1 | MEK1 | MEK1 | MEK1 | MEK1 | MEK1 | MEK1 | MEK1 | MEK1 | MEK1 |
| Unpaired t test | | | | | | | | | | | | |
| P value | <0.0001 | <0.0001 | 0.0011 | <0.0001 | <0.0001 | <0.0001 | <0.0001 | <0.0001 | 0.0287 | <0.0001 | <0.0001 | 0.0088 |
| P value summary | **** | **** | ** | **** | **** | **** | **** | **** | * | **** | **** | ** |
| Significantly different (P<0.05) | Yes | Yes | Yes | Yes | Yes | Yes | Yes | Yes | Yes | Yes | Yes | Yes |
| One- or two-tailed P value? | Two-tailed | Two-tailed | Two-tailed | Two-tailed | Two-tailed | Two-tailed | Two-tailed | Two-tailed | Two-tailed | Two-tailed | Two-tailed | Two-tailed |
| t, df | t=4.763 df=41 | t=5.274 df=49 | t=3.550 df=36 | t=7.236 df=41 | t=5.081 df=49 | t=3.567 df=36 | t=16.12 df=41 | t=20.14 df=49 | t=2.279 df=36 | t=18.40 df=41 | t=28.47 df=49 | t=2.770 df=36 |
| How big is the difference? | | | | | | | | | | | | |
| Mean±SEM of column A (MEK1) | | | | | | | | | | | | |
| Mean±SEM of column B | | | | | | | | | | | | |
| Difference between means | | | | | | | | | | | | |
| 95% confidence interval | | | | | | | | | | | | |
| R squared | 0.3581 | 0.3621 | 0.2683 | 0.5608 | 0.6278 | 0.4463 | 0.8637 | 0.8922 | 0.1261 | 0.892 | 0.943 | 0.1737 |
| F test to compare variances | | | | | | | | | | | | |
| F, DFn, Dfd | | | | | | | | | | | | |
| P value | 0.0002 | <0.0001 | 0.0119 | 0.0012 | 0.0709 | 0.6728 | <0.0001 | <0.0001 | 0.8404 | <0.0001 | <0.0001 | 0.0071 |
| P value summary | *** | *** | * | * | ns | ns | **** | **** | ns | **** | **** | ** |
| Significantly different (P<0.05) | Yes | Yes | Yes | Yes | Yes | No | Yes | Yes | No | Yes | Yes | Yes |

Figure: 71

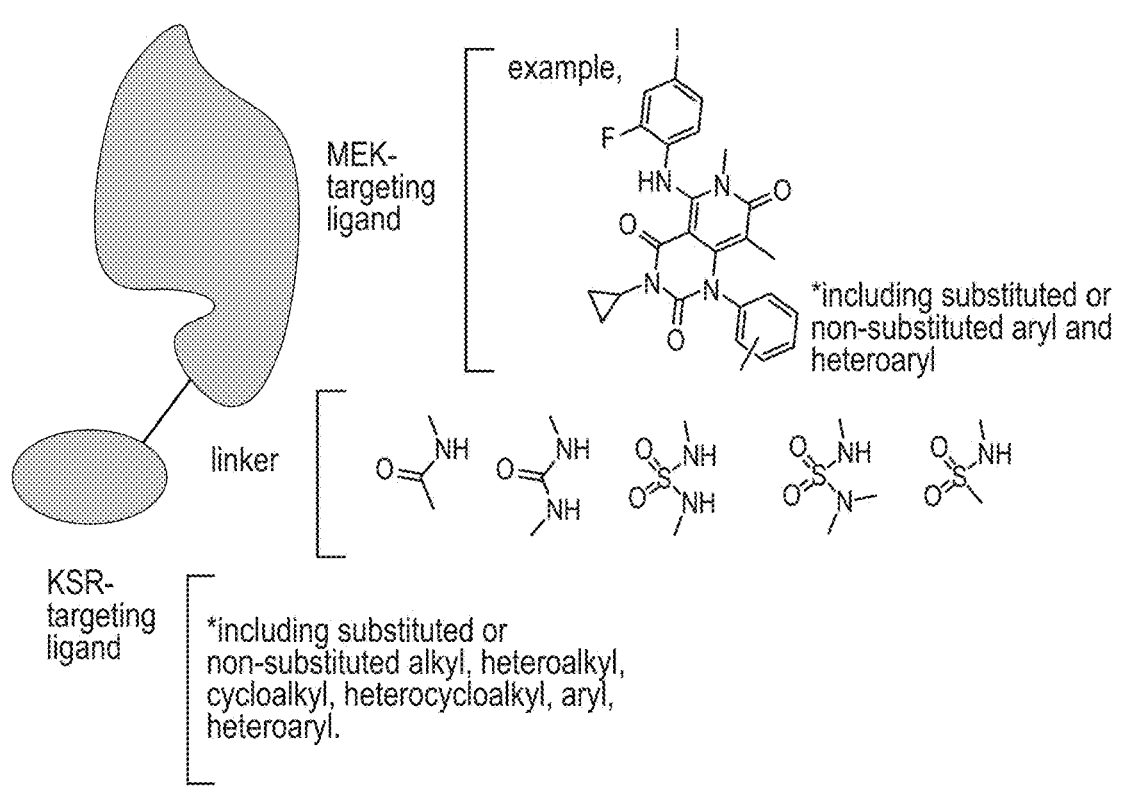
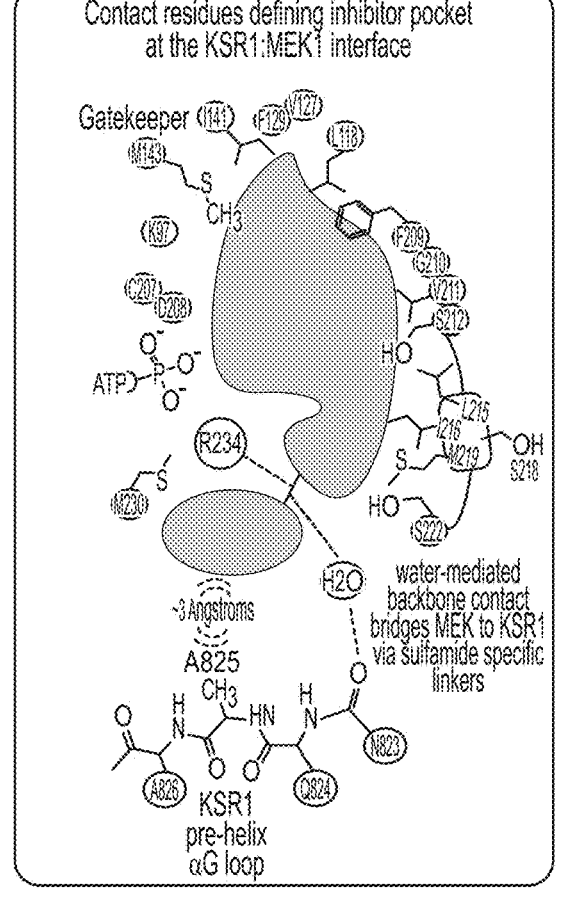
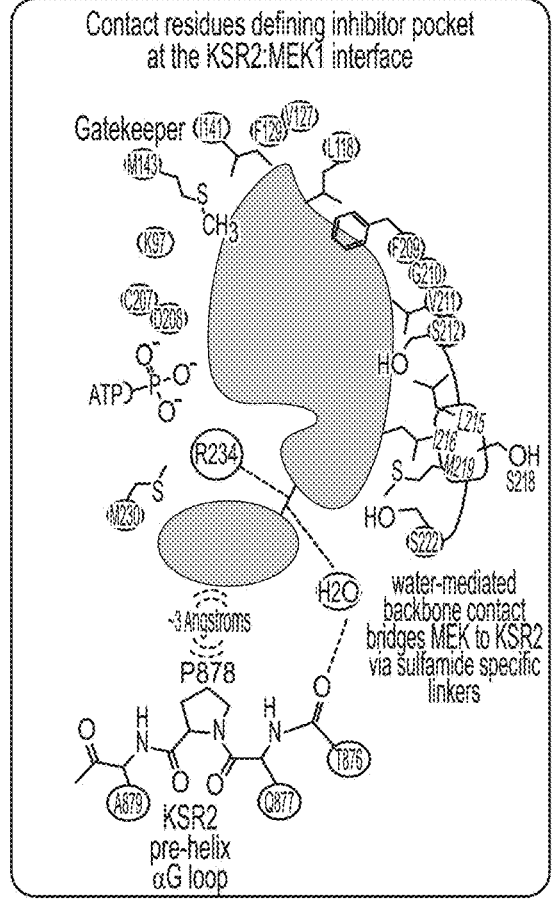
Figure: 72

Figure: 73

Data Table : X-ray Crystal Structure Data collection and Refinement Statistics (KSR2 : MEK1 : AMP-PNP)

| MEK-i | 1 | 2 | 3 | 4 | 5 | 6 |
|---|---|---|---|---|---|---|
| XDS-statistics | | | | | | |
| Space group | P 6(1) 2 2 | P 6(1) 2 2 | P 6(1) 2 2 | P 6(1) 2 2 | P 6(1) 2 2 | P 6(1) 2 2 |
| u.c. axis (Å) | 139.03, 139.03, 222.41 | 138.74, 138.74, 221.83 | 139.23  139.23 219.48 | 39.50  139.50 219.66 | 139.53  139.53 219.75 | 140.08  140.06 218.74 |
| u.c. angles (°) | 90 90 120 | 90 90 120 | 90 90 120 | 90 90 120 | 90 90 120 | 90 90 120 |
| Resolution (Å) | 50 - 3.22 | 50 - 3.35 | 50 - 3.25 | 50 - 3.17 | 50 - 3.46 | 50 - 2.58 |
| R-measure (%) | 9.9 (213.1) | 9.3 (194.1) | 19.6 (279.9) | 9.7 (221.9) | 14.7 (230.7) | 10.8 (231.1) |
| $<I/sI>$ | 20.86 (1.33) | 11.90 (1.27) | 12.45 (0.86) | 21.78 (1.24) | 13.42 (1.31) | 16.08 (1.14) |
| CC-1/2 (%) | 0.99 (0.51) | 0.99 (0.59) | 99.6 (65.3) | 100 (52.8) | 99.9 (49.8) | 99.9 (52.2) |
| Completeness (%) | 99.9 (100) | 99.7 (100) | 99.8 (100) | 99.6 (99.2) | 9935 (99.9) | 99.9 (100.0) |
| Multiplicity | 11.98 (12.37) | 11.02 (11.58) | 11.01 (11.56) | 10.99 (10.39) | 13.11 (14.05) | 13.28 (12.26) |
| Refinement statistics | | | | | | |
| Resolution (Å) | 3.22 | 3.35 | 3.25 | 3.18 | 3.56 | 2.59 |
| No. reflections | 21247 | 18480 | 20422 | 22052 | 14831 | 40064 |
| Rwork / Rfree (%) | 25.4 / 28.8 | 23.2 / 24.8 | 24.16 / 27.64 | 23.41 / 24.79 | 21.21 / 23.29 | 22.27 / 25.25 |
| No. atoms | | | | | | |
|    Protein | 4670 | 4662 | 4662 | 4662 | 4662 | 4651 |
|      Ligand/Ion | 55 | 103 | 104 | 107 | 105 | 105 |
|      Water | 2 | 12 | 14 | 17 | 8 | 20 |
| B-factors | | | | | | |
|    Protein | 118.88 | 107.46 | 112.79 | 110.38 | 140.52 | 92.18 |
|    Ligand/Ion | 108.17 | 106.73 | 114.17 | 110.55 | 140.57 | 91.35 |
|    Water | 78.87 | 62.91 | 79.81 | 75.32 | 94.17 | 70.37 |
| R.m.s. deviations | | | | | | |
|    Bond lengths (°) | 0.004 | 0.005 | 0.003 | 0.003 | 0.004 | 0.006 |
|    Bond angles (Å) | 0.994 | 0.965 | 0.70 | 0.70 | 0.92 | 1.04 |

* Values in parentheses are for highest-resolution shell.

Figure: 74

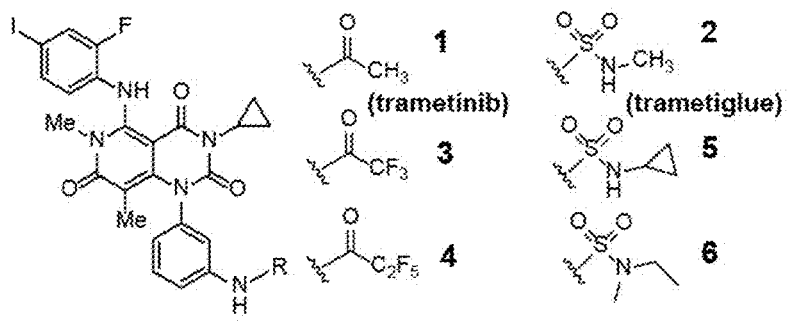
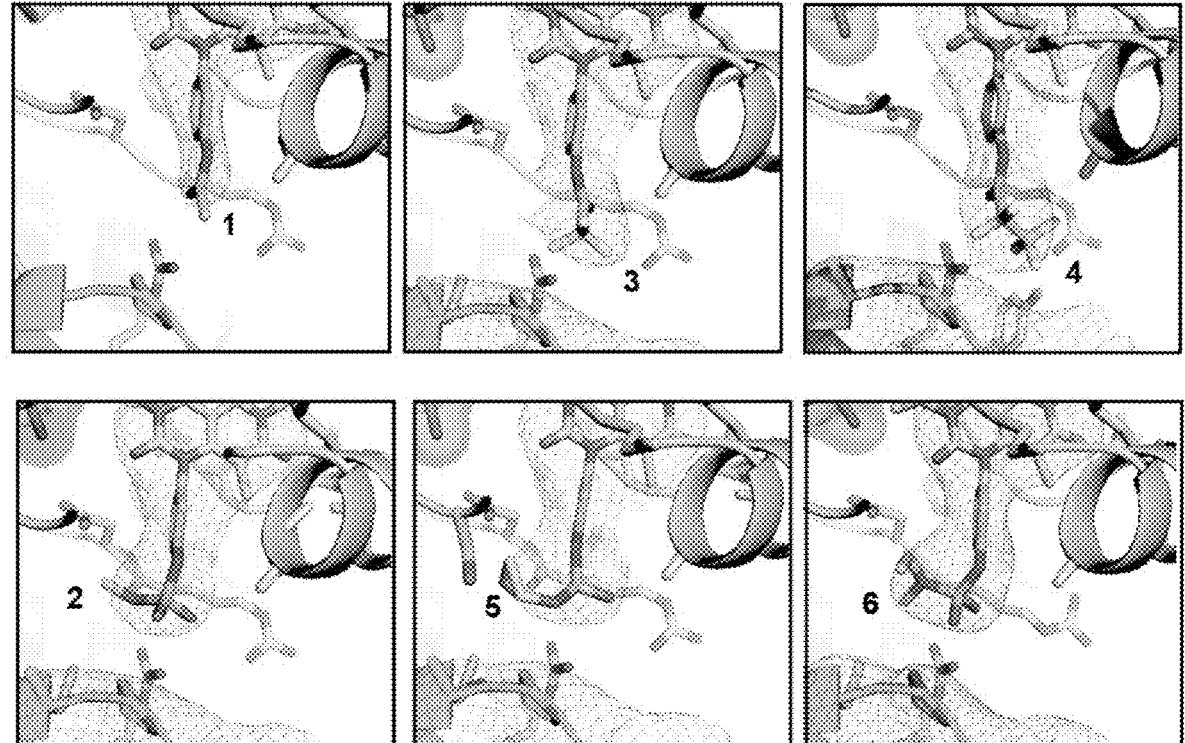
Figure: 75

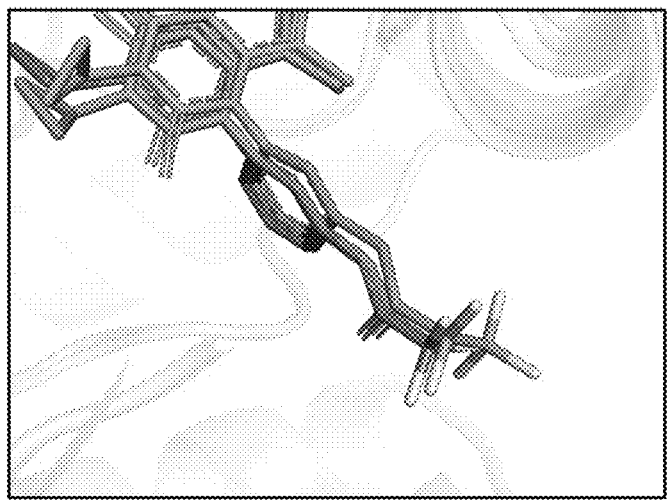
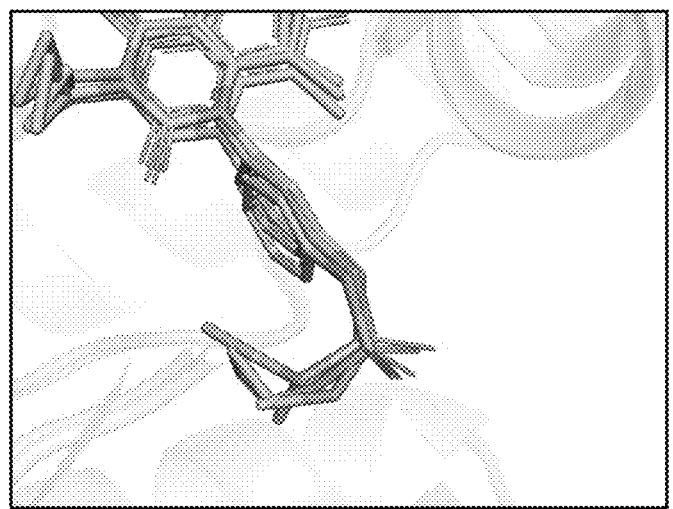
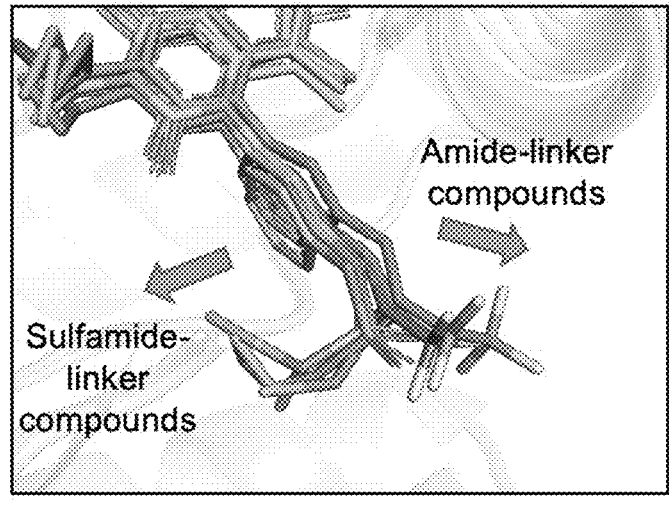
Figure: 76

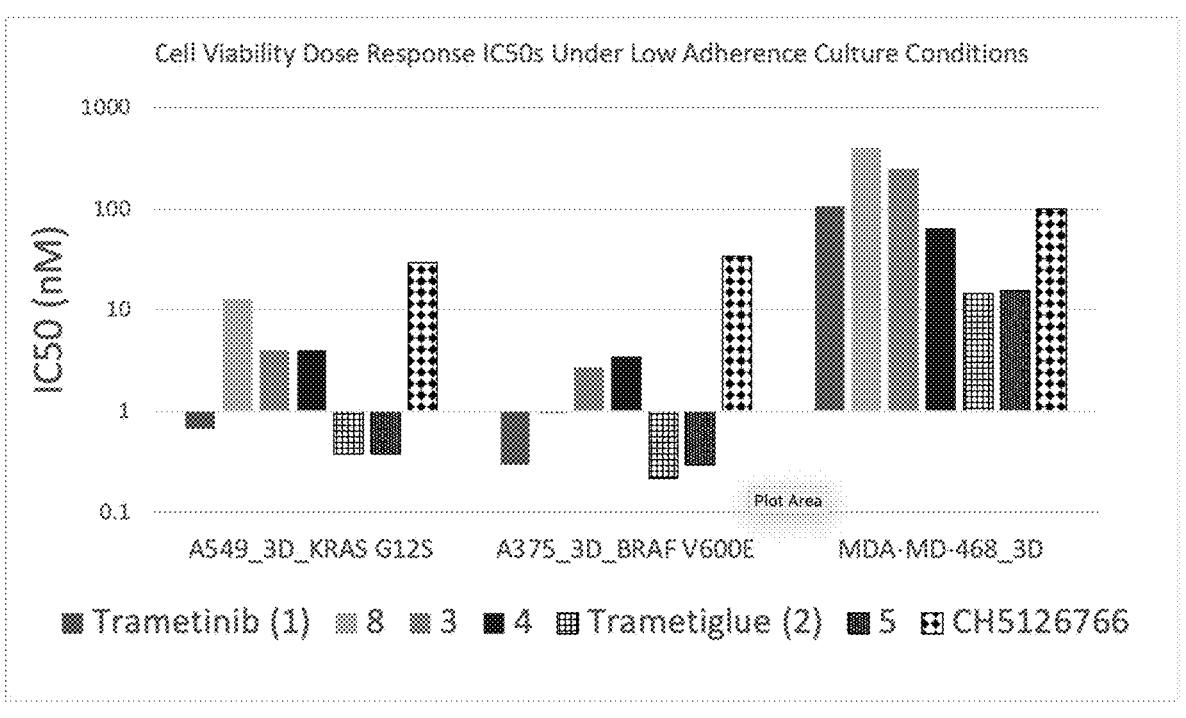
Figure: 77

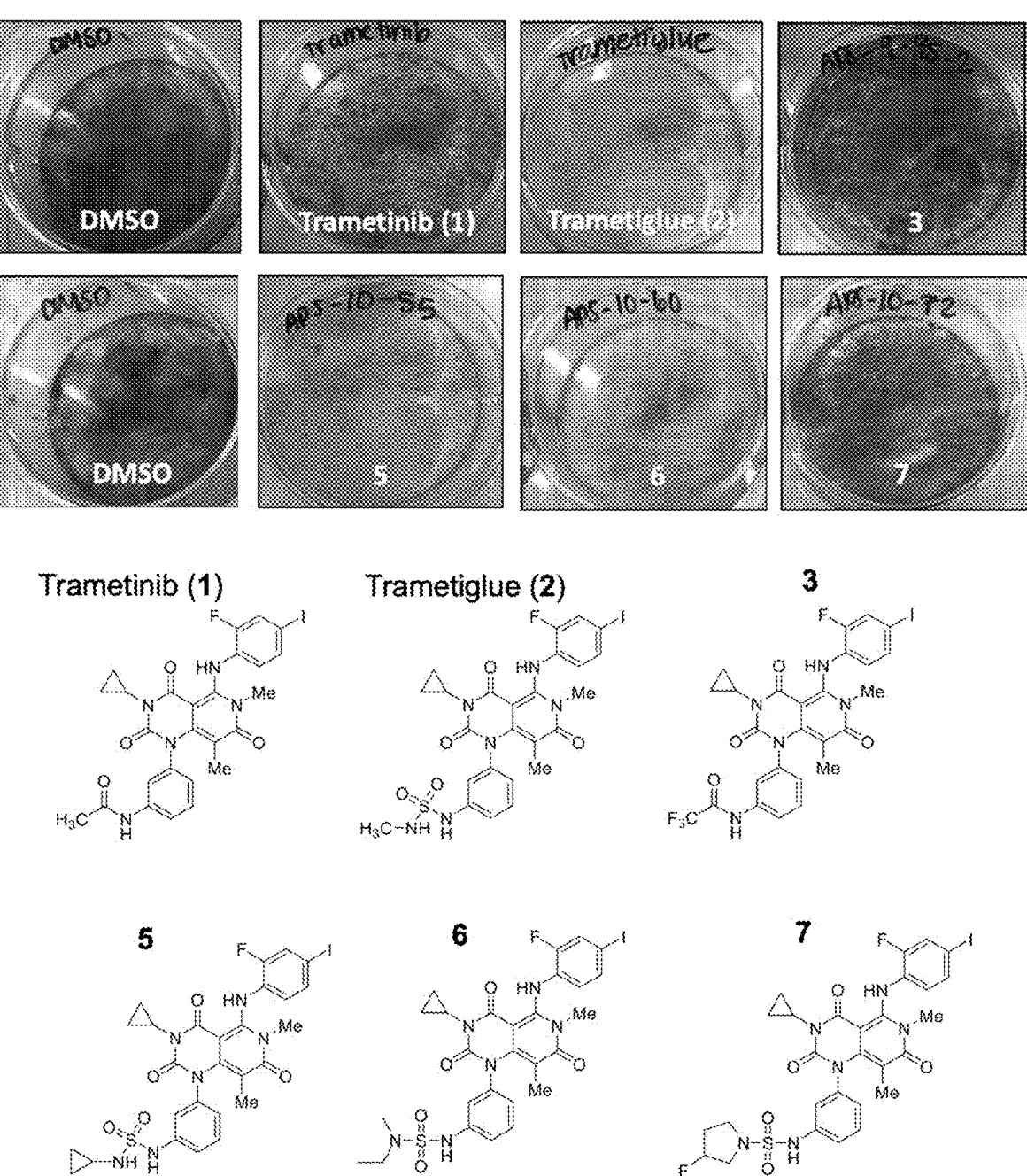
Figure: 78

Data Table : X-ray Crystal Structure Data collection and Refinement Statistics (BRAF : MEK1 : AMP-PNP) complex)

| MEK-i | Trametiglue (2) |
|---|---|
| | |
| XDS-statistics | |
| Space group | P 3(1) 2 1 |
| u.c. axis (Å) | 117.4; 117.4; 128.94 |
| u.c. angles (°) | 90; 90; 120 |
| Resolution (Å) | 50 - 3.55 |
| R-measure (%) | 20.4 (229.5) |
| <I/sI> | 9.15 (1.31) |
| CC-1/2 (%) | 99.8 (47.4) |
| Completeness (%) | 99.9 (100) |
| Multiplicity | 10.18 (9.62) |
| Refinement statistics | |
| Resolution (Å) | 3.55 |
| No. reflections | 12743 |
| Rwork / Rfree (%) | 24.46 / 29.28 |
| No. atoms | |
| Protein | 4531 |
| Ligand/Ion | 74 |
| B-factors | |
| Protein | 134.88 |
| Ligand/Ion | 131.72 |
| R.m.s. deviations | |
| Bond lengths (°) | 0.004 |
| Bond angles (Å) | 1.02 |

* Values in parentheses are for highest-resolution shell.

Figure: 79

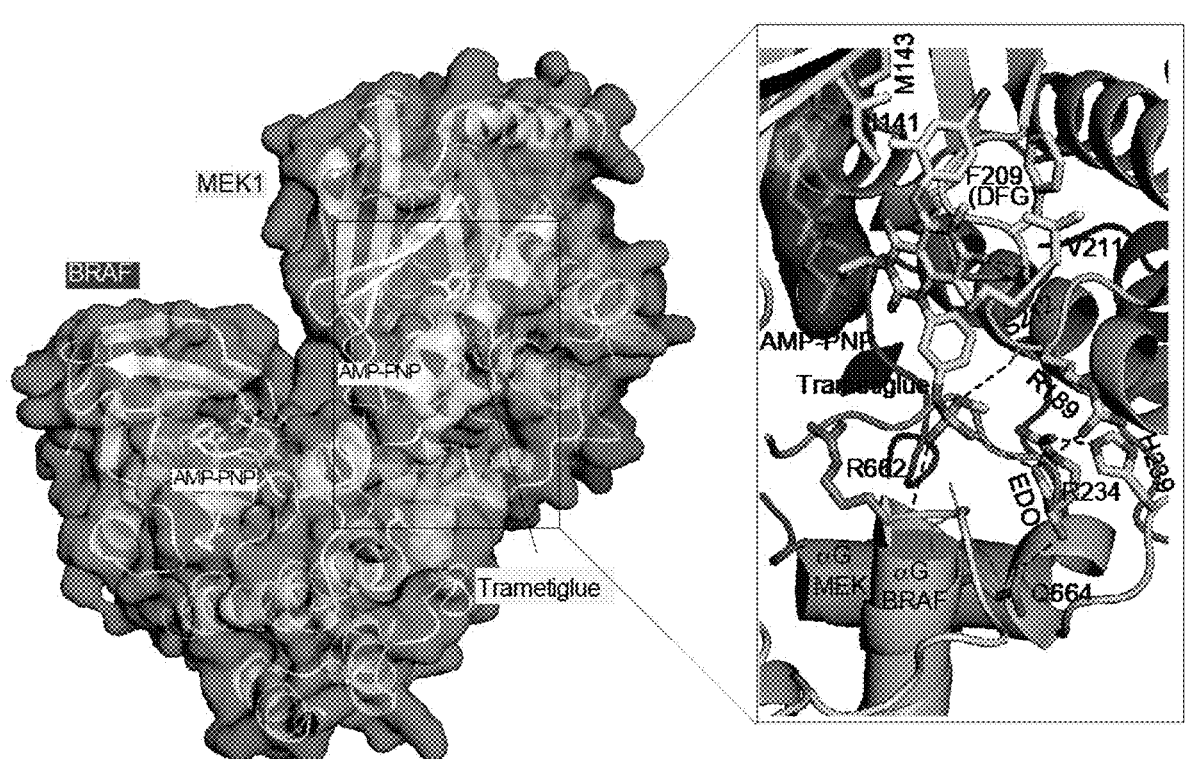
Figure: 80

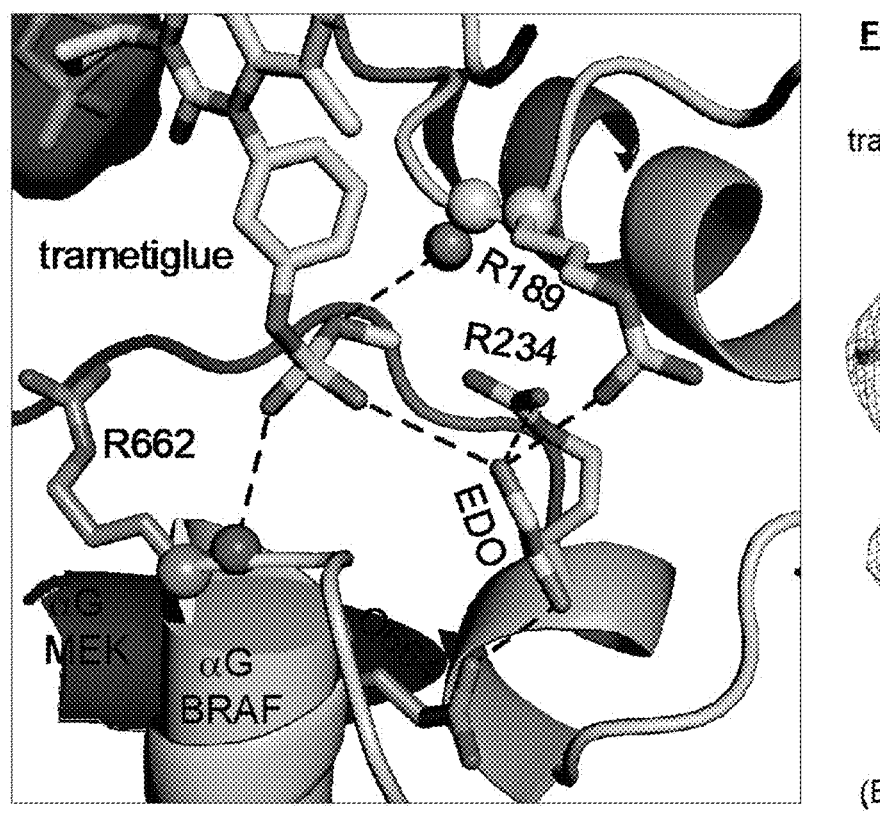
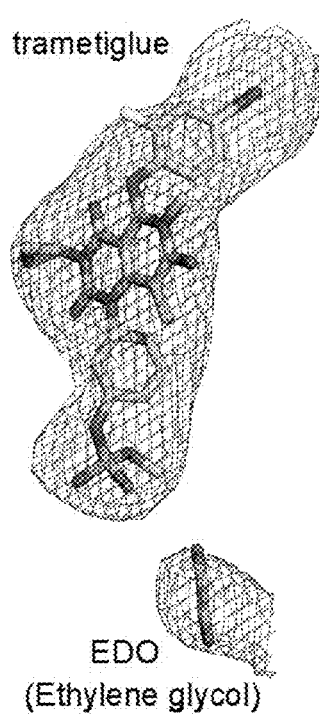
Fo-Fc omit maps
trametiglue
EDO
(Ethylene glycol)
Figure: 81

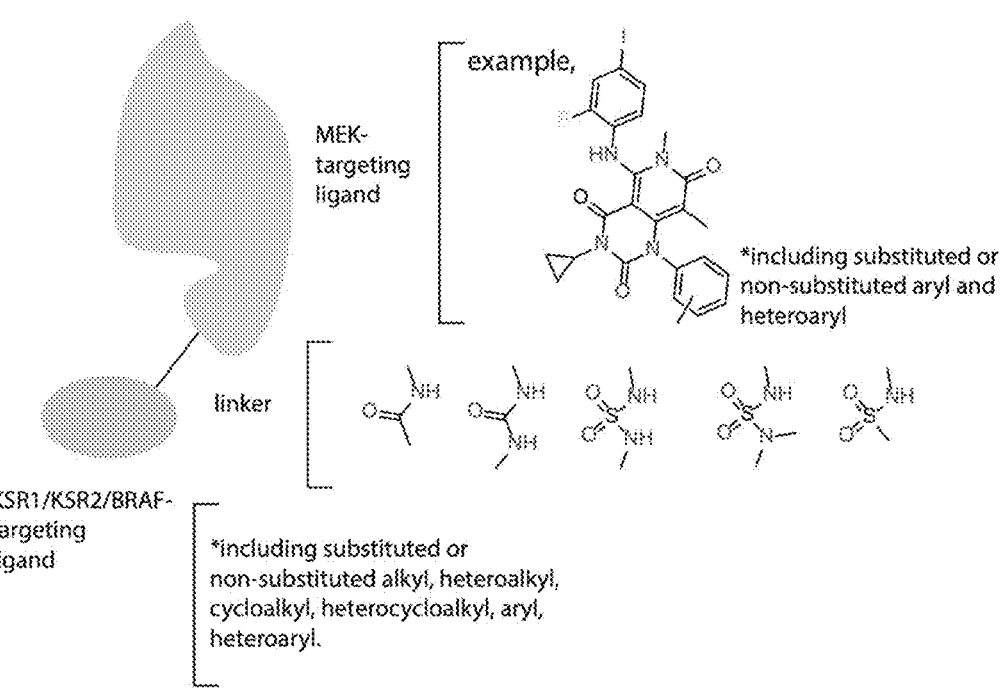
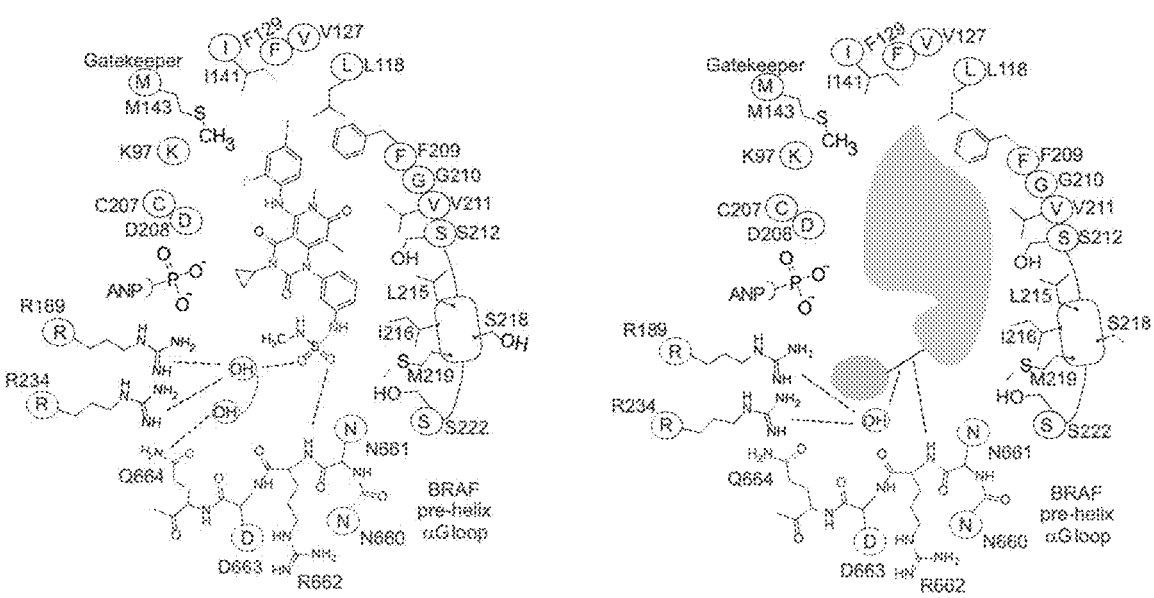
Figure: 82

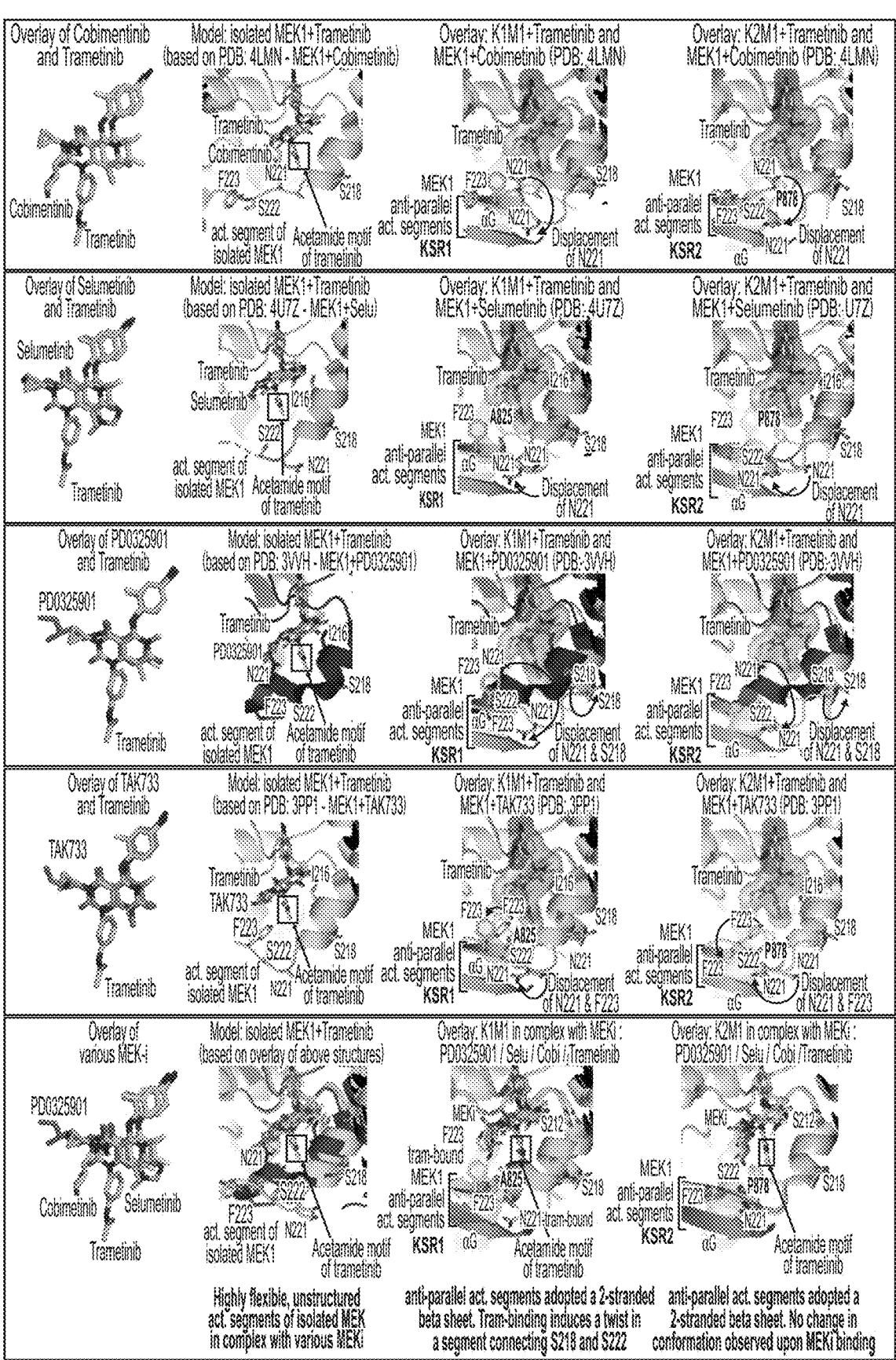
Figure: 83

SEQ ID NO:38
MPKKKPTPIQLNPAPDGSAVNGTSSAETNLEALQKKLEELELDEQQRKRLEAFLTQKQKV
GELKDDDFEKISELGAGNGGVVFKVSHKPSGLVMARKLIHLEIKPAIRNQIIRELQVLHE
CNSPYIVGFYGAFYSDGEISICMEHMDGGSLDQVLKKAGRIPEQILGKVSIAVIKGLTYL
REKHKIMHRDVKPSNILVNSRGEIKLCDFGVSGQLIDSMANSFVGTRSYMSPERLQGTHY
SVQSDIWSMGLSLVEMAVGRYPIPPPDAKELELMFGCQVEGDAAETPPRPRTPGRPLSSY
GMDSRPPMAIFELLDYIVNEPPPKLPSGVFSLEFQDFVNKCLIKNPAERADLKQLMVHAF
IKRSDAEEVDFAGWLCSTIGLNQPSTPTHAAGV

Figure: 84

SEQ ID NO:39
MLARRKPVLPALTINPTIAEGPSPTSEGASEANLVDLQKKLEELELDEQQKKRLEAFLTQ
KAKVGELKDDDFERISELGAGNGGVVTKVQHRPSGLIMARKLIHLEIKPAIRNQIIRELQ
VLHECNSPYIVGFYGAFYSDGEISICMEHMDGGSLDQVLKEAKRIPEEILGKVSIAVLRG
LAYLREKHQIMHRDVKPSNILVNSRGEIKLCDFGVSGQLIDSMANSFVGTRSYMAPERLQ
GTHYSVQSDIWSMGLSLVELAVGRYPIPPPDAKELEAIFGRPVVDGEEGEPHSISPRPRP
PGRPVSGHGMDSRPAMAIFELLDYIVNEPPPKLPNGVFTPDFQEFVNKCLIKNPAERADL
KMLTNHTFIKRSEVEEVDFAGWLCKTLRLNQPGTPTRTAV

Figure: 85

SEQ ID NO:40
MPKKKPTPIQLNPAPDGSAVNGTSSAETNLEALQKKLEELELDEQQRKRLEAFLTQKQKV
GELKDDDFEKISELGAGNGGVVFKVSHKPSGLVMARKLIHLEIKPAIRNQIIRELQVLHE
CNSPYIVGFYGAFYSDGEISICMEHMDGGSLDQVLKKAGRIPEQILGKVSIAVIKGLTYL
REKHKIMHRDVKPSNILVNSRGEIKLCDFGVSGQLIDSMANSFVGTRSYMSPERLQGTHY
SVQSDIWSMGLSLVEMAVGRYPIPPPDAKELELMFGCQVEGDAAETPPRPRTPGRPLSSY
GMDSRPPMAIFELLDYIVNEPPPKLPSAVFSLEFQDFVNKCLIKNPAERADLKQLMVHAF
IKRSDAEEVDFAGWLCSTIGLNQPSTPTHAAGV

Figure: 86

SEQ ID NO:41
MDRAALRAAAMGEKKEGGGGGDAAAAEGGAGAAASRALQQCGQLQKLIDISIGSLRGLRT
KCAVSNDLTQQEIRTLEAKLVRYICKQRQCKLSVAPGERTPELNSYPRFSDWLYTFNVRP
EVVQEIPRDLTLDALLEMNEAKVKETLRRCGASGDECGRLQYALTCLRKVTGLGGEHKED
SSWSSLDARRESGSGPSTDTLSAASLPWPPGSSQLGRAGNSAQGPRSISVSALPASDSPT
PSFSEGLSDTCIPLHASGRLTPRALHSFITPPTTPQLRRHTKLKPPRTPPPPSRKVFQLL
PSFPTLTRSKSHESQLGNRIDDVSSMRFDLSHGSPQMVRRDIGLSVTHRFSTKSWLSQVC
HVCQKSMIFGVKCKHCRLKCHNKCTKEAPACRISFLPLTRLRRTESVPSDINNPVDRAAE
PHFGTLPKALTKKEHPPAMNHLDSSSNPSSTTSSTPSSPAPFPTSSNPSSATTPPNPSPG
QRDSRFNFPAAYFIHHRQQFIFPVPSAGHCWKCLLIAESLKENAFNISAFAHAAPLPEAA
DGTRLDDQPKADVLEAHEAEAEEPEAGKSEAEDDEDEVDDLPSSRRPWRGPISRKASQTS
VYLQEWDIPFEQVELGEPIGQGRWGRVHRGRWHGEVAIRLLEMDGHNQDHLKLFKKEVMN
YRQTRHENVVLFMGACMNPPHLAIITSFCKGRTLHSFVRDPKTSLDINKTRQIAQEIIKG
MGYLHAKGIVHKDLKSKNVFYDNGKVVITDFGLFGISGVVREGRRENQLKLSHDWLCYLA
PEIVREMTPGKDEDQLPFSKAADVYAFGTVWYELQARDWPLKNQAAEASIWQIGSGEGMK
RVLTSVSLGKEVSEILSACWAFDLQERPSFSLLMDMLEKLPKLNRRLSHPGHFWKSADIN
SSKVVPRFERFGLGVLESSNPKM

Figure: 87

```
SEQ ID NO:42
MDEENMTKSEEQQPLSLQKALQQCELVQNMIDLSISNLEGLRTKCATSNDLTQKEIRTLE
SKLVKYFSRQLSCKKKVALQERNAELDGFPQLRHWFRIVDVRKEVLEEISPGQLSLEDLL
EMTDEQVCETVEKYGANREECARLNASLSCLRNVHMSGGNLSKQDWTIQWPTTETGKENN
PVCPPEPTPWIRTHLSQSPRVPSKCVQHYCHTSPTPGAPVYTHVDRLTVDAYPGLCPPPP
LESGHRSLPPSPRQRHAVRTPPRTPNIVTTVTPPGTPPMRKKNKLKPPGTPPPSSRKLIH
LIPGFTALHRSKSHEFQLGHRVDEAHTPKAKKKSKPLNLKIHSSVGSCENIPSQQRSPLL
SERSLRSFFVGHAPFLPSTPPVHTEANFSANTLSVPRWSPQIPRRDLGNSIKHRFSTKYW
MSQTCTVCGKGMLFGLKCKNCKLKCHNKCTKEAPPCHLLIIHRGDPARLVRTESVPCDIN
NPLRKPPRYSDLHISQTLPKTNKINKDHIPVPYQPDSSSNPSSTTSSTPSSPAPPLPPSA
TPPSPLHPSPQCTRQQKNFNLPASHYYKYKQQFIFPDVVPVPETPTRAPQVILHPVTSNP
ILEGNPLLQIEVEPTSENEEVHDEAEESEDDFEEMNLSLLSARSFPRKASQTSIFLQEWD
IPFEQLEIGELIGKGRFGQVYHGRWHGEVAIRLIDIERDNEDQLKAFKREVMAYRQTRHE
NVVLFMGACMSPPHLAIITSLCKGRTLYSVVRDAKIVLDVNKTRQIAQEIVKGMGYLHAK
GILHKDLKSKNVFYDNGKVVITDFGLFSISGVLQAGRREDKLRIQNGWLCHLAPEIIRQL
SPDTEEDKLPFSKHSDVFALGTIWYELHAREWPFKTQPAEAIIWQMGTGMKPNLSQIGMG
KEISDILLFCWAFEQEERPTFTKLMDMLEKLPKRNRRLSHPGHFWKSAEL
```

Figure: 88

SEQ ID NO:43
MDRAALRAAAMGEKKEGGGGGAAADGGAGAAVSRALQQCGQLQKLIDISIGSLRGLRTKC
SVSNDLTQQEIRTLEAKLVKYICKQQQSKLSVTPSDRTAELNSYPRFSDWLYIFNVRPEV
VQEIPQELTLDALLEMDEAKAKEMLRRWGASTEECSRLQQALTCLRKVTGLGGEHKMDSG
WSSTDARDSSLGPPMDMLSSLGRAGASTQGPRSISVSALPASDSPVPGLSEGLSDSCIPL
HTSGRLTPRALHSFITPPTTPQLRRHAKLKPPRTPPPPSRKVFQLLPSFPTLTRSKSHES
QLGNRIDDVTPMKFELPHGSPQLVRRDIGLSVTHRFSTKSWLSQVCNVCQKSMIFGVKCK
HCRLKCHNKCTKEAPACRITFLPLARLRRTESVPSDINNPVDRAAEPHFGTLPKALTKKE
HPPAMNLDSSSNPSSTTSSTPSSPAPFLTSSNPSSATTPPNPSPGQRDSRFSFPDISACS
QAAPLSSTADSTRLDDQPKTDVLGVHEAEAEEPEAGKSEAEDDEEDEVDDLPSSRRPWRG
PISRKASQTSVYLQEWDIPFEQVELGEPIGQGRWGRVHRGRWHGEVAIRLLEMDGHNQDH
LKLFKKEVMNYRQTRHENVVLFMGACMNPPHLAIITSFCKGRTLHSFVRDPKTSLDINKT
RQIAQEIIKGMGYLHAKGIVHKDLKSKNVFYDNGKVVITDFGLFGISGVVREERRENQLK
LSHDWLCYLAPEIVREMIPGRDEDQLPFSKAADVYAFGTVWYELQARDWPFKHQPAEALI
WQIGSGEGVRRVLASVSLGKEVGEILSACWAFDLQERPSFSLLMDMLERLPKLNRRLSHP
GHFWKSADINSSKVMPRFERFGLGTLESGNPKM

Figure: 89

SEQ ID NO:44
MAALSGGGGGGAEPGQALFNGDMEPEAGAGAGAAASSAADPAIPEEVWNIKQMIKLTQEH
IEALLDKFGGEHNPPSIYLEAYEEYTSKLDALQQREQQLLESLGNGTDFSVSSSASMDTV
TSSSSSSLSVLPSSLSVFQNPTDVARSNPKSPQKPIVRVFLPNKQRTVVPARCGVTVRDS
LKKALMMRGLIPECCAVYRIQDGEKKPIGWDTDISWLTGEELHVEVLENVPLTTHNFVRK
TFFTLAFCDFCRKLLFQGFRCQTCGYKFHQRCSTEVPLMCVNYDQLDLLFVSKFFEHHPI
PQEEASLAETALTSGSSPSAPASDSIGPQILTSPSPSKSIPIPQPFRPADEDHRNQFGQR
DRSSSAPNVHINTIEPVNIDDLIRDQGFRGDGGSTTGLSATPPASLPGSLTNVKALQKSP
GPQRERKSSSSSEDRNRMKTLGRRDSSDDWEIPDGQITVGQRIGSGSFGTVYKGKWHGDV
AVKMLNVTAPTPQQLQAFKNEVGVLRKTRHVNILLFMGYSTKPQLAIVTQWCEGSSLYHH
LHIIETKFEMIKLIDIARQTAQGMDYLHAKSIIHRDLKSNNIFLHEDLTVKIGDFGLATV
KSRWSGSHQFEQLSGSILWMAPEVIRMQDKNPYSFQSDVYAFGIVLYELMTGQLPYSNIN
NRDQIIFMVGRGYLSPDLSKVRSNCPKAMKRLMAECLKKKRDERPLFPQILASIELLARS
LPKIHRSASEPSLNRAGFQTEDFSLYACASPKTPIQAGGYGAFPVH

Figure: 90

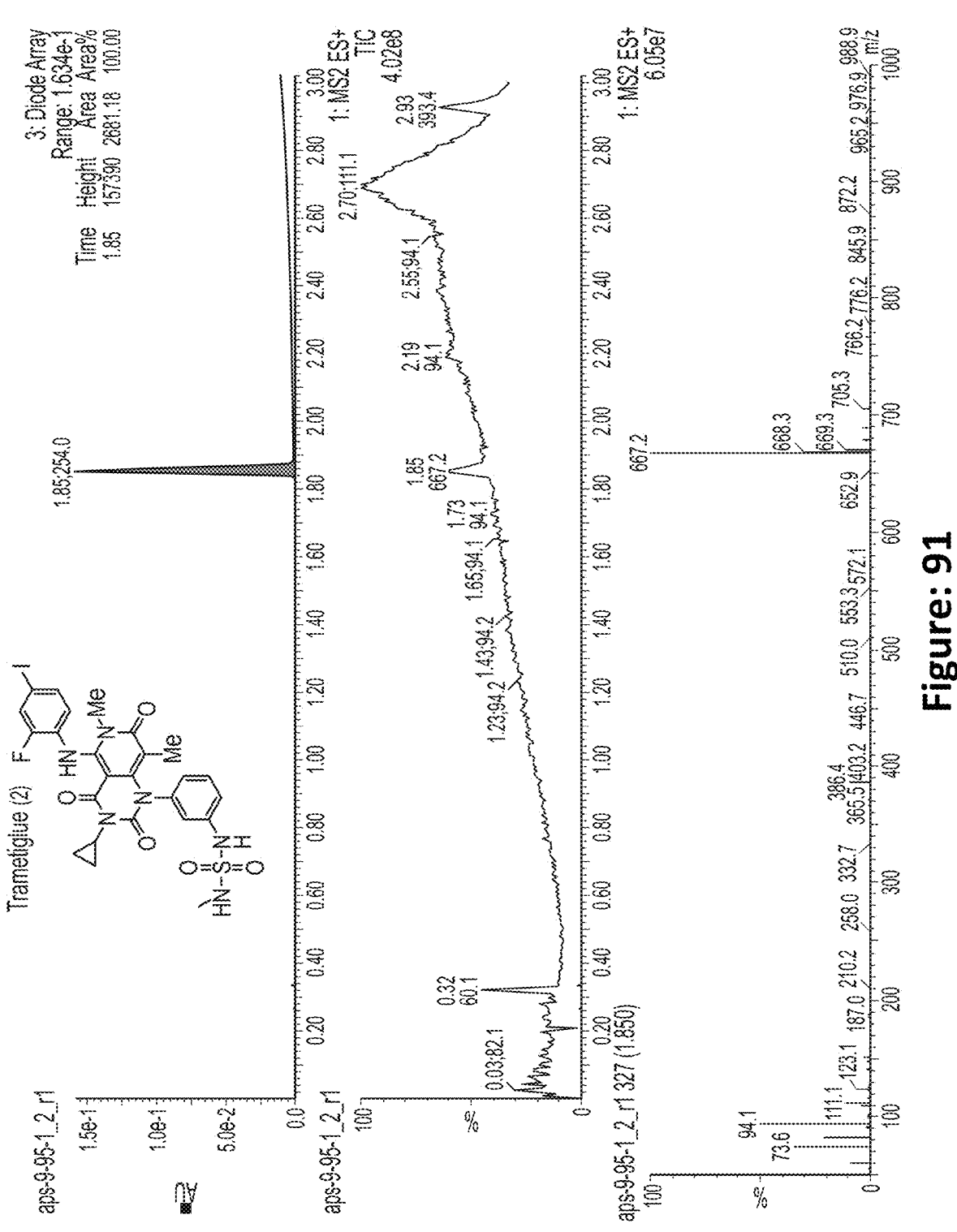
Figure: 91

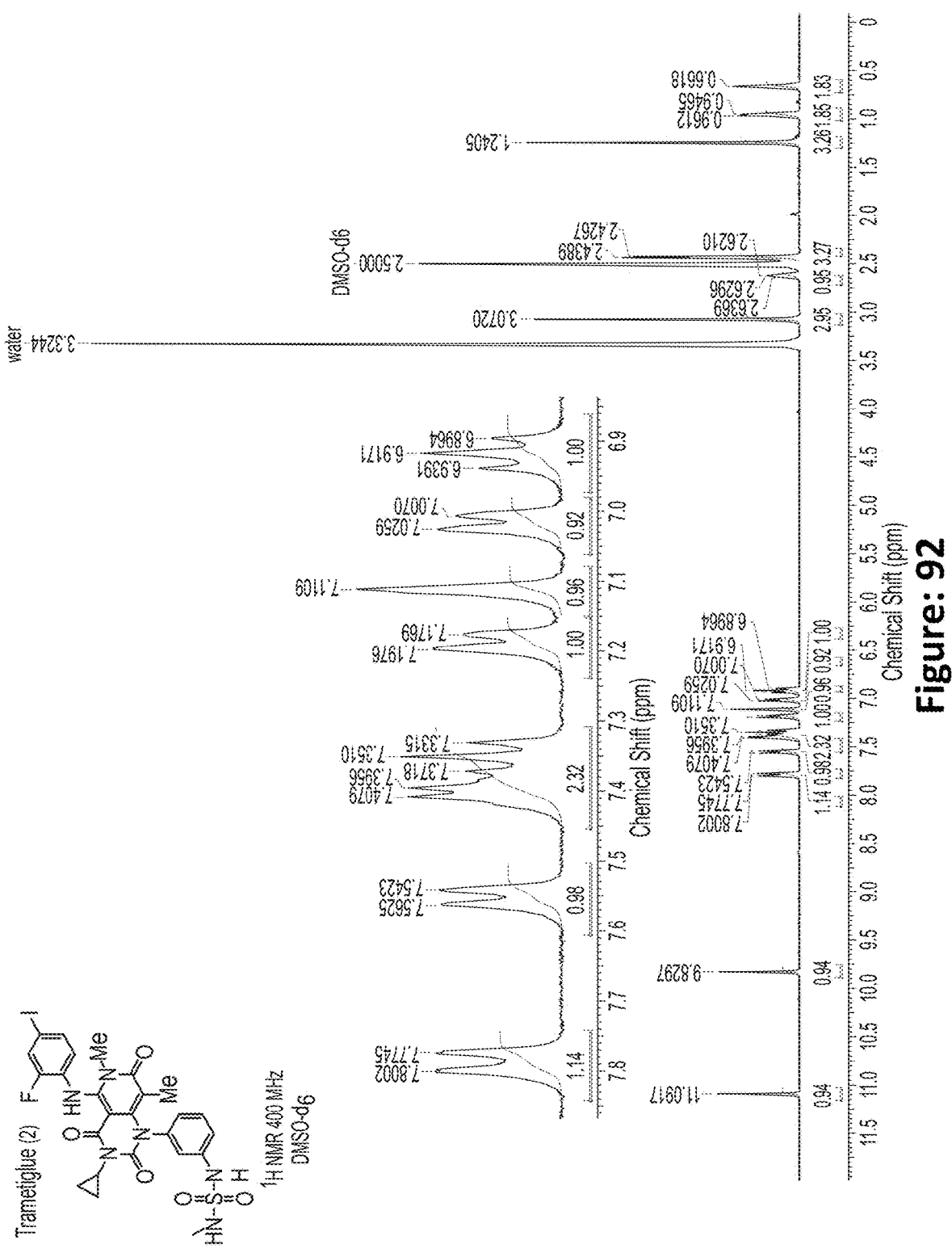
Figure: 92

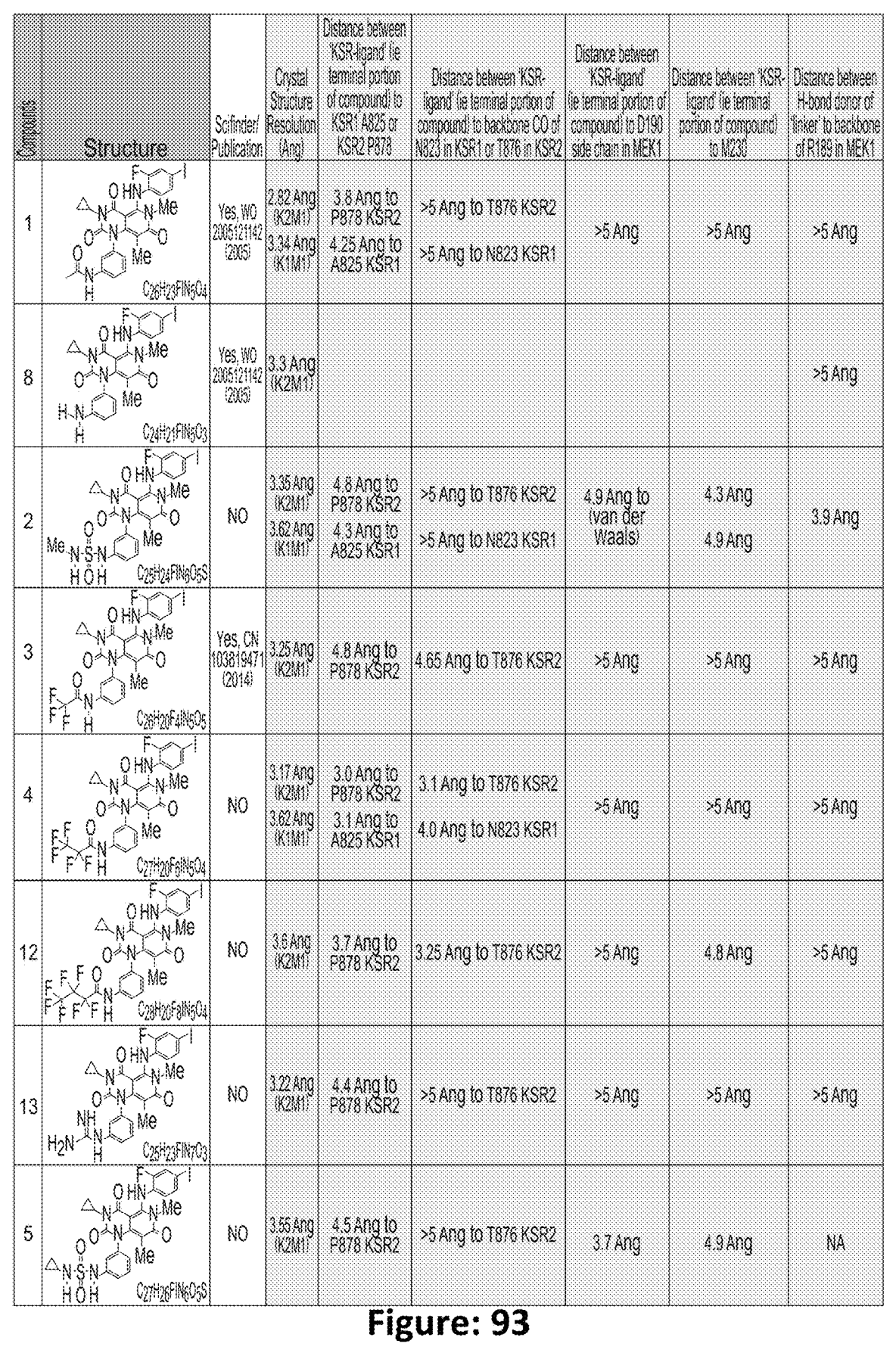

| Compounds | Structure | Scifinder/ Publication | Crystal Structure Resolution (Ang) | Distance between 'KSR-ligand' (ie terminal portion of compound) to KSR1 A825 or KSR2 P878 | Distance between KSR-ligand' (ie terminal portion of compound) to backbone CO of N823 in KSR1 or T876 in KSR2 | Distance between KSR-ligand' (ie terminal portion of compound) to D190 side chain in MEK1 | Distance between KSR-ligand' (ie terminal portion of compound) to M230 | Distance between H-bond donor of 'linker' to backbone of R189 in MEK1 |
|---|---|---|---|---|---|---|---|---|
| 1 | C26H23FIN5O4 | Yes, WO 2005121142 (2005) | 2.82 Ang (K2M1) 3.34 Ang (K1M1) | 3.8 Ang to P878 KSR2 4.25 Ang to A825 KSR1 | >5 Ang to T876 KSR2 >5 Ang to N823 KSR1 | >5 Ang | >5 Ang | >5 Ang |
| 8 | C24H21FIN5O3 | Yes, WO 2005121142 (2005) | 3.3 Ang (K2M1) | | | | | >5 Ang |
| 2 | C25H24FIN6O5S | NO | 3.35 Ang (K2M1) 3.62 Ang (K1M1) | 4.8 Ang to P878 KSR2 4.3 Ang to A825 KSR1 | >5 Ang to T876 KSR2 >5 Ang to N823 KSR1 | 4.9 Ang to (van der Waals) | 4.3 Ang 4.9 Ang | 3.9 Ang |
| 3 | C26H20F4IN5O5 | Yes, CN 103819471 (2014) | 3.25 Ang (K2M1) | 4.8 Ang to P878 KSR2 | 4.65 Ang to T876 KSR2 | >5 Ang | >5 Ang | >5 Ang |
| 4 | C27H20F6IN5O4 | NO | 3.17 Ang (K2M1) 3.62 Ang (K1M1) | 3.0 Ang to P878 KSR2 3.1 Ang to A825 KSR1 | 3.1 Ang to T876 KSR2 4.0 Ang to N823 KSR1 | >5 Ang | >5 Ang | >5 Ang |
| 12 | C28H20F8IN5O4 | NO | 3.6 Ang (K2M1) | 3.7 Ang to P878 KSR2 | 3.25 Ang to T876 KSR2 | >5 Ang | 4.8 Ang | >5 Ang |
| 13 | C26H23FIN7O3 | NO | 3.22 Ang (K2M1) | 4.4 Ang to P878 KSR2 | >5 Ang to T876 KSR2 | >5 Ang | >5 Ang | >5 Ang |
| 5 | C27H26FIN6O5S | NO | 3.55 Ang (K2M1) | 4.5 Ang to P878 KSR2 | >5 Ang to T876 KSR2 | 3.7 Ang | 4.9 Ang | NA |

Figure: 93

Figure 94:
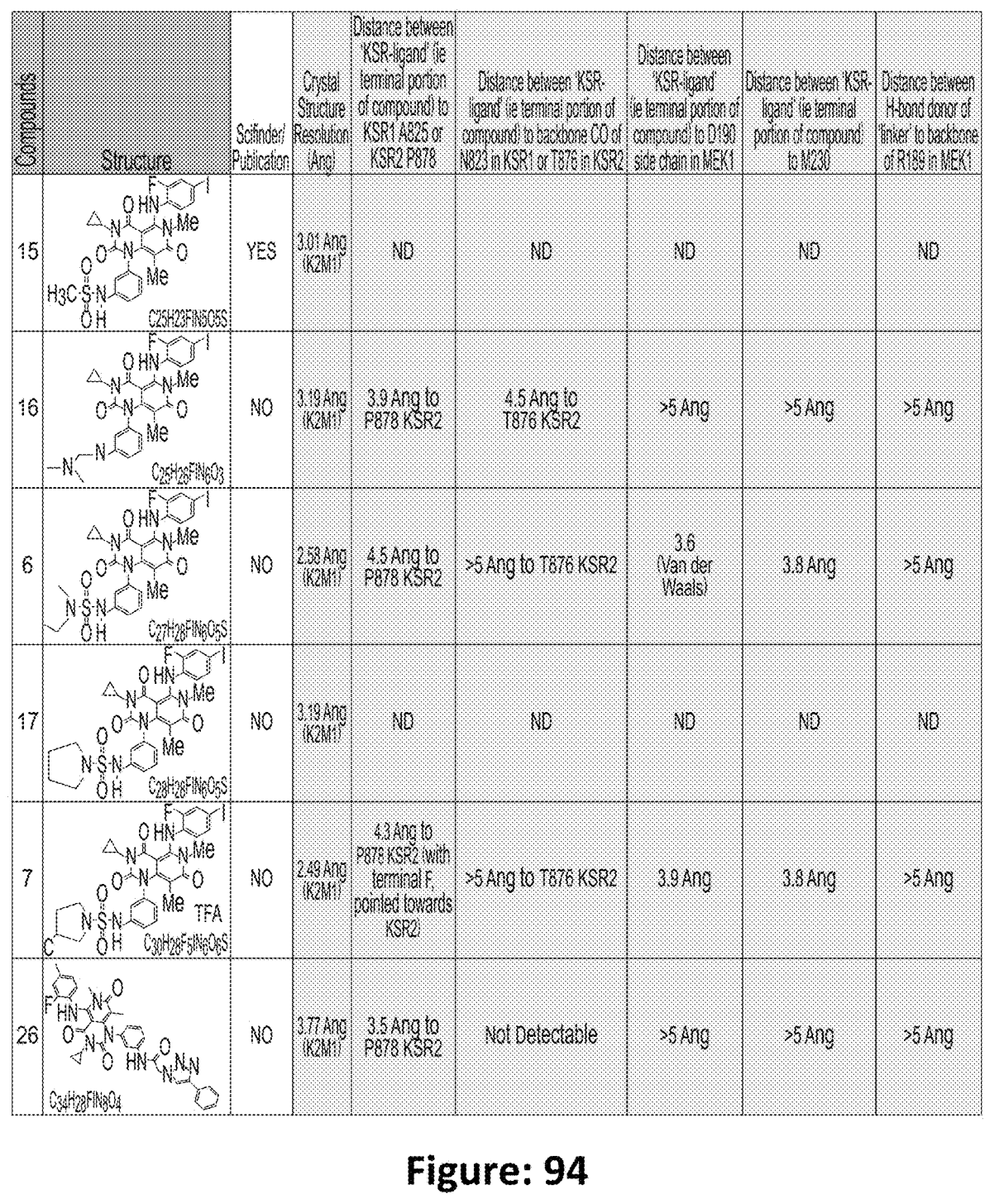

| Compounds | Structure | Scifinder/ Publication | Crystal Structure Resolution (Ang) | Distance between KSR-ligand (ie terminal portion of compound) to KSR1 A825 or KSR2 P878 | Distance between KSR-ligand (ie terminal portion of compound) to backbone CO of N823 in KSR1 or T876 in KSR2 | Distance between KSR-ligand (ie terminal portion of compound) to D190 side chain in MEK1 | Distance between KSR-ligand (ie terminal portion of compound) to M230 | Distance between H-bond donor of linker to backbone of R189 in MEK1 |
|---|---|---|---|---|---|---|---|---|
| 15 | C25H23FIN6O5S | YES | 3.01 Ang (K2M1) | ND | ND | ND | ND | ND |
| 16 | C26H26FIN6O3 | NO | 3.19 Ang (K2M1) | 3.9 Ang to P878 KSR2 | 4.5 Ang to T876 KSR2 | >5 Ang | >5 Ang | >5 Ang |
| 6 | C27H28FIN6O5S | NO | 2.58 Ang (K2M1) | 4.5 Ang to P878 KSR2 | >5 Ang to T876 KSR2 | 3.6 (Van der Waals) | 3.8 Ang | >5 Ang |
| 17 | C28H28FIN6O5S | NO | 3.19 Ang (K2M1) | ND | ND | ND | ND | ND |
| 7 | C30H28F5IN6O6S | NO | 2.49 Ang (K2M1) | 4.3 Ang to P878 KSR2 (with terminal F pointed towards KSR2) | >5 Ang to T876 KSR2 | 3.9 Ang | 3.8 Ang | >5 Ang |
| 26 | C34H28FIN8O4 | NO | 3.77 Ang (K2M1) | 3.5 Ang to P878 KSR2 | Not Detectable | >5 Ang | >5 Ang | >5 Ang |

Figure 95A:
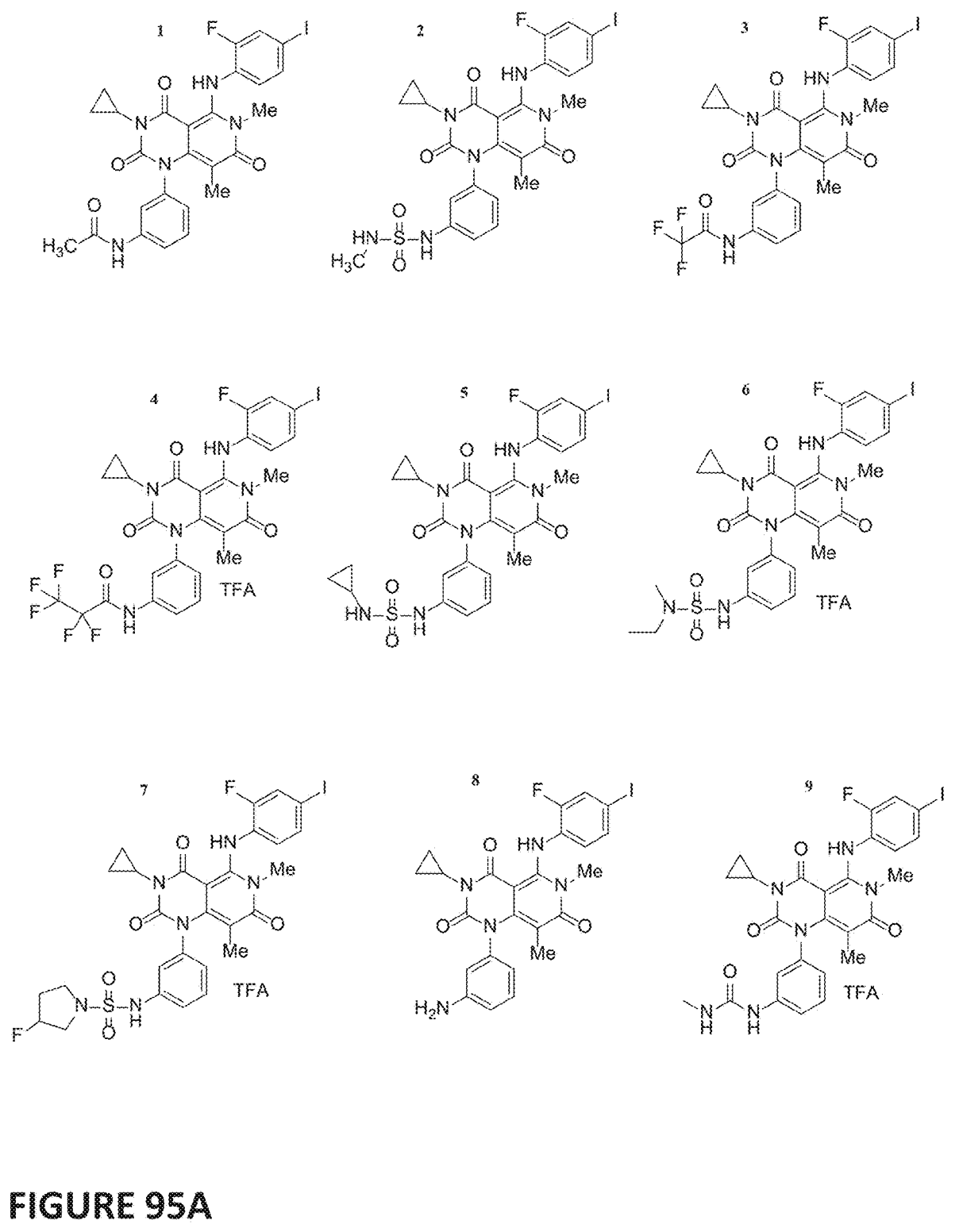

Figure 95B:
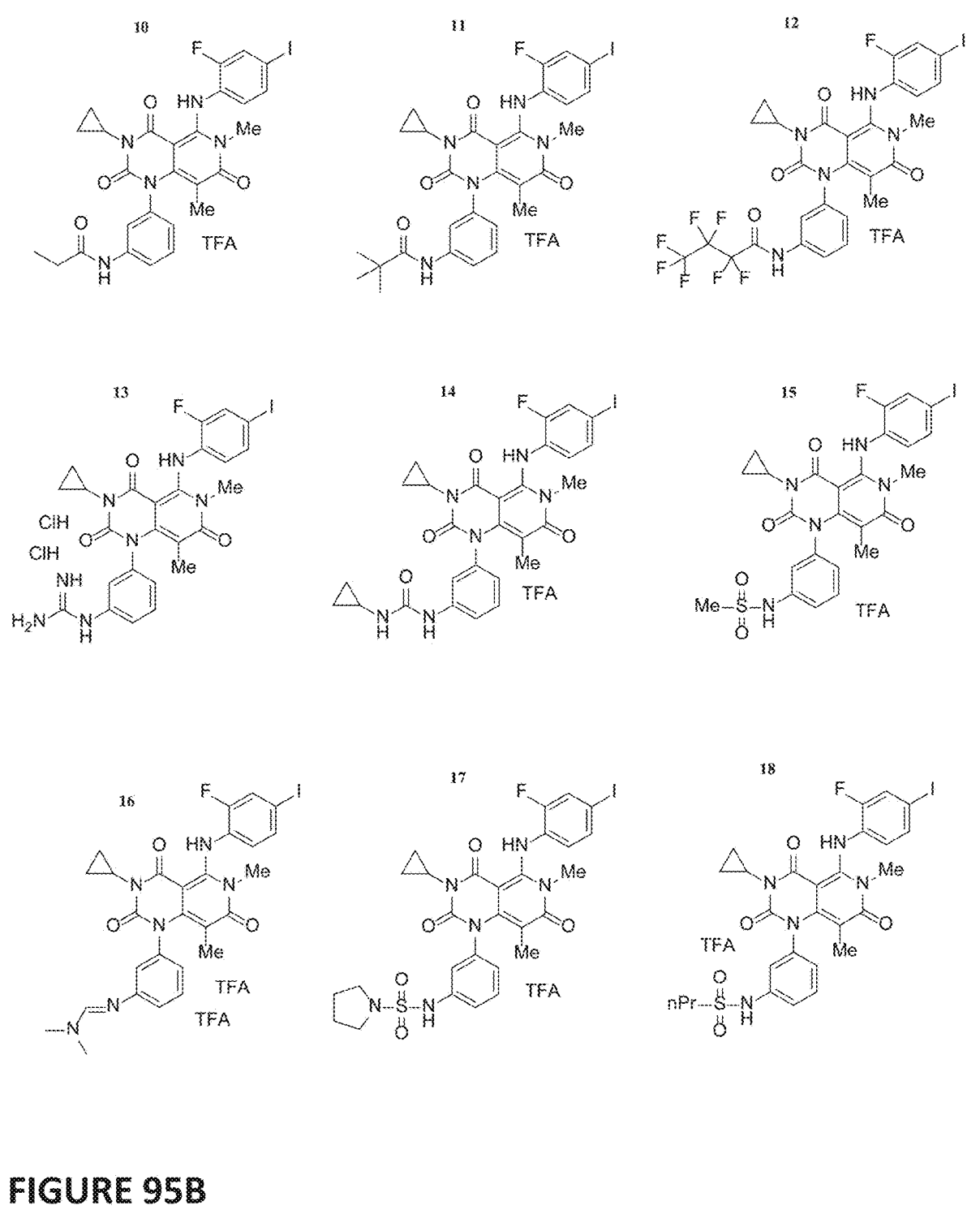

Figure 95C:
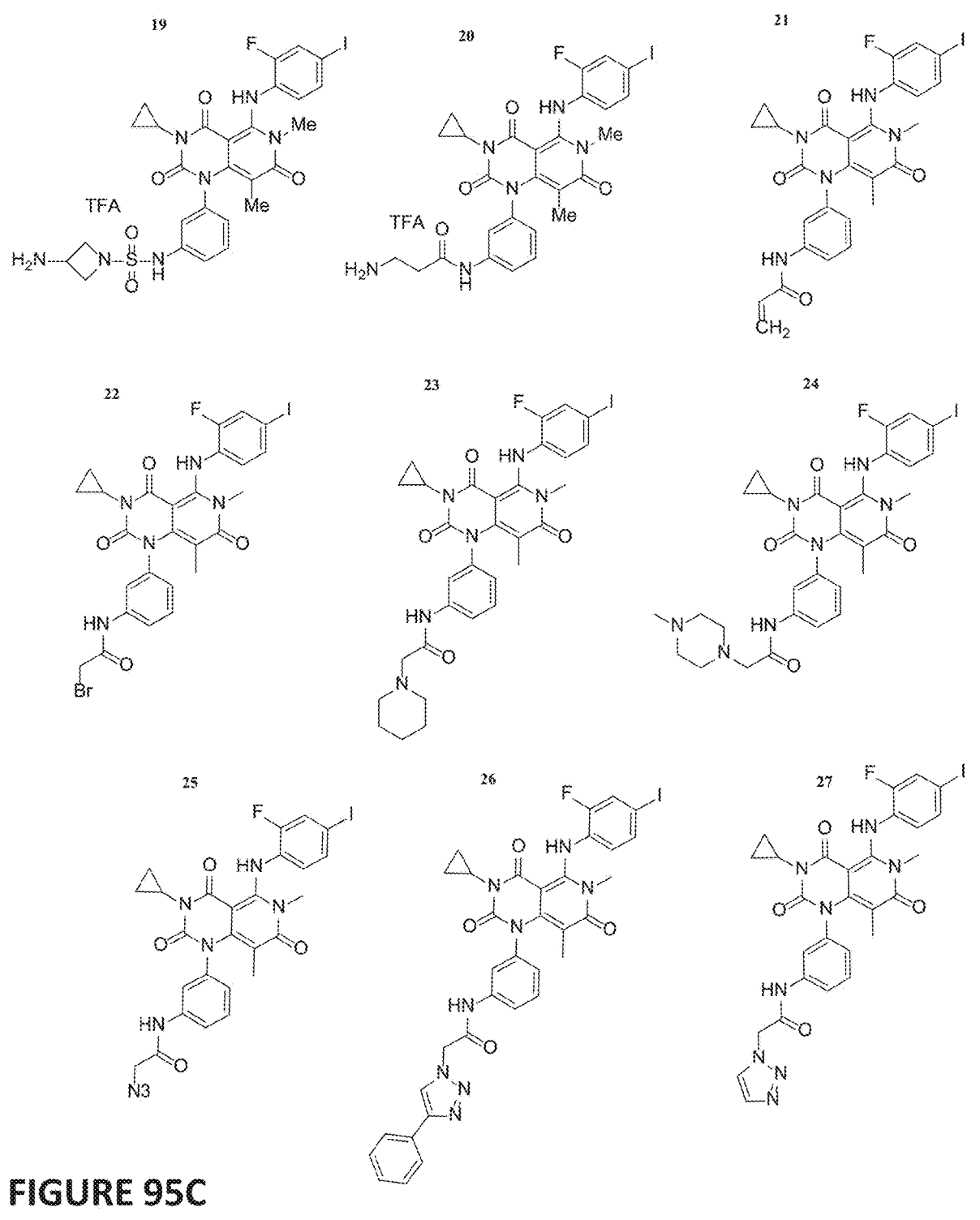

Figure 95D:
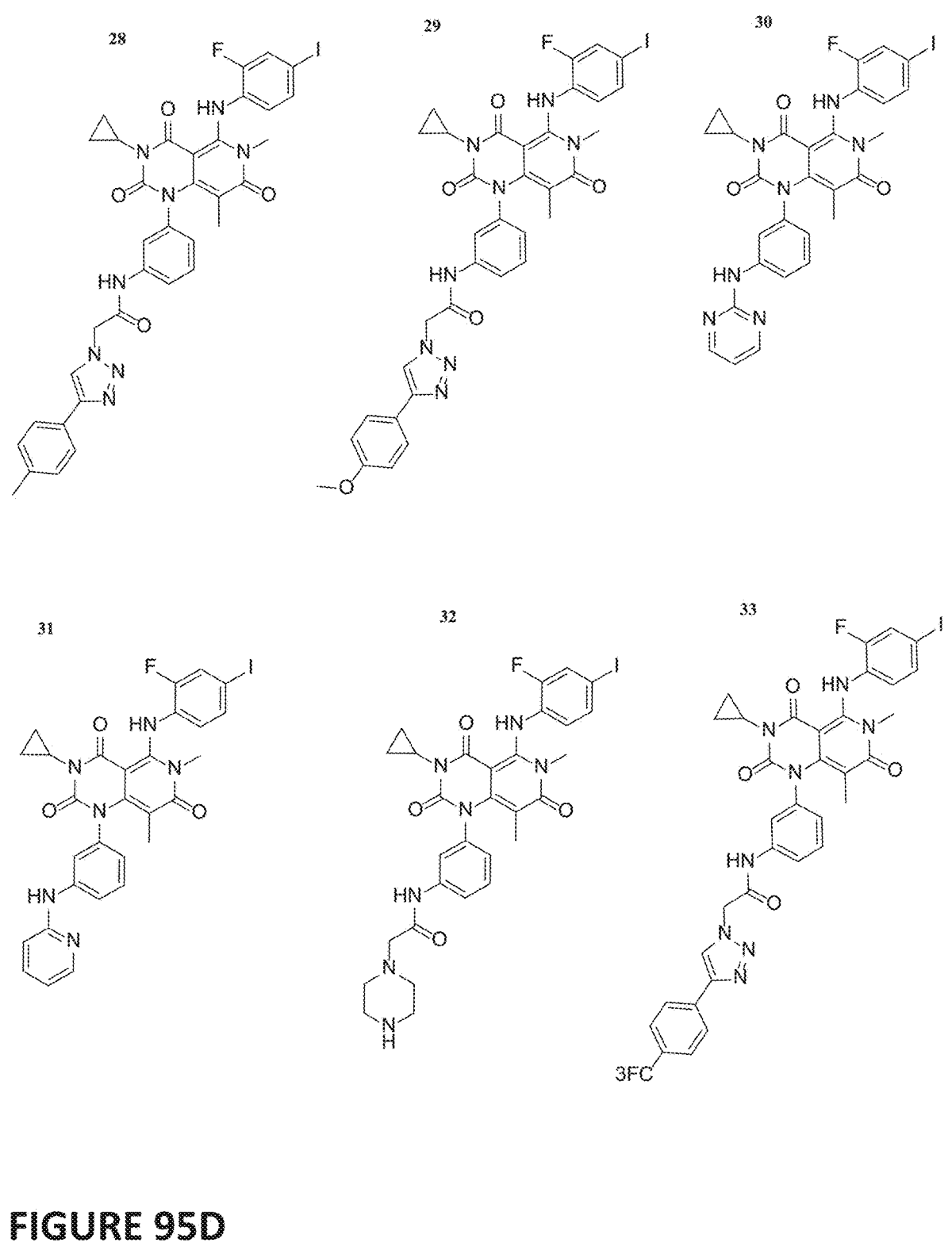

Figure 95E:
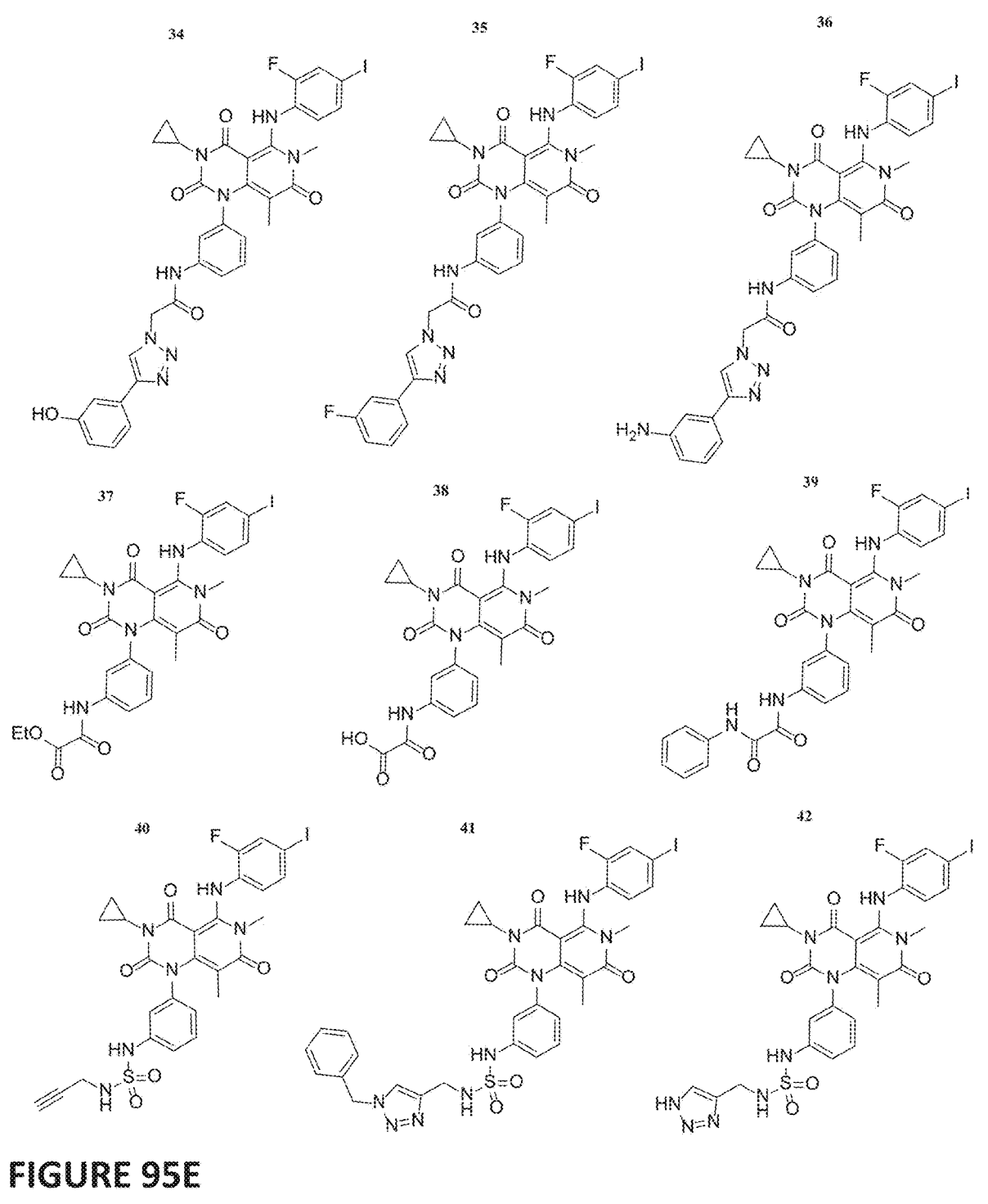

Figure 95F:
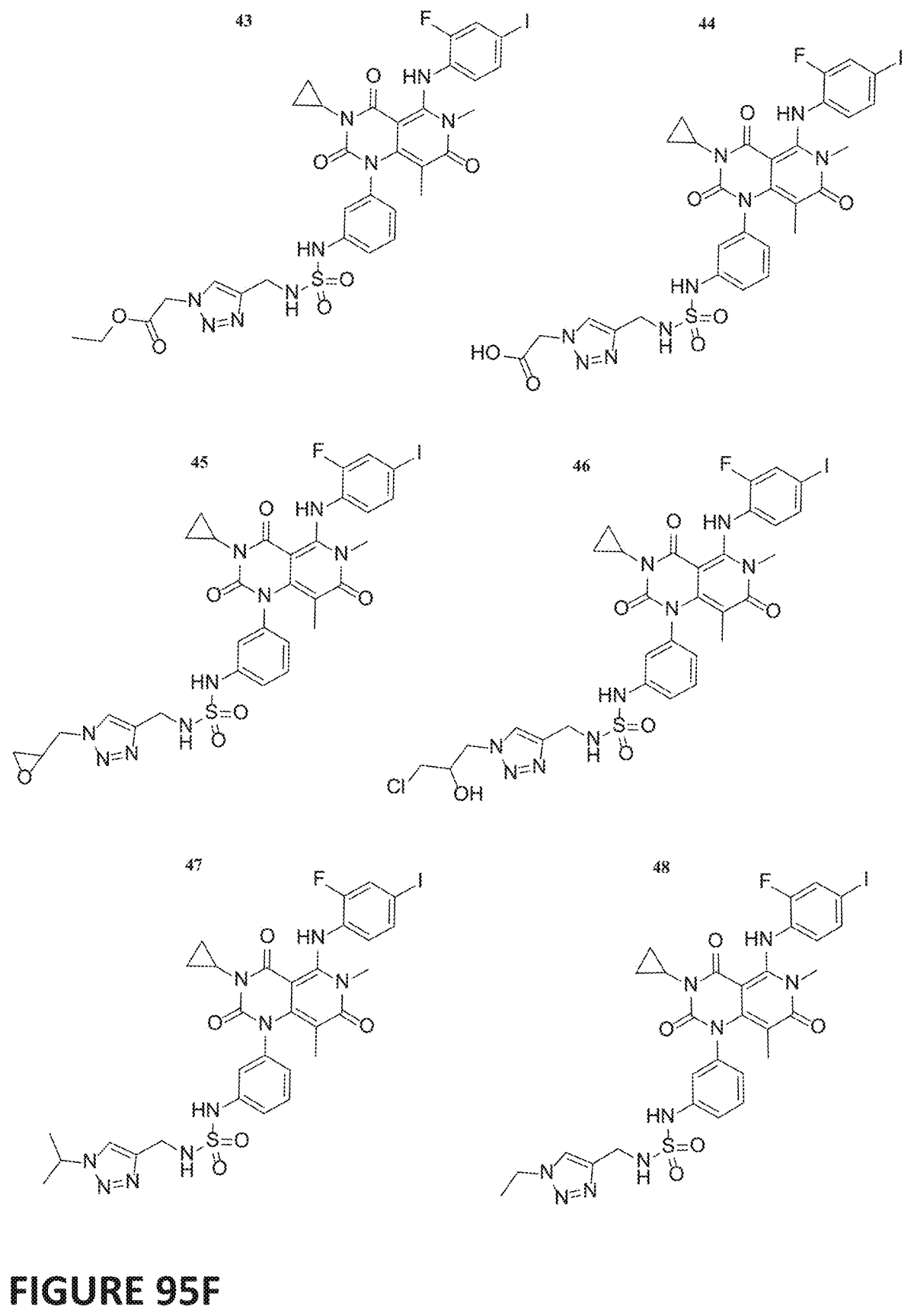

Figure 95G:
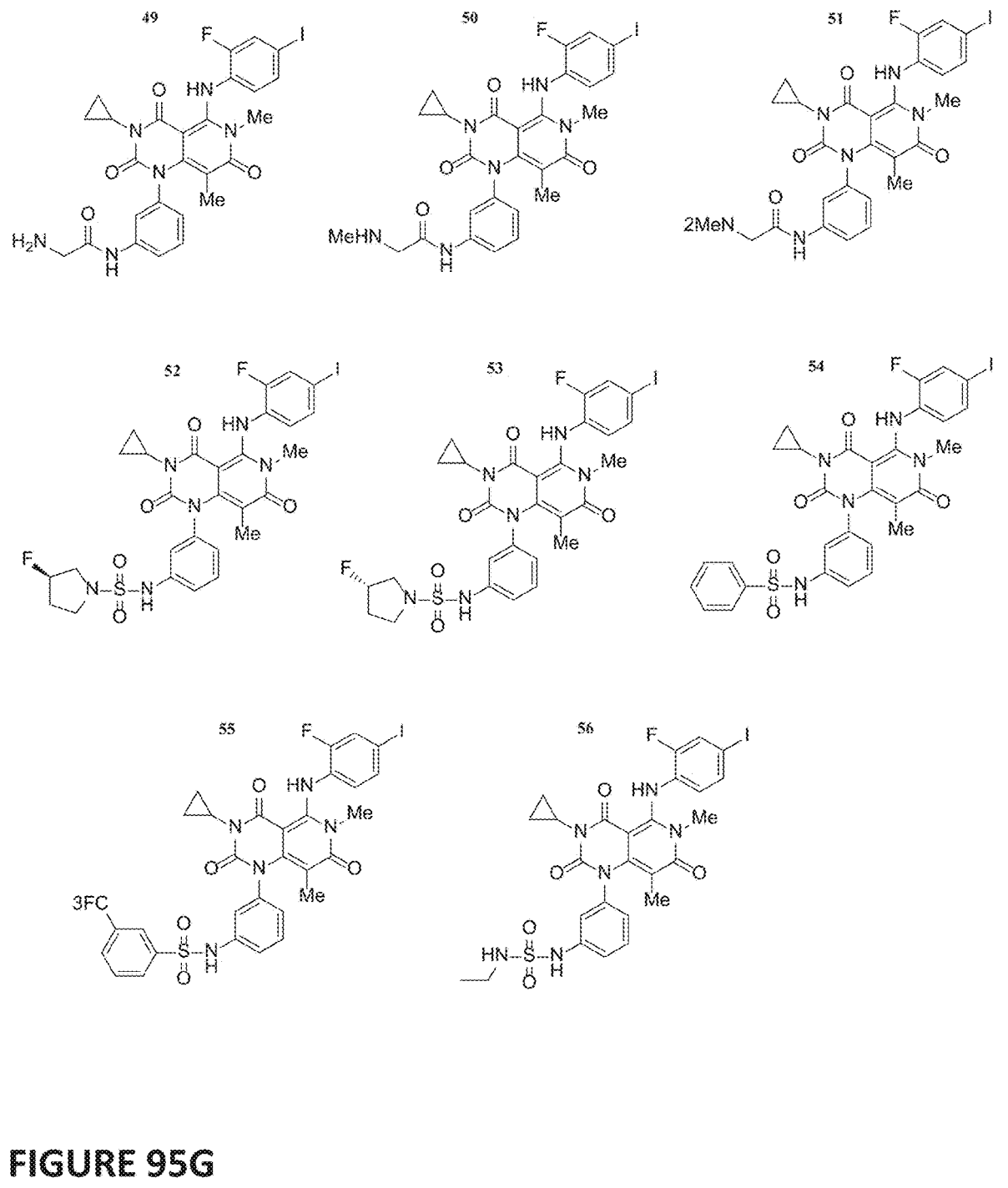

Figure 95H:
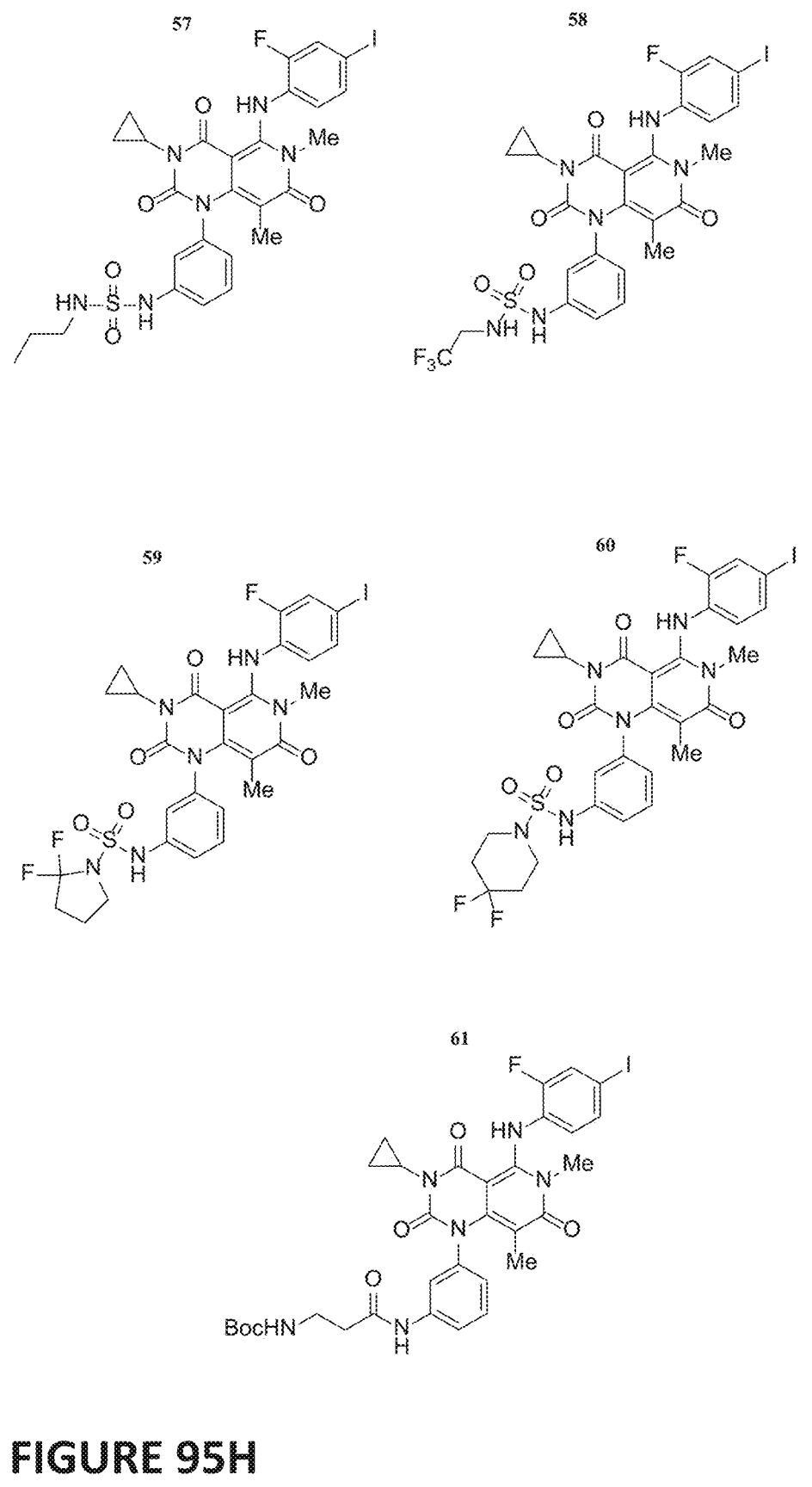

SMALL MOLECULE MODULATORS OF KSR-BOUND MEK

CROSS-REFERENCE TO APPLICATIONS STATEMENT

This application claims priority to commonly-owned U.S. Provisional Patent Application No. 62/958,626, filed on Jan. 8, 220, and U.S. Provisional Patent Application No. 63/044, 338, filed on Jun. 25, 2020, the disclosures of each of which are incorporated herein by reference in their entirety for all purposes.

STATEMENT REGARDING FEDERALLY SPONSORED RESEARCH OR DEVELOPMENT

This invention was made with government support under DP2CA186570 (NIH); RO1CA227636 (NIH); CA232454 (NIH); CA212474 (NIH); P30 CA196521 (NIH); and 5U54OD020353 NIH). The Government has certain rights in the invention.

SEQUENCE LISTING

The Sequence Listing text copy submitted herewith via EFS-Web was created on Aug. 5, 2023, is entitled 1045935022US_SeqList_ST25.txt, is 55 kilobytes in size and is herein incorporated by reference in its entirety.

FIELD AND BACKGROUND OF THE INVENTION

The MAPK/ERK kinase MEK is a shared effector of the frequent cancer drivers KRAS and BRAF that has long been pursued as a drug target in oncology[1], and more recently in immunotherapy[2,3] and aging[4]. However, many MEK inhibitors (MEKi) are limited owing to on-target toxicities[5-7] and drug resistance[8-10].

Among MEK inhibitors, the drugs trametinib, cobimetinib, selumetinib, and binemetinib, have been identified as therapeutics for cancer or Mendelian diseases referred to as RASopathies[1,11]. Trametinib was first approved by the US Food and Drug Administration (FDA) for the treatment of BRAF(V600E/K) mutant melanoma, and is now in development for several other cancers, including KRAS-positive cancers[12]. Trametinib forms the basis for several combination therapies, including with RAFi[13], autophagy inhibitors[14], checkpoint blockade[3,15], and KRAS(G12C) inhibitors[16]. However, unlike most targeted therapies, trametinib was serendipitously identified by phenotypic screens[17]. Despite its clinical utility, the mechanism of action for trametinib is not fully understood. Indeed, the structural and functional basis for the distinct pharmacological properties of trametinib relative to other MEK inhibitors remains elusive.

Molecular glue compounds provide a framework to overcome limitations in currently available MEKi through the rational design of next-generation drugs targeting the interfacial binding region of important regulatory complexes in the MAPK cascade. The concepts of molecular glue compounds are discussed and elucidated, e.g., by Stanton et al., Science 2018 Mar. 9; 359(6380); Gerry inter alia, Nat Chem Biol 2020 April; 16(4):369-378.

BRIEF SUMMARY OF THE INVENTION

The present invention answers multiple needs by providing a class of novel ATP non-competitive MEK inhibitors that stabilize or "glue" the complex formed between MEK and KSR. A compound according to the present invention: (i) allosterically binds an inhibitor pocket formed at an interaction interface between human MEK (MEK1 or MEK2) and human Kinase Suppressor of Ras (KSR1 or KSR2 or BRAF) adjacent to ATP in a physiological complex between MEK and KSR (or BRAF), forming an inhibitor-inhibitor pocket complex; (ii) is an ATP non-competitive kinase inhibitor; (iii) has a structure such that when bound to the inhibitor-inhibitor pocket complex, the complex comprises the structural elements: (a) at least one moiety of the inhibitor engaging A825 of KSR1, or P878 of KSR2; or R662 of BRAF (b) at least one moiety engaging R234 of MEK, wherein where R234 is within 5 Å from any atoms of KSR1 or KSR2 or BRAF is disclosed.

The inventors have elucidated the X-ray crystal structures of MEK bound to the scaffold KSR (Kinase Suppressor of Ras) with various MEKi, including the clinical drug trametinib. FIG. 1 shows the 3.3 Å and 2.8 Å structures of trametinib bound to the KSR1:MEK1 and KSR2:MEK1 complexes. Trametinib occupies the typical MEKi allosteric site adjacent to ATP[19,20], consistent with the characterization of trametinib as an ATP non-competitive kinase inhibitor[21] (FIG. 2). However, the inventors have discovered an unexpected mode of binding in which trametinib directly engages KSR at the MEK interface. Trametinib engages KSR through an extended sub-pocket that reaches the KSR interaction interface (FIG. 3). Through complexation, KSR remodels the prototypical MEKi allosteric pocket thereby impacting binding and kinetics, including drug-residence time. Moreover, trametinib binds KSR-MEK but disrupts the related RAF-MEK complex through a mechanism that exploits evolutionarily conserved interface residues that distinguish these subcomplexes. On the basis of these insights, the inventors have created a new class of MEKi, inter alia, trametiglue, which limit adaptive resistance to MEK inhibition through enhanced interfacial binding.

Trametinib is a 'bumped' MEKi with binding enabled through a conserved 'hole' found in KSR-family pseudokinases relative to the related RAF sub-family kinases. The targeting of trametinib to the KSR-MEK complex is the first example of a natural bump and hole system whereby a drug-binding site is remodelled by overlapping binding partners.

Overall, trametinib can be subdivided into 3 pharmacophores (FIG. 4). The A section, including the 2-fluoro, 4-iodo substituted phenyl group, is sandwiched between the gatekeeper Met143, conserved lysine (Lys97) of subdomain II, and several hydrophobic residues at the C-terminus of helix αC (Leu118) and beginning of β-strand 4 (Val127, F129) in MEK1. The second B section packs on one-side against the N-terminal end of the activation segment, including the DFG motif starting at Asp208. This portion of the inhibitor also generates a hydrogen bond to the backbone amide of Ser212, which is also key to several other MEKi2. The opposite side of the B section, including the cyclo-propyl ring, lies immediately adjacent to the phosphates of ATP. The unique portion of trametinib, not found in any other clinical MEK inhibitor, includes the 3-substituted phenyl acetamide group, which we refer to as section C. This section of trametinib is located in a pocket formed at the interface of MEK and KSR with contacts including the activation segment of MEK through direct interactions with a $3_{10}$-helix, Leu215, Ile216, and Met219, Arg189 and Asp190 of the HRD motif, an acetamide-Arg234 salt bridge located at the end of the activation segment, and on KSR at Ala825 and Pro878 in KSR1 and KSR2, respectively that emanate from the pre-αG loop (FIGS. 3, 4, 5, 6, 7). Highlighting the functional importance of this region, the pre-helix αG loop in KSR has previously been implicated in oncogenic signaling with the RAS$^{G12V}$ suppressor allele P696L in *Caenorhabditis elegans* ksr-12. Overall, the crystal structures suggest that the trametinib binding pocket is formed in part through the KSR-MEK interaction interface.

In various embodiments, the present invention provides an ATP non-competitive inhibitor of mitogen-activated protein kinase (MEK), inter alia, human MEK (MEK1 or MEK2) having the properties:

(i) allosterically binds an inhibitor pocket formed at an interaction interface between human MEK (MEK1 or MEK2) and human Kinase Suppressor of Ras (KSR1 or KSR2 or the KSR homolog BRAF) adjacent to ATP in a physiological complex between MEK and KSR or BRAF, forming an inhibitor-inhibitor pocket complex;

(ii) is an ATP non-competitive kinase inhibitor (iii) a structure such that when bound to the inhibitor-inhibitor pocket complex, the complex comprises the structural elements:

(a) at least one moiety of the inhibitor engaging A825 of hKSR1, or P878 of hKSR2 or R662 of BRAF;

(b) at least one moiety engaging R234 of hMEK, wherein R234 is within 5 Å from any atoms of hKSR1 or hKSR2 or hBRAF.

Also provided are salts, pharmaceutically acceptable salts, hydrates, prodrugs and bioisosteres of the compounds set forth herein.

Also provided are methods of using the compounds of the invention in therapeutic and analytical and/or diagnostic applications.

Other embodiments, objects and advantages of the current invention will be apparent from the detailed description that follows.

BRIEF DESCRIPTION OF THE DRAWINGS

FIG. 1. Summary of ligand bound complexes of KSR1-MEK1 and KSR2-MEK1. Resolution, number of reflections, and ligand omit maps for all described structures. Fo-Fc omit electron density maps are all contoured at 3.0 σ, with a 2.0 Å cutoff, around the ligands and shown as a blue mesh.

FIG. 2. Trametinib bound to KSR1-MEK-AMP-PNP.

FIG. 3 Trametinib contacts include A825 in the pre-helix αG loop of KSR1. Direct contacts of trametinib with MEK1 Lys97, Leu118, Val127, Ile141, Met143, Cys207, Arg189, Asp190, Phe209, Val211, Ser212, Ile216, Arg234 also highlighted.

FIG. 4 provides a 2D schematic of the trametinib-binding pocket in KSR1:MEK1.

FIG. 5 Trametinib bound to KSR2:MEK1:AMP-PNP.

FIG. 6 Trametinib contacts include P878 in the pre-helix αG loop of KSR2. Direct contacts of trametinib with MEK1 Lys97, Leu118, Val127, Ile141, Met143, Cys207, Arg189, Asp190, Phe209, Val211, Ser212, Ile216, Arg234 also highlighted.

FIG. 7 2D schematic of the trametinib binding pocket in KSR2:MEK1.

FIG. 8 Binding comparison of MEKi in KSR1-MEK1. Of the analysed MEKi, only trametinib directly engages KSR1.

FIG. 9 Close-up view of the trametinib interactions with KSR1 (left) and KSR2 (right). The terminal acetamide group of trametinib stacks between I216 in MEK1 and A825 in KSR1 or P878 in KSR2. Distances with hydrogens included in the models of trametinib and KSR measure 2.4 Å and 3.5 Å between alpha and beta hydrogens of A825 in KSR1 and the terminal —CH3 of trametinib. In comparison, the terminal —CH3 of trametinib measures 2.2 Å and 3.1 Å from beta and gamma hydrogens of P878. Measurements are marked by black arrows. Ser222 at one end of the anti-parallel activation segments between MEK and KSR is highlighted.

FIG. 10 Binding of KSR to MEK creates an enlarged allosteric binding pocket for inhibitors. Structures of isolated MEK1 bound to cobimetinib (PDB ID 4LMN), selumetinib (4U7Z) and PD0325901 (3VVH) compared to the KSR1-MEK1 complex for the indicated MEKi. In both the isolated and KSR-bound MEK structures, the inward and extended activation segment conformations, respectively, are highlighted as ribbons. Binding of KSR1 to MEK1 stabilizes an outward orientation of the MEK1 activation segment. See FIG. 13 for additional analysis and electron density maps.

FIG. 11 Conformational changes in MEK and KSR upon binding to trametinib. The MEKi allosteric pocket, and activation segment displacement, between the isolated state of MEK1 bound to PD0325901 relative to the KSR1:MEK1 complex bound to trametinib. The displacement in the activation segment was measured based on movement of residue Asn221 in the isolated and KSR1-bound state of MEK1.

FIG. 12 Conformational changes in MEK and KSR upon binding to trametinib. Left: distinct activation loop conformers of isolated MEK1 have been observed in complex with PD0325901 (PDB ID 3VVH), TAK733 (3PP1), selumetinib (4U7Z), and cobimetinib (4LMN). Middle and Right: overlay of the KSR1-MEK1 and KSR2-MEK1 structures bound to the indicated MEKi reveal near identical activation segment conformers, with the exception of the trametinib-bound complex of KSR1:MEK1

FIG. 13 Conformational changes in MEK and KSR upon binding to trametinib. Comparison of activation loop conformations in cobimetinib-bound (left) and trametinib-bound (right) states of the KSR1-MEK1 (top) and KSR-MEK1 (bottom) complexes. Fo-Fc omit electron density map, contoured at 2.0 σ, with a 3.0 Å cutoff, around the activation loop is shown as a blue mesh. Movement of the MEK activation loop between the two inhibitor-bound states of KSR1-MEK1 is highlighted by a arrow. Main chain H-bonds between the anti-parallel beta strands in KSR and MEK are shown as dotted lines.

FIG. 14 Conformational changes in MEK and KSR upon binding to trametinib. In the trametinib bound KSR1-MEK1 complex, a four-residue anti-parallel beta strand structure is formed between KSR1 and MEK1. In comparison, the same region forms a three-residue stretch in all other KSR1-MEK1 structures that we determined; the cobimetinib-bound complex is shown as an example for comparison. In contrast, a six-residue long anti-parallel beta strand is formed in the KSR2-MEK1 structures, irrespective of bound MEKi. The three- and four-residue long strands in KSR1-MEK1 include residues 769-771/772 for KSR1 and 222/223-225 for MEK1. The six residue long strands in KSR2-MEK1 include residues 820-825 for KSR2 and 221-226 for MEK1.

FIG. 15 Structural differences between human KSR1 and KSR2. Comparison of helices αG-αG' in the KSR1:MEK1 complex (left) and helix αG in KSR2:MEK1 complex.

FIG. 16 Structural differences between human KSR1 and KSR2. 2Fo-Fc omit electron density maps contoured at 1.0 σ, with a 2.0 Å cutoff, around helices αG-αG' in KSR1 (left) and αG in KSR2 (right).

FIG. 17 Structural differences between human KSR1 and KSR2. 2Fo-Fc omit electron density maps contoured at 1.0 σ, with a 2.0 Å cutoff, around strand $2 in KSR1 (left) and KSR2 (right).

FIG. 18 Structural differences between human KSR1 and KSR2. 2Fo-Fc omit electron density maps contoured at 1.0 σ, with a 2.0 Å cutoff, around the hinge region in KSR1 (left) and KSR2 (right).

FIG. 19 Structural differences between human KSR1 and KSR2. 2Fo-Fc omit electron density maps contoured at 1.0 σ, with a 2.0 Å cutoff, around helix αD in KSR1 (left) and KSR2 (right).

FIG. 20 Structural differences between human KSR1 and KSR2. Positionally equivalent residues H773 in KSR1 and N826 in KSR2 form distinct intra- and inter-molecular contacts, respectively. Specifically, H773 in KSR1 forms a hydrogen bond with the backbone carbonyl of L821 in the αF-αG loop of KSR1 (left). Whereas N826 in KSR2 forms a H-bond across the interfacial region of the KSR2-MEK1 complex via the backbone carbonyl of M219 in MEK1.

FIG. 21 Structural differences between human KSR1 and KSR2. Structure-based sequence alignment of the pseudokinase domains of KSR1 and KSR2 based on structures solved in this study. Boxed regions highlight the structural differences between KSR1 and KSR2, as shown in FIGS. 15-20.

FIG. 22 Intracellular target engagement on MEK and KSR-bound MEK via bioluminescence resonance energy transfer. Chemical structure of trametinib-bodipy. We refer to this fluorescent probe compound as 'tram-bo'.

FIG. 23 Intracellular target engagement on MEK and KSR-bound MEK via bioluminescence resonance energy transfer. Legend for schematics used in FIGS. 24-28.

FIG. 24 Intracellular target engagement on MEK and KSR-bound MEK via bioluminescence resonance energy transfer. Nano-luciferase tagged fusions of MEK1 (MEK-luc) and mouse KSR1 (KSR-luc).

FIG. 25 Intracellular target engagement on MEK and KSR-bound MEK via bioluminescence resonance energy transfer. BRET emission signal (squiggle arrow) between MEK-luc and tram-bo is expected to occur within multiple distinct states of MEK, including in the KSR-bound and free states of MEK as depicted.

FIG. 26 Intracellular target engagement on MEK and KSR-bound MEK via bioluminescence resonance energy transfer. BRET emission (squiggle arrow) between KSR-luc and tram-bo is expected to occur exclusively in the KSR-bound state of MEK as depicted.

FIG. 27 Intracellular target engagement on MEK and KSR-bound MEK via bioluminescence resonance energy transfer. Assay design for steady-state competition experiments.

FIG. 28 Intracellular target engagement on MEK and KSR-bound MEK via bioluminescence resonance energy transfer. Assay design for intracellular residence time experiments.

FIG. 29 Intracellular target engagement on MEK and KSR-bound MEK via bioluminescence resonance energy transfer. BRET signals between 1 μM tram-bo and the indicated luciferase tagged fusion proteins expressed in 293T cells. Increasing concentrations of free trametinib were added to these cells to determine $IC_{50}$ values. Dose-dependent competition for free trametinib was observed on MEK1-luc and mouse KSR1-luc. However, no discernible dose response for trametinib was observed on controls including RET-luc and SRC-luc using either tram-bo or previously established active site tracers K5 and K4, respectively.

FIG. 30 Intracellular target engagement on MEK and KSR-bound MEK via bioluminescence resonance energy transfer. A helix αG mutant, W781D in mouse KSR1, supports that the BRET signal between wild-type KSR1 and tram-bo depends on intact complex formation between KSR and MEK within cells. In particular, the KSR1-W781D mutant does not produce any dose dependent BRET signal (using 1 μM tram-bo) due to a predicted loss of complexation with MEK1; we previously demonstrated that the W781D mutant (W884D in KSR2 numbering) is a strong loss of function in KSR with respect to ERK pathway activation, and the analogous mutation in BRAF (F667E) prevents direct binding with purified MEK. W781 in mouse KSR1 is equivalent to W831 in human KSR1, W884 in human KSR2, and F667 in human BRAF. Structural depiction of the mouse W781 residue at the interface of KSR1-MEK1 complex is shown below.

FIG. 31 Table of IC50 values. Individual replicate data as well as averages and standard error measurements (S.E.M.) are listed for the indicated MEKi against KSR1-luc (also labeled KSR1), MEK1-luc (also labeled MEK1), and for co-expressions of MEK1-luc plus unlabelled KSR1-WT or KSR1-W781D, as indicated.

FIG. 32 Binding of KSR to MEK creates an enlarged allosteric binding pocket for inhibitors. Comparison of trametinib $IC_{50}$ values versus other MEKi on MEK1-luc and KSR1-luc. Data are mean±s.e.m. determined from three independent experiments. *P<0.05, each drug compared to trametinib using an unpaired two-tailed t-test. MEK-luc: T (trametinib) vs. C (cobimetinib) p<0.0001, t=16.85, df=4; T vs P (PD0325901) P=0.0004, t=11.26, df=4; T vs S (selumetinib) P=0.0081, t=4.985, df=4; KSR-luc: T vs C P=0.223, t=1.425, df=4; T vs P P=0.0046, t=5.735, df=4, T vs S P=0.0036, df=4.

FIG. 33 MEKi IC50 measurements and residence time are influenced by protein complex stoichiometry. $IC_{50}$ values plotted as a function of MEKi for MEK1-luc and KSR1-luc (left); mean and standard error (SEM) plotted from 3 independent experiments, each conducted in technical triplicate. CH5126766 was not plotted due to poor fit. MEK1-luc (middle) and KSR1-luc (right) dose-response curves for plotted $IC_{50}$ values using 1 μM Tram-bo; mean and SEM plotted for 3 independent experiments, each conducted in technical triplicates.

FIG. 34 MEKi IC50 measurements and residence time are influenced by protein complex stoichiometry. Comparison of MEKi $IC_{50}$ measurements and representative dose response curves of MEK1-luc, KSR1-luc, MEK1-luc co-expressed with KSR1-WT, and MEK1-luc co-expressed with KSR1-W781D. Co-expression of KSR1-WT with MEK1-luc gives rise to dose response curves and $IC_{50}$ values similar to that of KSR1-luc alone. This effect does not occur for the co-expression of MEK1-luc with KSR1-W781D, implying that $IC_{50}$ differences between MEK1-luc and KSR1-luc depend on the formation of the KSR-MEK complex mediated by helix αG. Mean and standard errors determined from 3 independent experiments, each conducted in technical duplicate. $IC_{50}$s derived from KSR1-luc, MEK1-luc co-expressed with KSR1-WT or W781D were compared to those of MEK1-luc for each MEKi using an ANOVA where an asterisk represents a P-value less than 0.05. For trametinib, data were subjected to a Kruskal-Wallis test and Dunn's multiple comparison post-hoc test (MEK1-luc vs KSR1-luc adjusted P>0.9999, MEK1-luc vs MEK1-luc+KSR1-WT adjusted P>0.9999, MEK1-luc vs MEK1-luc+KSR1-W781D adjusted P=0.4298). All other data were subjected to an ordinary one-way ANOVA and Dunnett's multiple comparison post-hoc test with a single pooled variance (Cobimetinib: MEK1-luc vs KSR1-luc adjusted P=0.0015, MEK1-luc vs MEK1-luc+KSR1-WT P=0.0021, MEK1-luc vs MEK1-luc+KSR1-W781D P=0.9940; PD0325901: MEK1-luc vs KSR1-luc adjusted P=0.0350, MEK1-luc vs MEK1-luc+KSR1-WT P=0.1524, MEK1-luc vs MEK1-luc+KSR1-W781D P=0.9920; Selumetinib: MEK1-luc vs KSR1-luc adjusted P=0.0578, MEK1-luc vs MEK1-luc+KSR1-WT P=0.0693, MEK1-luc vs MEK1-luc+KSR1-W781D P=0.9994. Cobimetinib displayed the largest difference in $IC_{50}$ value between MEK1-luc and KSR1-luc or MEK1-luc+KSR1-WT.

FIG. 35 Binding of KSR to MEK creates an enlarged allosteric binding pocket for inhibitors. Representative intracellular residence time plots for cells pre-treated with a range of sub-saturating levels of trametinib and cobimetinib that were transfected with MEK1-luc (left) and mouse KSR1-luc (right). The build-up signal (height and rate) is proportional to the dissociation of the indicated compounds on MEK1 or KSR1-bound MEK complex following the addition of Tram-bo (1 μM) on cells that were pre-treated and then washed of the MEKi. Note the DMSO curves are the same in both the trametinib and cobimetinib plots due to the experimental design in which all data was collected at once on one plate.

FIG. 36 MEKi IC50 measurements and residence time are influenced by protein complex stoichiometry. (Left) Schematic for the origin of the BRET signal under co-expression conditions. (Right) Tram-bo build-up curves for MEK1-luc, KSR1-luc, MEK1-luc co-expressed with KSR1-WT, and MEK1-luc co-expressed with KSR1-W781D. Co-expression of MEK1-luc+KSR1-WT resulted in a lower BRET signal and slower tram-bo build-up compared to MEK1-luc alone. Co-expression of MEK1-luc+KSR-W781D gave similar curves to MEK1-luc alone, suggesting that complex formation is disfavored under these conditions.

FIG. 37 KSR and RAF share complementary regulatory roles as MEK scaffolds and activators. KSR and RAF family members appear to have co-evolved. Phylogenetic tree diagrams for the indicated species were generated from reported kinome sequence data that can be found at www.kinase.com/web/current/kinbase/. All species that we analysed include at least one RAF and one KSR homolog.

FIG. 38 KSR and RAF share complementary regulatory roles as MEK scaffolds and activators. Structures of MEK1 in complex with KSR1 and KSR2 determined here, and previously determined structures of MEK1:BRAF-active conformation (PDB ID: 4MNE), and MEK1:BRAF-inactive conformation (PDB ID: 6U2G).

FIG. 39 KSR and RAF share complementary regulatory roles as MEK scaffolds and activators. Structural overlay of MEK1-associated complexes highlights variations in the quaternary arrangements of KSR-bound MEK and RAF-bound MEK. Shown are overlays of MEK1:KSR1 with MEK1:KSR2 (left); MEK1:BRAF (PDB ID: 4MNE) with MEK1:BRAF (PDB ID: 6U2G) (center); and MEK1:KSR1 with MEK1:BRAF (PDB ID: 4MNE). In particular, the N-lobe, including helix αC, in KSR and RAF proteins are significantly displaced between distinct complexes. However, in contrast, the lower C lobe, including helix αG, appears relatively fixed in all sets of complexes.

FIG. 40 KSR and RAF share complementary regulatory roles as MEK scaffolds and activators. Overlay of all structures from FIG. 39, using MEK1 C-lobe as an anchor (center), demonstrates helix αG as a common docking site for reciprocal kinase domain interactions between MEK and BRAF or KSR (left inset). Further, the pre-helix αG loop regions within BRAF and KSR proteins occupy a relatively fixed location relative to MEK (right inset).

FIG. 41 The trametinib binding site distinguishes KSR from RAF. Structural overlay of the BRAF-MEK1, KSR1-MEK1, and KSR2-MEK1 complexes predicts a clash between trametinib and the pre-helix αG loop of BRAF.

FIG. 42 Variance in the pre-helix αG loops of KSR and RAF proteins determines selectivity for trametinib. The pre-helix αG loop in BRAF (left; N660-N661-R662) includes an insertion and larger amino acid side chains compared to KSR1 (middle; GAP-A825-A826) and KSR2 (right; GAP-P878-A879), creating a clash with trametinib.

FIG. 43 The trametinib binding site distinguishes KSR from RAF. Sequence alignment of RAF kinases and KSR pseudokinases at the trametinib-binding site. Numbering for human KSR1, KSR2, and BRAF highlighted.

FIG. 44 Variance in the pre-helix αG loops of KSR and RAF proteins determines selectivity for trametinib. Sequence alignment highlighting conserved variations between RAF kinases and KSR pseudokinases at the trametinib-binding site. Native sequences and mutants in mouse KSR1 and human BRAF used for functional studies. Mouse KSR1 mutants include K1 (KSR1_P775N), K2 (KSR1_A776R), K3 (KSR1_P775N/A776R), and K4 (KSR1_insertionN/P775N/A776R). Human BRAF mutants include B1 (BRAF_N661A), B2 (BRAF_R662A), B3 (BRAF_N661A/R662A), and B4 (BRAF_N660deletion/N661A/R662A).

FIG. 45 The trametinib binding site distinguishes KSR from RAF. Immunoprecipitation and western blot (IP/WB) of endogenous MEK1 from lysates of HCT116 cells transfected with FLAG-tagged wild-type and mutant versions of full-length mouse KSR1. Cells were treated with DMSO or 200 nM trametinib for 1 hour prior to harvesting cells. IgG was used as a control for non-specific binding of proteins during IPs (lanes 1 versus 2). Transfected KSR1 was detected using anti-FLAG antibodies. All other western blot signals were detected using specific antibodies against endogenous proteins; note, the antibody against BRAF detects both endogenous and transfected FLAG-tagged BRAF. Blots are representative of three independent experiments with similar results.

FIG. 46 The trametinib binding site distinguishes KSR from RAF. Immunoprecipitation and western blot (IP/WB) of endogenous MEK1 from lysates of HCT116 cells transfected with FLAG-tagged wild-type and mutant versions of full-length or human BRAF. Cells were treated with DMSO or 200 nM trametinib for 1 hour prior to harvesting cells. IgG was used as a control for non-specific binding of proteins during IPs (lanes 1 versus 2). Transfected BRAF were detected using anti-FLAG antibodies. All other western blot signals were detected using specific antibodies against endogenous proteins; note, the antibody against BRAF detects both endogenous and transfected FLAG-tagged BRAF. Blots are representative of three independent experiments with similar results.

FIG. 47 Variance in the pre-helix αG loops of KSR and RAF proteins determines selectivity for trametinib. IP/WB of endogenous MEK1 from lysates of HCT116 cells transfected with (left) wild-type KSR1 and mutant K1 (P775N, mouse KSR1 numbering); (middle) wild-type BRAF and mutant B2 (R662A); (right) untransfected controls. Cells were treated with DMSO (D), 200 nM trametinib (T), or 200 nM cobimetinib (C) for 1 hour prior to harvesting cells. IgG was used as a control for non-specific binding of proteins during IPs. Transfected KSR1 or BRAF were detected using an anti-FLAG antibody. All other western blot signals were detected using specific antibodies against endogenous proteins. Blots are representative of three independent experiments. We conducted side-by-side analysis of cobimetinib as a control compound that does not generate direct interfacial contacts like trametinib but displays a similar $IC_{50}$ on the KSR:MEK complex. Note; compare the effects of cobimetinib addition on complex stability to the effects of trametinib in FIG. 45, 46. Unlike trametinib, cobimetinib does not impact the KSR1 or BRAF mutants in terms of pulldown through endogenous MEK similar to trametinib. This data supports that the 'bump-and-hole' model for trametinib selectivity between KSR-bound MEK and RAF-bound MEK. Further note from FIG. 45, 46 that all of the tested KSR1 alleles, and also the full swaps of the pre-helix $\alpha$G loops between RAF and KSR proteins, resulted in partial or complete loss of pulldown via MEK (FIG. 45, 46; lanes 2 vs 10 for mutants K4 and B4), which suggests that the length and composition of interfacial residues within both KSR and RAF proteins are critical and unique determinants of binding towards MEK.

FIG. 48 Variance in the pre-helix $\alpha$G loops of KSR and RAF proteins determines selectivity for trametinib. Overlay of four clinical MEKi highlights the phenyl acetamide group of trametinib as a unique 'bump' not found in the other compounds including cobimetinib.

FIG. 49 Variance in the pre-helix $\alpha$G loops of KSR and RAF proteins determines selectivity for trametinib. BRET buildup curves with increasing concentrations of tram-bo on the indicated luciferase-tagged versions of human KSR1, KSR2, ARAF, BRAF, and CRAF/RAF1. KSR1-luc and KSR2-luc both show higher BRET ratios, and also ~10-fold tighter binding, with tram-bo relative to ARAF-luc, BRAF-luc, and CRAF-luc. Lower inset is a y-axis magnification of the top inset. Data points represent the average of two technical replicates; experiments were conducted at least three independent times with similar results.

FIG. 50 In vitro binding of purified MEK, KSR:MEK, and RAF:MEK to trametinib. Representative binding sensograms for 500 nM each of isolated MEK1 or the indicated KSR-MEK and BRAF-MEK complexes on a biosensor immobilized with biotin-conjugated trametinib.

FIG. 51 In vitro binding of purified MEK, KSR:MEK, and RAF:MEK to trametinib. $K_D$ (M), $k_{on}$(1/Ms), and $k_{dis}$ (1/s) values for MEK1 (M), KSR11MEK1 (K1M1), KSR2-MEK1 (K2M2), BRAF-MEK1 (BRM1) on biotin-linked trametinib. Individual data points from independent binding experiments (n=29, 14, 22, and 9 for MEK1, KSR1-MEK1, KSR2-MEK1, and BRAF-MEK1, respectively) were used for statistical comparisons (** for p≤0.0001, respectively; FIG. 71**). Note, trametinib likely favours dissociation of BRAF from MEK1 for binding. For example, whereas the association and $K_D$ data between BRAF-MEK1 and isolated MEK1 markedly differ, the off rate and residence time calculations are similar. This data would be consistent with a model in which the equilibrium of BRAF-MEK1 shifts so as to populate the dissociated state under the conditions of the BLI assays.

FIG. 52 In vitro binding of purified MEK, KSR:MEK, and RAF:MEK to trametinib. Residence time values plotted as a function of protein concentration. MEK1 and BRAF-MEK1 display small variations in residence time over the concentrations tested. Whereas KSR2-MEK1 and KSR1-MEK1 demonstrate concentration-dependent changes in residence time. In particular, at low concentrations of KSR-MEK, where the complexes would be expected to more readily dissociate, the kinetic values of purified KSR1-MEK1 and KSR2-MEK1 approached isolated MEK1 and BRAF-MEK1.

FIG. 53 In vitro binding of purified MEK, KSR:MEK, and RAF:MEK to trametinib. Full binding curve experiment including loading of biotin-conjugated trametinib for 10 mins, followed by a wash step, and subsequently treating a low-density streptavidin (SA) sensor with a blocking agent, biocytin for 3 min. The sensors were washed extensively to acquire a zero baseline prior to binding analysis. Following, sensors were dipped in wells containing 500 nM of each protein for 15 min, followed by a dissociation in running buffer for 15 min.

FIG. 54 In vitro binding of purified MEK, KSR:MEK, and RAF:MEK to trametinib. A biotin conjugated version of trametinib was immobilized on sensor-heads and binding to MEK1, KSR1-MEK1, KSR2-MEK1 or BRAF-MEK1 was monitored using bio-layer interferometry. Increasing concentrations in 2-fold increments of proteins from 31.25 nM to 500 nM for MEK1, KSR1-MEK1, and KSR2-MEK1 and 500 nM to 2000 nM for BRAF-MEK1 were tested. A blank sensor head without immobilized trametinib was used as a control for non-specific binding. KD (M), kon (1/Ms), and kdis (1/s) values were derived from fitting each binding curve.

FIG. 55 KSR as a co-receptor for binding to trametinib. Literature data on CRISPR depletion screens highlight strong functional interactions between trametinib and KSR. For example, in a *Drosophila* cellular fitness model (left, reference 43) and a human BRAF V600E mutant cell line (right, reference 44), single-guide (sgRNAs) towards KSR generated relative outlier sensitivity or resistance to trametinib or a trametinib+dabrafenib combination, respectively. Raw data from Viswanatha inter alia was plotted based on the authors determination of a Z-score for log 2-fold change in sgRNA reads for S2 cells treated with trametinib versus a no treatment control (left). Raw data from Strub inter alia was plotted based on the authors determination of log 2-fold change in sgRNA reads for SKMEL-239 cells treated with a trametinib plus dabrafenib combination relative to a no treatment control (right). sgRNAs towards KSR are highlighted as a red dot; all other sgRNAs analysed in the respective studies are shown as grey dots. KSR emerged as a strong outlier beyond the mean plus standard deviation (black cross hairs) of all genes analysed in each respective study. These screens could be re-investigated based on the model that KSR functions as a direct co-receptor for binding to trametinib and MEK.

FIG. 56 KSR as a co-receptor for binding to trametinib. Model for the action of trametinib on KSR-MEK and RAF-MEK complexes. In the absence of drug, MEK activation depends on heterodimerization of both RAF and KSR, with phosphorylation on the sites S218/S222 occurring through active RAF kinases. This model is adapted from structural and biochemical studies in references 28,29, 45,46. Trametinib could down-regulate ERK signaling by impeding direct binding of MEK towards RAF in favor of KSR. In the KSR-bound state of MEK, trametinib would be expected to reside on target for extended periods of time.

FIG. 57 Trametiglue provides durable inhibition of RAS/ERK signaling in models of mutant KRAS and BRAF. (Left) Immunoblot of stable HCT116 (KRAS G13D) cancer cells including parental, scramble control (shSCR), and KSR1 knockdown (shKSR1). Cells were treated with 10 nM trametinib for the indicated time points and harvested for analysis on the indicated markers. (Right) Quantitative PCR was used to confirm specific knockdown of KSR1 in the shKSR1 cells. KSR1 knockdown slows the rebound of activated RAS-MAPK signaling in the presence of trametinib as measured by recovered phosphorylated-ERK1/2 over time (lanes 1-5 and 6-10 versus 11-15). This data supports that KSR1 plays a positive role in the adaptive resistance of HCT-116 cells to trametinib, suggesting that knockdown or trapping of the KSR-bound MEK complex could mitigate this intrinsic drug resistance mechanism. Experiment was conducted twice with similar results.

FIG. 58 Trametiglue provides durable inhibition of RAS/ERK signaling in models of mutant KRAS and BRAF. EC50 values for cell viability assays for the indicated compounds against a series of human cancer cell lines. Mean and standard deviation determined from three independent experiments, each conducted in technical triplicate.

Figure 59:
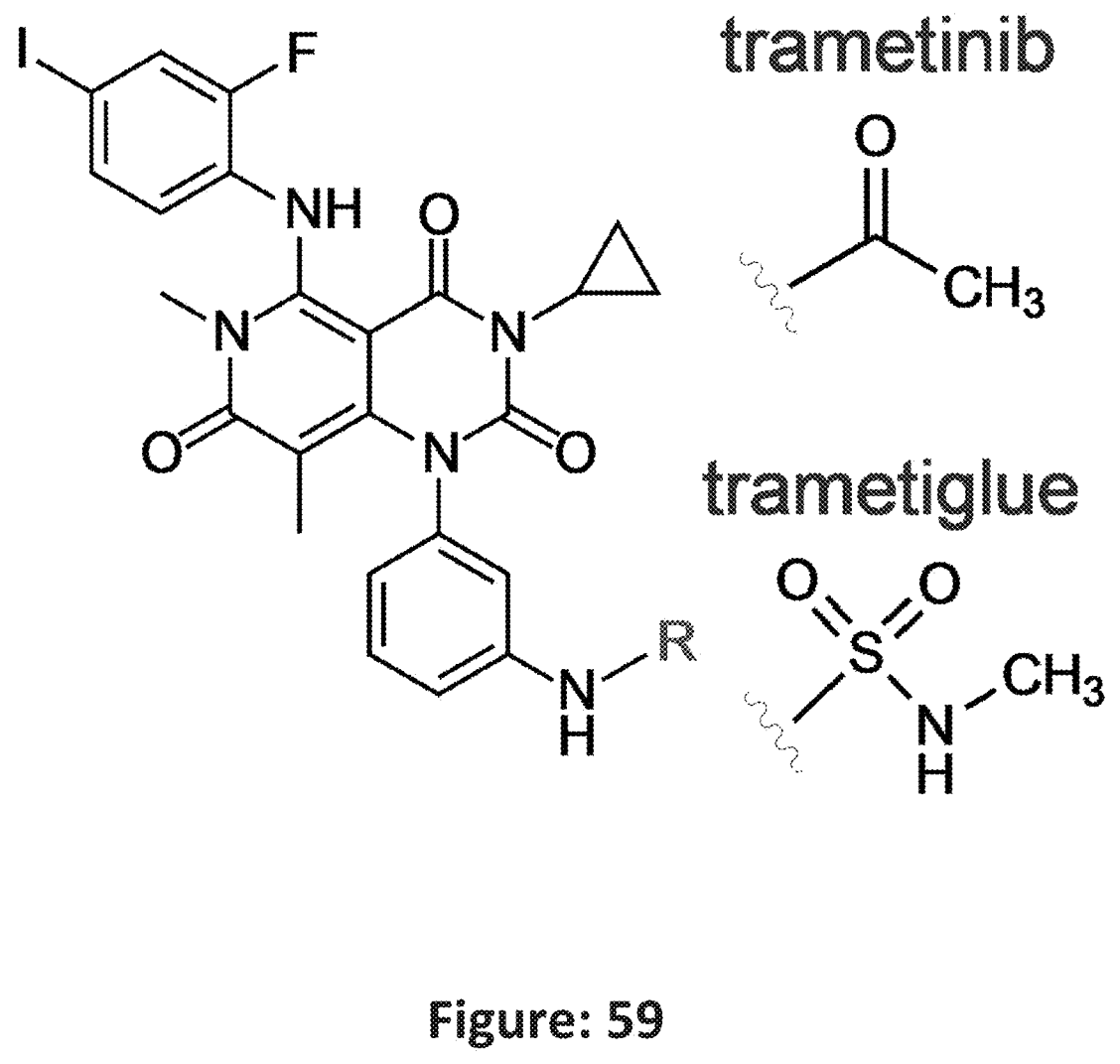

FIG. 59 Trametiglue targets both KSR-MEK and RAF-MEK with unprecedented potency and selectivity via unique interfacial binding interactions. Chemical structures of trametinib and trametiglue.

FIG. 60 Trametiglue targets both KSR-MEK and RAF-MEK with unprecedented potency and selectivity via unique interfacial binding interactions. X-ray crystal structure of trametiglue bound to KSR2-MEK1-AMP-PNP. Fo-Fc omit electron density map, contoured at 3.0σ with a 2.0 Å cut-off around ligand. Left panel shows the entire inhibitor binding pocket; right panel highlights contacts around the sulfamide group of trametiglue.

FIG. 61 Trametiglue provides durable inhibition of RAS/ERK signaling in models of mutant KRAS and BRAF. X-ray crystal structure of trametinib bound to the KSR2-MEK1-AMP-PNP complex. Trametinib is shown in stick representation. A Fo-Fc omit electron density map, contoured at 3.0σ with a 2.0 Å cutoff around ligand, is shown as a mesh. Left panel shows the entire inhibitor binding pocket; right panel highlights contacts around the phenyl acetamide group of trametinib.

FIG. 62 Trametiglue targets both KSR-MEK and RAF-MEK with unprecedented potency and selectivity via unique interfacial binding interactions. Overlay of trametinib and trametiglue. The sulfamide group of trametiglue, relative to the acetamide in trametinib, generates unique contacts at the interfacial binding region of KSR-bound MEK. In particular, the —NHSO$_2$NHCH$_3$ module of trametiglue facilitates unique space-filling via Met230 and the peptide backbone of Arg189 in MEK1 and a water-mediated H-bond towards the backbone of Thr876 in KSR2.

FIG. 63 Trametiglue targets both KSR-MEK and RAF-MEK with unprecedented potency and selectivity via unique interfacial binding interactions. Trametiglue retains the strong binding potency and residence time of trametinib on KSR-bound MEK as determined under steady-state conditions (left) and intracellular residence (right panel; all compounds tested at 6.25 nM) formats. Each point and error bars represent the mean and s.e.m. of three independent experiments. Data points for the intracellular residence time experiments represent the average of two technical replicates, each independently repeated three times.

FIG. 64 Trametiglue targets both KSR-MEK and RAF-MEK with unprecedented potency and selectivity via unique interfacial binding interactions. Trametiglue, unlike trametinib but similar to CH5126766, enhances interactions between endogenous BRAF and MEK1. IP/WB of endogenous MEK1 from HCT116 cells. Lanes 1-4 are cells transfected with FLAG-KSR1, and lanes 5-8 are untransfected samples. Cells were treated with DMSO, 200 nM CH5126766, 200 nM trametinib, or 200 nM trametiglue for 1 hour prior to harvesting cells and IPs. Blots are representative of three independent experiments with similar results.

FIG. 65 Trametiglue targets both KSR-MEK and RAF-MEK with unprecedented potency and selectivity via unique interfacial binding interactions. In vitro profiling of 1 μM trametiglue demonstrates high selectivity towards MEK1 and MEK2 in direct binding assays (top). Trametiglue also displays high selectivity in a panel of active kinases measured for inhibition of MEK1 and MEK2 substrate phosphorylation or direct MEK1 phosphorylation by the upstream kinases as indicated (bottom).

FIG. 66 Trametiglue targets both KSR-MEK and RAF-MEK with unprecedented potency and selectivity via unique interfacial binding interactions. Cell viability dose-responses on K-RAS and BRAF mutant lines. Assays conducted under low-adherence conditions and representative of three independent experiments, each conducted in technical triplicate. Mean and s.d. values in FIG. 58.

FIG. 67 Trametiglue provides durable inhibition of RAS/ERK signaling in models of mutant KRAS and BRAF. Clonogenic assay of KRAS-mutant and BRAF-mutant cancer cell lines treated with 10 nM trametinib or 10 nM trametiglue, and 10 nM or 50 nM CH5126766 for 10 days. Experiment was conducted twice with similar results.

FIG. 68 Trametiglue provides durable inhibition of RAS/ERK signaling in models of mutant KRAS and BRAF. Immunoblot analysis of the indicated cell lines treated for 1 hour with increasing concentrations of trametiglue and trametinib. This data supports that trametiglue, relative to trametinib, is a higher potency inhibitor of RAS-MAPK signaling as measured by phosphorylated ERK1/2 at residues T202 and Y204 (pERK). Experiment was conducted three times with similar results.

FIG. 69 Trametiglue provides durable inhibition of RAS/ERK signaling in models of mutant KRAS and BRAF. Immunoblot of KRAS-mutant and BRAF-mutant cancer cell lines treated with 10 nM trametinib or trametiglue for various times. Experiment was conducted twice with similar results.

FIG. 70 X-ray crystal data collection and refinement statistics table for the indicated MEKi bound to the indicated KSR-MEK complexes, including KSR1:MEK1 and KSR2: MEK1.

FIG. 71 Bioloayer interferometry (BLI) data and stastical comparison table for binding experiments of purified MEK1, BRAF:MEK1, KSR1:MEK1 and KSR2:MEK1 on a biotin-conjugated trametinib immobilized sensor.

FIG. 72 Genus of invention for an interfacial binder, including trametiglue and related analogs (MEK ligand-Linker-KSR ligand). (Top) General formula to define interfacial binders, such as trametiglue, of KSR1:MEK1 and KSR2:MEK1 complexes. (Bottom left and right) The sulfamide linker in trametiglue connects KSR1 or KSR2 to MEK proteins via multiple hydrogen bond contacts, including through engagement of both R234 in MEK1 and a water mediated H-bond to the backbone of the pre-helix αG loop; specifically, the carbonyl of T876 in KSR2 or N823 in KSR1. Note: S218 and S222 in MEK are shown because of the known functional importance of these residues.

Figure 73:
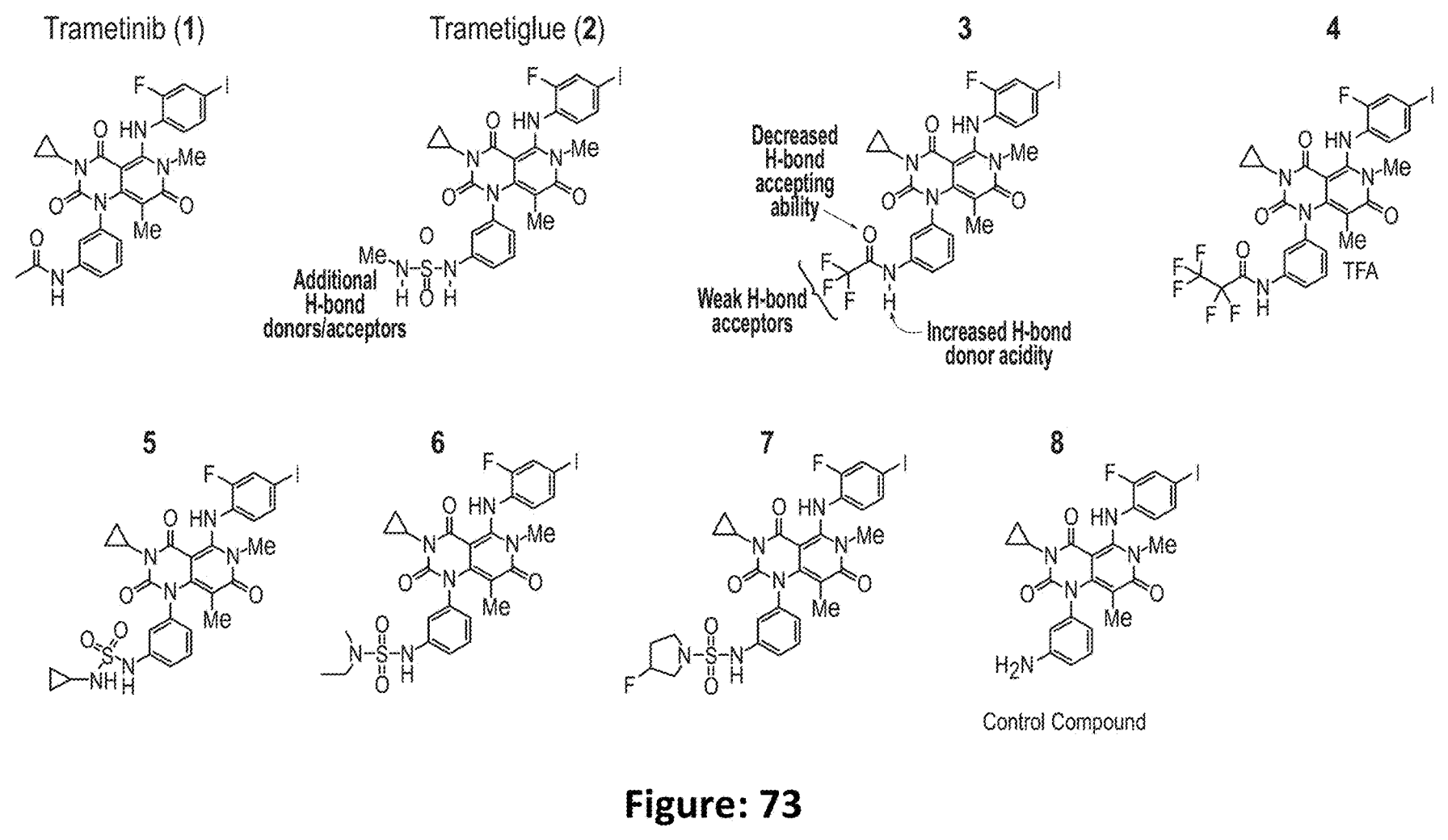

FIG. 73 Exemplary tool compounds for testing interfacial binding interactions on KSR-bound MEK generated through modifications localized to the linker and KSR-targeting ligand (FIG. 72) moieties of trametinib- and trametiglue-based analogs.

FIG. 74 X-ray crystal structure data collection and refinement statistics for the KSR2:MEK1:ANP-PNP complex bound to trametinib (1), trametiglue (2), 3, 4, 5, and 6.

FIG. 75 X-ray crystal structure analysis of Trametinib-Like and Trametiglue-Like Analogs. (Top) Chemical structures of trametinib (1) and related amide-linker analogs 3 and 4; chemical structures of trametiglue (2) and related sulfamide-linker analogs 5 and 6. (Middle) Co-crystal structures of KSR2-MEK1-ANP-PNP bound to 1, 3, and 4. (Bottom) Co-crystal structures of KSR2-MEK1-ANP-PNP bound to 2, 5, and 6. Note: Amide-linker analogs progress outwards toward solvent whereas sulfamide-linker analogs orient inwards. Thus, amide versus sulfamide linkers in trametinib-like and trametiglue-like analogs engender distinct interfacial binding contacts between KSR-bound MEK complexes.

FIG. 76 Overlay of KSR-MEK co-crystal structures bound to trametinib and trametiglue like analogs. (Top) Overlay of trametinib-like analogs 1, 3, and 4 bound in the KSR2-MEK1-ANP-PNP complex; each analog possess an amide (—NHCO—) linker. (Middle) Overlay of trametiglue-like analogs 2, 5, and 6 bound in the KSR2-MEK1-ANP-PNP complex; here, each analog possess a sulfamide (—NHSO₂NH—)

FIG. 77 Cell line proliferation structure-activity relationships (SAR) of analogs. (Top) Cell line IC50 values demonstrate that analogs possessing sulfamide-linkers (eg. 2, 5) give rise to distinct cell inhibition profiles from amide-linker compounds (eg. 1, 3, 4) and a control compound (8). Inhibitory effects of compounds on cell proliferation of KRAS-G12S (A549), BRAF-V600E (A375), and KRAS/BRAF WT (MDA-MD-468) cell lines. (Bottom) Structures of trametinib- (1, 3, 4) and trametiglue- (2 and 5) based analogs.

FIG. 78 Clonogenic assay SAR of analogs. (Top) Long-term clonogenic assays demonstrate several analogs possessing sulfamide-linkers (eg. 2, 5, and 6) that give rise to enhanced and durable growth inhibition in comparison to amide-linker compounds (eg. 1, 3). All compounds assayed at 10 nM final concentration in KRAS-G12S A549 cells. (Bottom) Chemical structures of analogs.

FIG. 79 Table: X-ray crystal data collection and refinement statistics for the structure of trametiglue bound to the BRAF:MEK1:ANP-PNP Complex.

FIG. 80 X-ray crystal structure of trametiglue bound to the BRAF:MEK1:ANP-PNP complex. This structures reveals the structural basis for binding at the BRAF:MEK1 interface and a network of H-bond donor and acceptor interactions mediated via the sulfamide linker in trametiglue.

FIG. 81 Zoom of the trametiglue binding pocket within the BRAF:MEK1:ANP-PNP complex. (Left) A network of H-bond donor/acceptor interactions centered around the linker (—NHSO₂NH—) of trametiglue (2), Arg189 of MEK1, Arg234 of MEK1, and the backbone —NH— of Arg662 in BRAF. (Right) Unbiased Fo-Fc electron density map centered around trametiglue (2).

FIG. 82 Extension of genus of invention for an interfacial binder, including trametiglue and related analogs (hMEK ligand-Linker-hKSR/BRAF ligand). (Top) General formula to define interfacial binders, such as trametiglue, of hKSR1:hMEK1, hKSR2:hMEK1, and hBRAF:hMEK1 complexes. (Bottom left and right) The sulfamide linker in trametiglue connects hBRAF to hMEK proteins via multiple hydrogen bond contacts, including through a water mediated H-bond to Arg189 and Arg234 in hMEK, as well as a direct H-bond to the backbone of the pre-helix αG loop —NH— of Arg662. Note: S218 and S222 in hMEK are shown because of the known functional importance of these residues.

FIG. 83 Overlay of trametinib from KSR-bound MEK1 structures determined in this work onto previously determined structures of isolated MEK1. This analysis suggests several hypothetical docking poses for trametinib within isolated MEK1. In all examples, the activation segment of isolated MEK1 or drug must re-orient to match the binding pose observed in the complex, including to avoid steric clashes that would otherwise occur. Therefore, a unique conformation of the MEK1 activation segment is likely required to accommodate trametinib within the allosteric pocket of isolated MEK1.

FIG. 84 Amino acid sequence of human MEK1 (uniprot ID Q02750)

FIG. 85 Amino acid sequence of human MEK2 (uniprot ID P36507)

FIG. 86 Amino acid sequence of rabbit MEK1 (uniprot ID P29678)

FIG. 87 Amino acid sequence of human KSR1 (uniprot ID Q8IVT5)

FIG. 88 Amino acid sequence of human KSR2 (uniprot ID Q6VAB6)

FIG. 89 Amino acid sequence of mouse KSR1 (uniprot ID Q61097)

FIG. 90 Amino acid sequence of human BRAF (uniprot ID P15056)

FIG. 91 Liquid chromatography mass spectrometry (LC-MS) characterization of trametiglue (2).

FIG. 92 Proton (1H) NMR spectra and characterization of trametiglue (2).

FIG. 93 Table specifying distances and contacts between the indicated compounds within either the hKSR2:hMEK1 (K2M1) or hKSR1:hMEK1(K1M1) complexes as determined by co-crystallography. Column headers specify criteria and features between analogs within the defined interfacial binding pocket of KSR-bound MEK.

FIG. 94 Continuation of table from FIG. 93 specifying distances and contacts between the indicated compounds within either the KSR2:MEK1 (K2M1) or hKSR1.hMEK1 (K1M1) complexes as determined by co-crystallography. Column headers specify criteria and features between analogs within the defined interfacial binding pocket of hKSR-bound hMEK.

DETAILED DESCRIPTION OF THE INVENTION

I. Introduction

Reference will now be made in detail to implementation of exemplary embodiments of the present disclosure as illustrated in the accompanying drawings. The same reference indicators will be used throughout the drawings and the following detailed description to refer to the same or like parts. Those of ordinary skill in the art will understand that the following detailed description is illustrative only and is not intended to be in any way limiting. Other embodiments of the present disclosure will readily suggest themselves to such skilled persons having benefit of this disclosure.

In the interest of clarity, not all of the routine features of the implementations described herein are shown and described. It will be appreciated that, in the development of any such actual implementation, numerous implementation-specific decisions are made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Many modifications and variations of the exemplary embodiments set forth in this disclosure can be made without departing from the spirit and scope of the exemplary embodiments, as will be apparent to those skilled in the art. The specific exemplary embodiments described herein are offered by way of example only, and the disclosure is to be limited only by the terms of the appended claims, along with the full scope of equivalents to which such claims are entitled.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing embodiments of the present invention, the following abbreviations and terms will be employed, and are intended to be defined as indicated below.

IIa. Abbreviations

"FET", as used herein, refers to "Fluorescence Energy Transfer."

"FRET", as used herein, refers to "Fluorescence (Foerster) Resonance Energy Transfer." These terms are used herein to refer to both radiative and non-radiative energy transfer processes. For example, processes in which a photon is emitted and those involving long-range electron transfer are included within these terms. Throughout this specification, both of these phenomena are subsumed under the general term "donor-acceptor energy transfer."

"Bioluminescence resonance energy transfer technology" (BRET) is similar to fluorescence resonance energy transfer (FRET), in that both are powerful tools for reporting molecular interaction events. BRET technology takes advantage of energy donors, which are products of a bioluminescent reaction (i.e., enzymatic reduction). A comparison of FRET vs. BRET shows that the analysis of BRET signals can be simpler due to lack of fluorescent bleedthrough, auto-fluorescence as well as photo-bleaching in FRET. BRET has the advantage of producing a simple meaningful analysis from simple apparatus.

Probes of use in characterizing structural and functional aspects of the inhibitors of the invention and a complex formed between such an inhibitor and an inhibitor binding can be a component of an FET or FRET or BRET pair as either the donor or acceptor. Conjugating a compound of the invention and a donor or acceptor fluorophore through reactive functional groups on the conjugation partners and an appropriate linker, adaptor, carrier molecule or a combination thereof is well within the abilities of those of skill in the art.

The symbol "R", as used herein, refers to moiety which is a member selected from the moieties defined in the following section, inter alia, substituted or unsubstituted alkyl, substituted or unsubstituted heteroalkyl, substituted or unsubstituted aryl, substituted or unsubstituted heteroaryl, etc. as well as those groups set forth as substituents of these moieties.

As used herein "MEK" and "hMEK" are used interchangeably to refer to human mitogen activated protein kinase.

As used herein, "KSR" and hKSR" are used interchangeably to refer to human kinase suppressor of Ras.

As used herein, "BRAF" and hBRAP" are used interchangeably to refer to human B-RAF.

IIb. Definitions

Unless defined otherwise, all technical and scientific terms used herein generally have the same meaning as commonly understood by one of ordinary skill in the art to which this invention belongs. Generally, the nomenclature used herein and the laboratory procedures in organic chemistry, pharmaceutical formulation, and medical imaging are those well known and commonly employed in the art.

The articles "a" and "an" are used herein to refer to one or to more than one (i.e. to at least one) of the grammatical object of the article. By way of example, "an element" means one element or more than one element.

In characterizing the MEK-KSR-inhibitor complexes of the invention, light emitting probes, inter alia, fluorescent probes, and luminescent probes, find use. Fluorescent labels have the advantage of requiring few precautions in handling, and being amenable to high-throughput visualization techniques (optical analysis including digitization of the image for analysis in an integrated system comprising a computer). Exemplary labels exhibit one or more of the following characteristics: high sensitivity, high stability, low background, low environmental sensitivity, high specificity in labeling, and a broader range of excitation/emission spectra. Many fluorescent labels based upon the cyanine-nucleus are commercially available from the SIGMA chemical company (Saint Louis, MO), Molecular Probes (Eugene, OR), R&D systems (Minneapolis, MN), Pharmacia LKB Biotechnology (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), and Applied Biosystems (Foster City, CA), as well as many other commercial sources known to one of skill. Furthermore, those of skill in the art will recognize how to select an appropriate cyanine-based fluorophore for a particular application and, if it not readily available commercially, will be able to synthesize the necessary fluorophore de novo or synthetically modify commercially available cyanine compounds to arrive at the desired fluorescent label.

The compounds, probes, complexes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

Where chemical moieties are specified by their conventional chemical formulae, written from left to right, they optionally equally encompass the moiety which would result from writing the structure from right to left, inter alia, —CH$_2$O— is intended to also recite —OCH$_2$—; —NHS (O)$_2$— is also intended to optionally represent. —S(O)$_2$ HN—, etc. Moreover, where compounds can be represented as free acids or free bases or salts thereof, the representation of a particular form, inter alia, carboxylic or sulfonic acid, also optionally discloses the other form, inter alia, the deprotonated salt form, inter alia, the carboxylate or sulfonate salt. Appropriate counterions for salts are well-known in the art, and the choice of a particular counterion for a salt of the invention is well within the abilities of those of skill in the art. Similarly, where the salt is disclosed, this structure also optionally discloses the compound in a free acid or free base form. Methods of making salts and free acids and free bases are well-known in the art.

"A component of a reactive functional group" refers to a leaving group or to a component of the reactive functional group that is itself reactive. Exemplary leaving groups include halogens of an acyl or alkyl halide, the alcohol component of an ester (inter alia, an active ester, inter alia, N-hydroxysuccinimide), an imidazole and the like. An exemplary reactive component of the reactive functional group is an unsaturated bond (inter alia, the double bond of a maleimide, or the unsaturated bond of an alkyne). Additional exemplary components include those forming bonds through coupling reactions (inter alia, oxidative coupling, inter alia, S—S bond formation).

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers and d and l isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, Drug Metabolism Reviews 165 (1988) and Bundgaard, Design of Prodrugs, Elsevier (1985).

Prodrugs of the compounds described herein include, but are not limited to, esters, ethers, carbonates, thiocarbonates, N-acyl derivatives, N-acycloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. inter alia, Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acycloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups.

Metabolites of the compounds disclosed herein are optionally identified either by administration of compounds to a host and analysis of tissue samples from the host, or by incubation of compounds with hepatic cells in vitro and analysis of the resulting compounds.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Amino acid," as used herein refers to the genus encompassing hydrophilic amino acids, acidic amino acids, basic amino acids, polar amino acids, hydrophobic amino acids, aromatic amino acids, non-polar amino acids and aliphatic amino acids, including the genus and the species therein. A "peptide" is formed from such amino acids linked via peptide bonds. Amino acids also encompass amino-carboxylic acid species other than α-amino acids, inter alia, aminobutyric acid (aba), aminohexanoic acid (aha), aminomethylbenzoic acid (amb) etc. In an exemplary embodiment, the cyanine dye of the invention is conjugated to a carrier molecule through a linker having one or more than one amino acid. Exemplary amino acids of use in such linkers include lysine, proline and acidic amino acids.

As used herein, "KSR" (and its equivalents) refers to KSR1, KSR2 and other closely related homologs. Similarly, "MEK" as used herein, refers to MEK (and its equivalents) refers to MEK1, MEK2. "BRAF" as used herein refers to BRAF itself and closely related homologs of BRAF. Amino acid sequences and uniprot identification numbers for KSR, MEK and BRAF are included in FIGS. 84 to 90.

"Activated derivatives of carboxyl moieties," and equivalent species, refers to moiety on a precursor component of a conjugate of the invention (inter alia, dye, adaptor, linker, polyvalent moiety) having a leaving group, inter alia, an active ester, acyl halide, acyl imidazole, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, optionally, those derivatives of alkyl defined in more detail below, such as "alkenyl", "alkynyl", "alkyldiyl", "alkyleno" and "heteroalkyl."

"Alkenyl", refers to an unsaturated branched, straight-chain or cyclic alkyl radical having at least one carbon-carbon double bond derived by the removal of one hydrogen atom from a single carbon atom of a parent alkane. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en- 1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc., and the like. In exemplary embodiments, the alkenyl group is ($C_2$-$C_6$) alkenyl.

"Alkynyl" refers to an unsaturated branched, straight-chain or cyclic alkyl radical having at least one carbon-carbon triple bond derived by the removal of one hydrogen atom from a single carbon atom of a parent alkene. Typical alkynyl groups include, but are not limited to, ethynyl; propynyls such as prop-1-yn-1-yl, prop-2-yn-1-yl, etc.; butynyls such as but-1-yn-1-yl, but-3-yn-1-yl, etc., and the like. In exemplary embodiments, the alkynyl group is ($C_2$-$C_6$) alkynyl.

"Alkyldiyl", refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,3-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In preferred embodiments, the alkyldiyl group is ($C_2$-$C_6$) alkyldiyl. Also preferred are saturated acyclic alkanyldiyl radicals in which the radical centers are at the terminal carbons, inter alia, methandiyl (methano); ethan-1,2-diyl(ethano); propan-1,3-diyl (propano); butan-1,4-diyl(butano), and the like (also referred to as alkylenos, defined infra).

"Alkyleno", refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1, 2]dieno, prop[1]yno, etc.; butylenos such as butano, but[1]eno, but[2]eno, buta[1,3]dieno, but[1]yno, but[2]yno, but[1, 3]diyno, etc., and the like. Where specific levels of saturation are intended, the nomenclature alkano, alkeno and/or alkyno is used. In preferred embodiments, the alkyleno group is ($C_2$-$C_6$) alkyleno.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P and S, and wherein the nitrogen and sulfur atoms may optionally be oxidized and the nitrogen heteroatom may optionally be quaternized. The heteroatom(s) O, N, S, P and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N ($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—OCH$_3$, and —CH=CH—N($CH_3$)—$CH_3$. Up to two heteroatoms may be consecutive, such as, for example, —$CH_2$—NH—OCH$_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di- and multi-valent species such as "cycloalkylene." Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a poly-unsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes aryl and, optionally, heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: $-OR'$, $=O$, $=NR'$, $=N-OR'$, $-NR''R''$, $-SR'$, -halogen, $-SiR'R''R'''$, $-OC(O)R'$, $-C(O)R'$, $-CO_2R'$, $-CONR'R''$, $-OC(O)NR'R''$, $-NR''C(O)R'$, $SO_3R'$, $-NR'-C(O)NR''R'''$, $-NR''C(O)_2R'$, $-NR-C(NR'R''R''')=NR''''$, $-NR-C(NR'R'')=NR'$, $-S(O)R'$, $-S(O)_2R'$, $-S(O)_2NR'R''$, $-NRSO_2R'$, $-CN$ and $-NO_2$ in a number ranging from zero to (2 m'+1), where m' is the total number of carbon atoms in such radical. R', R", R''' and R'''' each preferably independently refer to hydrogen, substituted or unsubstituted heteroalkyl, substituted or unsubstituted aryl, inter alia, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, $-NR'R''$ is meant to include, but not be limited to, 1-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., $-CF_3$ and $-CH_2CF_3$) and acyl (e.g., $-C(O)CH_3$, $-C(O)CF_3$, $-C(O)CH_2OCH_3$, and the like).

The substituents set forth in the paragraph above are referred to herein as "alkyl group substituents."

Similar to the substituents described for the alkyl radical, substituents for the aryl and heteroaryl groups are varied and are selected from, for example: halogen, $-OR'$, $=O$, $=NR'$, $=N-OR'$, $-NR'R''$, $-SR'$, -halogen, $-SiR'R''R'''$, $-OC(O)R'$, $-C(O)R'$, $-CO_2R'$, $-CONR'R''$, $-OC(O)NR'R''$, $-NR''C(O)R'$, $-NR'-C(O)NR''R'''$, $-NR''C(O)_2R'$, $-NR-C(NR'R'')=NR'$, $-S(O)R'$, $-S(O)_2R'$, $SO_3R'$, $-S(O)_2NR'R''$, $-NRSO_2R'$, $-CN$ and $-NO_2$, $-R'$, $-N_3$, $-CH(Ph)_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, ($C_1$-$C_5$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently $-NR-$, $-O-$, $-CRR'-$ or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently $-CRR'-$, $-O-$, $-NR-$, $-S-$, $-S(O)-$, $-S(O)_2-$, $-S(O)_2NR'-$ or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $-(CRR')_s$—X—(CR"R''')$_d$—, where s and d are independently integers of from 0 to 3, and X is $-O-$, $-NR'-$, $-S-$, $-S(O)-$, $-S(O)_2-$, or $-S(O)_2NR'-$. The substituents R, R', R" and R''' are preferably independently selected from hydrogen or substituted or unsubstituted ($C_1$-$C_6$)alkyl.

The substituents set forth in the two paragraphs above are referred to herein as "aryl group substituents."

A "planar moiety" is a substituted or unsubstituted aryl or heteroaryl moiety.

"Bioisostere" or "Isostere" means a compound or functional group resulting from the exchange of an atom or of a group of atoms with another, broadly similar, atom or group of atoms. The objective of a bioisosteric replacement is to create a new compound with similar biological and improved physio-chemical properties to the parent compound or a functional group which provides similar biological properties as the parent functional group before the exchange. In general, two isosteric groups will have the same number of valence electrons and the same electronic configuration but differing in the kinds and numbers of atoms. Meanwell, N. J Med Chem 2011 Apr. 28; 54(8): 2529-91; St Laurent inter alia, Biorg Med Chem 1995 August; 3(8): 1145-56; www.cambridgemedchemconsulting.com/resources/bioisoteres/.

A "linkage fragment" is a bond formed by reaction of two reactive functional groups of complementary reactivity. An exemplary linkage fragment is an amide formed by the reaction of an amine and an activated derivative of a carboxylic acid (inter alia, acyl halide, acyl imidazole, active ester, etc.).

The term "linker" or "L", as used herein, refers to a single covalent bond or a series of stable covalent bonds incorporating 1-40, inter alia, 10-30 nonhydrogen atoms selected from the group consisting of C, N, O, S and P that covalently attach a moiety of the inhibitor to another moiety. Exemplary linkers include one or more linkage fragment, inter alia, $-C(O)NH-$, $-C(O)O-$, $-NH-$, $-S-$, $-O-$.

"Analyte", as used herein, means any compound or molecule of interest for which a diagnostic test is performed, such as a biopolymer or a small molecular bioactive material. An analyte can be, for example, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation. An exemplary analyte is a physiological complex between MEK and KSR.

A "signal generating moiety" refers to a molecular species generating a signal detectable visually or via various standard instrumental modalities (UV/Vis, fluorescence or luminescence detection). The signal may either be a positive signal (inter alia, emission, change in wavelength of emission) or it can be a negative signal (inter alia, quenching). An exemplary signal generating moiety is referred to herein as a "dye".

As used herein, a "dye" is a detectable molecular structure (moiety) or a component of a detectable "energy transfer pair". Exemplary dyes include fluorophores, lumiphores, components of luminescence generating systems, and moieties shifting the wavelength of energy or quenching the energy generated by these species. Exemplary dyes are incorporated into a conjugate with an inhibitor of the invention ("first signal generating moiety"). In various embodiments, a dye is attached to MEK, KSR or a combination thereof ("second signal generating moiety") and utilized to probe properties of the inhibitors of the invention, inter alia, with respect to their interaction with the MEK-KSR complex. In various embodiments, a dye is attached to its conjugation partner (inter alia, inhibitor, MEK, KSR) via a linker linking the two partners. Compounds of use as dyes are widely known in the art. An exemplary dye is a boron-containing species. Exemplary boron-containing dyes include the bora-diazaindacenes compounds, inter alia, BODIPY.

As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena.

As used herein, "energy transfer pair" refers to any two molecules that participate in detectable energy transfer. Typically, one of the molecules acts as a signal generating group (inter alia, fluorophore), and the other acts as a signal-modifying group (inter alia, quencher). In various embodiments, the choice of members of an energy transfer pair is limited only by the requirement that the members engage in detectable energy transfer when brought into operative proximity by the formation of an inhibitor-inhibitor pocket complex. All that is required is that the spectroscopic properties of the energy transfer pair as a whole change in some measurable way if the distance between the individual members is altered by some critical amount. An exemplary energy transfer pair is formed between an inhibitor of the invention conjugated to a first signal generating moiety, and a second signal generating moiety conjugated to MEK, KSR or a combination thereof. The first and second signal generating moiety are brought into operative proximity by formation of an inhibitor-inhibitor pocket complex, such that energy is detectably transferred from one member of the energy transfer pair to the other.

Structural and functional characteristics (kinetics, thermodynamics) of the inhibitors of the invention, and the complex formed between such an inhibitor and an inhibitor pocket are probable using an energy transfer pair formed between an inhibitor of the invention conjugated to a first signal generating moiety and a second energy transfer moiety conjugated to MEK, KSR or both in a complex formed between the labeled inhibitor and the inhibitor pocket formed by the interaction of MEK and KSR.

As used herein, "fluorescence-modifying group" refers to a molecule of the invention that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, and a change in fluorescence lifetime. One example of a fluorescence-modifying group is a quenching group.

"Fluorescence resonance energy transfer" or "FRET" is used interchangeably with FET, and refers to an energy transfer phenomenon in which the light emitted by the excited fluorescent group is absorbed at least partially by a fluorescence-modifying group of the invention. If the fluorescence-modifying group is a quenching group, then that group will preferably not radiate a substantial fraction of the absorbed light as light of a different wavelength, and will preferably dissipate it as heat. FRET depends on an overlap between the emission spectrum of the fluorescent group and the absorption spectrum of the quenching group. FRET also depends on the distance between the quenching group and the fluorescent group.

As used herein, "fluorophore" refers to a fluorescent species.

"Moiety" refers to the radical of a molecule that is attached to another moiety.

A "disease" is a state of health of an animal wherein the animal cannot maintain homeostasis, and wherein if the disease is not ameliorated then the animal's health continues to deteriorate.

As used herein a "non-ATP competitive inhibitor refers" to an inhibitor of MEK that does not bind in the ATP pocket of MEK, or does not displace ATP from the MEK active site, and can form direct contacts when co-bound to the MEK-ATP complex. Non-ATP competitive inhibition by a compound of the invention can be confirmed by art-recognized methods such as enzymology studies, competition assays, biophysical methods, including X-ray co-crystallography. An exemplary non-ATP competitive inhibitor of the invention inhibits recombinant MEK1 or MEK2 with an $IC_{50}$ of from about 1 nM to about 1000 nM, inter alia, from about 5 nM to about 500 nM, inter alia, from about 10 nM to about 100 nM.

An "inhibitor pocket", as used herein, refers to a structure formed at the interface of the interaction between MEK and KSR or BRAF with which an inhibitor of the invention is engaged. An exemplary "inhibitor pocket" is shown in FIG. 72.

As used herein, a compound of the invention "allosterically binds an inhibitor pocket" when a compound binds outside the active site (inter alia, outside or adjacent to the ATP-binding site of a kinase).

An "inhibitor-inhibitor pocket complex" describes a species in which an inhibitor of the invention allosterically binds an inhibitor pocket formed at an interaction interface between human MEK (MEK1 or MEK2) and human Kinase Suppressor of Ras (KSR1, KSR2, or the KSR homolog BRAF) adjacent to ATP in a physiological complex between MEK and KSR.

As used herein, "adjacent to ATP", refers to a portion of the inhibitor pocket in which critical inhibitor binding amino acid residues of the MEK-KSR or MEK-BRAF complex are from about 2 Å to about 5 Å from the ATP binding site of MEK.

The concepts of molecular glue-like features and proximity are discussed and elucidated in the art, e.g., Stanton et al., Science 2018 Mar. 9; 359(6380); Gerry et al., Nat Chem Biol 2020 April; 16(4):369-378.

As used herein "substantially fills the space" refers to a structural characteristic of a complex formed between MEK-KSR or MEK-BRAF and an inhibitor of the invention engaged in the inhibitor pocket. An inhibitor "substantially fills the space" when moieties on the inhibitor which interact with amino acid residues on a protein of the complex are from about 2 Å to about 5 Å from the amino acid with which they engage.

When a moiety on an inhibitor "engages" an amino acid residue of MEK and/or KSR in an inhibitor pocket, this interaction is detectable by X-ray crystallography, or similar structural methods, such as cryo-elctron microscopy, NMR, or in silico docking, including fragment binding and computational simulations, which demonstrates that the interaction defining the engagement is a separation between the inhibitor moiety and the amino acid residue of not more than about 5 Å, inter alia, from about 2 Å to about 5 Å.

The distances provided herein allow for the implicit inclusion of hydrogen atoms; however, hydrogen atoms were not included in the present crystallographic models, which is appropriate unless crystals diffract to very high resolutions (ie. better than 1.5 Angstroms). Literature surveys of drug-receptor atom pairs across all structures in the protein data bank have used 4-5 Angstrom distance cutoffs (PMID 29308120, 26517868, 19221587) to evaluate reasonable small molecule hydrophobic bonding interactions and have found that intermolecular carbon-carbon interactions similar to the trametinib-KSR contacts are among the most highly represented drug-receptor atom pairs within the protein data bank. With respect to the interactions between the inhibitors of the invention and the MEK-KSR complex, a 4 Angstrom contact is reasonable based on the nature of the trametinib-KSR interaction and precedence of known drug-receptor complexes. This contact is within the range of known contacts as defined by several independent groups (PMID 29308120, 26517868, 19221587).

Further characteristics of an inhibitor engaging an amino acid of MEK and/or KSR or BRAF in an inhibitor pocket include:

(a) the inhibitor has an IC50 less than about 500 nM, inter alia, less than about 250 nM, inter alia, less than about 100 nM. on KSR-bound MEK using KSR reporters (inter alia, FIG. 31, 33; Example 2.14);

(b) the inhibitor has a residence time in the inhibitor pocket greater than about 60 min, inter alia, greater than about 90 min, inter alia, greater than about 120 min in washout assays (inter alia, FIG. 35, 63; Example 2.14); and (c) the inhibitor induces the BRAF-MEK complex relative to vehicle as assessed by co-IP (FIG. 64, lanes 5 versus 8; Example 2.8).

In an exemplary embodiment, the inhibitors of the invention meet each of these three criteria. By way of contrast, the art-recognized compound trametinib meets only criteria (a) and (b).

As used herein, "pharmaceutically acceptable carrier" includes any material, which when combined with a compound of the invention substantially retains the activity of the compound and is substantially non-reactive with the subject's immune system. Examples include, but are not limited to, any of the standard pharmaceutical carriers such as a phosphate buffered saline solution, water, emulsions such as oil/water emulsion, and various types of wetting agents. Other carriers may also include sterile solutions. Typically, such carriers contain excipients such as starch, milk, sugar, sorbitol, methylcellulose, certain types of clay, gelatin, stearic acid or salts thereof, magnesium or calcium stearate, talc, vegetable fats or oils, gums, glycols, or other known excipients. Such carriers may also include flavor, texture, and color additives or other ingredients. Pharmaceutical formulations comprising such carriers are formulated by well-known, conventional methods.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (inter alia, methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the compounds described herein include the N-oxide forms.

The terms "administer," "administering", "administration," and the like, as used herein, refer to methods that may be used to enable delivery of agents or compositions to the desired site of biological action. These methods include, but are not limited to oral routes, intraduodenal routes and rectal administration. Administration techniques that are optionally employed with the agents and methods described herein are found in sources inter alia, Goodman and Gilman, The Pharmacological Basis of Therapeutics, current ed.; Pergamon; and Remington's, Pharmaceutical Sciences (current edition), Mack Publishing Co., Easton, Pa. In certain embodiments, the agents and compositions described herein are administered orally. As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The terms "prevent," "preventing" or "prevention," and other grammatical equivalents as used herein, include preventing additional symptoms, preventing the underlying metabolic causes of symptoms, inhibiting the disease or condition, inter alia, arresting the development of the disease or condition and are intended to include prophylaxis. The terms further include achieving a prophylactic benefit. For prophylactic benefit, the compositions are optionally administered to a patient at risk of developing a particular disease, to a patient reporting one or more of the physiological symptoms of a disease, or to a patient at risk of reoccurrence of the disease.

The term "subject", "patient" or "individual" may be used interchangeably herein and refer to mammals and non-mammals, inter alia, suffering from a disorder described herein. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, amphibians, and the like. In one embodiment of the methods and compositions provided herein, the mammal is a human.

The terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating a disease or condition symptoms, ameliorating the underlying metabolic causes of symptoms, inhibiting the disease or condition, inter alia, arresting the development of the disease or condition, relieving the disease or condition, causing regression of the disease or condition, relieving a condition caused by the disease or condition, or stopping the symptoms of the disease or condition. The terms further include achieving a therapeutic benefit. Therapeutic benefit means eradication or amelioration of the underlying disorder being treated, and/or the eradication or amelioration of one or more of the physiological symptoms associated with the underlying disorder, such that an improvement is observed in the patient. As used herein, the terms "co-administration," "administered in combination with," and their grammatical equivalents, are meant to encompass administration of the selected therapeutic agents to a single patient, and are intended to include treatment regimens in which the agents are administered by the same or different route of administration or at the same or different times. In some embodiments the agents described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the agents described herein and the other agent(s) are administered in a single composition. In some embodiments, the agents described herein and the other agent(s) are admixed in the composition.

The terms "effective amount," "pharmaceutically effective amount" or "therapeutically effective amount" as used herein, refer to a sufficient amount of at least one agent being administered to achieve a desired result, inter alia, to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case can be determined using any suitable technique, such as a dose escalation study.

III. Exemplary Embodiments

A. Compositions

In various embodiments, the present invention provides an ATP non-competitive inhibitor of mitogen-activated protein kinase (MEK), inter alia, human MEK (MEK1 or MEK2) having the properties:

(i) allosterically binds an inhibitor pocket formed at an interaction interface between human MEK (MEK1 or MEK2) and human Kinase Suppressor of Ras (KSR1 or KSR2 or the KSR homolog BRAF) adjacent to ATP in a physiological complex between MEK and KSR or BRAF, forming an inhibitor-inhibitor pocket complex;

(ii) is an ATP non-competitive kinase inhibitor (iii) a structure such that when bound to the inhibitor-inhibitor pocket complex, the complex comprises the structural elements:

(a) at least one moiety of the inhibitor engaging A825 of hKSR1, or P878 of hKSR2 or R662 of BRAF;

(b) at least one moiety engaging R234 of hMEK, wherein where R234 is within 5 Å from any atoms of hKSR1 or hKSR2 or BRAF.

In an exemplary embodiment, the inhibitor is not trametinib. In an exemplary embodiment, the inhibitor does not engage one or more than one of I216 in MEK1 and A825 in KSR1 or P878 in KSR2

In an exemplary embodiment, the at least one moiety according to (a) is an H-bond acceptor, inter alia, an oxygen or nitrogen atom, or an H bond donor. In various embodiments, the at least one moiety according to (a) is a moiety of a linker, inter alia, "L", infra, engaging the backbone of A825 of hKSR1, or P878 of hKSR2, or R662 of hBRAF, directly or through a water-mediated contact.

In various embodiments, there is provided an ATP non-competitive inhibitor comprising one or more of the following:

(c) at least one moiety engaging M230 of hMEK, wherein M230 is within 5 Å from terminal atom (CB) of A825 of KSR1 or (CG) of P878 of hKSR2 or (CG) N661 of hBRAF;

(d) at least one moiety is a H-bond acceptor or donor engaging the backbone carbonyl of N823 of hKSR1, or T876 of hKSR2 through a water-mediated contact or backbone amino group of R662 of hBRAF directly;

(e) at least one moiety engaging Q824 of hKSR1 or Q877 of hKSR2 or Q664 of hBRAF;

(f) at least one moiety engaging a side chaing atom of A826 of hKSR1 or A879 of hKSR2 or R662 of BRAF;

(g) at least one moiety is a heteroaryl group engaging M143 of hMEK;

(h) at least one moiety is a heteroaryl group engaging F209 of hMEK;

(i) at least one moiety (inter alia, a H-bond acceptor) is engaging the backbone amino group of S212 of hMEK;

(j) at least one moiety engaging L215 of hMEK;

(k) at least one moiety engaging I216 of hMEK; and (l) at least one moiety engaging M219 of hMEK where hMEK residues 215-219 adopt a helical conformation; and the inhibitor is not trametinib.

In various embodiments, the moiety corresponding to (c) is selected from substituted or unsubstituted alkyl or cycloalkyl In various embodiments, there is provided an ATP non-competitive inhibitor wherein T876 of hKSR2 or N823 of hKSR1 is engaged by the inhibitor at a backbone CO residue.

An exemplary ATP non-competitive inhibitor engaging binding pocket is lined by the MEK residues R234 and M230, and P877 of KSR2 or A825 of KSR1 or R662 of BRAF.

In various embodiments an ATP non-competitive inhibitor of the invention engages the binding pocket via multiple hydrogen bond contacts, including through a water mediated H-bond to Arg189 and Arg234 in hMEK, as well as a direct H-bond to the backbone of the pre-helix αG loop —NH— of Arg662.

Some exemplary ATP non-competitive inhibitors engage A825 of hKSR1 or P878 of hKSR2 or R662 of BRAF does so within a distance of less than or equal to about 5 Å from the at least one moiety to A825 of hKSR1 or P878 of hKSR2 or R662 of BRAF.

In various embodiments, the ATP non-competitive inhibitor has the formula:

wherein

α is a moiety interacting with at least one of M143, F209 and a combination thereof of hMEK;

β is a planar moiety engaging R234 R189 and I216 in hMEK; and R is a planar moiety not engaging F223 or Ser222

χ is a moiety engaging ATP, selected from substituted or unsubstituted alkyl, substituted or unsubstituted cycloalkyl substituted or unsubstituted heteroalkyl, substituted or unsubstituted heterocycloalkyl;

L is a linker of 0 (bond), 1, 2, or 3 non-hydrogen atoms in length engaging R234 of hMEK; and δ is a moiety engaging A825 of hKSR1 or P878 of hKSR2 or N661 of hBRAF.

In various embodiments, 6 substantially fills the space between MEK and KSR1 or KSR2 or BRAF when the interfacial binding space is formed upon binding of MEK with KSR1 or KSR2 or BRAF.

In various embodiments, the inhibitor of the invention has the formula:

in which $X^1$, $X^2$, $X^3$, $X^4$ and $X^5$ are each independently selected from N and C;

$R^1$, $R^2$, $R^3$, $R^4$ and $R^5$ are each independently selected from H, substituted or unsubsituted alkyl, halogen, $OR^{13}$, —$NR^{13}R^{14}$, —$SR^{13}$, halogen, —$SiR^{13}R^{14}R^{15}$, $OC(O)R^{13}$, —$C(O)R^{13}$, $CO_2R^{13}$, —$CONR^{13}R^{14}$, —$OC(O)NR^{13}R^{14}$, —$NR^{13}C(O)R^{14}$, $NR^{13}C(O)NR^{14}R^{15}$, —$NR^{13}C(O)_2R^{14}$, $NR^{13}C(NR^{14}R'')$=$NR'''$, —$S(O)R'$, —$S(O)_2R'$, $SO_3R'$, —$S(O)_2NR^{13}R^{14}$, $NRSO_2R^{13}$, —CN and —$NO_2$, —$N_3$, fluoro($C_1$-$C_4$) alkoxy, and fluoro($C_1$-$C_4$)alkyl, —$NHS(O)_2$—$R^{13}$ wherein $R^{13}$, $R^{14}$ and $R^{15}$ are each independently selected from H, substituted or unsubstituted alkyl, substituted or unsubstituted heteroalkyl, substituted or unsubstituted aryl, and substituted or unsubsituted heteroaryl;

$R^6$ and $R^7$ are independently selected from H, substituted or unsubstituted ($C_1$-$C_6$)alkyl, substituted or unsubstituted ($C_1$-$C_6$)heteroalkyl, substituted or unsubstituted ($C_1$-$C_6$)fluoroalkyl, halogen, CN, and $NO_2$; and $R^8$, $R^9$, and $R^{10}$ are each independently selected from H, substituted or unsubstituted ($C_1$-$C_6$) alkyl, and substituted or unsubstituted ($C_1$-$C_6$) heteroalkyl.

In various embodiments, $R^8$ and $R^9$ are independently selected from substituted or unsubstituted ($C_1$-$C_4$) alkyl and substituted or unsubstituted ($C_1$-$C_4$) heteroalkyl.

In an exemplary embodiment, $R^8$ is selected from substituted or unsubstituted $C_3$-$C_6$ cycloalkyl, and substituted or unsubstituted $C_3$-$C_6$ heterocycloalkyl.

In various embodiments, $R^6$ and $R^7$ are independently selected from F and I. In an exemplary embodiment, $R^6$ is F and $R^7$ is I.

In an exemplary embodiment, $R^8$ is selected from $C_3$-$C_6$ substituted or unsubstituted cycloalkyl and $C_3$-$C_6$ substituted or unsubstituted heterocycloalkyl.

In an exemplary embodiment, neither $R^2$ or $R^4$ is:

In an exemplary embodiment, none of $R^1$, $R^2$, $R^3$, $R^4$ and $R^5$ is:

In an exemplary embodiment, at least one of $R^2$ and $R^4$ is:

In an exemplary embodiment, L is a zero-order linker (bond).

In various embodiments, the inhibitor of the invention is of the structure:

In certain embodiments, $R^{11}$, $R^{12}$ and $R^{13}$ are independently selected from H, substituted or unsubstituted alkyl, substituted or unsubstituted heteroalkyl, substituted or unsubstituted heterocyclyl, substituted or unsubstituted aryl, and substituted or unsubstituted heteroaryl.

In various embodiments, the inhibitor of the invention has the structure:

In various embodiments, the inhibitor of the invention has the formula:

wherein $R^1$, $R^2$ and $R^3$ are independently selected from H, and the structure:

wherein
at least one of $R^1$, $R^2$ and $R^3$ is a moiety other than H.

In exemplary embodiment, ATP non-competitive inhibitors of the invention, 6 is selected from fluoroalkyl (haloalkyl), substituted or unsubstituted, saturated or unsaturated alkyl, substituted or unsubstituted alkyl heteroalkyl, substituted or unsubstituted cycloalkyl, substituted or unsubstituted aryl and substituted or unsubstituted heteroaryl having 1-4 heteroatoms independently selected from the group consisting of nitrogen, oxygen, or sulfur.

In some embodiments, the ATP non-competitive inhibitor, 6 is a hydrocarbon of a size selected for substantially fill a space formed by binding MEK with KSR1 or KSR2 or BRAF.

An exemplary ATP non-competitive inhibitor includes as 6σ saturated, partially unsaturated, straight-chain, branched-chain, alkyl, haloaklyl, substituted or unsubstituted heteroalkyl, substituted or unsubstituted aryl and substituted or unsubstituted heteroaryl having 1-4 heteroatoms independently selected from the group consisting of nitrogen, oxygen, or sulfur.

In various embodiments, the ATP non-competitive inhibitor of the invention, further comprises one or more of the following:

(i) δ fills the space between M230 of MEK and A825 of KSR1 or P878 of KSR2 or N661 of BRAF;

(ii) δ fills the space between R189 or D190 of MEK and A825 of KSR1 or P878 of KSR2 or R662 of BRAF;

(iii) δ fills the space between D190 of MEK and E827 of KSR1 or E880 of KSR2 or D663 of BRAF.

(iv) δ fills the space between K192 of MEK and E827 of KSR1 or E880 of KSR2 or D663 of BRAF.

(v) δ fills the space between Y229 of MEK and E827 of KSR1 or E880 of KSR2 or D663 of BRAF.

(vi) δ fills the space between R234 of MEK and A825 of KSR1 or P878 of KSR2 or R662 of BRAF.

(vii) δ fills the space between R234 of MEK and Q824 of KSR1 or Q877 of KSR2 or Q664 of BRAF.

(viii) δ fills the space between Y240 of MWK and N823 of KSR1 or T876 of KSR2 or N658 of BRAF.

(ix) δ fills the space between S222 of MEK and A825 of KSR1 or P878 of KSR2 or R662 of BRAF.

(x) δ fills the space between F223 of MEK and A825 of KSR1 or P878 of KSR2 or R662 of BRAF.

(xi) δ fills the space between S222 of MEK and E827 of KSR1 or E880 of KSR2 or D663 of BRAF.

In some ATP non-competitive inhibitors, at least one of $R^1$, $R^2$ and $R^3$ comprises a moiety engaging R234 in MEK, and either A825 in hKSR1 or P878 in hKSR2 or R662 of BRAF at a distance of less than or equal to about 5 Å from the at least one of $R^1$, $R^2$ and $R^3$ to A825 of hKSR1 or P878 of hKSR2 or R662 of BRAF.

Exemplary species for L include a member selected from the following or bioisosteres thereof:

In various embodiments, the linker is selected from:

i. a moiety that connects the beta structure and one of several delta motif, ii. a N-acetamide group or N-sulfamide group or bioisosteres thereof;

iii. a linker connecting beta and delta portions of the ATP non-competitive inhibitor to simultaneously engage MEK and KSR1 or KSR2 or BRAF;

iv. a linker engaging R234 of MEK when MEK is bound to KSR1 or KSR2 or BRAF v. a linker engaging A825 of KSR1 or P878 of KSR2 or R662 of BRAF; and vi. a linker engaging N823 of KSR1 or T876 of KSR2 or Q664 of BRAF via a water-mediated H-bond.

In an exemplary embodiment, L-δ is —$S(O)_2NR^{13}R^{14}$.

In an exemplary embodiment, $R^2$ is —$S(O)_2NR^{13}R^{14}$.

A.2 Pharmaceutical Formulations

In various embodiments, the invention provides a pharmaceutical formulation comprising an inhibitor of the invention in combination with a pharmaceutically acceptable carrier.

The non-conventional role of KSR as a catalytically compromised kinase (i.e. pseudokinase) has slowed drug development projects (see e.g., Dar, *Biochem Soc. Trans.* 2013, 41(4), 987-994 and Brennan inter alia, *Nature,* 2011, 472(7343), 366-369). Current models suggest that KSR functions as a scaffold to potentiate Ras signaling through the formation of macromolecular signaling complexes that include the Ras effector kinases RAF and MEK. In one state, KSR likely forms a high affinity complex with inactive forms of MEK but once engaged by active RasGTP-RAF complexes, KSR adopts a distinct state where it can instead drive MEK phosphorylation by RAF. Small molecules antagonizing KSR dependent activities would be valuable tools that could be used to functionally annotate the pharmacology of this class of protein in Ras or RAF dependent cancers. Accordingly, the present application provides compounds that are useful as KSR antagonists, pharmaceutical formulations including such antagonists and methods of using the same.

Genetic screens conducted in *Drosophila* and *C. elegans* suggested KSR as selectively essential for Ras driven tumors (see e.g., Downward, *Cell,* 1995, 83(6), 831-834; Kornfeld inter alia, *Cell,* 1995, 83(6), 903-913; Sundaram inter alia, *Cell,* 1995, 83(6), 889-901; and Therrien inter alia, *Cell,* 1995, 83(6), 879-888). This phenotype, where point mutations in KSR disable Ras-driven tumors but not other aspects of Ras related biology such as normal growth and division, likely stems from KSR's function as a scaffold for core enzymes in multiple Ras pathways. For example, KSR controls Ras-dependent proliferation via direct interactions with several kinases in the MAPK cascade and also metabolism via AMP-activated protein kinase signaling (see e.g., Costanzo-Garvey inter alia, *Cell Metab.* 2009, 10(5), 366-378; Roy inter alia, *Genes Dev.* 2002, 16(4), 427-438; and Ritt inter alia, *Methods Enzymol.* 2006, 407, 224-237).

KSR belongs to a family of highly related kinases, including KSR1 and KSR2, and the human RAF kinases (A-RAF, B-RAF, C-RAF). KSR1 and KSR2 share 61% overall amino acid identity, and 71% amino acid identity between kinase domains. While both KSR1 and KSR2 can interact with RAF, MEK, and ERK, KSR1 has been shown to be prominently involved in MAPK signaling, while KSR2 was shown to impact cell growth through its interaction and functional impact on AMPK (see e.g., Fernandez inter alia, *Mol. Cell. Biol.* 2012, 32(18), 3718-3731). This has been further supported by the fact that KSR1 knockout mice exhibit a rough hair phenotype, while KSR2 knockout mice display a severe obese phenotype (see e.g., Costanzo-Garvey inter alia, *Cell Metab.* 2009, 10(5), 366-378; Fernandez inter alia, *Mol. Cell. Biol.* 2012, 32(18), 3718-3731; and Lozano inter alia, *Cancer Res.* 2003, 63(14), 4232-4238). Knockout of KSR1 in RAS-driven tumor mouse models completely blocks tumorigenesis. Therefore, unlike MEK1/2 and ERK1/2, in which knockdown is lethal in adult mice, KSR1 appears to be essential for RAS-driven tumorigenesis but not required for normal homeostasis (see e.g., Blasco inter alia, *Cancer Cell,* 2011, 19(5), 652-653).

Combination drugs are increasingly recognized as a therapeutic modality for a variety of complex diseases including cancer (see, e.g., Glickman inter alia, Cell, 2012, 148(6), 1089-1098). In particular, in areas where rapid development of resistance to monotherapy is a major concern, drug combinations may be required to improve treatment responses, minimize adverse events, or minimize development of resistance. In the setting of cancer, combination approaches have primarily focused on three strategies including co-targeting of a single pathway (see e.g., Chapman inter alia, Cancer Cell, 2014, 26(5), 603-604), different pathways (see e.g., Vora inter alia, Cancer Cell, 2014, 26(1), 136-149), or compensatory pathways (see e.g., Carver inter alia, Cancer Cell, 2011, 19(5), 575-586).

In various exemplary embodiments, an inhibitor of the invention is combined with one or more additional pharmaceutically active agent in a pharmaceutical formulation of the invention.

The present invention also includes pharmaceutically acceptable salts of the compounds described herein, and pharmaceutical formulations of these salts. When employed as pharmaceuticals, the compounds provided herein can be administered in the form of pharmaceutical compositions; thus, the methods described herein can include administering pharmaceutical compositions provided herein. In some embodiments, the present application provides a pharmaceutical composition comprising a compound provided herein (inter alia, a compound of Formula I), or a pharmaceutically acceptable salt thereof and at least one pharmaceutically acceptable carrier.

These compositions can be prepared as described herein or elsewhere, and can be administered by a variety of routes, depending upon whether local or systemic treatment is desired and upon the area to be treated. Administration may be pulmonary (inter alia, by inhalation or insufflation of powders or aerosols, including by nebulizer; intratracheal or intranasal), oral, or parenteral. Parenteral administration may include, but is not limited to intravenous, intraarterial, subcutaneous, intraperitoneal, intramuscular injection or infusion; or intracranial, (inter alia, intrathecal, intraocular, or intraventricular) administration. Parenteral administration can be in the form of a single bolus dose, or may be, for example, by a continuous perfusion pump. Conventional pharmaceutical carriers, aqueous, powder or oily bases, thickeners and the like may be necessary or desirable.

In making the formulations provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The inhibitors of the invention can be effective over a wide dosage range and are generally administered in a therapeutically effective amount. It will be understood, however, that the amount of the compound actually administered and the schedule of administration will usually be determined by a physician, according to the relevant circumstances, including the condition to be treated, the chosen route of administration, the actual compound administered, the age, weight, and response of the individual subject, the severity of the subject's symptoms, and the like.

A.3 Preparing the Compounds

As will be appreciated, the compounds provided herein, including salts thereof, can be prepared using known organic synthesis techniques and can be synthesized according to any of numerous possible synthetic routes.

It will be appreciated by one skilled in the art that the processes described herein for preparing the formulations provided herein, or a pharmaceutically acceptable salt thereof, are not the exclusive means by which compounds and salts provided herein may be synthesized and that a broad repertoire of synthetic organic reactions is available to be potentially employed in compounding formulations provided herein. The person skilled in the art knows how to select and implement appropriate formulation and synthetic routes. Suitable synthetic methods of starting materials, intermediates and products may be identified by reference to the literature, including reference sources such as: Advances in Heterocyclic Chemistry, Vols. 1-107 (Elsevier, 1963-2012); Journal of Heterocyclic Chemistry Vols. 1-49 (Journal of Heterocyclic Chemistry, 1964-2012); Carreira, et al. (Ed.) Science of Synthesis, Vols. 1-48 (2001-2010) and Knowledge Updates KU2010/1-4; 2011/1-4; 2012/1-2 (Thieme, 2001-2012); Katritzky, et al. (Ed.) Comprehensive Organic Functional Group Transformations, (Pergamon Press, 1996); Katritzky et al. (Ed.); Comprehensive Organic Functional Group Transformations II (Elsevier, $2^{nd}$ Edition, 2004); Katritzky et al. (Ed.), Comprehensive Heterocyclic Chemistry (Pergamon Press, 1984); Katritzky et al., Comprehensive Heterocyclic Chemistry II, (Pergamon Press, 1996); Smith et al., March's Advanced Organic Chemistry: Reactions, Mechanisms, and Structure, $6^{th}$ Ed. (Wiley, 2007); Trost et al. (Ed.), Comprehensive Organic Synthesis (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (inter alia, temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (inter alia, $^1H$ or $^{13}C$), infrared spectroscopy, spectrophotometry (inter alia, UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

A.3a Preparing the Compounds: Reactive Functional Groups

The compounds and conjugates of the invention are assembled via covalent bonding reactions between precursors bearing a reactive functional group, which is a locus for formation of a covalent bond between the precursors. The precursors of compounds of the invention bear a reactive functional group, which can be located at any position on the compound. The finished inhibitor, and conjugates of the inhibitor (inter alia, probes) can include a further reactive functional group at any point on the molecule. In various embodiments, a reactive functional group on the inhibitor is reacted with a reactive functional group on a dye, linker, or carrier molecule (or a linker attached to a carrier molecule) to couple the two components together covalently through a linkage fragment, thereby forming a conjugate of the invention.

Exemplary species include a reactive functional group attached directly to an inhibitor nucleus or to a linker attached to a component of a dye moiety. An exemplary reactive functional group is attached to an alkyl or heteroalkyl moiety. When the reactive group is attached a substituted or unsubstituted alkyl or substituted or unsubstituted heteroalkyl linker moiety, the reactive group is preferably located at a terminal position of the alkyl or heteroalkyl chain. Reactive groups and classes of reactions useful in practicing the present invention are generally those that are well known in the art of bioconjugate chemistry. Currently favored classes of reactions available with reactive dye-based compounds of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and derivatives thereof including, but not limited to activated esters, inter alia, N-hydroxysuccinimide esters, N-hydroxyphthalimide, N-hydroxybenztriazole esters, p-nitrophenyl esters; acid halides; acyl imidazoles; thioesters; alkyl, alkenyl, alkynyl and aromatic esters; and activating groups used in peptide synthesis;

(b) hydroxyl groups and hydroxylamines, which can be converted to esters, sulfonates, phosphoramidates, ethers, aldehydes, etc.

(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, allowing derivatization via formation of carbonyl derivatives, inter alia, imines, hydrazones, semicarbazones or oximes, or via such mechanisms as Grignard addition or alkyllithium addition;

(f) sulfonyl halide groups for reaction with amines, for example, to form sulfonamides;

(g) thiol groups, which can be converted to disulfides or reacted with acyl halides, for example;

(h) amine, hydrazine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

In various embodiments, the reactive functional group is a member selected from:

-continued in which each r is independently selected from the integers from 1 to 10; G is a halogen; and $R^{30}$ and $R^{31}$ are members independently selected from H and halogen and at least one of $R^{30}$ and $R^{31}$ is halogen.

The reactive functional groups can be chosen such that they do not participate in, or interfere with, the reactions necessary to assemble or utilize the reactive dye analogue. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Energy donors and acceptors can also be attached by indirect means. In various embodiments, a ligand molecule (e.g., biotin) is covalently bound to the probe species. The ligand then binds to another molecules (e.g., streptavidin) molecule, which is either inherently detectable or covalently bound to a signal system, such as a fluorescent compound, or an enzyme that produces a fluorescent compound by conversion of a non-fluorescent compound. Useful enzymes of interest as labels include, for example, hydrolases, particularly phosphatases, esterases and glycosidases, hydrolases, peptidases or oxidases, and peroxidases.

In various embodiments, the donor or acceptor is attached to the inhibitor through a linkage fragment. Exemplary linkage fragments include a bond and a moiety that includes at least one heteroatom, which is formed by the reaction of two reactive functional groups of complementary reactivity. Exemplary linkage fragments of use in the conjugates of the invention include, without limitation:

$-(CH_2)_xS(CH_2)_z-$, $\quad -(CH_2)_xSC(O)NR(CH_2)_z-$,
$-(CH_2)_xSC(O)O(CH_2)_z-$, $\quad -(CH_2)_xNR(CH_2)_z-$,
$-(CH_2)_xNRC(O)(CH_2)_z-$, $\quad -(CH_2)_xNRC(O)O$
$(CH_2)_z-$, $\quad -(CH_2)_xO(CH_2)_z-$, $\quad -(CH_2)_oT\text{-PEG-}$,
$-(CH_2)_xC(O)CH_2S-$, $-S\text{-maleimide-N}-$, $-RNC$
$(O)NR-$, $-RNS(O)NR-$, $-S(O)_2NR-$, Wherein T is a member selected from S, NH, NHC(O), C(O)NH, NHC(O)O, OC(O)NH, and O. The index o is an integer from 1 to 50; and the indices t and z are independently selected from the integers from 0 to 10.

The linkage fragments can also be formed via "Click Chemistry between one component having an azide moiety and another component with an alkyne moitey. The donor or acceptor can be derivatized with either reactive functional group as can the carrier molecule.

B. Assays

B1. Binding Assays

Inhibitors with the structural and MEK-KSR complex engagement properties set forth in the present disclosure can be readily identified using assays able to detect engagement of the inhibitors with the inhibitor binding pocket of the MEK-KSR complex ("target"). Such engagement is at a statistically significant level, with a confidence level of at least 90%, or at least 95, 97, 98, 99% or greater confidence level that the assay signal represents engagement of the compound with the target, i.e., is distinguished from background. In some embodiments, controls are used to distinguish target engagement from non-specific binding. A large variety of assays indicative of engagement are known for different targets are useful to assay engagement of the inhibitors of the invention with the target.

Inhibitors engaging the target can be characterized by their effect on the activity of the the MEK-KSR complex or one of its components. Thus, a "low activity" inhibitor has an inhibitory concentration (IC50) or effective concentration (EC50) of greater than 1 μM under standard conditions. By "very low activity" is meant an IC50 or EC50 of above 100 μM under standard conditions. By "extremely low activity" is meant an IC50 or EC50 of above 1 mM under standard conditions. By "moderate activity" is meant an IC50 or EC50 of 200 nM to 1 μM under standard conditions. By "moderately high activity" is meant an IC50 or EC50 of 1 nM to 200 nM. By "high activity" is meant an IC50 or EC50 of below 1 nM under standard conditions.

The IC50 or EC50 is defined as the concentration of inhibitor at which 50% of the activity of the MEK-KSR complex or one of its components (inter alia enzyme or other protein) activity being measured is lost relative to the range of activity observed when no inhibitor is present. Activity can be measured using methods known to those of ordinary skill in the art, inter alia, by measuring any detectable product or signal produced by occurrence of an enzymatic reaction, or other activity by a protein being measured.

By "background signal" in reference to an assay for determining engagement of the target by an inhibitor is meant the signal that is recorded under standard conditions for the particular assay in the absence of a test compound, molecular scaffold, or ligand that binds to the target. Persons of ordinary skill in the art will realize that accepted methods exist and are widely available for determining background signal.

B1a. Surface Plasmon Resonance

Inhibitor engagement parameters with the target can be measured using surface plasmon resonance, for example, with a BIAcore® chip (Biacore, Japan) coated with one or more immobilized components of the MEK-KSR complex, the complex itself and the inhibitor. Surface plasmon resonance is used to characterize the microscopic association and dissociation constants of reaction between the inhibitor directed against the target. Such methods are generally described in the following references which are incorporated herein by reference. Vely F. inter alia, (2000) BIAcore® analysis to test phosphopeptide-SH2 domain interactions, *Methods in Molecular Biology*. 121:313-21; Liparoto inter alia, (1999) Biosensor analysis of the interleukin-2 receptor complex, *Journal of Molecular Recognition*. 12:316-21; Lipschultz inter alia, (2000) Experimental design for analysis of complex kinetics using surface plasmon resonance, *Methods*. 20(3):310-8; Malmqvist., (1999) BIACORE: an affinity biosensor system for characterization of biomolecular interactions, *Biochemical Society Transactions* 27:335-40; Alfthan, (1998) Surface plasmon resonance biosensors as a tool in antibody engineering, *Biosensors & Bioelectronics*. 13:653-63; Fivash inter alia, (1998) BIAcore for macromolecular interaction, *Current Opinion in Biotechnology*. 9:97-101; Price inter alia; (1998) Summary report on the ISOBM TD-4 Workshop: analysis of 56 monoclonal antibodies against the MUC1 mucin. *Tumour Biology* 19 Suppl 1:1-20; Malmqvist et al, (1997) Biomolecular interaction analysis: affinity biosensor technologies for functional analysis of proteins, *Current Opinion in Chemical Biology*. 1:378-83; O'Shannessy inter alia, (1996) Interpretation of deviations from pseudo-first-order kinetic behavior in the characterization of ligand binding by biosensor technology, *Analytical Biochemistry*. 236:275-83; Malmborg inter alia, (1995) BIAcore as a tool in antibody engineering, *Journal of Immunological Methods*. 183:7-13; Van Regenmortel, (1994) Use of biosensors to characterize recombinant proteins, Developments in Biological Standardization. 83:143-51; and O'Shannessy, (1994) Determination of kinetic rate and equilibrium binding constants for macromolecular interactions: a critique of the surface plasmon resonance literature, *Current Opinions in Biotechnology*. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (inter alia by ligand binding to the bound protein) a shift occurs in the resonance angle. This angle shift can be measured and is expressed as resonance units (RUs) such that 1000 RUs is equivalent to a change in surface protein concentration of 1 ng/mm². These changes are displayed with respect to time along the y-axis of a sensorgram, which depicts the association and dissociation of any biological reaction.

B1b. High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator.

B1c. Measuring Engagement During Screening Assays

Spectrophotometric and spectrofluorometric assays are well known in the art. Examples of such assays are described in the art. See, inter alia, Gordon, A. J. and Ford, R. A., (1972) The Chemist's Companion: A Handbook Of Practical Data, Techniques, And References, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford inter alia, (1987) Spectrophotometry and Spectrofluorometry: A Practical Approach, pp. 91-114, IRL Press Ltd.; and Bell, (1981) Spectroscopy In Biochemistry, Vol. I, pp. 155-194, CRC Press.

Spectrometric methods are of use in characterizing the compounds of the invention and complexes formed between a compound of the invention and a MEK-KSR complex in which a compound of the invention is engaged with an inhibitor binding pocket of the MEK-KSR complex. An exemplary assay is based on the transfer of energy from an energy donor member of an energy transfer pair to an energy acceptor member of the energy transfer pair.

Fluorescence resonance energy transfer (FRET) is a useful assay for detecting interaction and has been described. See, inter alia, Heim inter alia, (1996) Curr. Biol. 6:178-182; Mitra inter alia, (1996) Gene 173:13-17; and Selvin inter alia, (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman inter alia, (1997) J. Lipid Res. 38:2365-2373; Kahl inter alia, (1996) Anal. Biochem. 243: 282-283; Undenfriend inter alia, (1987) Anal. Biochem. 161:494-500). See also U.S. Pat. Nos. 4,626,513 and 4,568, 649, and European Patent No. 0,154,734. One commercially available system uses FLASHPLATE™ scintillant-coated plates (NEN Life Science Products, Boston, Mass.).

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases described assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phospho-specific antibody.

B. Methods

B1. Assays

The invention also provides methods of utilizing the compounds of the invention to detect various properties of a formation of an inhibitor-inhibitor pocket complex formed between a physiological complex of MEK-KSR and an ATP non-competitive inhibitor of MEK complexed with KSR.

In an exemplary embodiment, there is provided an assay for determining formation of an interaction interface between MEK and Kinase Suppressor of Ras (KSR) in a physiological complex between MEK and KSR, forming an inhibitor-inhibitor pocket complex, the assay comprising, spectrophotometrically querying a solution comprising a detectable inhibitor-inhibitor pocket complex MEK and KSR, generating a signal determining formation of the interaction interface.

In various embodiments, the invention provides a method of determining if an ATP non-competitive inhibitor of the invention binds preferentially to an interaction interface between MEK and Kinase Suppressor of Ras (KSR) in a physiological complex between MEK and KSR relative to a compound being queried for its binding to the interaction interface, the method comprising, contacting the interaction interface in solution with the ATP non-competitive inhibitor and the compound being queried; and determining a spectrophotometric property of the resulting solution.

The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

In an exemplary embodiment, the assay is formatted to detect formation of a physiological complex between MEK and KSR. In various embodiments, the assay is formatted to detect the binding and the affinity of binding of a small molecule of the invention to the physiological complex formed between MEK and KSR. In some embodiments, the assay confirms whether a compound bind to the interface formed by MEK and KSR in the physiological complex.

Assays based on specific binding reactions are used for detecting a wide variety of substances such as drugs, hormones, enzymes, proteins, antibodies, and infectious agents in various biological fluids and tissue samples. In general, the assays consist of an analyte, a recognition moiety for the analyte, and a detectable label. Competitive assay modalities generally utilize a binding partner in addition to these components. In an exemplary embodiment, the binding partner is a molecule that interacts with a recognition moiety to form a complex that is inherently less stable than a similar complex formed between the recognition moiety and the analyte, and is subsequently displaced by the incoming analyte.

Because the results of specific binding interactions are frequently not directly observable, a variety of fluorescent labels have been devised for determining the presence of an interaction. The fluorophores of the invention are detected by use of fluorescence spectroscopy or by the naked eye. An introduction to labels, labeling procedures and detection of labels, such as are useful in practicing the present invention, is found in Polak et al., INTRODUCTION TO IMMUNOCYTOCHEMIS-TRY, $2^{nd}$ Ed., Springer Verlag, NY, (1977), and in Haugland, HANDBOOK OF FLUORESCENT PROBES AND RESEARCH CHEMICALS, a combined handbook and catalogue Published by Molecular Probes, Inc., Eugene, OR. (1996)

In certain embodiments, the assay is a competitive assay. In practice, the components of the assay (i.e., recognition moiety, binding partner and analyte) can have substantially any chemical structure, however in a preferred embodiment, the recognition moiety, the binding partner and the analyte are members independently selected from the group consisting of small molecular bioactive agents, biomolecules and combinations thereof. When a component of the assay is a biomolecule, the biomolecule is preferably a member selected from the group consisting of haptens, antibodies, antigens, carbohydrates, nucleic acids, peptides, enzymes and receptors.

In a competitive assay format, one or more than one of the components is labeled with a compound of the invention. For example, in one embodiment, the binding partner is labeled with a compound of the invention and its displacement from an immobilized recognition moiety is detected by the appearance of fluorescence in a liquid phase of the assay. In another competitive assay format, an immobilized enzyme is complexed with a substrate conjugated to a compound of the invention. The complex is then contacted with a putative antagonist. The displacement of fluorescence from the immobilized enzyme into a liquid phase of the assay is indicative of displacement of the substrate by the putative antagonist. These embodiments are offered by way of example only and it will be plain to one of skill in the art that many other competitive assay formats can utilize and benefit from the compounds of the invention.

In addition to ascertaining a binding event, it is frequently desired to quantitate the magnitude of the affinity between two or more binding partners. Thus, it is also within the scope of the present invention to utilize the compounds disclosed herein as a support for such assays.

Most typically, the amount of analyte present is measured by quantitating the amount of label fixed to a binding partner, analyte or recognition moiety following a binding event. Means of detecting and quantitating fluorescent labels are well known to those of skill in the art.

In another preferred embodiment, the affinity between two or more assay constituents is measured by quantifying a population selected from the group consisting of the analyte-recognition moiety complex, free analyte, free binding partner, binding partner-recognition moiety complex and combinations thereof.

The format of an assay for extracting affinity data for two molecules can be understood by reference to an embodiment in which a ligand that is known to bind to a receptor is displaced by an antagonist to that receptor. Other variations on this format will be apparent to those of skill in the art. The competitive format is well known to those of skill in the art. See, for example, U.S. Pat. Nos. 3,654,090 and 3,850,752.

The binding of an antagonist to a receptor can be assayed by a competitive binding method using a ligand for that receptor and the antagonist. The binding assay can be performed, for example, in a 96-well filtration plate assembly (Millipore Corporation, Bedford, Mass.). One of the three binding partners (i.e., the ligand, antagonist or receptor) is generally bound to the well or to a particulate material contained within the well.

The assays of the invention can be practiced with some or all components in solution. Alternatively, one or more components can be substantially insoluble in the assay medium. In a preferred embodiment, one or more members selected from the group consisting of the recognition moiety, the binding partner and the analyte are attached to a surface, i.e., a solid support. Useful surfaces include, but are not limited to, glass or polymeric beads, sheets, fibers, membranes (e.g. nylon, nitrocellulose), slides (e.g. glass, quartz) and the like.

Following the displacement of the binding partner from the binding partner-recognition moiety complex, the remaining steps of the assay can be performed on the mixture that is formed by the displacement or one or more of the components of the mixture can be removed. In a preferred embodiment, the method further includes separating the free binding partner from a member of the group consisting of the recognition-binding partner pair, the analyte-recognition moiety pair and combinations thereof.

In another embodiment, the present invention provides methods of using the compounds described herein to detect an analyte in a sample, inter alia, a physiological complex between MEK and KSR.

In a further aspect, there is provided a method for determining the presence or absence of analyte in a sample. The method includes: a) contacting the sample with a compound of the invention; b) incubating the labeled sample for a sufficient amount of time to allow the peroxide to react with the fluorogenic compound to produce a fluorescent product; c) illuminating the sample from b) with light of an appropriate wavelength; and d) observing the presence or absence of fluorescence from the sample, whereby the presence or absence of the analyte in the sample is determined.

In other embodiments, the compounds of the invention are utilized to stain a sample to give a detectable optical response under desired conditions by first preparing a dye solution comprising a dye compound described above, at a concentration sufficient to yield a detectable optical response under the desired conditions. Specifically the methods for staining a sample include: a) contacting the sample with a compound of the invention; b) incubating the labeled sample for a sufficient amount of time to allow reaction between the compound and the sample; c) illuminating the sample from b) with light of an appropriate wavelength to excite the fluorophore; and d) detecting fluorescence in the sample.

For example, a compound of the invention is used to monitor specific components of the sample with respect to their spatial and temporal distribution in the sample.

In one embodiment, the compounds of the present invention are cell permeant, and can be introduced into the sample cell or cells by incubation of the cell or cells in a solution containing the compounds. Any other method of introducing the compound into the sample cell, such as microinjection of a solution of the fluorogen, scrape loading techniques (short mechanical disruption of the plasma membrane where the plasma membrane is peeled away from the cytoplasm, the dye is perfused through the sample and the plasma membrane reassembled), or patch clamp methods (where an opening is maintained in the plasma membrane for long periods) can be used. Any other treatment that will permeabilize the plasma membrane, such as electroporation, shock treatments or high extracellular ATP can be used to accelerate introduction of the fluorogen into the cellular cytoplasm. Microinjection of a fluorogen solution is of particular use when analysis of a single cell is desired, within a colony of other sample cells.

B2. Sample Preparation

The end user will determine the choice of the sample and the way in which the sample is prepared. The sample includes, without limitation, any biological derived material or aqueous solution that is thought or known to contain a target analyte.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, beta-cells, hepatocytes, and neurons.

Various buffers may be used that do not interfere with the generation of a fluorescent signal by conversion of the fluorogen. These buffers include PBS, Tris, MOPS, HEPES, phosphate, etc. The pH will vary depending upon the particular monooxygenase being assayed, generally being in the range of about 7.0-7.5.

B3. Methods of Treatment

In some embodiments, the method comprises administering to a patient in need thereof a therapeutically effective amount of a compound provided herein, a prodrug, a hydrate, a solvate, a metabolite or a pharmaceutically acceptable salt thereof.

In some embodiments, the method further comprises co-administering an additional therapeutic agent to the patient. Example additional therapeutic agents include, but are not limited to antibiotic agents, antiviral agents, antifungal agents, anesthetics (e.g., for use in combination with a surgical procedure), anti-inflammatory agents, anti-allergic agents, and chemotherapeutic agents. In some embodiments, the additional therapeutic agent comprises radiation therapy. In some embodiments, a compound provided herein is administered in combination with an additional therapeutic agent during a surgical procedure.

In various embodiments, the method includes co-administering to the subject a compound of of the invention and another chemotherapeutic agent of known utility in treating the disease. In various embodiments, this combination therapy provides synergistic effects in treating the disease.

In some embodiments, the additional therapeutic agent is administered simultaneously with a compound provided herein. In some embodiments, the additional therapeutic agent is administered after administration of a compound provided herein. In some embodiments, the additional therapeutic agent is administered prior to administration of a compound provided herein.

In some embodiments, the additional therapeutic agent is selected from the group consisting of an antibiotic agent, an antiviral agent, an antifungal agent, an anesthetic, or an anti-inflammatory agent (e.g., steroidal and non-steroidal anti-inflammatories), and an anti-allergic agent. Examples of suitable medicaments include, but are not limited to, coriticosteroids such as dexamethasone or prednisone, aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

In some embodiments, the additional therapeutic agent is a chemotherapeutic agent. In some embodiments, the additional therapeutic agent is a kinase inhibitor (e.g., KSR, MEK, Bcr-Abl, Flt-3, EGFR, HER2, JAK, c-MET, VEGFR, PDGFR, PI3K, cKit, IGF-1R, RAF, FAK, Akt mTOR, PIM, and AKT). For example, the additional therapeutic agent can be a MEK inhibitor or a KSR inhibitor. In some embodiments, the additional therapeutic agent is selected from the group consisting of a cytostatic agent, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, tipifarnib, gefitinib, erlotinib hydrochloride, antibodies to EGFR, imatinib mesylate, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, epirubicin, idarubicin, mithramycin, deoxycoformycin, mitomycin-C, L-asparaginase, teniposide, $17\alpha$-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, porfimer, erbitux, thiotepa, altretamine, trastuzumab, fulvestrant, exemestane, rituximab, alemtuzumab, clofarabine, cladribine, aphidicolin, sunitinib, dasatinib, tezacitabine, triapine, didox, trimidox, amidox, bendamustine, ofatumumab, and idelalisib.

In some embodiments, the disease is cancer. In some embodiments, the cancer is selected from the group consisting of breast cancer, prostate cancer, esophageal cancer, colon cancer, endometrial cancer, brain cancer, bladder cancer, skin cancer, cancer of the uterus, cancer of the ovary, lung cancer, pancreatic cancer, renal cancer, prostate cancer, gastric cancer, stomach cancer, and hematological cancer. In some embodiments, the lung cancer is selected from the group consisting of non-small cell lung cancer, small cell lung cancer, and lung carcinoid tumor.

In some embodiments, the hematological cancer is selected from the group consisting of leukemia, lymphoma, and multiple myeloma.

In some embodiments, the hematological cancer is acute myeloblastic leukemia, chronic myeloid leukemia, B cell lymphoma, chronic lymphocytic leukemia (CLL), Non-Hodgkins lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma.

In some embodiments, the leukemia is selected from the group consisting of acute lymphoblastic leukemia (ALL), chronic lymphocytic leukemia (CLL), acute myelogenous leukemia (AML), chronic myeloid leukemia (CML), hairy cell leukemia, T-cell prolymphocytic leukemia, juvenile myelomonocytic leukemia, and follicular lymphoma.

In some embodiments, the lymphoma is Hodgkin's lymphoma or non-Hodgkin's lymphoma (NHL).

In some embodiments, the non-Hodgkin lymphoma (NHL) is selected from relapsed NHL, refractory NHL, and recurrent follicular NHL.

The following Examples are offered to illustrate exemplary embodiments of the invention and do not define or limit its scope.

EXAMPLES

Example 1

General Chemical Methods. All solvents were purchased from Sigma-Aldrich and were used as received; anhydrous solvents were used for chemical reactions, and HPLC grade solvents were used for aqueous work-ups, recrystallizations and chromatography. Reagents were purchased from various vendors and were used as received. Reactions were run as described in the individual procedures using standard double manifold and syringe techniques. Glassware was dried by baking in an oven at 130° C. for 12 h prior to use, or was flame-dried. The pH of aqueous solutions was estimated using pH paper. Vacuum filtrations were carried out using a house vacuum line (~100 torr). In the individual procedures, the phrases "concentration under vacuum" and "concentrated to dryness" mean that solvent was removed on a rotary evaporator using a diaphragm pump (with an automatic vacuum regulator) and remaining traces of volatiles were removed on a high-vacuum (<1 torr) oil pump. Unless specified otherwise, the term "flask" refers to the round-bottomed variety. Reactions were monitored by TLC using EMD silica gel 60 $F_{254}$ (250 μm) glass-backed plates (visualized by UV fluorescence quenching and stained with basic KMnO$_4$ solution) and by liquid chromatography-tandem mass spectrometry (LC-MS). Analysis by reverse-phase LC-MS was carried out on a Waters Acquity I-Class UPLC system, with a C$_{18}$ column (2.1×30 mm; 1.7 μm particle size), heated at 50° C., eluted at 0.6 mL/min, and using a 3 min linear gradient method with a mobile phase consisting of water/acetonitrile (0.1% v/v formic acid added to each): 95:5→1:99(0-2.5 min), then 1:99(2.5-3 min). Sample runs were monitored using alternating positive/negative electrospray ionization (50-1000 amu) and UV detection at 254 nm. Automated preparative normal- and reverse-phase chromatography was carried out with an Interchim PuriFlash 450 purification system with a diode array detector (runs were monitored at 220-400 nm). Pre-packed silica gel cartridges (12, 25 and 40 g; 15 μm particle size) were employed for normal-$_{phase}$ (silica gel) chromatography, eluting at 20-30 mL/min. Preparative reverse-phase chromatography was carried out with an Agilent 1260 Infinity using a C$_{18}$ column (30×100 mm; 5 μm particle size) with a multiwavelength detector, eluting at 40 mL/min with a pressure limit of 200 bar; crude samples were injected with an autosampler, typically in a 90:10 mixture of MeOH/DMSO (1.5 mL/injection). Carbon-decoupled $^1$H NMR spectra were recorded at 400 MHz on a Bruker spectrometer and are reported in ppm using the residual solvent signal (dimethylsulfoxide-d$_6$=2.50 ppm; methanol-d4=3.31 ppm) as an internal standard. Data are reported as: {(shift), [(s=singlet, d=doublet, dd=doublet of doublets, ddd=doublet of a doublet of doublets, t=triplet, dt=doublet of triplets, q=quartet, m=multiplet, br=broad, ap=apparent), (J=coupling constant in Hz), (integration)]}. Proton-decoupled $^{13}$C NMR spectra were recorded at 100 MHz on a Bruker spectrometer and are reported in ppm using the residual solvent signal (dimethylsulfoxide-d6=39.5 ppm) as an internal standard. $^{19}$F NMR spectra were recorded at 376 MHz on a Bruker spectrometer and are reported in ppm using added CFCl$_3$ (0.00 ppm) as an internal standard; compounds with only one signal were integrated relative to a known amount of the internal standard.

Trametinib (1)

52

-continued

8a

8b

8

Synthetic route to 8 from trametinib (1).

(8)

1-(3-Aminophenyl)-3-cyclopropyl-5-((2-fluoro-4-iodophenyl)amino)-6,8-dimethylpyrido[4,3-d]py-rimidine-2,4,7(1H,3H,6H)-trione (8)

To a solution of trametinib (1; 250 mg, 0.406 mmol), 4-(dimethylamino)pyridine (DMAP; 99.2 mg, 0.812 mmol) and DMF (dimethylformamide; 3 mL), in an 8 mL vial, was added a solution of di-tert-butyl dicarbonate (Boc$_2$O; 266 mg, 1.22 mmol) and DMF (1.5 mL) dropwise over 1 min. The vial was sealed under Ar and the solution was stirred for 1 h. The solution was transferred to a 50 mL flask and concentrated to dryness. The remaining solid (2a) was dissolved in MeOH (3 mL) and then an aqueous solution of KOH (2.0 mL, 1.0 M solution, 2.0 mmol) was added. The solution was stirred for 4 h, then diluted with brine (30 mL) and extracted with CH$_2$Cl$_2$ (3×30 mL). The organic extracts were pooled, dried (Na$_2$SO$_4$), filtered and concentrated to dryness. The remaining solid (2b) was dissolved in trifluoroacetic acid (TFA; 3.0 mL, 39 mmol). The solution was stirred for 30 min and then concentrated to dryness from toluene (3×3 mL). The remaining material was partitioned between CH$_2$Cl$_2$ (50 mL) and saturated NaHCO$_3$ solution (50 mL), and transferred to a separatory funnel. The layers were separated and the aqueous phase was extracted with CH$_2$Cl$_2$ (25 mL). The organic extracts were pooled, dried (Na$_2$SO$_4$), filtered and concentrated to dryness. The remaining solid was purified by silica gel chromatography (25 g cartridge), eluting at 25 mL/min and using a linear gradient of CH$_2$Cl$_2$/MeOH: 100:0→90:10 over 37 column volumes to yield 189 mg (81% over 3 steps) of the title compound as an off-white solid: 1H NMR (400 MHz, DMSO-d6) δ 11.06 (s, 1H), 7.78 (dd, J=10.3, 2.0 Hz, 1H), 7.54 (dd, J=8.6, 1.0 Hz, 1H), 7.05 (t, J=7.8 Hz, 1H), 6.90 (t, J=8.7 Hz, 1H), 6.50-6.59 (m, 2H), 6.46 (dd, J=7.8, 1.0 Hz, 1H), 5.25 (s, 2H), 3.07 (s, 3H), 2.61 (tt, J=7.2, 3.7 Hz, 1H), 1.35 (s, 3H), 0.89-1.00 (m, 2H), 0.59-0.69 (m, 2H); $^{19}$F NMR (376 MHz, DMSO-d$_6$) δ –124.0-–123.9 (m, 1F); LC-MS (ESI+) m/z: [M+H]$^+$ Calcd for C$_{24}$H$_{22}$FIN$_5$O$_3$ 574.1; Found 574.3.

(2)

Trametiglue

N-(3-(3-Cyclopropyl-5-((2-fluoro-4-iodophenyl)amino)-6,8-dimethyl-2,4,7-trioxo-3,4,6,7-tetrahydro-pyrido[4,3-d]pyrimidin-1(2H)-yl)phenyl)methylami-nosulfonamide (2; trametiglue)

To a mixture of 8 (25.0 mg, 0.044 mmol) and CH$_2$Cl$_2$ (0.6 mL), in a 4 mL vial, was added methylsulfamoyl chloride (4.5 µL, 0.052 mmol), followed by pyridine (11.0 µL, 0.136 mmol). The reaction was stirred for 6 h and then was purified directly by silica gel chromatography (25 g cartridge), eluting at 25 mL/min and using a linear gradient of: 100:0→90:10 CH$_2$Cl$_2$/MeOH over column 30 volumes to yield 16.4 mg (56%) of the title compound as an off-white solid: 1H NMR (400 MHz, DMSO-d$_6$) δ 11.09 (s, 1H), 9.83 (s, 1H), 7.79 (d, J=10.3 Hz, 1H), 7.55 (d, J=8.1 Hz, 1H), 7.29-7.46 (m, 2H), 7.19 (d, J=8.3 Hz, 1H), 7.11 (s, 1H), 7.02 (d, J=7.6 Hz, 1H), 6.92 (t, J=8.6 Hz, 1H), 3.07 (s, 3H), 2.58-2.67 (m, 1H), 2.43 (d, J=4.9 Hz, 3H), 1.24 (s, 3H), 0.95 (d, J=5.9 Hz, 2H), 0.66 (br s, 2H); $^{19}$F NMR (376 MHz, DMSO-d$_6$) δ –124.0-–123.8 (m, 1F); LC-MS (ESI+) m/z: [M+H]$^+$ Calcd for C$_{25}$H$_{25}$FIN$_6$O$_5$S 667.1; Found 667.2.

(3)

N-(3-(3-Cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)-2,2,2-trif-
luoroacetamide (3)

To a mixture of 8 (25.0 mg, 0.044 mmol) and $CH_2Cl_2$ (0.6 mL), in a 4 mL vial, was added trifluoroacetic anhydride (7.5 µL, 0.054 mmol), followed by pyridine (11.0 µL, 0.136 mmol). The reaction was stirred for 6 h and then was purified directly by silica gel chromatography (25 g cartridge), eluting at 25 mL/min and using a linear gradient of: 100:0→90:10 $CH_2Cl_2$/MeOH over 30 column volumes to yield 18.3 mg (62%) of the title compound as an off-white solid: $^1H$ NMR (400 MHz, DMSO-$d_6$) δ 11.42 (br s, 1H), 11.06 (br s, 1H), 7.79 (dd, J=10.3, 1.7 Hz, 1H), 7.66-7.74 (m, 2H), 7.55 (dd, J=8.3, 1.2 Hz, 1H), 7.49 (t, J=8.1 Hz, 1H), 7.25 (dd, J=8.1, 1.0 Hz, 1H), 6.93 (t, J=8.7 Hz, 1H), 3.08 (s, 3H), 2.62 (tt, J=7.1, 3.8 Hz, 1H), 1.25 (s, 3H), 0.95 (q, J=7.1 Hz, 2H), 0.63-0.71 (m, 2H); $^{19}F$ NMR (376 MHz, DMSO-$d_6$) δ −124.0–−123.8 (m, 1F); LC-MS (ESI+) m/z: $[M+H]^+$ Calcd for $C_{26}H_{21}F_4IN_5O_4$ 670.1; Found 670.1.

N-(3-(3-Cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)-2,2,3,3,3-
pentafluoropropanamide 2,2,2-trifluoroacetate (4)

To a mixture of 8 (50.0 mg, 0.087 mmol) and DMF (1.5 mL), in an 8 mL vial, was added pyridine (8.5 µL, 0.105 mmol), followed by 2,2,3,3,3-pentafluoropropanoic anhydride (19.0 µL, 0.097 mmol). The reaction was stirred for 16 h and then was purified directly by reverse-phase chromatography, eluting at 40 mL/min and using a linear gradient of $H_2O$ (with 0.1% TFA)/MeCN (with 0.1% TFA): 90:10→1:99 over 20 minutes to yield 39.8 mg (56%) of the title compound as a white solid: $^1H$ NMR (400 MHz, DMSO-$d_6$) δ 11.47 (s, 1H), 11.07 (s, 1H), 7.79 (dd, J=10.3, 2.0 Hz, 1H), 7.66-7.74 (m, 2H), 7.55 (dd, J=8.4, 1.1 Hz, 1H), 7.50 (t, J=8.1 Hz, 1H), 7.27 (ddd, J=8.1, 2.0, 1.0 Hz, 1H), 6.93 (t, J=8.7 Hz, 1H), 3.08 (s, 3H), 2.61 (tt, J=7.2, 3.7 Hz, 1H), 1.25 (s, 3H), 0.95 (q, J=7.0 Hz, 2H), 0.62-0.73 (m, 2H); $^{19}F$ NMR (376 MHz, DMSO-$d_6$) δ −74.1 (s, 3F), −81.7–−81.5 (m, 3F), −120.7–−120.5 (m, 2F), −124.0–−123.8 (m, 1F); LC-MS (ESI+) m/z: $[M+H]^+$ Calcd for $C_{27}H_{21}F_6IN_5O_4$ 720.1; Found 720.2.

N-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)cyclopro-
pylaminosulfonamide (5)

To a mixture of 8 (50.0 mg, 0.087 mmol) and $CH_2Cl_2$ (1.5 mL), in an 8 mL vial, was added triethylamine (15.0 µL, 0.108 mmol), followed by cyclopropylsulfamoyl chloride (10.0 µL, mmol). The reaction was stirred for 16 h and then the product was isolated by vacuum filtration; washed solid with $CH_2Cl_2$. Air-drying yielded 47.0 mg (78%) of the title compound as a white solid: $^1H$ NMR (400 MHz, DMSO-$d_6$) δ 11.09 (s, 1H), 10.01 (s, 1H), 7.91 (s, 1H), 7.79 (d, J=10.5 Hz, 1H), 7.55 (d, J=8.6 Hz, 1H), 7.30-7.37 (m, 1H), 7.14 (d, J=8.6 Hz, 1H), 7.11 (s, 1H), 6.98 (d, J=8.3 Hz, 1H), 6.92 (t, J=8.6 Hz, 1H), 3.07 (s, 3H), 2.59-2.66 (m, 1H), 2.22-2.29 (m, 1H), 1.24 (s, 3H), 0.95 (d, J=6.8 Hz, 2H), 0.65 (br s, 2H), 0.49 (m, J=5.1 Hz, 2H), 0.34 (br s, 2H); $^{19}F$ NMR (376 MHz, DMSO-$d_6$) δ −123.96–−123.81 (m, 1F); LC-MS (ESI+) m/z: $[M+H]^+$ Calcd for $C_{27}H_{27}FIN_6O_5S$ 693.1; Found 693.3.

N-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)-N'-ethyl
(methyl)sulfonamide 2,2,2-trifluoroacetate (6)

To a mixture of 8 (50.0 mg, 0.087 mmol) and pyridine (0.5 mL), in a 4 mL vial, was added ethyl(methyl)sulfamoyl chloride (24.0 μL, 0.204 mmol). The reaction was heated at 50° C. and stirred for 16 h. The reaction was cooled to room temperature, diluted with EtOAc (50 mL) and water (50 mL), and transferred to a separatory funnel. The layers were separated and the organic phase was washed with water (50 mL) and brine (2×50 mL), dried (Na$_2$SO$_4$), filtered and concentrated to dryness. The remaining residue was purified by reverse-phase chromatography, eluting at 40 mL/min and using a linear gradient of H$_2$O (with 0.1% TFA)/MeCN (with 0.1% TFA): 90:10→1:99 over 20 minutes to yield 22.1 mg (32%) of the title compound as a white solid: $^1$H NMR (400 MHz, DMSO-d$_6$) δ 11.07 (s, 1H), 10.00 (s, 1H), 7.78 (dd, J=10.3, 2.0 Hz, 1H), 7.55 (dd, J=8.3, 1.2 Hz, 1H), 7.32-7.41 (m, 1H), 7.10-7.19 (m, 2H), 7.02-7.08 (m, 1H), 6.91 (t, J=8.7 Hz, 1H), 3.02-3.16 (m, 5H), 2.67 (s, 3H), 2.58-2.65 (m, 1H), 1.23 (s, 3H), 0.89-1.06 (m, 5H), 0.62-0.70 (m, 2H); $^{19}$F NMR (376 MHz, DMSO-d$_6$) δ −73.8 (s, 3F), −123.9 (t, J=9.2 Hz, 1F); LC-MS (ESI+) m/z: [M+H]$^+$ Calcd for C$_{27}$H$_{29}$FIN$_6$O$_5$S 695.1; Found 695.3.

3-Fluoropyrrolidine-1-sulfonyl chloride (7a)

To a mixture of 3-fluoropyrrolidine hydrochloride (200 mg, 1.59 mmol) and CH$_2$Cl$_2$ (4 mL) was added DIPEA (555 μL, 3.19 mmol). The mixture was cooled to −30° C. (small chunks of dry ice/2-PrOH) and sulfuryl chloride (390 μL, 4.81 mmol) was added dropwise over 5 min. The reaction was allowed to warm to room temperature over 2.5 h and was stirred for an additional 20 h. The reaction was poured into a mixture of 1 M HCl (20 mL) and CH$_2$Cl$_2$ (20 mL), and transferred to a separatory funnel. The layers were separated and the aqueous layer was extracted with CH$_2$Cl$_2$ (20 mL). The organic extracts were pooled, washed with 1 M HCl (20 mL), dried (MgSO$_4$) and filtered. Concentration under vacuum gave 212 mg of a white solid, which was used without further purification (see 7).

N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-3-fluoropyrrolidine-1-sulfonamide (7)

A 4 mL vial was charged with 8 (50.0 mg, 0.087 mmol), 3-fluoropyrrolidine-1-sulfonyl chloride (7a; 97.9 mg, 0.522 mmol) and pyridine (0.5 mL). The reaction mixture was heated at 50° C. and stirred for 18 h. The reaction was cooled to room temperature, diluted with EtOAc (50 mL) and water (50 mL), and transferred to a separatory funnel. The layers were separated and the organic phase was washed with water (50 mL) and brine (2×50 mL), dried (Na$_2$SO$_4$), filtered and concentrated to dryness. The remaining material was purified by silica gel chromatography (25 g cartridge), eluting at 25 mL/min and using a linear gradient of CH$_2$Cl$_2$/EtOAc: 100:0→20:80 over 35 column volumes to yield 24.6 mg (39%) of the title compound as an off-white solid: $^1$H NMR (400 MHz, DMSO-d$_6$) δ 11.07 (s, 1H), 10.10 (s, 1H), 7.78 (dd, J=10.4, 1.8 Hz, 1H), 7.55 (dd, J=8.3, 1.2 Hz, 1H), 7.33-7.40 (m, 1H), 7.15-7.24 (m, 2H), 7.03-7.10 (m, 1H), 6.92 (t, J=8.7 Hz, 1H), 3.22-3.30 (m, 1H), 3.07 (s, 3H), 2.57-2.65 (m, 1H), 1.98 (m, J=7.8 Hz, 2H), 1.22 (s, 3H), 0.91-1.00 (m, 2H), 0.63-0.70 (m, 2H), (signals corresponding to four protons overlap with the water peak); $^{19}$F NMR (376 MHz, DMSO-d$_6$) δ −124.01--123.77 (m, 1F), −174.42--173.93 (m, 1F); LC-MS (ESI+) m/z: [M+H]$^+$ Calcd for C$_{28}$H$_{28}$F$_2$IN$_6$O$_5$S 725.1;

1-(3-(3-Cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-3-methylurea 2,2,2-trifluoroacetate (9)

To a mixture of 8 (50.0 mg, 0.087 mmol) and DMF (1 mL), in an 8 mL vial, was added pyridine (8.5 μL, 0.105 mmol), followed by a solution of methylcarbamic chloride (9.0 mg, 0.096 mmol) and DMF (0.5 mL). The reaction was stirred for 16 h and then was purified directly by reverse-phase chromatography, eluting at 40 mL/min and using a linear gradient of H$_2$O (with 0.1% TFA)/MeCN (with 0.1% TFA): 90:10→1:99 over 20 minutes to yield 14.6 mg (23%) of the title compound as an off-white solid: $^1$H NMR (400 MHz, DMSO-d$_6$) δ 11.08 (s, 1H), 8.70 (s, 1H), 7.78 (dd, J=10.3, 2.0 Hz, 1H), 7.55 (d, J=9.8 Hz, 1H), 7.47 (t, J=2.0 Hz, 1H), 7.33-7.40 (m, 1H), 7.27 (t, J=8.1 Hz, 1H), 6.84-6.97 (m, 2H), 6.03 (m, J=4.6 Hz, 1H), 3.07 (s, 3H), 2.57-2.66 (m, 4H), 1.28 (s, 3H), 0.90-1.00 (m, 2H), 0.62-0.70 (m, 2H); $^{19}$F NMR (376 MHz, DMSO-d$_6$) δ −73.2 (s, 3F), −124.0−−123.8 (m, 1F); LC-MS (ESI+) m/z: [M+H]$^+$ Calcd for C$_{26}$H$_{25}$FIN$_6$O$_4$ 631.1; Found 631.2.

N-(3-(3-Cyclopropyl-5-((2-fluoro-4-iodophenyl)amino)-6,8-dimethyl-2,4,7-trioxo-3,4,6,7-tetrahydro-pyrido[4,3-d]pyrimidin-1(2H)-yl)phenyl)propiona-mide 2,2,2-trifluoroacetate (10)

To a mixture of 8 (50.0 mg, 0.087 mmol) and DMF (1.5 mL), in an 8 mL vial, was added pyridine (8.5 µL, 0.105 mmol), followed by propionyl chloride (8.5 µL, 0.097 mmol). The reaction was stirred for 16 h and then was purified directly by reverse-phase chromatography, eluting at 40 mL/min and using a linear gradient of H$_2$O (with 0.1% TFA)/MeCN (with 0.1% TFA): 90:10→1:99 over 20 minutes to yield 20.9 mg (33%) of the title compound as a white solid: $^1$H NMR (400 MHz, DMSO-d$_6$) δ 11.07 (s, 1H), 10.02 (s, 1H), 7.78 (dd, J=10.3, 2.0 Hz, 1H), 7.64 (t, J=2.0 Hz, 1H), 7.59 (d, J=8.3 Hz, 1H), 7.55 (dd, J=8.4, 1.1 Hz, 1H), 7.35 (t, J=8.1 Hz, 1H), 7.02 (ddd, J=8.0, 2.0, 1.0 Hz, 1H), 6.92 (t, J=8.7 Hz, 1H), 3.07 (s, 3H), 2.58-2.65 (m, 1H), 2.32 (q, J=7.6 Hz, 2H), 1.25 (s, 3H), 1.07 (t, J=7.6 Hz, 3H), 0.90-0.99 (m, 2H), 0.62-0.70 (m, 2H); $^{19}$F NMR (376 MHz, DMSO-d$_6$) δ −74.3 (s, 3F), −124.0−−123.8 (m, 1F); LC-MS (ESI+) m/z: [M+H]$^+$ Calcd for C$_{27}$H$_{26}$FIN$_5$O$_4$ 630.1; Found 630.3.

N-(3-(3-Cyclopropyl-5-((2-fluoro-4-iodophenyl)amino)-6,8-dimethyl-2,4,7-trioxo-3,4,6,7-tetrahydro-pyrido[4,3-d]pyrimidin-1(2H)-yl)phenyl)pivalamide 2,2,2-trifluoroacetate (11)

To a mixture of 8 (50.0 mg, 0.087 mmol) and CH$_2$Cl$_2$ (1.5 mL), in an 8 mL vial, was added triethylamine (15.0 µL, 0.108 mmol), followed by pivaloyl chloride (12.0 µL, 0.097 mmol). The reaction was stirred for 16 h and then was concentrated to dryness. The remaining residue was purified by reverse-phase chromatography, eluting at 40 mL/min and using a linear gradient of H$_2$O (with 0.1% TFA)/MeCN (with 0.1% TFA): 90:10→1:99 over 20 minutes to yield 25.0 mg (38%) of the title compound as a white solid: 1H NMR (400 MHz, DMSO-d$_6$) δ 11.08 (s, 1H), 9.37 (s, 1H), 7.78 (dd, J=10.3, 2.0 Hz, 1H), 7.63-7.70 (m, 2H), 7.55 (dd, J=8.3, 1.2 Hz, 1H), 7.35 (t, J=8.3 Hz, 1H), 7.04 (dt, J=7.6, 1.2 Hz, 1H), 6.92 (t, J=8.6 Hz, 1H), 3.08 (s, 3H), 2.62 (tt, J=7.2, 3.7 Hz, 1H), 1.27 (s, 3H), 1.22 (s, 9H), 0.90-1.00 (m, 2H), 0.62-0.71 (m, 2H); $^{19}$F NMR (376 MHz, DMSO-d$_6$) δ −74.4 (s, 3F), −123.9−−123.8 (m, 1F); LC-MS (ESI+) m/z: [M+H]$^+$ Calcd for C$_{29}$H$_{30}$FIN$_5$O$_4$ 658.1; Found 658.4.

N-(3-(3-Cyclopropyl-5-((2-fluoro-4-iodophenyl)amino)-6,8-dimethyl-2,4,7-trioxo-3,4,6,7-tetrahydro-pyrido[4,3-d]pyrimidin-1(2H)-yl)phenyl)-2,2,3,3,4,4-heptafluorobutanamide 2,2,2-trifluoroacetate (12)

To a mixture of 8 (50.0 mg, 0.087 mmol) and DMF (1.5 mL), in an 8 mL vial, was added pyridine (8.5 µL, 0.105 mmol), followed by 2,2,3,3,4,4-heptafluorobutanoic anhydride (24.0 µL, 0.097 mmol). The reaction was stirred for 16 h and then was purified directly by reverse-phase chromatography, eluting at 40 mL/min and using a linear gradient of H$_2$O (with 0.1% TFA)/MeCN (with 0.1% TFA): 90:10→1:99 over 20 minutes to yield 48.3 mg (64%) of the title compound as a white solid: $^1$H NMR (400 MHz, DMSO-d$_6$) δ 11.46 (s, 1H), 11.07 (s, 1H), 7.78 (dd, J=10.4, 1.8 Hz, 1H), 7.71 (d, J=8.1 Hz, 1H), 7.67 (t, J=1.8 Hz, 1H), 7.55 (d, J=8.3 Hz, 1H), 7.50 (t, J=8.1 Hz, 1H), 7.28 (dd, J=8.1, 1.0 Hz, 1H), 6.92 (t, J=8.7 Hz, 1H), 3.08 (s, 3H), 2.61 (tt, J=7.1, 3.6 Hz, 1H), 1.25 (s, 3H), 0.91-0.99 (m, 2H), 0.63-0.71 (m, 2H); $^{19}$F NMR (376 MHz, DMSO-d$_6$) δ −73.9 (s, 3F), −79.6 (t, J=9.2 Hz, 3F), −118.7−−118.4 (m, 2F), −124.0−−123.8 (m, 1F), −126.0−−125.9 (m, 2F); LC-MS (ESI+) m/z: [M+H]$^+$ Calcd for C$_{28}$H$_{21}$F$_8$IN$_5$O$_4$ 770.1; Found 770.3.

1-(3-(3-Cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)guanidine
2,2,2-trifluoroacetate (13)

To a mixture of 8 (50.0 mg, 0.087 mmol), cyanamide (4.0 mg, 0.095 mmol) and 1,4-dioxane (0.5 mL), in an 8 mL vial, was added hydrogen chloride (25.0 μL, 4.0 M solution in 1,4-dioxane, 0.100 mmol). The reaction was heated at 80° C. and stirred for 6 h. The reaction was cooled to room temperature and then triethylamine (20 μL, 0.14 mmol) was added. The solution was concentrated to dryness and the remaining material was purified by reverse-phase chromatography, eluting at 40 mL/min and using a linear gradient of H$_2$O (with 0.1% TFA)/MeCN (with 0.1% TFA): 90:10→1:99 over 20 minutes to yield 31.7 mg (51%) of the title compound as a white solid: $^1$H NMR (400 MHz, DMSO-d$_6$) δ 11.00 (s, 1H), 9.92 (s, 1H), 7.79 (dd, J=10.3, 2.0 Hz, 1H), 7.46-7.59 (m, 6H), 7.27-7.36 (m, 2H), 7.23 (t, J=2.0 Hz, 1H), 6.94 (t, J=8.6 Hz, 1H), 3.08 (s, 3H), 2.62 (tt, J=7.2, 3.7 Hz, 1H), 1.26 (s, 3H), 0.96 (q, J=6.4 Hz, 2H), 0.63-0.72 (m, 2H); $^{19}$F NMR (376 MHz, DMSO-d$_6$) δ −73.7 (s, 3F), −123.9--123.8 (m, 1F); LC-MS (ESI+) m/z: [M+H]$^+$ Calcd for C$_{25}$H$_{24}$FIN$_7$O$_3$ 616.1; Found 616.2.

1-Cyclopropyl-3-(3-(3-cyclopropyl-5-((2-fluoro-4-
iodophenyl)amino)-6,8-dimethyl-2,4,7-trioxo-3,4,6,
7-tetrahydropyrido[4,3-d]pyrimidin-1(2H)-yl)phe-
nyl)urea 2,2,2-trifluoroacetate (14)

To a −5° C. (ice/brine) solution of CDI (24.5 mg, 0.151 mmol) and CH$_2$Cl$_2$ (0.5 mL), in an 8 mL vial, was added 8

(80.0 mg, 0.140 mmol) as a suspension in a 50:50 mixture of DMF/CH$_2$Cl$_2$ (2 mL), over 3 min. The reaction was allowed to warm to room temperature overnight and was stirred for 12 h. Cyclopropyl amine (10.5 μL, 0.152 mmol) was added and the reaction was stirred for an additional 5 h. Concentration under vacuum left a solid, which was purified by reverse-phase chromatography, eluting at 40 mL/min and using a linear gradient of H$_2$O (with 0.1% TFA)/MeCN (with 0.1% TFA): 90:10→1:99 over 20 minutes to yield 27.5 mg (26%) of the title compound as an off-white solid: $^1$H NMR (400 MHz, DMSO-d$_6$) δ 11.08 (s, 1H), 8.51 (s, 1H), 7.78 (d, J=10.5 Hz, 1H), 7.55 (d, J=8.8 Hz, 1H), 7.50 (s, 1H), 7.32-7.41 (m, 1H), 7.24-7.32 (m, 1H), 6.86-6.96 (m, 2H), 6.42 (br s, 1H), 3.07 (s, 3H), 2.58-2.66 (m, 1H), 1.28 (s, 3H), 0.95 (m, J=6.8 Hz, 2H), 0.56-0.72 (m, 4H), 0.36-0.44 (m, 2H), (one signal overlaps with the DMSO-d$_5$ peak); $^{19}$F NMR (376 MHz, DMSO-d$_6$) δ −73.95 (s, 3F), −123.97--123.86 (m, 1F); LC-MS (ESI+) m/z: [M+H]$^+$ Calcd for C$_{28}$H$_{27}$FIN$_6$O$_4$ 657.1; Found 657.3.

N-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)methane-
sulfonamide 2,2,2-trifluoroacetate (15)

To a mixture of 8 (50.0 mg, 0.087 mmol) and pyridine (0.5 mL), in a 4 mL vial, was added methanesulfonyl chloride (8.0 μL, mmol). The reaction was heated at 50° C. and stirred for 12 h. The reaction was cooled to room temperature, diluted with EtOAc (50 mL) and water (50 mL), and transferred to a separatory funnel. The layers were separated and the organic phase was washed with water (50 mL) and brine (2×50 mL), dried (Na$_2$SO$_4$), filtered and concentrated to dryness. The remaining residue was purified by reverse-phase chromatography, eluting at 40 mL/min and using a linear gradient of H$_2$O (with 0.1% TFA)/MeCN (with 0.1% TFA): 90:10→1:99 over 20 minutes to yield 41.1 mg (63%) of the title compound as a white solid: $^1$H NMR (400 MHz, DMSO-d$_6$) δ 11.08 (s, 1H), 9.89 (s, 1H), 7.78 (dd, J=10.3, 1.7 Hz, 1H), 7.55 (dd, J=8.4, 1.1 Hz, 1H), 7.37-7.45 (m, 1H), 7.19-7.26 (m, 2H), 7.08-7.14 (m, 1H), 6.92 (t, J=8.6 Hz, 1H), 3.08 (s, 3H), 3.00 (s, 3H), 2.57-2.65 (m, 1H), 1.25 (s, 4H), 0.95 (q, J=6.7 Hz, 2H), 0.62-0.71 (m, 2H); $^{19}$F NMR (376 MHz, DMSO-d$_6$) δ −73.5 (s, 3F), −123.9 (t, J=9.2 Hz, 1F); LC-MS (ESI+) m/z: [M+H]$^+$ Calcd for C$_{25}$H$_{24}$FIN$_5$O$_5$S 652.1; Found 652.2.

(E)-N'-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)-N,N-dim-
ethylformimidamide 2,2,2-trifluoroacetate (16)

To a mixture of 8 (50.0 mg, 0.087 mmol) and DMF (1 mL), in an 8 mL vial, was added methanesulfonyl chloride (13.5 μL, 0.174 mmol). The reaction was stirred for 16 h and then was purified directly by reverse-phase chromatography, eluting at 40 mL/min and using a linear gradient of $H_2O$ (with 0.1% TFA)/MeCN (with 0.1% TFA): 90:10→1:99 over 20 minutes to yield 29.7 mg (47%) of the title compound as a yellow solid: $^1$H NMR (400 MHz, DMSO-$d_6$) δ 10.97-11.16 (m, 2H), 8.72 (br. s., 1H), 7.79 (dd, J=10.3, 1.7 Hz, 1H), 7.55 (t, J=8.8 Hz, 2H), 7.43-7.50 (m, 2H), 7.30 (d, J=8.3 Hz, 1H), 6.94 (t, J=8.7 Hz, 1H), 3.22 (s, 3H), 3.08 (s, 3H), 2.59-2.66 (m, 1H), 1.26 (s, 3H), 0.97 (d, J=7.6 Hz, 2H), 0.67 (br s, 2H), (one signal overlaps with the water peak); $^{19}$F NMR (376 MHz, DMSO-$d_6$) δ −73.1 (s, 3F), −123.9-−123.7 (m, 1F); LC-MS (ESI+) m/z: [M+H]$^+$ Calcd for $C_{27}H_{27}FIN_6O_3$ 629.1; Found 629.3.

N-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)pyrrolidine-
1-sulfonamide 2,2,2-trifluoroacetate (17)

To a mixture of 8 (50.0 mg, 0.087 mmol) and pyridine (0.5 mL), in a 4 mL vial, was added pyrrolidine-1-sulfonyl chloride (40.0 μL, 0.349 mmol). The reaction was heated at 50° C. and stirred for 14 h. The reaction was cooled to room temperature, diluted with EtOAc (50 mL) and water (50 mL), and transferred to a separatory funnel. The layers were separated and the organic phase was washed with water (50 mL) and brine (2×50 mL), dried (Na$_2$SO$_4$), filtered and concentrated to dryness. The remaining residue was purified by reverse-phase chromatography, eluting at 40 mL/min and using a linear gradient of $H_2O$ (with 0.1% TFA)/MeCN (with 0.1% TFA): 90:10→1:99 over 20 minutes to yield 28.7 mg (41%) of the title compound as a white solid: 1H NMR (400 MHz, DMSO-$d_6$) δ 11.07 (s, 1H), 9.99 (s, 1H), 7.78 (dd, J=10.3, 2.0 Hz, 1H), 7.55 (dd, J=8.3, 1.0 Hz, 1H), 7.32-7.40 (m, 1H), 7.15-7.22 (m, 2H), 7.03-7.08 (m, 1H), 6.92 (t, J=8.6 Hz, 1H), 3.14 (br. s., 4H), 3.07 (s, 3H), 2.62 (m, J=7.2, 7.2, 3.4 Hz, 1H), 1.66-1.80 (m, 4H), 1.23 (s, 3H), 0.95 (q, J=6.7 Hz, 2H), 0.60-0.72 (m, 2H); $^{19}$F NMR (376 MHz, DMSO-$d_6$) δ −73.5 (s, 3F), −123.9-−123.8 (m, 1F); LC-MS (ESI+) m/z: [M+H]$^+$ Calcd for $C_{28}H_{29}FIN_6O_5S$ 707.1; Found 707.2.

N-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)propane-1-
sulfonamide 2,2,2-trifluoroacetate (18)

To a mixture of 8 (50.0 mg, 0.087 mmol) and pyridine (0.5 mL), in a 4 mL vial, was added propane-1-sulfonyl chloride (15.0 μL, 0.133 mmol). The reaction was heated at 50° C. and stirred for 16 h. The reaction was cooled to room temperature, diluted with EtOAc (50 mL) and water (50 mL), and transferred to a separatory funnel. The layers were separated and the organic phase was washed with water (50 mL) and brine (2×50 mL), dried (Na$_2$SO$_4$), filtered and concentrated to dryness. The remaining residue was purified by reverse-phase chromatography, eluting at 40 mL/min and using a linear gradient of $H_2O$ (with 0.1% TFA)/MeCN (with 0.1% TFA): 90:10→1:99 over 20 minutes to yield 43.9 mg (65%) of the title compound as an off-white solid: 1H NMR (400 MHz, DMSO-$d_6$) δ 11.08 (s, 1H), 9.95 (s, 1H), 7.78 (dd, J=10.4, 1.6 Hz, 1H), 7.55 (d, J=8.3 Hz, 1H), 7.35-7.44 (m, 1H), 7.18-7.28 (m, 2H), 7.09 (d, J=7.6 Hz, 1H), 6.92 (t, J=8.6 Hz, 1H), 3.00-3.16 (m, 5H), 2.57-2.66 (m, 1H), 1.67 (dq, J=15.2, 7.5 Hz, 2H), 1.24 (s, 3H), 0.88-0.99 (m, 5H), 0.67 (br s, 2H); $^{19}$F NMR (376 MHz, DMSO-$d_6$) δ −74.0 (s, 3F), −124.0-−123.8 (m, 1F); LC-MS (ESI+) m/z: [M+H]$^+$ Calcd for $C_{27}H_{28}FIN_5O_5S$ 680.1; Found 680.2.

7.36-7.44 (m, 1H), 7.23 (ddd, J=8.1, 2.1, 1.0 Hz, 1H), 7.19 (t, J=2.1 Hz, 1H), 7.10-7.15 (m, 1H), 6.93 (t, J=8.7 Hz, 1H), 3.81-4.04 (m, 5H; overlaps with water peak), 3.08 (s, 3H), 2.62 (tt, J=7.1, 3.7 Hz, 1H), 1.25 (s, 3H), 0.96 (q, J=6.8 Hz, 2H), 0.64-0.71 (m, 2H); $^{19}$F NMR (376 MHz, DMSO-d$_6$) δ −73.5 (s, 3F), −123.9−−123.8 (m, 1F); LC-MS (ESI+) m/z: [M+H]$^+$ Calcd for C$_{27}$H$_{28}$FIN$_7$O$_5$S 708.1; Found 708.1.

19a tert-Butyl (1-(chlorosulfonyl)azetidin-3-yl)carbamate (19a)

To a −78° C. solution of sulfuryl chloride (130 μL, 1.60 mmol) and CH$_2$Cl$_2$ (6 mL), in a 50 mL flask, was added tert-butyl azetidin-3-ylcarbamate hydrochloride and triethylamine (500 μL, 3.59 mmol) as a slurry in MeCN (6 mL), dropwise over 5 min. The reaction was allowed to warm to room temperature overnight and was stirred for 16 h. The reaction mixture was concentrated to dryness from toluene (3×5 mL) and then dried further under high vacuum to leave ~750 mg of a white solid. This material was used without further purification (see 19) and was assumed to be 19a+2 (Et$_3$N·HCl).

19

3-Amino-N-(3-(3-cyclopropyl-5-((2-fluoro-4-iodo-phenyl)amino)-6,8-dimethyl-2,4,7-trioxo-3,4,6,7-tetrahydropyrido[4,3-d]pyrimidin-1(2H)-yl)phenyl) azetidine-1-sulfonamide 2,2,2-trifluoroacetate (19)

A 4 mL vial was charged with 8 (60.0 mg, 0.105 mmol), tert-butyl (1-(chlorosulfonyl)azetidin-3-yl)carbamate (19a+2(Et$_3$N·HCl); 173 mg, 0.317 mmol) and pyridine (0.5 mL). The reaction mixture was heated at 50° C. and stirred for 16 h. The reaction was cooled to room temperature, diluted with EtOAc (50 mL) and water (50 mL), and transferred to a separatory funnel. The layers were separated and the organic phase was washed with water (50 mL) and brine (2×50 mL), dried (Na$_2$SO$_4$), filtered and concentrated to dryness. The remaining solid was treated with TFA (2 mL), stirred for 30 min and then concentrated to dryness from toluene (3×2 mL). The remaining material was purified by reverse-phase chromatography, eluting at 40 mL/min and using a linear gradient of H$_2$O (with 0.1% TFA)/MeCN (with 0.1% TFA): 90:10→1:99 over 20 minutes to yield 20.3 mg (24%) of the title compound as an off-white solid: $^1$H NMR (400 MHz, DMSO-d$_6$) δ 11.09 (s, 1H), 10.25 (br s, 1H), 8.39 (br s, 3H), 7.79 (dd, J=10.4, 1.8 Hz, 1H), 7.56 (dd, J=8.2, 1.3 Hz, 1H),

20

3-Amino-N-(3-(3-cyclopropyl-5-((2-fluoro-4-iodo-phenyl)amino)-6,8-dimethyl-2,4,7-trioxo-3,4,6,7-tetrahydropyrido[4,3-d]pyrimidin-1(2H)-yl)phenyl) propanamide 2,2,2-trifluoroacetate (20)

A 25 mL flask was charged with 61 (88.2 mg, 0.118 mmol) and TFA (1 mL). The solution was stirred for 1 h and then concentrated to dryness from toluene (3×3 mL). The remaining residue was purified by reverse-phase chromatography, eluting at 40 mL/min and using a linear gradient of H$_2$O (with 0.1% TFA)/MeCN (with 0.1% TFA): 90:10→1:99 over 20 minutes to yield 80.6 mg (>99%) of the title compound as a tan solid: $^1$H NMR (400 MHz, DMSO-d$_6$) δ 11.07 (s, 1H), 10.32 (s, 1H), 7.69-7.84 (m, 4H), 7.66 (t, J=2.0 Hz, 1H), 7.58 (dd, J=16.6, 8.3 Hz, 2H), 7.39 (t, J=8.1 Hz, 1H), 7.06 (dd, J=7.9, 1.1 Hz, 1H), 6.92 (t, J=8.6 Hz, 1H), 3.04-3.14 (m, 5H), 2.71 (t, J=6.7 Hz, 2H), 2.62 (tt, J=7.2, 3.7 Hz, 1H), 1.25 (s, 3H), 0.90-1.00 (m, 2H), 0.61-0.70 (m, 2H); $^{19}$F NMR (376 MHz, DMSO-d$_6$) δ −73.2 (s, 3F), −123.9−−123.8 (m, 1F); LC-MS (ESI+) m/z: [M+H]$^+$ Calcd for C$_{27}$H$_{27}$FIN$_6$O$_4$ 645.1; Found 645.3.

21

N-(3-(3-cyclopropyl-5-((2-fluoro-4-iodophenyl) amino)-6,8-dimethyl-2,4,7-trioxo-3,4,6,7-tetrahydro-pyrido[4,3-d]pyrimidin-1(2H)-yl)phenyl)acrylamide (21)

To a 20 mL reaction vial, 8 (30 mg, 0.052 mmol) was dissolved in DCM (5 mL). To this solution, $K_2CO_3$ (14 mg, 0.104 mmol) was added and the reaction mixture was cooled to 0° C. followed by addition of acroyl chloride (4.2 μL, 0.052 mmol, pre-dissolved in DCM) dropwise over a period of 10 minutes. The reaction was stirred at 0° C. for 2 hours and warmed to room temperature and stirred for an additional 8 hours. Reaction was quenched with saturated $NaHCO_3$ (5 mL) solution and worked up with DCM/water. Combined organic layers were dried over anhydrous $Na_2SO_4$, filtered, concentrated to give the crude product, which was purified by flash chromatography using eluent from pure DCM to 3% MeOH/DCM to afford the product as off-white solid. $^1H$ NMR (400 MHz, DMSO-$d_6$) δ ppm 0.64-0.71 (m, 2H) 0.92-1.00 (m, 2H) 1.20-1.30 (m, 6H) 2.57-2.68 (m, 1H) 3.09 (s, 3H) 5.75-5.81 (m, 1H) 6.21-6.31 (m, 1H) 6.38-6.50 (m, 1H) 6.93 (t, J=8.68 Hz, 1H) 7.06-7.12 (m, 1H) 7.36-7.44 (m, 1H) 7.56 (dt, J=8.50, 1.01 Hz, 1H) 7.67-7.73 (m, 2H) 7.79 (dd, J=10.39, 1.83 Hz, 1H) 10.24-10.37 (m, 1H) 11.08 (br. s., 1H); $^{13}C$ NMR (100 MHz, DMSO-$d_6$) δ ppm 164.14, 162.80, 150.97, 150.81, 144.85, 140.34, 139.22, 133.97, 131.63, 128.81, 128.10, 127.24, 124.94, 124.51, 120.40, 118.63, 101.97, 90.30, 33.92, 31.27, 29.01, 24.85, 22.08, 13.94, 13.03, 8.16; LCMS (ESI+) m/z: [M+H]+ Calcd for C27H24FIN5O4 628.2; Found 628.2

8

22

2-Bromo-N-(3-(3-cyclopropyl-5-((2-fluoro-4-iodo-phenyl)amino)-6,8-dimethyl-2,4,7-trioxo-3,4,6,7-tetrahydropyrido[4,3-d]pyrimidin-1(2H)-yl)phenyl) acetamide (22; APS-11-15)

To a 0° C. mixture of 8 (150 mg, 0.261 mmol), $NaHCO_3$ (65.8 mg, 0.783 mmol) and $CH_2Cl_2$ (3 mL), in an 8 mL vial, was added bromoacetyl bromide (25.0 μL, 0.287 mmol). The reaction was stirred for 1 h and then was poured into a 50:50 mixture (50 mL) of ice and saturated $NaHCO_3$ solution, and then was extracted with EtOAc (2×50 mL). The organic extracts were pooled, dried ($Na_2SO_4$) and filtered. Concentration under vacuum yielded 178 mg (98%) of the title compound as a white solid, which was used without further purification: LC-MS (ESI+) m/z: [M+H]+ Calcd for $C_{26}H_{23}BrFIN_5O_4$ 694.0; Found 694.1.

22

2-bromo-N-(3-(3-cyclopropyl-5-((2-fluoro-4-iodo-phenyl)amino)-6,8-dimethyl-2,4,7-trioxo-3,4,6,7-tetrahydropyrido[4,3-d]pyrimidin-1(2H)-yl)phenyl) acetamide (22; YJ-04-37)

To a 20 mL reaction vial, 1-(3-aminophenyl)-3-cyclopropyl-5-((2-fluoro-4-iodophenyl)amino)-6,8-dimethylpyrido[4,3-d]pyrimidine-2,4,7(1H,3H,6H)-trione (85 mg, 0.148 mmol) was dissolved in DCM (5 mL). To this solution, $K_2CO_3$ (40 mg, 0.296 mmol) was added and the reaction mixture was cooled to 0° C. followed by addition of bromo acetylbromide (14.2 μL, 0.168 mmol, pre-dissolved in DCM) dropwise over a period of 10 minutes. The reaction was stirred at 0° C. for 2 hours and warmed to room temperature and stirred for an additional 8 hours. Reaction was quenched with saturated $NaHCO_3$ (5 mL) solution and worked up with DCM/water. Combined organic layers were dried over anhydrous $Na_2SO_4$, filtered, concentrated to give the crude product, which was purified by flash chromatography using eluent from pure DCM to 30% EtOAc/DCM to afford the product as white solid. $^1H$ NMR (400 MHz, DMSO-$d_6$) δ ppm 0.63-0.71 (m, 2H) 0.91-0.99 (m, 2H) 1.23-1.26 (m, 4H) 2.57-2.66 (m, 1H) 3.08 (s, 3H) 4.04 (s, 2H) 6.92 (t, J=8.68 Hz, 1H) 7.06-7.14 (m, 1H) 7.36-7.45 (m, 1H) 7.51-7.64 (m, 3H) 7.78 (dd, J=10.27, 1.96 Hz, 1H) 10.55 (s, 1H) 11.07 (s, 1H); $^{13}C$ NMR (100 MHz, DMSO-$d_6$) δ ppm 164.94, 164.15, 162.80, 155.36, 152.86, 150.97, 150.82, 144.84, 140.41, 138.79, 134.01, 128.92, 128.08, 124.96, 120.36, 118.54, 101.89, 90.31, 88.27, 34.18, 33.92, 30.94, 30.32, 28.46, 24.85, 22.05, 13.95, 13.06, 8.15; LCMS (ESI+) m/z. [M+H]+ Calcd for $C_{26}H23BrFIN5O4$ 796.1; Found 796.2

N-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)-2-(piperi-
din-1-yl)acetamide (23)

To a 20 mL reaction vial, 22 (30 mg, 0.043 mmol) was dissolved in DCM (5 mL). To this solution, $K_2CO_3$ (11 mg, 0.086 mmol) was added and the reaction mixture was cooled to 0° C. followed by addition of piperidine (4.65 mL, 0.047 mmol, pre-dissolved in DCM) dropwise over a period of 10 minutes. The reaction was stirred at 0° C. for 2 hours and warmed to room temperature and stirred for an additional 8 hours. Reaction was quenched with saturated $NaHCO_3$ (5 mL) solution and worked up with Ethylacetate/water. Combined organic layers was dried over anhydrous $Na_2SO_4$, filtered, concentrated to give the crude product, which was purified by flash chromatography using eluent from pure DCM to 5% MeOH/DCM to afford the product as pale yellow solid. $^1H$ NMR (400 MHz, DMSO-$d_6$) δ ppm 0.63-0.70 (m, 2H) 0.91-0.99 (m, 2H) 1.24-1.28 (m, 3H) 1.34-1.43 (m, 2H) 1.56 (quin, J=5.56 Hz, 4H) 2.46 (br. s., 4H) 2.62 (tt, J=7.15, 3.73 Hz, 1H) 3.32 (s, 2H) 5.75 (s, 1H) 6.92 (t, J=8.68 Hz, 1H) 7.04-7.10 (m, 1H) 7.37 (t, J=8.19 Hz, 1H) 7.51-7.58 (m, 1H) 7.63-7.70 (m, 2H) 7.78 (dd, J=10.39, 1.83 Hz, 1H) 9.82 (s, 1H) 11.09 (s, 1H); $^{13}C$ NMR (100 MHz, DMSO-$d_6$) δ ppm 168.88, 164.15, 162.80, 155.34, 152.86, 150.98, 150.83, 144.81, 140.28, 138.89, 133.96, 128.64, 124.95, 124.50, 120.36, 118.76, 101.89, 90.23, 62.62, 54.89, 54.05, 33.93, 25.38, 24.83, 23.51, 13.01, 8.15; LCMS (ESI+) m/z: [M+H]+ Calcd for $C_{31}H33FIN6O4$ 799.4; Found 799.4

2-azido-N-(3-(3-cyclopropyl-5-((2-fluoro-4-iodophe-
nyl)amino)-6,8-dimethyl-2,4,7-trioxo-3,4,6,7-tetra-
hydropyrido[4,3-d]pyrimidin-1(2H)-yl)phenyl)acet-
amide (25)

22 (5.30 g, 13.1 mmol) was dissolved in acetone (50 mL) in a 250 mL round bottom flask. To this solution sodium azide (3.20 g, 0.13 mol) was added and the reaction mixture was stirred for 12 hours under refluxing condition. Acetone was removed under reduced pressure and the resulting residue was dissolved in water and then extracted with ethyl acetate. The combined organic layers were washed with brine, dried over anhydrous $Na_2SO_4$, filtered and concentrated to afford the crude. It was then purified by flash chromatography using a gradient of solvent system of EtOAc:hexane from 1:4 to 1:1. The desired product was obtained as a white solid (4.60 g, 94%), (Rf ¼ 0.7 in 70% EtOAc/hexane). $^1H$ NMR (400 MHz, DMSO-$d_6$) δ ppm 0.65-0.71 (m, 2H) 0.93-0.99 (m, 2H) 1.26 (s, 3H) 2.59-2.66 (m, 1H) 3.08 (s, 3H) 4.06 (s, 2H) 6.93 (t, J=8.56 Hz, 1H) 7.10 (dd, J=7.95, 1.10 Hz, 1H) 7.41 (t, J=8.07 Hz, 1H) 7.54-7.63 (m, 2H) 7.66 (t, J=1.96 Hz, 1H) 7.79 (dd, J=10.27, 1.96 Hz, 1H) 10.32 (s, 1H) 11.09 (s, 1H); $^{13}C$ NMR (100 MHz, DMSO-$d_6$) δ ppm 166.56, 164.15, 162.80, 115.35, 152.86, 150.96, 150.82, 144.84, 140.40, 138.63, 133.97, 128.89, 128.08, 124.94, 124.68, 120.42, 118.57, 101.89, 90.31, 51.22, 33.93, 24.85, 22.05, 13.03, 8.15; LCMS (ESI+) m/z: [M+H]+ Calcd for $C_{26}H23FIN8O4$ 657.2; Found 657.2

N-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)-2-(4-phe-
nyl-1H-1,2,3-triazol-1-yl)acetamide (26)

To a 20 mL reaction vial, 25 (30 mg, 0.045 mmol) and Phenylacetylene (5.8 μL, 0.049 mmol) were dissolved in tBuOH:Water: 1:1 (4 mL). To this solution copper (II) sulfate (0.0045 mmol) and L-ascorbic sodium salt (0.0045 mmol) were added. Reaction was stirring at room temperature for 24 h. Reaction was monitored using TLC and LC-MS. The solvents were evaporated under reduced pressure. The resulting residue was dissolved in ethylacetate (10 mL), washed with water (2 mL) and the crude product was purified using flash chromatography on silica gel by EtOAc: DCM (40:60) The desired product was obtained as a white solid. $^1H$ NMR (400 MHz, DMSO-$d_6$) δ ppm 0.62-0.69 (m, 2H) 0.90-0.98 (m, 2H) 1.26 (s, 3H) 2.53-2.55 (m, 1H) 2.57-2.65 (m, 1H) 3.07 (s, 3H) 5.40 (s, 2H) 6.91 (t, J=8.68

Hz, 1H) 7.08-7.13 (m, 1H) 7.31-7.37 (m, 1H) 7.39-7.49 (m, 3H) 7.52-7.62 (m, 2H) 7.68 (t, J=1.96 Hz, 1H) 7.78 (dd, J=10.39, 1.83 Hz, 1H) 7.84-7.90 (m, 2H) 8.59 (s, 1H) 10.70 (s, 1H) 11.06 (s, 1H); $^{13}$C NMR (100 MHz, DMSO-d$_6$) δ ppm 164.49, 162.80, 155.36, 152.86, 150.96, 150.82, 146.21, 144.86, 140.47, 138.60, 134.02, 130.71, 128.94, 127.86, 125.13, 123.06, 120.51, 118.55, 101.91, 90.31, 52.33, 40.42, 33.93, 24.85, 13.07, 8.15; LCMS (ESI+) m/z: [M+H]+ Calcd for C$_{34}$H29FIN8O4 659.3; Found 659.3

N-(3-(3-cyclopropyl-5-((2-fluoro-4-iodophenyl) amino)-6,8-dimethyl-2,4,7-trioxo-3,4,6,7-tetrahydro-pyrido[4,3-d]pyrimidin-1(2H)-yl)phenyl)-2-(4-(p-tolyl)-1H-1,2,3-triazol-1-yl)acetamide (28)

To a 20 mL reaction vial, 25 (30 mg, 0.045 mmol) and 4-Ethylnyltoluene (6.95 μL, 0.054 mmol) were dissolved in tBuOH:Water: 1:1 (4 mL). To this solution copper (II) sulfate (0.0045 mmol) and L-ascorbic sodium salt (0.0045 mmol) were added. Reaction was stirring at room temperature for 24 h. Reaction was monitored using TLC and LC-MS. The solvents were evaporated under reduced pressure. The resulting residue was dissolved in ethylacetate (10 mL), washed with water (2 mL) and the crude product was purified using flash chromatography on silica gel by EtOAc:Hexane (95:5) or DCM:MeOH (97:3). The desired product was obtained as a white solid. The other compounds were synthesized and purified similarly. $^1$H NMR (400 MHz, DMSO-d$_6$) δ ppm 0.64-0.70 (m, 2H) 0.91-0.99 (m, 2H) 1.25-1.28 (m, 3H) 2.46 (s, 3H) 2.56-2.67 (m, 1H) 3.03-3.10 (m, 3H) 5.40-5.45 (m, 2H) 6.92 (t, J=8.56 Hz, 1H) 7.08-7.14 (m, 1H) 7.24-7.35 (m, 3H) 7.43 (t, J=8.19 Hz, 1H) 7.52-7.63 (m, 2H) 7.69 (t, J=2.08 Hz, 1H) 7.74-7.82 (m, 2H) 8.43 (s, 1H) 10.71 (s, 1H) 11.07 (s, 1H); $^{13}$C NMR (100 MHz, DMSO-d$_6$) δ ppm 164.55, 164.14, 162.80, 152.86, 150.95, 150.82, 145.35, 144.85, 140.46, 138.63, 134.83, 130.87, 129.96, 128.12, 126.06, 124.95, 124.72, 120.46, 101.89, 90.30, 52.20, 33.93, 24.84, 21.13, 13.06, 8.14; LCMS (ESI+) m/z: [M+H]+ Calcd for C$_{35}$H31FIN8O4 773.3; Found 773.3

N-(3-(3-cyclopropyl-5-((2-fluoro-4-iodophenyl) amino)-6,8-dimethyl-2,4,7-trioxo-3,4,6,7-tetrahydro-pyrido[4,3-d]pyrimidin-1(2H)-yl)phenyl)-2-(4-(4-methoxyphenyl)-1H-1,2,3-triazol-1-yl)acetamide (29)

To a 20 mL reaction vial, 25 (30 mg, 0.045 mmol) and 4-Ethylnylanesole (7.11 μL, 0.054 mmol) were dissolved in tBuOH:Water: 1:1 (4 mL). To this solution copper (II) sulfate (0.0045 mmol) and L-ascorbic sodium salt (0.0045 mmol) were added. Reaction was stirring at room temperature for 24 h. Reaction was monitored using TLC and LC-MS. The solvents were evaporated under reduced pressure. The resulting residue was dissolved in ethylacetate (10 mL), washed with water (2 mL) and the crude product was purified using flash chromatography on silica gel by EtOAc:Hexane (95:5) or DCM:MeOH (97:3). The desired product was obtained as a white solid. $^1$H NMR (400 MHz, DMSO-d$_6$) δ ppm 0.62-0.69 (m, 2H) 0.91-0.98 (m, 2H) 1.24-1.28 (m, 3H) 2.58-2.65 (m, 1H) 3.05-3.08 (m, 3H) 3.82 (s, 3H) 5.40 (s, 2H) 6.88-6.94 (m, 2H) 7.08-7.12 (m, 1H) 7.33-7.40 (m, 1H) 7.41-7.46 (m, 3H) 7.52-7.62 (m, 2H) 7.68 (t, J=2.08 Hz, 1H) 7.78 (dd, J=10.27, 1.96 Hz, 1H) 8.62 (s, 1H) 10.70 (s, 1H) 11.06 (s, 1H); $^{13}$C NMR (100 MHz, DMSO-d$_6$) δ ppm 164.46, 164.14, 162.78, 159.68, 155.35, 152.86, 150.95, 150.82, 146.11, 144.84, 140.46, 138.59, 134.00, 132.04, 130.06, 128.98, 128.18, 123.30, 120.51, 117.46, 113.62, 110.29, 101.90, 90.30, 88.27, 55.11, 52.34, 33.92, 24.84, 13.07, 8.15; LCMS (ESI+) m/z: [M+H]+ Calcd for C$_{35}$H31FIN8O5 789.3; Found 789.3.

3-cyclopropyl-5-((2-fluoro-4-iodophenyl)amino)-6,8-dimethyl-1-(3-(pyrimidin-2-ylamino)phenyl)pyrido[4,3-d]pyrimidine-2,4,7(1H,3H,6H)-trione (30)

To a an oven-dried pressure reaction tube containing 1,4-dioxane:acetic acid (2.6 mL:1 mL), 2-bromo-pyrimidine (27.6 mg, 0.17 mmol), 8 (20 mg, 0.034 mmol) was added. The reaction mixture was stirred at 110° C. for 24 h and monitored by TLC. Upon completion, saturated NaHCO$_3$ was added, and the reaction mixture was extracted with ethyl acetate (3×10 mL). The combined organic phase was washed with brine and dried over Na$_2$SO$_4$. Solvent was evaporated in a vacuum to give the crude product which was purified by column chromatography on silica gel DCM:EtOAc (80:20) to give the product as an off-white solid. $^1$H NMR (400 MHz, DMSO-d$_6$) δ 0.64-0.71 (m, 2H) 0.92-0.99 (m, 2H) 1.31 (s, 3H) 2.63 (tt, J=7.24, 3.64 Hz, 1H) 3.06-3.09 (m, 3H) 6.86 (t, J=4.77 Hz, 1H) 6.89-6.97 (m, 2H) 7.34 (t, J=8.07 Hz, 1H) 7.55 (dd, J=8.44, 1.10 Hz, 1H) 7.63 (t, J=4.89 Hz, 1H) 7.75-7.82 (m, 3H) 8.48 (d, J=4.89 Hz, 2H) 8.73 (d, J=4.89 Hz, 1H) 9.74 (s, 1H) 11.10 (s, 1H); $^{13}$C NMR (100 MHz, DMSO-d$_6$) δ ppm 164.15, 162.82, 160.48, 158.06, 155.34, 152.86, 144.81, 140.79, 140.18, 134.00, 128.45, 124.94, 122.26, 121.26, 119.87, 101.99, 90.19, 33.92, 24.85, 12.92, 10.34, 8.18; LCMS (ESI+) m/z: [M+H]+ Calcd for C$_{28}$H$_{24}$FIN$_7$O$_3$ 652.3; Found 652.3

31

3-cyclopropyl-5-((2-fluoro-4-iodophenyl)amino)-6,8-dimethyl-1-(3-(pyridin-2 ylamino)phenyl)pyrido[4,3-d]pyrimidine-2,4,7(1H,3H,6H)-trione (31)

To a an oven-dried pressure reaction tube containing 2-bromopyridine (32.5 mL, 0.34 mmol), 8 (20 mg, 0.034 mmol) was added. The reaction mixture was stirred at 160° C. for 7 h and monitored by TLC. Upon completion, saturated NaHCO$_3$ was added, and the reaction mixture was extracted with ethyl acetate (3×10 mL). The combined organic phase was washed with brine and dried over Na$_2$SO$_4$. After that, the solid was filtered off through a thin pad of Celite, and the filtrate was evaporated in a vacuum to give the crude product which was purified by column chromatography on silica gel DCM:EtOAc (30:70) to give the product as a off-white solid. $^1$H NMR (400 MHz, DMSO-d$_6$) δ ppm 0.63-0.71 (m, 2H) 0.90-1.00 (m, 2H) 1.33 (s, 3H) 2.57-2.69 (m, 1H) 3.08 (s, 3H) 6.72-6.78 (m, 1H) 6.80-6.95 (m, 3H) 7.27-7.35 (m, 1H) 7.52-7.62 (m, 3H) 7.75-7.84 (m, 2H) 8.14 (dd, J=5.01, 1.34 Hz, 1H) 9.19 (s, 1H) 11.08 (s, 1H); $^{13}$C NMR (100 MHz, DMSO-d$_6$) δ ppm 164.21, 162.87, 155.65, 155.39, 151.03, 150.84, 147.24, 144.95, 142.05, 140.27, 137.39, 134.05, 128.61, 124.98, 124.76, 121.16, 118.92, 117.16, 114.66, 110.96, 102.13, 90.31, 33.94, 24.89, 12.94, 8.22; LCMS (ESI+) m/z: [M+H]+ Calcd for C$_{29}$H25FIN6O3 651.3; Found 651.3

32

N-(3-(3-cyclopropyl-5-((2-fluoro-4-iodophenyl)amino)-6,8-dimethyl-2,4,7-trioxo-3,4,6,7-tetrahydro-pyrido[4,3-d]pyrimidin-1(2H)-yl)phenyl)-2-(piperazin-1-yl)acetamide (32)

To a 20 mL reaction vial, 22 (35 mg, 0.050 mmol) was dissolved in DCM (5 mL). To this solution, K$_2$CO$_3$ (14 mg, 0.10 mmol) was added and the reaction mixture was cooled to 0° C. followed by addition of piperazine (5 mg, 0.06 mmol, pre-dissolved in DCM) dropwise over a period of 10 minutes. The reaction was stirred at 0° C. for 2 hours and warmed to room temperature and stirred for an additional 8 hours. Reaction was quenched with saturated NaHCO$_3$ (5 mL) solution and worked up with Ethylacetate/water. Combined organic layers was dried over anhydrous Na$_2$SO$_4$, filtered, concentrated to give the crude product, which was purified by flash chromatography using eluent from pure DCM to 40% MeOH/DCM to afford the product as pale yellow solid. $^1$H NMR (400 MHz, DMSO-d$_6$) δ ppm 0.63-0.69 (m, 2H) 0.91-0.99 (m, 2H) 1.23-1.29 (m, 3H) 2.58-2.65 (m, 1H) 2.82-2.90 (m, 3H) 3.13 (s, 2H) 5.76 (s, 1H) 6.92 (t, J=8.56 Hz, 1H) 7.04-7.11 (m, 1H) 7.33-7.42 (m, 1H) 7.54 (dd, J=8.56, 1.22 Hz, 1H) 7.62-7.71 (m, 2H) 7.78 (dd, J=10.27, 1.71 Hz, 1H) 9.81-9.94 (m, 1H); $^{13}$C NMR (100 MHz, DMSO-d$_6$) δ ppm 168.52, 163.96, 162.85, 151.03, 150.88, 144.90, 140.32, 138.87, 128.64, 124.89, 124.50, 120.41, 62.08, 54.90, 52.76, 44.69, 33.72, 24.83, 13.01, 8.17; LCMS (ESI+) m/z: [M+H]+ Calcd for C$_{30}$H32FIN7O4 700.4; Found 700.4

N-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)-2-(4-(4-
(trifluoromethyl)phenyl)-1H-1,2,3-triazol-1-yl)
acetamide (33)

To a 20 mL reaction vial, 25 (40 mg, 0.06 mmol) and 1-Ethynyl-4-(trifluoromethyl)benzene (20 μL, 0.12 mmol) were dissolved in tBuOH:Water: 1:1 (4 mL). To this solution copper (II) sulfate (0.006 mmol) and L-ascorbic sodium salt (0.006 mmol) were added. Reaction was stirring at room temperature for 24 h. Reaction was monitored using TLC and LC-MS. The solvents were evaporated under reduced pressure. The resulting residue was dissolved in ethylacetate (10 mL), washed with water (2 mL) and the crude product was purified using flash chromatography on silica gel by EtOAc:DCM (95:5). The desired product was obtained as a white solid. $^1$H NMR (400 MHz, DMSO-d$_6$) δ ppm 0.60-0.71 (m, 2H) 0.88-1.00 (m, 2H) 1.26 (s, 3H) 2.53-2.67 (m, 1H) 3.06 (s, 3H) 5.44 (s, 2H) 6.91 (t, J=8.68 Hz, 1H) 7.07-7.15 (m, 1H) 7.42 (t, J=8.07 Hz, 1H) 7.50-7.64 (m, 2H) 7.68 (t, J=1.96 Hz, 1H) 7.73-7.88 (m, 3H) 8.10 (d, J=8.07 Hz, 2H) 8.78 (s, 1H) 10.72 (s, 1H) 11.06 (s, 1H); $^{13}$C NMR (100 MHz, DMSO-d$_6$) δ ppm 164.37, 164.14, 162.80, 155.35, 152.86, 150.95, 144.85, 140.47, 138.57, 134.67, 133.97, 128.99, 125.96, 125.65, 124.36, 122.90, 120.51, 118.55, 101.91, 90.30, 88.28, 52.42, 33.92, 24.84, 13.07, 8.15; LCMS (ESI+) m/z: [M+H]+ Calcd for C$_{35}$H28F4IN8O4 827.4; Found 827.4

N-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)-2-(4-(3-
hydroxyphenyl)-1H-1,2,3-triazol-1-yl)acetamide
(34)

To a 20 mL reaction vial, 25 (40 mg, 0.06 mmol) and 1-Ethynylphenol (14.3 μL, 0.12 mmol) were dissolved in tBuOH:Water: 1:1 (4 mL). To this solution copper (II) sulfate (0.006 mmol) and L-ascorbic sodium salt (0.006 mmol) were added. Reaction was stirring at room temperature for 24 h. Reaction was monitored using TLC and LC-MS. The solvents were evaporated under reduced pressure. The resulting residue was dissolved in ethylacetate (10 mL), washed with water (2 mL) and the crude product was purified using flash chromatography on silica gel by EtOAc:DCM (95:5). The desired product was obtained as a white solid. $^1$H NMR (400 MHz, DMSO-d$_6$) δ ppm 0.60-0.67 (m, 2H) 0.90-0.97 (m, 2H) 1.20-1.27 (m, 3H) 2.56-2.64 (m, 1H) 3.05 (s, 3H) 5.37 (s, 2H) 6.69-6.76 (m, 1H) 6.90 (t, J=8.56 Hz, 1H) 7.06-7.12 (m, 1H) 7.20-7.29 (m, 3H) 7.42 (t, J=8.07 Hz, 1H) 7.51-7.59 (m, 2H) 7.66 (t, J=2.08 Hz, 1H) 7.76 (dd, J=10.27, 1.96 Hz, 1H) 8.49 (s, 1H) 9.65 (s, 1H) 10.71 (s, 1H) 11.04 (s, 1H); $^{13}$C NMR (100 MHz, DMSO-d$_6$) δ ppm 164.68, 164.30, 163.05, 157.88, 153.04, 151.18, 151.01, 146.48, 145.09, 140.62, 138.72, 134.22, 132.00, 130.23, 129.21, 128.23, 125.17, 123.21, 120.67, 118.79, 116.26, 115.14, 112.01, 102.10, 90.51, 88.38, 52.43, 34.36, 34.13, 25.02, 13.23, 8.33; LCMS (ESI+) m/z: [M+H]+ Calcd for C$_{34}$H29FIN8O5 775.2; Found 775.2

N-(3-(3-cyclopropyl-5-((2-fluoro-4-iodophenyl)
amino)-6,8-dimethyl-2,4,7-trioxo-3,4,6,7-tetrahydro-
pyrido[4,3-d]pyrimidin-1(2H)-yl)phenyl)-2-(4-(3-
fluorophenyl)-1H-1,2,3-triazol-1-yl)acetamide (35)

To a 20 mL reaction vial, 25 (40 mg, 0.06 mmol) and 3-Fluorophenylacetylene (14.6 μL, 0.12 mmol) were dissolved in tBuOH:Water: 1:1 (4 mL). To this solution copper (II) sulfate (0.006 mmol) and L-ascorbic sodium salt (0.006 mmol) were added. Reaction was stirring at room temperature for 24 h. Reaction was monitored using TLC and LC-MS. The solvents were evaporated under reduced pressure. The resulting residue was dissolved in ethylacetate (10 mL), washed with water (2 mL) and the crude product was purified using flash chromatography on silica gel by EtOAc:DCM (95:5). The desired product was obtained as a white solid. $^1$H NMR (400 MHz, DMSO-d$_6$) δ ppm 0.61-0.67 (m, 2H) 0.90-0.97 (m, 2H) 1.22-1.26 (m, 3H) 2.56-2.64 (m, 1H)

3.05 (s, 3H) 5.41 (s, 2H) 6.90 (t, J=8.68 Hz, 1H) 7.07-7.12 (m, 1H) 7.13-7.20 (m, 1H) 7.42 (t, J=8.07 Hz, 1H) 7.47-7.59 (m, 3H) 7.63-7.69 (m, 2H) 7.69-7.80 (m, 2H) 8.63-8.67 (m, 1H) 10.74 (s, 1H) 11.04 (s, 1H); $^{13}$C NMR (100 MHz, DMSO-d$_6$) δ ppm 164.57, 164.30, 163.05, 161.56, 155.53, 153.05, 151.18, 151.01, 145.35, 145.09, 140.62, 138.69, 134.22, 133.19, 131.35, 131.26, 129.21, 128.34, 123.97, 121.39, 121.36, 120.69, 114.90, 111.96, 111.74, 102.10, 90.50, 88.38, 88.31, 52.53, 34.12, 25.02, 20.77, 13.23, 8.13; LCMS (ESI+) m/z: [M+H]+ Calcd for C$_{34}$H28F2IN8O4 777.3; Found 777.3

2-(4-(3-aminophenyl)-1H-1,2,3-triazol-1-yl)-N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide (36)

To a 20 mL reaction vial, 25 (40 mg, 0.06 mmol) and 3-Ethynylaniline (14.2 mg, 0.12 mmol) were dissolved in tBuOH:Water: 1:1 (4 mL). To this solution copper (II) sulfate (0.006 mmol) and L-ascorbic sodium salt (0.006 mmol) were added. Reaction was stirring at room temperature for 24 h. Reaction was monitored using TLC and LC-MS. The solvents were evaporated under reduced pressure. The resulting residue was dissolved in ethylacetate (10 mL), washed with water (2 mL) and the crude product was purified using flash chromatography on silica gel by MeOH:DCM (7:93). The desired product was obtained as a off-white solid. $^1$H NMR (400 MHz, DMSO-d$_6$) δ ppm 0.66 (br. s., 2H) 0.94 (d, J=6.60 Hz, 2H) 1.26 (s, 3H) 2.55-2.67 (m, 1H) 3.07 (s, 3H) 5.19 (br. s., 1H) 5.37 (s, 2H) 6.53 (d, J=7.82 Hz, 1H) 6.86-6.98 (m, 2H) 7.01-7.17 (m, 3H) 7.42 (t, J=8.07 Hz, 1H) 7.51-7.63 (m, 2H) 7.67 (s, 1H) 7.78 (dd, J=10.27, 1.96 Hz, 1H) 8.41 (s, 1H) 10.68 (s, 1H) 11.06 (s, 1H); $^{13}$C NMR (100 MHz, DMSO-d6) δ ppm 164.54, 164.14, 162.79, 152.86, 150.95, 150.81, 146.86, 144.84, 140.46, 138.61, 133.98, 131.16, 129.35, 128.97, 124.97, 122.58, 120.48, 118.52, 113.55, 112.99, 110.45, 101.91, 90.30, 52.23, 33.92, 24.84, 13.06, 8.14; LCMS (ESI+) m/z: [M+H]+ Calcd for C$_{34}$H30FIN9O4 774.4; Found 774.4

Ethyl 2-((3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)amino)-2-oxoacetate (37)

To a 20 mL reaction vial, 8 (100 mg, 0.17 mmol) was dissolved in DCM (5 mL). To this solution, K$_2$CO$_3$ (48 mg, 0.34 mmol) was added and the reaction mixture was cooled to 0° C. followed by addition of Ethyl chloroglyoxylate (19.3 μL, 0.17 mmol, pre-dissolved in DCM) dropwise over a period of 10 minutes. The reaction was stirred at 0° C. for 2 hours and warmed to room temperature and stirred for an additional 8 hours. Reaction was quenched with saturated NaHCO$_3$ (5 mL) solution and worked up with DCM/water. Combined organic layers were dried over anhydrous Na$_2$SO$_4$, filtered, concentrated to give the crude product, which was purified by flash chromatography using eluent from pure DCM to 32% EtOAc/DCM to afford the product as white solid. $^1$H NMR (400 MHz, DMSO-d$_6$) δ ppm 0.64-0.69 (m, 2H) 0.92-0.98 (m, 2H) 1.31 (t, J=7.21 Hz, 3H) 2.56-2.69 (m, 1H) 3.08 (s, 3H) 4.30 (q, J=7.09 Hz, 2H) 6.92 (t, J=8.56 Hz, 1H) 7.12-7.22 (m, 1H) 7.38-7.49 (m, 1H) 7.55 (dd, J=8.31, 1.22 Hz, 1H) 7.70-7.84 (m, 3H) 10.91 (s, 1H) 11.07 (s, 1H); $^{13}$C NMR (100 MHz, DMSO-d$_6$) δ ppm 164.12, 162.80, 160.36, 155.67, 152.86, 150.95, 150.83, 144.74, 140.29, 137.69, 134.00, 128.80, 128.19, 128.08, 124.95, 121.61, 119.82, 101.97, 90.27, 88.27, 88.20, 62.40, 34.17, 33.91, 30.94, 28.46, 24.84, 22.04, 20.59, 13.82, 13.06, 8.14; LCMS (ESI+) m/z: [M+H]+ Calcd for C$_{28}$H26FIN5O6 674.4; Found 674.4

2-Amino-N-(3-(3-cyclopropyl-5-((2-fluoro-4-iodo-phenyl)amino)-6,8-dimethyl-2,4,7-trioxo-3,4,6,7-tetrahydropyrido[4,3-d]pyrimidin-1(2H)-yl)phenyl)acetamide (49)

A mixture of 22 (50.0 mg, 0.072 mmol), THE (1 mL) and aqueous ammonium hydroxide (0.50 mL, 30% w/w solution in water, 3.9 mmol) was sealed in a 15 mL pressure tube and heated at 60° C. for 20 h. The reaction was cooled to room temperature, the tube was opened and the reaction was diluted with water (1 mL). The mixture was stirred for 5 min and the solid was isolated by vacuum filtration; washed solid with water (1 mL). Air-drying yielded 19.6 mg (43%) of the title compound as a white solid: $^1H$ NMR (400 MHz, DMSO-$d_6$) δ 7.78 (d, J=10.3 Hz, 1H), 7.62-7.67 (m, 1H), 7.55 (d, J=8.6 Hz, 1H), 7.39-7.43 (m, 1H), 7.07 (d, J=7.3 Hz, 1H), 6.92 (t, J=8.6 Hz, 1H), 3.07 (s, 3H), 1.20-1.30 (m, 5H), 0.95 (d, J=6.6 Hz, 2H), 0.66 (br s, 2H); LC-MS (ESI+) m/z: [M+H]$^+$ Calcd for $C_{26}H_{25}FIN_6O_4$ 631.1; Found 631.3.

2-(Methylamino)-N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide (50)

To a mixture of 22 (50.0 mg, 0.072 mmol) and THE (1 mL), in an 4 mL vial, was added methylamine (180 µL, 2.0 M solution in THF, 0.36 mmol). The reaction was stirred for 1 h and then was concentrated to dryness. The remaining solid was purified by silica gel chromatography (25 g cartridge), eluting at 25 mL/min and using a linear gradient of CH$_2$Cl$_2$/EtOAc: 100:0→0:100 over 30 column volumes to yield 32.0 mg (69%) of the title compound as a white solid: $^1H$ NMR (400 MHz, DMSO-$d_6$) δ 7.78 (dd, J=10.3, 1.7 Hz, 1H), 7.64-7.69 (m, 2H), 7.55 (d, J=8.3 Hz, 1H), 7.38 (t, J=8.3 Hz, 1H), 7.06 (d, J=7.6 Hz, 1H), 6.92 (t, J=8.7 Hz, 1H), 3.08 (s, 3H), 2.57-2.65 (m, 1H), 2.33 (s, 3H), 1.20-1.29 (m, 4H), 0.95 (q, J=6.9 Hz, 2H), 0.61-0.70 (m, 2H); LC-MS (ESI+) m/z: [M+H]$^+$ Calcd for $C_{27}H_{27}FIN_6O_4$ 645.1; Found 645.2.

2-(Dimethylamino)-N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide (51)

To a mixture of 22 (50.0 mg, 0.072 mmol) and THE (1 mL), in an 4 mL vial, was added dimethylamine (180 µL, 2.0 M solution in THF, 0.36 mmol). The reaction was stirred for 1 h and then was concentrated to dryness. The remaining solid was purified by silica gel chromatography (25 g cartridge), eluting at 25 mL/min and using a linear gradient of CH$_2$Cl$_2$/EtOAc: 100:0→0:100 over 20 column volumes to yield 39.5 mg (83%) of the title compound as a white solid: $^1H$ NMR (400 MHz, DMSO-$d_6$) δ 11.08 (s, 1H), 9.89 (s, 1H), 7.78 (dd, J=10.3, 1.7 Hz, 1H), 7.66-7.73 (m, 2H), 7.55 (dd, J=8.4, 1.3 Hz, 1H), 7.37 (t, J=8.4 Hz, 1H), 7.02-7.10 (m, 1H), 6.92 (t, J=8.6 Hz, 1H), 3.02-3.14 (m, 5H), 2.62 (tt, J=7.2, 3.7 Hz, 1H), 2.28 (s, 6H), 1.19-1.30 (m, 4H), 0.90-0.99 (m, 2H), 0.61-0.71 (m, 2H); LC-MS (ESI+) m/z: [M+H]$^+$ Calcd for $C_{28}H_{29}FIN_6O_4$ 659.1; Found 659.4.

(R)—3-Fluoropyrrolidine-1-sulfonyl chloride (52a)

To a −78° C. solution of sulfuryl chloride (390 µL, 4.81 mmol) and CH$_2$Cl$_2$ (3 mL) was added a mixture of (R)—3-fluoropyrrolidine hydrochloride (200 mg, 1.59 mmol), DIPEA (840 µL, 4.82 mmol) and CH$_2$Cl$_2$ (2 mL). The reaction was allowed to warm to room temperature overnight. After a total of 16 h, the reaction was poured into a mixture of 1 M HCl (20 mL) and CH$_2$Cl$_2$ (20 mL), and transferred to a separatory funnel. The layers were separated and the aqueous layer was extracted with CH$_2$Cl$_2$ (20 mL). The organic extracts were pooled, washed with 1 M HCl (20 mL), dried (MgSO$_4$) and filtered. Concentration under vacuum gave 253 mg of a white solid, which was used without further purification (see 52).

(R)—N-(3-(3-Cyclopropyl-5-((2-fluoro-4-iodophe-nyl)amino)-6,8-dimethyl-2,4,7-trioxo-3,4,6,7-tetra-hydropyrido[4,3-d]pyrimidin-1(2H)-yl)phenyl)-3-fluoropyrrolidine-1-sulfonamide (52)

A 15 mL pressure vessel was charged with 8 (50.0 mg, 0.087 mmol), 52a (81.6 mg, 0.435 mmol) CH$_2$Cl$_2$ (1 mL) pyridine (350 µL, 4.33 mmol). The reaction mixture was sealed under Ar and heated at 50° C. for 16 h. After cooling to room temperature, the reaction was concentrated to dryness and the remaining material was purified by silica gel chromatography (25 g cartridge), eluting at 25 mL/min and using a linear gradient of CH$_2$Cl$_2$/EtOAc: 100:0→0:100 over 35 column volumes to yield 24.7 mg (39%) of the title compound as a white solid: $^1$H NMR (400 MHz, DMSO-d$_6$) δ 11.06 (s, 1H), 10.10 (s, 1H), 7.78 (d, J=10.0 Hz, 1H), 7.55 (d, J=8.6 Hz, 1H), 7.32-7.42 (m, 1H), 7.14-7.25 (m, 2H), 7.07 (d, J=7.6 Hz, 1H), 6.91 (t, J=8.6 Hz, 1H), 3.07 (s, 3H), 2.61 (dt, J=6.7, 3.2 Hz, 1H), 1.22 (s, 3H), 0.95 (d, J=6.6 Hz, 2H), 0.66 (br s, 2H); LC-MS (ESI+) m/z: [M+H]$^+$ Calcd for C$_{28}$H$_{28}$F$_2$IN$_6$O$_5$S 725.1; Found 725.2.

(S)—3-Fluoropyrrolidine-1-sulfonyl chloride (53a)

To a −78° C. solution of sulfuryl chloride (390 µL, 4.81 mmol) and CH$_2$Cl$_2$ (3 mL) was added a mixture of (S)—3-fluoropyrrolidine hydrochloride (200 mg, 1.59 mmol), DIPEA (840 µL, 4.82 mmol) and CH$_2$Cl$_2$ (2 mL). The reaction was allowed to warm to room temperature overnight. After a total of 16 h, the reaction was poured into a mixture of 1 M HCl (20 mL) and CH$_2$Cl$_2$ (20 mL), and transferred to a separatory funnel. The layers were separated and the aqueous layer was extracted with CH$_2$Cl$_2$ (20 mL). The organic extracts were pooled, washed with 1 M HCl (20 mL), dried (MgSO$_4$) and filtered. Concentration under vacuum gave 254 mg of a white solid, which was used without further purification (see 53).

(S)—N-(3-(3-Cyclopropyl-5-((2-fluoro-4-iodophe-nyl)amino)-6,8-dimethyl-2,4,7-trioxo-3,4,6,7-tetra-hydropyrido[4,3-d]pyrimidin-1(2H)-yl)phenyl)-3-fluoropyrrolidine-1-sulfonamide (53)

A 15 mL pressure vessel was charged with 8 (50.0 mg, 0.087 mmol), 53a (81.6 mg, 0.435 mmol) CH$_2$Cl$_2$ (1 mL) pyridine (175 µL, 2.16 mmol). The reaction mixture was sealed under Ar and heated at 50° C. for 16 h. After cooling to room temperature, the reaction was concentrated to dryness and the remaining material was purified by silica gel chromatography (25 g cartridge), eluting at 25 mL/min and using a linear gradient of CH$_2$Cl$_2$/EtOAc: 100:0→0:100 over 35 column volumes to yield 45.7 mg (73%) of the title compound as a white solid: $^1$H NMR (400 MHz, DMSO-d$_6$) δ 11.07 (s, 1H), 10.10 (s, 1H), 7.78 (dd, J=10.3, 1.7 Hz, 1H), 7.55 (d, J=8.3 Hz, 1H), 7.33-7.41 (m, 1H), 7.15-7.26 (m, 2H), 7.07 (d, J=7.8 Hz, 1H), 6.91 (t, J=8.6 Hz, 1H), 3.07 (s, 3H), 2.61 (tt, J=7.0, 3.7 Hz, 1H), 1.22 (s, 3H), 0.87-1.01 (m, 2H), 0.66 (br s, 2H); LC-MS (ESI+) m/z: [M+H]$^+$ Calcd for C$_{28}$H$_{28}$F$_2$IN$_6$O$_5$S 725.1; Found 725.3.

N-(3-(3-Cyclopropyl-5-((2-fluoro-4-iodophenyl) amino)-6,8-dimethyl-2,4,7-trioxo-3,4,6,7-tetrahydro-pyrido[4,3-d]pyrimidin-1(2H)-yl)phenyl)benzene-sulfonamide 2,2,2-trifluoroacetate (54)

To a mixture of 8 (50.0 mg, 0.087 mmol), pyridine (175 µL, 2.16 mmol) and CH$_2$Cl$_2$ (1 mL), in an 8 mL vial, was added benzenesulfonyl chloride (20.0 μL, 0.157 mmol). The reaction mixture was stirred at room temperature for 1 h. Concentration under vacuum left a semi-solid, which was purified by reverse-phase chromatography, eluting at 40 mL/min and using a linear gradient of $H_2O$ (with 0.1% TFA)/MeCN (with 0.1% TFA): 90:10→1:99 over 20 minutes to yield 50.3 mg (81%) of the title compound as an off-white solid: $^1$H NMR (400 MHz, DMSO-d6) δ 11.04 (s, 1H), 10.41 (s, 1H), 7.78 (dd, J=10.4, 1.8 Hz, 1H), 7.70-7.76 (m, 2H), 7.58-7.64 (m, 1H), 7.53 (q, J=7.4 Hz, 4H), 7.25-7.32 (m, 1H), 7.15 (t, J=2.0 Hz, 1H), 7.06-7.12 (m, 1H), 7.01 (d, J=7.1 Hz, 1H), 6.90 (t, J=8.6 Hz, 1H), 3.07 (s, 3H), 2.55-2.63 (m, 1H), 0.93 (d, J=7.1 Hz, 2H), 0.65 (br s, 2H); LC-MS (ESI+) m/z: $[M+H]^+$ Calcd for $C_{30}H_{26}FIN_5O_5S$ 714.1; Found 714.2.

N-(3-(3-cyclopropyl-5-((2-fluoro-4-iodophenyl)amino)-6,8-dimethyl-2,4,7-trioxo-3,4,6,7-tetrahydro-pyrido[4,3-d]pyrimidin-1(2H)-yl)phenyl)-3-(trifluoromethyl)benzenesulfonamide 2,2,2-trifluoroacetate (55)

To a mixture of 8 (50.0 mg, 0.087 mmol), pyridine (175 μL, 2.16 mmol) and $CH_2Cl_2$ (1 mL), in an 8 mL vial, was added 3-(trifluoromethyl)benzenesulfonyl chloride (25.0 μL, 0.157 mmol). The reaction mixture was stirred at room temperature for 1 h. Concentration under vacuum left a semi-solid, which was purified by reverse-phase chromatography, eluting at 40 mL/min and using a linear gradient of $H_2O$ (with 0.1% TFA)/MeCN (with 0.1% TFA): 90:10→1:99 over 20 minutes to yield 54.8 mg (81%) of the title compound as a white solid: 1H NMR (400 MHz, DMSO-d$_6$) δ 11.04 (s, 1H), 10.59 (s, 1H), 7.98-8.08 (m, 3H), 7.74-7.84 (m, 2H), 7.54 (d, J=8.3 Hz, 1H), 7.27-7.36 (m, 1H), 7.17 (t, J=2.0 Hz, 1H), 7.11 (d, J=8.1 Hz, 1H), 7.04 (d, J=7.3 Hz, 1H), 6.90 (t, J=8.7 Hz, 1H), 3.06 (s, 3H), 2.55-2.63 (m, 1H), 0.93 (d, J=7.3 Hz, 2H), 0.86 (s, 3H), 0.65 (br s, 2H); LC-MS (ESI+) m/z: $[M+H]^+$ Calcd for $C_{31}H_{25}F_4IN_5O_5S$ 782.1; Found 782.3.

N-(3-(3-Cyclopropyl-5-((2-fluoro-4-iodophenyl)amino)-6,8-dimethyl-2,4,7-trioxo-3,4,6,7-tetrahydro-pyrido[4,3-d]pyrimidin-1(2H)-yl)phenyl)ethylaminosulfonamide 2,2,2-trifluoroacetate (56)

To a mixture of 8 (50.0 mg, 0.087 mmol), pyridine (175 μL, 2.16 mmol) and $CH_2Cl_2$ (1 mL), in an 8 mL vial, was added ethylsulfamoyl chloride (12.5 μL, 0.131 mmol). The reaction mixture was stirred at room temperature for 14 h. Concentration under vacuum left a semi-solid, which was purified by reverse-phase chromatography, eluting at 40 mL/min and using a linear gradient of $H_2O$ (with 0.1% TFA)/MeCN (with 0.1% TFA): 90:10→1:99 over 30 minutes to yield 18.9 mg (32%) of the title compound as a white solid: $^1$H NMR (400 MHz, DMSO-d$_6$) δ 11.09 (s, 1H), 9.82 (s, 1H), 7.78 (d, J=9.0 Hz, 1H), 7.55 (d, J=8.3 Hz, 1H), 7.49 (t, J=5.5 Hz, 1H), 7.30-7.39 (m, 1H), 7.09-7.20 (m, 2H), 6.99 (d, J=8.3 Hz, 1H), 6.92 (t, J=8.6 Hz, 1H), 3.07 (s, 3H), 2.84 (quin, J=6.5 Hz, 2H), 2.62 (m, J=6.4, 3.0, 3.0 Hz, 1H), 0.95 (t, J=7.2 Hz, 2H), 0.66 (br s, 2H); LC-MS (ESI+) m/z: $[M+H]^+$ Calcd for $C_{26}H_{27}FIN_6O_5S$ 681.1; Found 681.1.

N-(3-(3-Cyclopropyl-5-((2-fluoro-4-iodophenyl)amino)-6,8-dimethyl-2,4,7-trioxo-3,4,6,7-tetrahydro-pyrido[4,3-d]pyrimidin-1(2H)-yl)phenyl)propylaminosulfonamide 2,2,2-trifluoroacetate (57)

To a mixture of 8 (50.0 mg, 0.087 mmol), pyridine (175 μL, 2.16 mmol) and $CH_2Cl_2$ (1 mL), in an 8 mL vial, was added propylsulfamoyl chloride (15.0 µL, 0.134 mmol). The reaction mixture was stirred at room temperature for 18 h. Concentration under vacuum left a semi-solid, which was purified by reverse-phase chromatography, eluting at 40 mL/min and using a linear gradient of $H_2O$ (with 0.1% TFA)/MeCN (with 0.1% TFA): 90:10→1:99 over 30 minutes to yield 23.3 mg (39%) of the title compound as a white solid: $^1H$ NMR (400 MHz, DMSO-$d_6$) δ 11.08 (s, 1H), 9.82 (s, 1H), 7.78 (dd, J=10.3, 1.7 Hz, 1H), 7.48-7.59 (m, 2H), 7.30-7.38 (m, 1H), 7.17 (d, J=8.3 Hz, 1H), 7.09-7.14 (m, 1H), 6.99 (d, J=9.0 Hz, 1H), 6.92 (t, J=8.6 Hz, 1H), 3.07 (s, 3H), 2.75 (q, J=6.8 Hz, 2H), 2.62 (dt, J=7.2, 3.4 Hz, 1H), 1.28-1.41 (m, 2H), 1.25 (s, 3H), 0.95 (d, J=7.1 Hz, 2H), 0.76 (t, J=7.3 Hz, 3H), 0.66 (br s, 2H); LC-MS (ESI+) m/z: [M+H]$^+$ Calcd for $C_{27}H_{29}FIN_6O_5S$ 695.1; Found 695.2.

61 tert-Butyl (3-((3-(3-cyclopropyl-5-((2-fluoro-4-iodo-phenyl)amino)-6,8-dimethyl-2,4,7-trioxo-3,4,6,7-tetrahydropyrido[4,3-d]pyrimidin-1(2H)-yl)phenyl)amino)-3-oxopropyl)carbamate (61)

To a solution of 1-[bis(dimethylamino)methylene]—1H-1,2,3-triazolo[4,5-b]pyridinium 3-oxide hexafluorophosphate (HATU; 58.6 mg, 0.154 mmol), N,N-diisopropylethylamine (DIPEA; 55.0 µL, 0.316 mmol) and DMF (0.5 mL), in a 4 mL vial, was added a solution of 3-((tert-butoxycarbonyl)amino)propanoic acid (29.1 mg, 0.154 mmol) and DMF (0.5 mL) dropwise over 1 min. The dark orange solution was stirred for 30 min and then 8 (80.0 mg, 0.140 mmol) was added in one portion. The reaction was initially heterogeneous, but became clear over 1 h, and was stirred for a total of 14 h. The solution was concentrated to dryness and purified by silica gel chromatography (25 g cartridge), eluting at 25 mL/min and using a linear gradient of $CH_2Cl_2$/EtOAc: 100:0→0:100 over 30 column volumes to yield 103 mg (>99%) of the title compound as an off-white solid: $^1H$ NMR (400 MHz, DMSO-$d_6$) δ 11.07 (s, 1H), 10.09 (s, 1H), 7.79 (d, J=10.3 Hz, 1H), 7.50-7.70 (m, 3H), 7.36 (t, J=8.1 Hz, 1H), 7.03 (d, J=7.8 Hz, 1H), 6.81-6.98 (m, 2H), 3.21 (q, J=6.4 Hz, 2H), 3.07 (s, 3H), 2.62 (tt, J=6.9, 3.8 Hz, 1H), 2.43-2.51 (m, 2H; signal overlaps with DMSO-$d_5$ peak), 1.37 (s, 9H), 1.26 (s, 3H), 0.95 (d, J=6.1 Hz, 2H), 0.67 (br s, 2H); $^{19}F$ NMR (376 MHz, DMSO-$d_6$) δ −124.0-−123.8 (m, 1F); LC-MS (ESI+) m/z: [M+H]$^+$ Calcd for $C_{32}H_{35}FIN_6O_6$ 745.2; Found 745.3.

Example 2

Methods 2.1 Data Reporting

No statistical methods were used to predetermine sample size. The experiments were not randomized, and the investigators were not blinded to allocation during experiments and outcome assessment.

2.2 Expression and Purification of KSR:MEK1 and BRAF: MEK1 Complexes.

Codon optimized versions of human KSR1 (residues 591-899; Uniprot ID:Q8IVT5), human KSR2 (residues 634-950; Uniprot ID: Q6VAB6), human BRAF (residues 432-726; Uniprot ID: P15056), and rabbit MEK1 (residues 35-393; Uniprot ID: P29678) were synthesized with N-terminal hexahistidine tags and TEV-cleavage site (HHIHHENLYFQG). Each KSR-MEK1 pair, as well as BRAF-MEK1, was sub-cloned into the pFastBac Dual expression vector, with KSR1, KSR2, or BRAF under the influence of a late polyhedron (PH) promoter and MEK1 under an early p10 promoter. A mutant version of MEK1, Ser298Asn/Ser299Lys/Tyr300Phe was used based on a previous report that these mutations eliminate a degradation site and thereby increase protein yields[19]. For recombinant expression and purification of KSR1, KSR2, BRAF, or MEK1, it is understood that we refer to the fragments mentioned above. Similarly, all MEK1 proteins used for expression, purification, crystallization, and biochemical studies include the Ser298Asn/Ser299Lys/Tyr300Phe mutations. The pseudokinase domains of either human KSR1 or human KSR2, or the kinase domain of human BRAF, were co-expressed with rabbit MEK1 using the baculovirus expression system (Clontech). SF21 cells were infected with baculovirus expressing the KSR1-MEK1, KSR2-MEK1, or BRAF-MEK1 complex for 72 hours and harvested typically with a cell viability of ~50-60% and density of 3-4×10$^6$ cells/mL. Cell pastes were lysed by freeze-thawing and sonication. Following, cobalt resin (Clontech) was used to capture protein complexes, and eluted proteins were subsequently dialyzed in 20 mM Tris pH 7.8, 200 mM NaCl, 10% glycerol, and 5 mM DTT. The dialyzed sample was further purified by ion exchange chromatography using HiPrep SP HP column (GE Healthcare) for the KSR2-MEK1 or BRAF-MEK1 complex, and a HiPrep Q HP column (GE Healthcare) for the KSR1-MEK1 complex. Dialysis retentates were diluted at least five-fold and then applied to the respective columns, and eluted with linear salt gradients (50 to 500 mM NaCl) used to isolate free MEK1, and the 1:1 KSR-MEK1 complexes. Following separation, fractions containing stoichiometric KSR1-MEK1, KSR2-MEK1, or BRAF-MEK1 were confirmed by gel electrophoresis and coomassie staining. Selected fractions were then pooled, and subsequently applied to a Hiprep Superdex 200 10/300 GL size exclusion column for final purification in a buffer consisting of 20 mM Tris pH 7.8, 150 mM NaCl, 5 mM DTT, 1 mM TCEP. Each of the KSR1-MEK1 complex, KSR2-MEK1, and BRAF-MEK1 complex eluted in two peaks, representing heterodimer (minor) and heterotetramer (major) species. Excess MEK1, which was purified separately over a Hiprep Superdex 200 10/300 GL size exclusion column eluted as a monomer. For crystallization, samples of the KSR1-MEK1 or KSR2-MEK1 complex were incubated overnight with trypsin (1:1000 ratio). These samples were then subsequently applied to a Hiprep Superdex 200 10/300 GL size exclusion column for final purification in the same buffer as described above. Trypsinized samples of both the KSR1-MEK1 complex and KSR2-MEK1 complex demonstrated similar elution profile as non-trypsinized samples, with heterotetramer as the major species. Typical yields were 0.2 mg of tetrameric complex from 50 grams of pellet for KSR1-MEK1 and 0.8 mg from 50 grams of pellet for KSR2-MEK1.

2.3 Crystallization and Structure Determination of Inhibitor-Bound KSR1/2:MEK1 Complexes.

Co-crystals of isolated MEK1 with trametinib could not be obtained, however, when purified in complex with human KSR1 or KSR2, the structures of trametinib bound to the KSR1:MEK1 and KSR2:MEK1 complexes were determined at 3.3 Å and 2.8 Å, respectively (FIG. 1). In the trametinib-bound structures, the compound occupies the MEKi allosteric site adjacent to ATP[19,20], consistent with the characterization of trametinib as an ATP non-competitive kinase inhibitor[21] (FIG. 2). However, trametinib also engages an extended sub-pocket that reaches the KSR interaction interface (FIG. 3).

The tetrameric complex of both KSR1-MEK1 and KSR2-MEK1 were concentrated to 6-9 mg/ml and incubated with 5 mM AMP-PNP in a buffer supplemented with 10 mM MgCl$_2$. After an incubation period of approximately 10 minutes, aggregates were removed through centrifugation at 14,000 g for 10 minutes. Following, the complexes were crystallized using the hanging drop method at 20 deg C. in a 1:1 ratio of protein and crystallization buffer [12% PEG-3350, 100 mM MES pH 6.25, 200 mM Magnesium Acetate]. Hexagonal shaped crystals appeared within 24 hours, and these grew to the maximum size of approximately 200 microns within 48-72 hours. Initial crystals were then transferred to a fresh solution containing MEK inhibitors (Selleckchem: Trametinib-52673, Cobimetinib-58041, Selumetinib-S1008, and PD0325901-S1036). Finally, the MEKi soaked crystals were back soaked into a cryosolution of 25% ethylene glycol in mother liquor prior to flash-freezing in liquid nitrogen. X-ray diffraction data was collected at the Advanced Photon Source sector 21 (Argonne National Laboratory, IL), Advanced Light Source (Lawrence Berkeley National Laboratory, CA), or the National Synchrotron Light Source II (Brookhaven, NY). Diffraction images were indexed and scaled using XDS[37], and structures were solved by molecular replacement using Phaser[38] based on searches of KSR2 (chain B) and MEK1 (chain C) models derived from the KSR2(KD):MEK1:ATP crystal structure (PDB code: 2Y4I). Model building was performed with Coot[39]. The crystallographic information files (CIF) for all the ligands were generated using Phenix based Electronic Ligand Builder and Optimization Workbench (ELBOW), and were used subsequently in the refinement process[40]. Rigid body and maximum likelihood-based refinement protocols were implemented through Phenix with ligands omitted from early rounds of refinement[41]. All crystal structures were found to share similar unit cell dimensions, space group symmetry, and X-ray diffraction properties. Pymol Molecular Graphics System (Schrödinger) was used to generate images for all structural figures presented in the manuscript. Detailed data collection and refinement statistics are included in FIG. 70. Electron density omit maps for ligands are included in FIG. 1.

This research used resources of the Life Sciences Collaborative Access Team beamline (sector 21) of the Advanced Photon Source, a U.S. Department of Energy (DOE) Office of Science User Facility operated for the DOE Office of Science by Argonne National Laboratory under Contract No. DE-AC02-06CH11357. Use of the LS-CAT Sector 21 was supported by the Michigan Economic Development Corporation and the Michigan Technology Tri-Corridor (Grant 085P1000817). Also, this research used resources of the National Synchrotron Light Source beamline (17-ID-1&2), a U.S. Department of Energy (DOE) Office of Science User Facility operated for the DOE Office of Science by Brookhaven National Laboratory under Contract No. DE-AC02-98CH10886. Also, this research used resources from Beamline 8.2.2 of the Advanced Light Source, a U.S. DOE Office of Science User Facility under Contract No. DE-AC02-05CH11231, which is supported in part by the ALS-ENABLE program funded by the National Institutes of Health, National Institute of General Medical Sciences, grant P30 GM124169-01.

2.4 Modeling of Trametinib onto Isolated MEK and Distance Calculations.

Docking of trametinib onto the previously determined structures of isolated MEK was performed through structural overlays using the coordinates derived from our experimental structures of KSR2-MEK1 in complex with trametinib. This analysis suggests that either the activation segment of isolated MEK or the compound must undergo significant rearrangements so as to enable drug binding (FIG. 83). Distances in FIG. 8 were measured with hydrogens included in the ligand and KSR1 and were found to measure 2.4 Å and 3.5 Å between alpha and beta hydrogens of A825 and the terminal —CH$_3$ of trametinib. In comparison, PD0325901, selumetinib, and cobimetinib are at the closest distance of approximately 10 Å, 9 Å, and 6 Å, respectively, within the KSR1-MEK1 complex.

2.5 Binding Analysis as Measured by Bio-Layer Interferometry (BLI).

Figure 53:
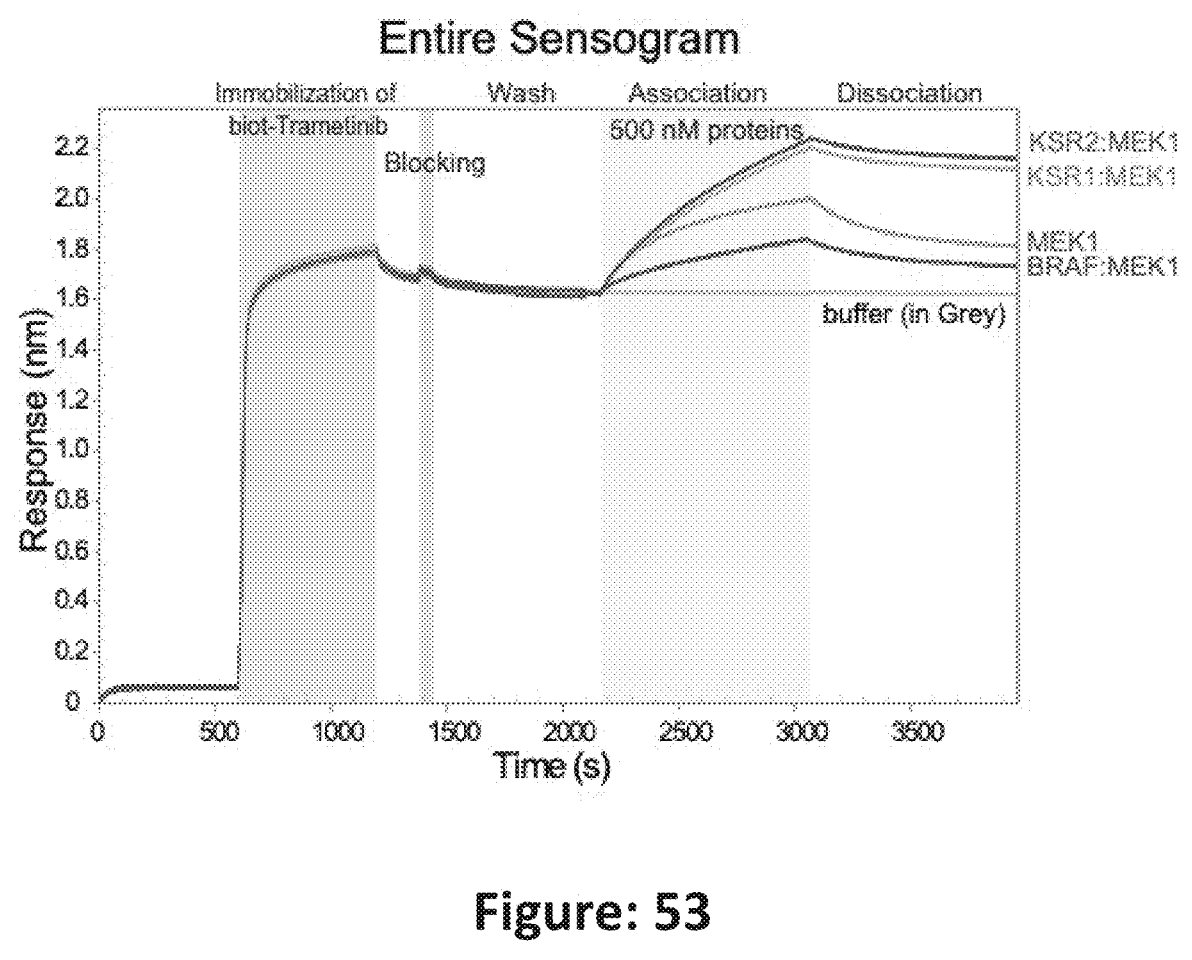

BLI measurements were performed using an Octet Red96 (Forte Bio, Inc.) system. All experiments were conducted at 25° C. with shaking at 1000 rpm, and in a buffer containing 20 mM Hepes pH 7.5, 200 mM NaCl, 1 mM ATP, 5 mM MgCl2, 0.02% Tween-20, 1% DMSO. In the first step, biotin-linked trametinib was loaded onto a streptavidin (SA; Product number 18-5019 ForteBio) Dip-and-Read sensor head to saturation. This amount of immobilization typically achieved 1.5-2.0 nm binding signal. Biosensors were then washed in buffer, treated in a solution of biocytin for 3 min, and then again washed extensively to achieve a normalized baseline signal of ~0 nm. Following, for kinetic analysis, biosensors were dipped in solutions of free MEK1, BRAF: MEK1, KSR1:MEK1, or KSR2:MEK1. Association was measured for 10 or 15 minutes, following a dissociation phase in buffer of 15 minutes. Blank sensors and buffer only data, which displayed no discernible binding, were included as controls (FIG. 53, 54). Varying the load of biotin-linked trametinib did not influence binding kinetics discernibly and therefore all experiments were conducted with 1000 nM biotin linked trametinib immobilized to saturation. All experiments were performed at least three independent times, with raw data processed and analyzed using global fit binding models in Fortebio software to derive KD (M), K$_{on}$(1/M·s), and K$_{dis}$ (1/s) values. Drug target lifetimes ($\tau$) were determined as the reciprocal of K$_{dis}$; titration analysis suggested dissociation of the KSR1:MEK1 and KSR2: MEK1 complexes below 500 nM (FIG. 52) and therefore only binding data at 500 nM or above was used to determine $\tau$(min) for KSR1:MEK1 and KSR2:MEK1. $\tau$(min) for MEK1 and BRAF:MEK1 was also determined from binding data with protein at a concentration of 500 nM or greater. One-to-one binding models provided a high agreement with the measured binding signals based on chi-squared and R-squared values. Raw data and fitting, mean and standard deviation determinations, as well as statistical analysis, for K$_D$, k$_{on}$(1/M·s), k$_{dis}$(1/s), and $\tau$(min) are included in FIG. 71.

2.6 Cell Culture and Antibodies.

HCT116, A549, and A375 cells were acquired from American Type Culture Collection. SKMEL-239 cells were generously provided by the Emily Bernstein laboratory (Mount Sinai) via Memorial Sloan Kettering Cancer Center. HCT116, A549, and A375 cells were maintained in DMEM supplemented with 10% fetal bovine serum and penicillin/streptomycin. SKMEL-239 cells were cultured in RPMI supplemented with 10% fetal bovine serum and penicillin/streptomycin. Antibodies detecting MEK1/2 (Product number: 4694S) at 45 kDa, ERK1/2 (Product number: 4695S) at 42/44 kDa, phospho-ERK1/2 (T202/Y204; Product number: 9101S) at 42/44 kDa and GAPDH (Product number: 2118S) at 37 kDa were obtained from Cell Signaling Technology. Antibodies detecting BRAF (Product number: sc-5284) at 85 kDa and FLAG (Product number: F1804) were purchased from Santa Cruz Biotechnology and Sigma-Aldrich, respectively. FLAG-tagged BRAF was detected at 85 kDa, and FLAG-tagged KSR was detected at 97 kDa. For antibody detection, blots were incubated at 4° C. overnight in primary antibodies in 5% BSA in Tris-buffered saline 0.1% Tween 20 detergent (TBST) at the following dilutions: MEK1/2 (1:5, 000), GAPDH (1:10,000), BRAF (1:200), FLAG (1:5000), ERK1/2 (1:1000), phospho-ERK 1/2 (1:1000). The next day, blots were washed five times with TBS-T and probed for 1 hour with anti-mouse-HRP (Product number: 7076S) or anti-rabbit-IRP (Product number: 7074P2) antibodies from Cell Signaling in 5% BSA TBST at a dilution of 1:5,000. Endogenous MEK1 was immunoprecipitated (IP) with a MEK1 specific antibody from Millipore-Sigma (Product number: 07-641). Normal rabbit IgG (Product number: 12-370) also acquired from Millipore-Sigma was used as an IP control antibody at final concentrations of 1 µg antibody per 50 µg input sample lysate. Precision Plus Protein Dual Color Standard from Bio-Rad (Product number: 1610375) was used as a reference ladder to confirm band sizes.

2.7 Plasmids and Transfections.

Full-length mouse KSR1-FLAG (Addgene ID: 25970) plasmid was acquired from Addgene, and full-length human BRAF-FLAG plasmid was generously provided by the Poulikos Poulikakos laboratory (Mount Sinai). Mutant KSR1 and BRAF constructs were generated using the QuickChange Site-Directed Mutagenesis Kit from Agilent Technologies. To normalize protein expression levels across KSR1-FLAG and BRAF-FLAG constructs for experiments shown in FIGS. 3C and D, the following masses of plasmids were transfected into HCT116 cells: KSR1(WT)—2.3 µg, KSR1 mutant K1 (P775N)—12 µg, KSR1 mutant K2 (A776R)—8 µg, KSR1 mutant K3 (P775N/A776R)—15 µg, KSR1 mutant K4 (—InsN/P775N/A776R)—15 µg, KSR1 (R$^{615}$H)—12 µg, BRAF(WT)—10 µg, BRAF mutant B1 (N661A)—10 µg, BRAF mutant B2 (R662A)—3.5 µg, BRAF mutant B3 (N661A/R662A)—5 µg, BRAF mutant B4 (delN/N661A/R662A)—5 µg. DNA transfections were performed using Lipofectamine 3000 (Invitrogen) according to the manufacturer's instructions with a ratio of P3000 enhancer reagent:L3000 transfection reagent of 6:3.75.

2.8 Immunoprecipitation of MEK1 Associated Complexes from Cancer Cell Lines.

Immunoprecipitation (IP) experiments (as shown in FIGS. 45, 46, and 64) were performed by plating 450,000 HCT116 cells per well in 6-well plates. Cells were plated for 48 hours so as to reach approximately 70% confluency prior to transfection. Following 24 hours post-transfection, cells were treated with vehicle (0.1% DMSO) or trametinib (200 nM) for 1 hour. Cells were then washed two times in cold PBS and then transferred to a pre-chilled tube in 0.6 mL of PBS solution. Cells were spun at 1,800× gin a cold centrifuge for 10 minutes, and supernatant was aspirated. To lyse cells, pellets were resuspended in NP-40 buffer (50 mM Tris pH 7.8, 100 mM NaCl, 0.5% [v/v] NP-40, 10% [v/v] glycerol, 1 mM EDTA) supplemented with Protease and Phosphatase Inhibitor Cocktail (Thermo Fisher, product number 78440) and incubated on ice for 30 minutes. Lysates were centrifuged for 20 minutes at 2,100×g, and supernatants were collected. Cleared lysates were quantified using BCA reagent (Pierce, 23225), with BSA as a standard. 5 µg of rabbit anti-MEK1 antibody (07-641 from Millipore-Sigma), or rabbit IgG (12-370 from Millipore Sigma), was immobilized on 50 µL of Sepharose Protein A Resin (Thermo Fisher, 53139) and washed three times in 300 µL NP-40 buffer prior to initiating IPs. Following, for MEK1 immunoprecipitation, 250 µg of total cell lysate in a total volume of 0.6 mL was mixed with the pre-immobilized anti-MEK1 antibody pre-conjugated to Protein A Resin. Samples were incubated at 4° C. on an end-over-end rotator for 4 hours, followed by three washes in 0.6 ml volume of NP-40 buffer. Following, proteins were denatured and released from resin by the addition of 80 µl volume of 1×SDS sample buffer. Samples were boiled at 90 degrees Celsius for two minutes, spun, and then applied to a 4-12% bis-tris glycine gel (Bio-Rad, 3450125) run in MOPS-SDS buffer (Thermo Fisher, NP0001) for 60 minutes at 150 volts. After, gels were transferred onto nitrocellulose in 20% methanol in tris-glycine buffer (95 volts, 250 amps). Transfers were confirmed using Ponceau red and then analysed by Western blot. Signals for MEK, FLAG-tagged proteins, BRAF, and GAPDH were detected by enhanced chemiluminescence on a ChemDoc XRS+ imaging system (Biorad).

2.9 Cell Proliferation Assays.

A375, A549, HCT116, and SKMEL-239 cells were plated in Corning Costar Ultra-Low Attachment 96-well plates (Reference number 3434). After 24 hours of incubation at 37° C., cells were treated with inhibitors (0.1% DMSO in final volume). Cells were grown for five days, and resazurin sodium salt was added at a final concentration of 0.01 µg/µL. Fluorescence was measured using a Molecular Devices SpectraMax M5 spectrophotometer after a 4-24-hour incubation with resazurin solution. Technical triplicate values were averaged for each experiment, and biological replicate values are represented as average+/−standard deviation. For each cell line, log EC$_{50}$ values of inhibitors were statistically compared using the extra sum-of-squares F test in GraphPad Prism 8 (FIG. 57, 58, 67, 68, 69).

2.10 Clonogenic Assays.

Cells were plated at a density of 6,000 cells per well in 6-well plates in 3 mL of culture medium. Twenty-four hours after seeding, compounds dissolved in DMSO or DMSO-only vehicles were added directly to the culture media at a 1:1000 dilution. Following 10 days of culture, cells were washed 2× in PBS, fixed in ice-cold methanol for 10 minutes, stained with crystal-violet at room temperature for 10 minutes, and subsequently washed three times in water. Plates were allowed to dry overnight before imagining with an Epson V600 scanner.

2.11 Time Course Experiments to Assess RAS/ERK Pathway Inhibition by Immunoblot.

Cells were plated at a density of 300,000 cells per well in 6-well plates in 2 mL of culture medium. 24 hours after seeding, cells were treated with compounds or DMSO at a 1:1000 dilution (0.1% DMSO in final volume). At harvest, media from cells was first aspirated and washed 2× in ice-cold PBS, and either lysed directly in wells using RIPA buffer or transferred to a pre-chilled tube in 0.5 mL ice-cold PBS, centrifuged for 10 minutes at 1,800×g, then lysed in 120 μl of Pierce RIPA buffer (PI89901) supplemented with protease and phosphatase inhibitor cocktail (Thermo Fisher, product number 78440). Cleared lysates were quantified using BCA reagent (Pierce, 23225) or DC Protein Assay (Bio-Rad 5000111) with BSA as a standard. Samples were normalized to a protein content of 5 μg/μL in 100 μL total volume, and 20 μL of 6×SDS was added. Samples were boiled at 90 degrees Celsius for two minutes, spun, and then applied to either 4-12% or 4-15% bis-tris glycine gels (Bio-Rad, 3450125) run in MOPS-SDS buffer (Thermo Fisher, NP0001) for 60 minutes at 150 volts. After, gels were transferred onto nitrocellulose in 20% methanol in tris-glycine buffer (95 volts, 250 amps). Transfers were confirmed using ponceau red, washed, and then blocked for 1 hour with 5% BSA TBS-T, prior to overnight incubation with primary antibodies including phospho-ERK1/2 T202/Y204 and total ERK1/2 (Cell Signaling Technologies (CST) 9101S and 4695S, respectively) in 5% BSA TBS-T. The next day, blots were washed extensively, and incubated in secondary antibody (Anti-Rabbit IgG HRP-Linked CST 7074S). Signals for phospho-ERK1/2, total ERK and/or GAPDH were detected by enhanced chemiluminescence on a ChemDoc XRS+ imaging system (Biorad).

2.12 Generation of Stable shRNA HCT-116 Knockdown Lines

Scramble control shRNA (CCTAAGGT-TAAGTCGCCCTCGCTCGAGCGAGGGCGACT-TAACCTTA GG; TRCN000000622) and KSR1-shRNA (CCGGGCCTCCTTATTGCAGAAAGTTCTCGAGAA-CTT TCTGCAATAAGGAGGCTTTTT; Addgene:1864) constructs were packaged into lentivirus in HEK293T cells using the Lipofectamine 3000 transfection reagent (Thermofisher L3000001) and 10 μg of vector, 1.5 μg of VSV-G, and 5 μg of delta8.9, and incubated for 48 hours before supernatant collection. Virus-containing supernatant was then concentrated using Lenti-X Concentrator (Takara 631231) and quantified via Lenti-X GoStix Plus (Takara 631280). HCT-116 parental cells were spin-infected with concentrated virus at a MOI of 6 in media supplemented with polybrene (6 ug/mL). After 2 days, cells were selected for stable knockdown of KSR1 using puromycin (2 ug/mL). After a further 4-6 days, cells were passaged for experimentation.

2.13 RNA Preparation, cDNA Preparation, and Quantitative PCR Analysis

Total RNA was extracted with Trizol (Invitrogen 15596026) and purified using the RNeasy Mini Kit (Qiagen). cDNA was generated using the Superscript IV First-Strand Synthesis System (Invitrogen 18091050) according to the manufacturer's instructions. Quantitative RT-PCR was performed with gene-specific primers, using the Power SYBR-Green Master Mix (Applied Biosystems). For measurement of KSR1 mRNA by RT-qPCR, primers (Forward—AGTTTCTCCAG CATGTCCATC, Reverse—GAATGAAGCGTGTCCTGACT) specific to the KSR1 mRNA were utilized, and 18S rRNA (Forward—ACCCGTTGAACCCCATTCGTGA, Reverse—GCCT-CACTAAACCATCCAATCGG) was used as a reference gene.

2.14 Intracellular Target Engagement Assays Via Nano-BRET 2.14a In-Cell $IC_{50}$ Measurements to Determine Steady-State Binding of MEKi Measurements of $IC_{50}$ values for MEKi (that is, trametinib analogs and clinical compounds) were carried out according to the protocol provided by Promega for the in-cell kinase assay, and as previously reported[24], with some modifications. Briefly, HEK293T cells were transfected with either human MEK1-luc (Uniprot Q02750), mouse KSR1-luc (wild-type Uniprot Q61097), mouse KSR1-luc (W781D; Uniprot Q61097), Src-luc (Uniprot P12931), and RET-luc (Uniprot 07949) constructs at a concentration of 1 μg/mL in combination with 9 μg/mL of carrier DNA (part of the Promega kit) at a density of 200,000 cells/mL and Fugene HD. RET and Src constructs were obtained from Promega. For co-transfections (1:1), each construct was used at a concentration of 1 μg/mL in combination with 8 μg/mL of carrier DNA. Transfected cells were incubated overnight at 37° C. Cells were then trypsinized and plated into white low adherence 96 well plates (Corning-3990) in Opti-MEM (Gibco-31985-070) at a density of 20,000 cells/well. All compounds (Selleckchem: Trametinib-52673, Cobimetinib-58041, Selumetinib-S1008, PD0325901-S1036, CH5126766-S7170 and Trametiglue) were first dissolved in DMSO as concentrated stocks (10 mM), then further diluted in a transfer plate using Opti-MEM to a 10× concentration relative to final dose levels as indicated in each experiment; final concentrations for dose responses ranged from 10 μM down to 1 μM, in 10-fold dilutions. Following the addition of the compounds to cells, a 20× tram-bo solution (final concentration of 1 μM) in a mixture of DMSO/Tracer dilution buffer (Promega) was added to each well and the plate was incubated at 37° C. for 2 hrs. Alternatively, K4 and K5 tracers were used as positive controls for BRET with Src-luc and RET-luc, respectively. The order of addition for all experiments was drug/compound first, followed by tracer, which was very important to produce dose response curves that gave robust BRET ratio separation between the highest and lowest doses tested. To generate dose response curves, a 33.3× solution of NanoLuc inhibitor and Nano-Glo substrate in Opti-MEM was added to each well, and plates were read on a GloMax plate reader using the standard protocol on the GloMax software for BRET assays. All data were analyzed in Prism 8 (GraphPad).

2.14b Washout Experiments to Determine Intracellular Residence Time of MEKi

Given the potency of the analysed MEKi, we could not accurately distinguish residence time on MEK1-luc and KSR1-luc under typical saturating assay conditions (ie. 15×$IC_{50}$; Supplementary FIG. 2, page 8 compares wash versus no-wash pretreatment). Therefore, washout assays were conducted with pre-incubation of MEKi at 50, 25, 12.5 and 6.25 nM, or as otherwise noted, prior to cell washing and addition of tram-bo. Specifically, transfections of MEK1-luc and KSR1-luc, and construction of the drug transfer plates were carried out as mentioned above. For washout experiments, cells were first removed from adherent plates by trypsin treatment. Following, cells were harvested, spun, and resuspended in Opti-MEM (270 μL total) in centrifuge tubes at 450,000 cells/tube. 30 μL of drug solutions were then added to final indicated concentrations to give 300 μL total volume; then tubes were incubated at 37° C. for 2 hours, spun down at 1200× g for 5 min, aspirated of supernatant, resuspended in Opti-MEM, and plated into white low adherence 96 well plates at a density of 150,000 cells/well. A 20× solution of tram-bo was added to the plate (final concentration of 1 μM), followed immediately by the addition of a 33.3× solution of NanoLuc inhibitor and Nano-Glo substrate in Opti-MEM. Plates were then read on a GloMax plate reader for 175 minutes using 75 reads each with 0.3s/well integration time.

2.14c RAF Family Tram-Bo Buildup Curves

Human c-terminal NanoLuc fusions versions of ARAF (Uniprot P10398), BRAF (UniProt P15056), CRAF (Uniprot P04049), KSR1 (Uniprot Q8IVT5), and KSR2 (Uniprot Q6VAB6) were transfected as mentioned above at a concentration of 0.1 µg/mL in combination with 9.9 µg/mL of carrier DNA. All RAF constructs from Promega. Following incubation at 37° C. overnight, cells were trypsinized and plated into white low adherence 96 well plates in Opti-MEM at a density of 20,000 cells/well. A 20× tram-bo solution was added to each well to give final concentrations of 4, 1, 0.5, 0.1, 0.05, 0.01, 0.001, 0.0001 µM. The plate was incubated for 2 hrs at 37° C., and buildup curves were generated using the standard GloMax protocol upon the addition of a 33.3× solution of NanoLuc inhibitor and Nano-Glo substrate in Opti-MEM. All data were analyzed using Prism 8 (GraphPad).

2.2 Discussion 2.2a KSR Modulates Target Engagement of MEK Inhibitors

To understand the unique properties of trametinib, we also solved structures of KSR2-MEK1 and KSR1-MEK1 bound to cobimetinib (2.99 Å and 3.10 Å, respectively), selumetinib (3.09 Å and 3.21 Å, respectively), and PD0325901 (3.19 Å and 3.63 Å, respectively) (FIG. 1).

Unlike trametinib, KSR1 and KSR2 do not directly interact with the other MEKi ligands that we analysed, which suggests that the direct engagement of KSR is a unique feature of trametinib (FIG. 9). Indeed, whereas the terminal —CH$_3$ group within trametinib is within a bonding distance of approximately 3 Å to KSR1 or KSR2 (FIG. 9), the other MEKi that we analysed are up to 10 Å from direct contact with the KSR-MEK interaction interface.

Compared with isolated MEK1, the MEKi pocket differs in shape and size when MEK1 is in complex with KSR1 or KSR2 (FIG. 10). Unlike isolated MEK1 bound to PD0325901 (PDB code: 3VVH), selumetinib (4U7Z), and cobimetinib (4LMN), MEK1 displays substantial structural differences in the N-terminal end of the activation loop, $3_{10}$-helix, and Ser218-Ser222 sites, as these motifs extend up to around 9 Å away from the active site of MEK1 after complexation to KSR (FIG. 11). This large shift in activation loop conformation, and concomitant increase in the size of the MEKi allosteric pocket, is stabilized through the pre-helix αG loop on KSR, and also through the formation of unique anti-parallel β-sheets shared between MEK1 and KSR1 or KSR2 (FIG. 12). Specific to KSR1-MEK1, the three-residue antiparallel β-sheet structure within the activation segment extends to a 4-residue stretch after complexation with trametinib (FIG. 9, 11-14). This structural change, which occurs in a segment connecting the key phospho-regulatory sites Ser218 and Ser222 in MEK1, creates a further expanded pocket so as to accommodate the phenyl-acetamide group in trametinib. The same rearrangement does not occur within KSR2-MEK1, as the antiparallel activation segments adopt an extended six-residue sheet irrespective of MEKi engagement (FIG. 13, 14). KSR1 also differs from KSR2 by a unique helical extension (αG') and at several motifs (FIG. 15-21).

Figure 22:
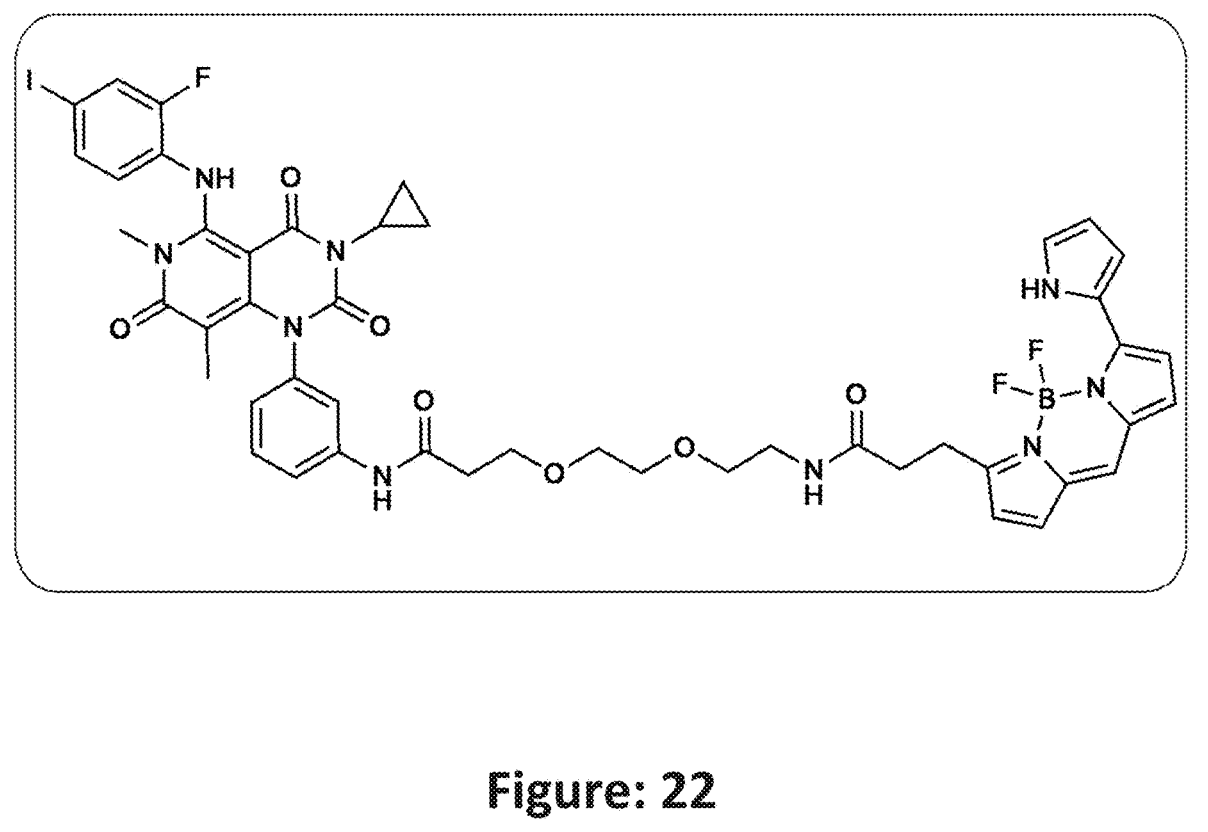

Together, the structural comparisons suggest that the MEKi allosteric pocket differs substantially between isolated MEK, in which the activation segment adopts an 'inward' configuration, and the KSR-bound state, in which the same region adopts an 'extended' conformation (FIG. 10). Additionally, in the complex, trametinib is accommodated by an enlarged allosteric binding pocket in MEK that is remodelled through direct contacts with KSR. To investigate pharmacological readouts of MEK and KSR-bound MEK in vivo, we adapted a target engagement assay[24] to measure MEKi interactions within a cellular context. In brief, we synthesized a bodipy-conjugated version of trametinib (tram-bo) to serve as a fluorescent small molecule tracer for bioluminescence resonance energy transfer (BRET) with nanoluciferase (luc) tagged versions of KSR1 or MEK1 (FIG. 22-28). When expressed in cells, both KSR1-luc or MEK1-luc, but not control kinases, generated BRET with tram-bo that could be competed with free trametinib, which suggests that tram-bo binds the same allosteric pocket as trametinib (FIG. 29). Furthermore, a KSR1(W781D) mutant at the MEK1 interaction interface ablated the BRET dose response (FIG. 30). MEK1-luc therefore serves as a reporter for several states of MEK that are accessible within live cells, including free MEK. Whereas energy transfer between KSR1-luc and tram-bo depends on the formation of the KSR-MEK complex in vivo.

Under equilibrium binding conditions, we obtained near identical steady-state IC$_{50}$ values of 6.7±0.5 and 7.6±1.1 nM for trametinib against KSR1-luc and MEK1-luc, respectively (FIG. 31). However, with cobimetinib, PD0325901, and selumetinib, we obtained markedly distinct potency values, differing by as much as 20-fold for cobimetinib (IC$_{50}$=5.1±0.7 nM on KSR1-luc and 102.8±5 nM on MEK1-luc; FIG. 12). Furthermore, PD0325901, cobimetinib, and selumetinib all competed tram-bo with more potent IC$_{50}$ values on KSR1-luc over MEK1-luc (FIG. 33), which suggests that KSR-bound MEK represents a high-affinity target for these MEK inhibitors in vivo. The only exception we found was the compound CH5126766 with relatively low micromolar IC$_{50}$ values in comparison to other MEKi (FIG. 31), which may reflect the unique mechanism of action proposed for this compound[25].

The significantly distinct IC$_{50}$ values for MEK1-luc and KSR1-luc with the MEKi PD0325901, cobimetinib, and selumetinib would be consistent with a model in which these compounds bind multiple distinct configurations of MEK as represented by 'inward' and 'extended' conformations observed in crystal structures (FIG. 11). Moreover, the presence of KSR1 could hinder the dissociation of PD0325901, cobimetinib, and selumetinib from MEK1 by sterically occluding drug release, potentially favoring drug 'rebinding'[26] that leads to more potent apparent IC$_{50}$ values observed within the complex; as supported by co-expression analysis (FIG. 34). Whereas, the near-identical IC$_{50}$s for trametinib on KSR1-luc and MEK1-luc, would be consistent with this compound engaging a single target configuration in vivo. In particular, we propose that under the conditions of our competition assays within engineered cell lines, trametinib is unique in demonstrating selectivity for the extended activation segment conformation that we observe in structures of KSR-bound MEK.

We next performed washout experiments on cells pretreated with the different MEKi to which we then added tram-bo (FIG. 28). In these experiments, the velocity of the BRET build-up curve, as measured by the association of fluorescent tracer over time, is proportional to the dissociation and intracellular residence time of free-ligand[24]. Over a range of MEKi concentrations both above and near the IC$_{50}$ values, we observed varying dissociation kinetics among the MEKi on both MEK1-luc and KSR1-luc (FIG. 31). Trametinib demonstrated the slowest dissociation kinetics with no detectable BRET signal recovery over a 175-minute time course on KSR1-luc, and to a lesser extent MEK1-luc, over a range of inhibitor concentrations (FIG. 13, top); this was also observed through MEK1-luc and KSR1 co-expression (FIG. 36). In comparison, cobimetinib dissociated more readily from both MEK1-luc and KSR1-luc, despite similar $IC_{50}$ values on the complex relative to trametinib (FIG. 13, bottom). These data suggest that within the nonequilibrium conditions of a washout experiment, which may mimic target occupancy and pharmacology under the dynamic conditions typically observed in vivo[24], certain MEKi specifically engage KSR-bound MEK for extended periods of time.

2.2b Trametinib Binds KSR-MEK and Disrupts RAF-MEK

KSR belongs to the larger family of RAF kinases[27]. However, unlike BRAF, CRAF/RAF1, or ARAF, KSR1 and KSR2 are characterized as pseudokinases owing to mutations in the active site. Notably, KSR and RAF pairs co-exist across a variety of metazoan species (FIG. 37). Further, much like the KSR-MEK complexes, BRAF and MEK1 can form a similar complex centred on reciprocal helix αG interactions (FIG. 38-40[28-31])

Previous work on several clinical MEKi have suggested that trametinib weakens the interaction of MEK towards RAF[9], yet our crystal structures and functional analysis clearly demonstrate binding of trametinib to MEK in the presence of KSR. We therefore next sought to understand how trametinib may impede binding of MEK to RAF yet favor binding towards KSR. For this, we superimposed the BRAF-MEK1 crystal structure onto the KSR-MEK1-trametinib structures that we determined, which revealed a putative steric clash between the phenyl acetamide of trametinib and the pre-helix αG loop in BRAF (FIG. 15). In particular, the N660-N661-R662 motif in human BRAF is predicted to effectively reduce the size of the trametinib binding pocket, thereby preventing binding of BRAF to MEK in the presence of drug (FIG. 42). In contrast, the equivalent motif in KSR includes a gap followed by residues with relatively small side chains. For example, human KSR1 includes the sequence GAP-A825-A826 at the pre-helix αG loop. Notably, the 'small' versus 'large' pre-helix αG loops in KSR and RAF family kinases are highly conserved (FIG. 16). Thus, our structural analysis suggested that the mechanism of action for trametinib could depend, at least in part, on exploiting evolutionarily conserved differences in the size and composition of the pre-helix αG loop among KSR pseudokinases and RAF sub-family kinases.

To test the hypothesis that trametinib acts differentially upon KSR and RAF proteins at the MEK interaction interface, we generated a reciprocal set of mutants in which we systematically altered the sequences in the pre-helix αG loop of KSR and RAF to a set of 'RAF-like' and 'KSR-like' alleles, respectively (FIG. 44). The mutants, along with wild-type (WT) controls, were transfected into cells and evaluated for binding to endogenous MEK, in the presence and absence of trametinib, via co-immunoprecipitation (co-IP). The addition of trametinib to cells expressing wild-type KSR1 led to sustained pulldown of KSR1 (FIG. 17; lanes 2 versus 3), but as expected based on previously published results[9], diminished binding of BRAF (FIG. 18; lanes 2 versus 3).

Mutations that made KSR1 more 'RAF-like' largely resulted in loss of function with respect to pulldown via MEK1 (FIG. 17; compare lanes 2 versus 4, 6, 8, or 10). However, one KSR allele, mutant K1(P775N) demonstrated diminished pulldown relative to WT-KSR1 at baseline, and further complex destabilization in the presence of trametinib much like wild-type BRAF (FIG. 17; compare lanes 4 versus 5 to 2 versus 3). Two of the tested 'KSR-like' alleles in BRAF (mutants B2-R662 Å and B3-N$_{661}$A/R662A) allowed for sustained pulldown in the presence of trametinib relative to WT-BRAF (FIG. 18, compare lanes 2 versus 3 to 6 versus 7 and 8 versus 9). By contrast, cobimetinib, which does not possess an analogous phenyl acetamide 'bump' as trametinib, did not alter complex stability towards the K1 and B2 mutants of KSR1 and BRAF, respectively (FIG. 47, 48). Thus, space-creating mutations R662A(B2) and N661A/R662A(B3) in the pre-helix αG loop of BRAF enable binding of trametinib to stable RAF-MEK complexes, whereas a space-reducing mutation P775N(K1) in KSR1 diminished the stability of mutant KSR-MEK complexes, which was further hindered in the presence of trametinib.

Together, the results of our structural and functional analysis support a model in which the natural residues within the pre-helix αG loops of RAF and KSR disfavor or favor, respectively, direct binding to MEK in the presence of trametinib. Consistent with this model and predicted selectivity differences among isoforms, tram-bo generated strong BRET binding signals for human KSR2-luc and KSR1-luc in cells, and much weaker BRET signals towards ARAF-luc, BRAF-luc, and CRAF-luc (FIG. 49).

To further examine trametinib interactions with MEK when isolated or in complex with KSR or RAF, we used in vitro binding analysis (FIG. 50-54). For these studies, we generated a biotinylated version of trametinib similar in structure to the conjugated version of the drug[21] used to pull-down and identify MEK as a target of the compound. For isolated MEK1 or MEK1-BRAF, we obtained dissociation constant ($K_D$) values of 131±9.4 nM and 217±3.2 nM, respectively. Whereas, we measured $K_D$ values of 63.9±4.7 and 70.4±4.4 nM against KSR1-MEK1 and KSR2-MEK1, respectively. Further, we found significant differences in off rates ($k_{dis}$(1/s); FIG. 51), which relates to drug residence time[32], with drug-target lifetimes of 23.1±0.6 and 27.6±2.2 minutes for isolated MEK1 and BRAF-MEK1, respectively, compared to 90.1±5.2 and 84.8±2.4 minutes for KSR1-MEK1 and KSR2-MEK1, respectively. Thus, in vitro binding kinetics of trametinib towards MEK1 are distinctly enhanced in the presence of bound KSR1 or KSR2.

Searching publicly available datasets, we identified two CRISPR screens in which KSR1 emerged as a strong modifier of potency for trametinib or a trametinib-plus-dabrafenib combination within cellular models, which is supportive of an in vivo role for endogenous KSR in the mechanism of action of trametinib (FIG. 55). Given our structural insights, the results of these screens may indicate a model in which KSR serves as a direct co-receptor for trametinib. We propose that KSR pseudokinases and RAF kinases share an overlapping binding site towards MEK, and that through these interactions centred around helix αG, trametinib is able to sustain binding of MEK directly towards KSR over RAF (FIG. 56). Through this biochemical mechanism, and reported differences in circulating half-life[33], trametinib would display greater specificity and residence time towards KSR-bound states of MEK.

2.2c A New-Generation Trametinib Analog

A significant limitation of trametinib, and several clinical MEKi, is the susceptibility of this class of compounds to adaptive forms of drug-resistance[34]. For example, because trametinib is unable to effectively 'trap' RAF kinases within inactive complexes with MEK, it has been proposed that the efficacy of trametinib is lost over time due to release of negative feedback signaling downstream of RAS and drug escape via active RAF kinases, including BRAF and CRAF[9]. The adaptive resistance to MEKi is also KSR1-dependent[35], which we confirmed (FIG. 57). A MEKi that has been reported to effectively promote, and thereby trap, RAF-bound MEK is the compound CH5126766[25]. However, unlike trametinib, CH5126766 is orders of magnitude weaker in terms of biochemical and cellular potency (FIG. 33, 58); thus, a compound that would retain the potency and slow off-rate kinetics of trametinib combined with the functional impact of CH5126766 on higher-order MAPK signaling complexes could represent a potential therapeutic advance. To test whether we could overcome adaptive resistance to MEKi by alterations at the interfacial binding site of KSR-MEK, and potentially RAF-MEK, we created a derivative of trametinib, which we term trametiglue (FIG. 22).

Trametiglue possesses a sulfamide group in place of the key acetamide moiety within trametinib. We focused on sulfamide based on (i) the common use of this moiety as an acetamide bioisostere, (ii) the lack of previously-reported sulfamide-containing derivatives of trametinib, and (iii) our analysis of the MEK inhibitor CH5126766 that suggested that an analogous motif may enable the unique trapping of RAF-bound MEK.

Co-crystal structures confirmed binding of trametiglue to KSR-MEK complexes, with the compound adopting an overall similar binding-orientation as trametinib (FIG. 23). However, by virtue of the sulfamide moiety, trametiglue both directly contacts Arg234 in MEK and reinforces a water-mediated contact to the backbone carbonyl of Thr876 in KSR2. Thus, trametiglue places two hydrogen-bond donors and acceptors in exchange of the acetamide of trametinib (FIG. 61), thereby generating distinct trajectory and space-filling interactions at the interface of KSR-MEK (FIG. 62), and we speculate possibly also RAF-MEK.

In cellular target engagement assays using the KSR-luc or MEK-luc reporters, trametiglue retained similar potency and off-rate kinetics as trametinib (FIG. 63), suggesting that the alterations at the interfacial region revealed within our crystal structures of trametiglue did not significantly affect binding to the KSR-bound state of MEK. However, in co-immunoprecipitation assays via endogenous MEK, treatment with trametiglue, unlike trametinib, markedly enhanced capture of BRAF relative to untreated samples (FIG. 64; lanes 5 versus 8, BRAF blot). This effect of trametiglue in co-IP experiments was very similar to CH5126766 (FIG. 64; lanes 5 to 6), suggesting that trametiglue, much like CH5126766 but unlike trametinib, has an ability to favour binding of BRAF towards MEK. To characterize trametiglue further, we profiled the compound in conventional in vitro kinase assays. In binding experiments, trametiglue demonstrated strong selectivity towards MEK1 and MEK2, with no direct interactions towards isolated BRAF or CRAF (FIG. 65, top). However, in substrate phosphorylation assays, trametiglue not only inhibited MEK1 and MEK2, but also upstream kinases, including inhibition of both BRAF and CRAF phosphorylation of MEK1 as substrate (FIG. 65, bottom). This profile resembles the published in vitro kinome profile of CH5126766[25], and supports the idea that trametiglue shares pharmacological properties with CH5126766.

In summary, trametiglue combines the potency and off-rate kinetics of trametinib on KSR-bound MEK with the functional ability of CH5126766 to promote, and potentially trap, inactive states of RAF-bound MEK. To test the impact of combining two distinct MEKi activities into a single compound, we screened trametiglue across a series of KRAS- and BRAF-mutant cell lines. For example, under low-adherence conditions in the cell line HCT 116, trametiglue produced an $IC_{50}$ of $0.07\pm0.04$ nM, which is an approximately 7-fold and 200-fold improvement in potency relative to trametinib and CH5126766, respectively (FIG.

66). This increase in activity also translated to long-term clonogenic assays (FIG. 67), with marked enhancements in phospho-ERK inhibition over both short and long term treatments (FIG. 67, 69). Together, our data suggest trametiglue, and the simultaneous targeting of both KSR- and RAF-bound MEK with a high-potency compound, as an effective strategy to mitigate adaptive resistance via feedback upregulation of RAS-MAPK signaling.

The comparative analysis revealed trametinib as a 'bumped' MEKi with binding enabled through a conserved 'hole' found in KSR-family pseudokinases relative to the related RAF sub-family kinases. To our knowledge, the targeting of trametinib to the KSR-MEK complex is the first example of a natural bump and hole system whereby a drug-binding site is remodelled by overlapping binding partners. Given the prevalence of enzyme and pseudoenzyme pairs[36], more opportunities to exploit natural bump and hole systems probably exist but have yet to be uncovered. Furthermore, these studies highlight KSR as a critical missing piece in the mechanism of action for clinical MEK inhibitors. Targeting sub-populations of MEK with compounds that possess molecular glue-like features offers a new therapeutic path for selectively antagonizing RAS-driven malignancies in patients. Indeed, the finding of trametiglue provides a framework to overcome limitations in currently available MEKi through the rational design of next-generation drugs targeting the interfacial binding region of important regulatory complexes in the MAPK cascade.

The present invention has been illustrated by reference to various exemplary embodiments and examples. As will be apparent to those of skill in the art other embodiments and variations of this invention may be devised by others skilled in the art without departing from the true spirit and scope of the invention. The appended claims are to be construed to include all such embodiments and equivalent variations.

The disclosures of each and every patent, patent application, and publication cited herein are hereby incorporated herein by reference in their entirety.

REFERENCES

1. Zhao, Y. & Adjei, A. A. The clinical development of MEK inhibitors. *Nat. Rev. Clin. Oncol.* 11, 385-400 (2014).
2. Ebert, P. J. R. et al. MAP Kinase Inhibition Promotes T Cell and Anti-tumor Activity in Combination with PD-L1 Checkpoint Blockade. *Immunity* 44, 609-621 (2016).
3. Liu, L. et al. The BRAF and MEK Inhibitors Dabrafenib and Trametinib: Effects on Immune Function and in Combination with Immunomodulatory Antibodies Targeting PD-1, PD-L1, and CTLA-4. *Clin. Cancer Res.* 21, 1639-1651 (2015).
4. Slack, C. et al. The Ras-Erk-ETS-Signaling Pathway Is a Drug Target for Longevity. *Cell* 162, 72-83 (2015).
5. LoRusso, P. M. et al. Phase I pharmacokinetic and pharmacodynamic study of the oral MAPK/ERK kinase inhibitor PD-0325901 in patients with advanced cancers. *Clin. Cancer Res.* 16, 1924-1937 (2010).
6. Huang, W. et al. PD0325901, a mitogen-activated protein kinase kinase inhibitor, produces ocular toxicity in a rabbit animal model of retinal vein occlusion. *J. Ocul. Pharmacol. Ther.* 25, 519-530 (2009).
7. Infante, J. R. et al. Safety and efficacy results from the first-in-human study of the oral MEK 1/2 inhibitor GSK1120212. *J. Clin. Orthod.* 28, 2503-2503 (2010).

8. Emery, C. M. et al. MEK1 mutations confer resistance to MEK and B-RAF inhibition. *Proc. Natl. Acad. Sci. U.S.A* 106, 20411-20416 (2009).

9. Lito, P. et al. Disruption of CRAF-mediated MEK activation is required for effective MEK inhibition in KRAS mutant tumors. *Cancer Cell* 25, 697-710 (2014).

10. Gao, Y. et al. V21 ID Mutation in MEK1 Causes Resistance to MEK Inhibitors in Colon Cancer. *Cancer Discov.* 9, 1182-1191 (2019).

11. Simanshu, D. K., Nissley, D. V. & McCormick, F. RAS Proteins and Their Regulators in Human Disease. *Cell* 170, 17-33 (2017).

12. Moore, A. R., Rosenberg, S. C., McCormick, F. & Malek, S. RAS-targeted therapies: is the undruggable drugged? *Nat. Rev. Drug Discov.* 19, 533-552 (2020).

13. Long, G. V. et al. Dabrafenib and trametinib versus dabrafenib and placebo for Val600 BRAF-mutant melanoma: a multicentre, double-blind, phase 3 randomised controlled trial. *Lancet* 386, 444-451 (2015).

14. Kinsey, C. G. et al. Protective autophagy elicited by RAF→MEK→ERK inhibition suggests a treatment strategy for RAS-driven cancers. *Nat. Med.* 1 (2019).

15. Ribas, A. et al. Phase I study combining anti-PD-L1 (MEDI4736) with BRAF (dabrafenib) and/or MEK (trametinib) inhibitors in advanced melanoma. *J. Clin. Orthod.* 33, 3003-3003 (2015).

16. Canon, J. et al. The clinical KRAS(G12C) inhibitor AMG 510 drives anti-tumour immunity. *Nature* 575, 217-223 (2019).

17. Yamaguchi, T. et al. Identification of JTP-70902, a p15(INK4b)-inductive compound, as a novel MEK1/2 inhibitor. *Cancer Sci.* 98, 1809-1816 (2007).

18. Westbrook, J. D. & Burley, S. K. How Structural Biologists and the Protein Data Bank Contributed to Recent FDA New Drug Approvals. *Structure* 27, 211-217 (2019).

19. Fischmann, T. O. et al. Crystal structures of MEK1 binary and ternary complexes with nucleotides and inhibitors. *Biochemistry* 48, 2661-2674 (2009).

20. Ohren, J. F. et al. Structures of human MAP kinase kinase 1 (MEK1) and MEK2 describe novel noncompetitive kinase inhibition. *Nat. Struct. Mol. Biol.* 11, 1192-1197 (2004).

21. Yoshida, T. et al. Identification and characterization of a novel chemotype MEK inhibitor able to alter the phosphorylation state of MEK1/2. *Oncotarget* 3, 1533-1545 (2012).

22. Hatzivassiliou, G. et al. Mechanism of MEK inhibition determines efficacy in mutant KRAS-versus BRAF-driven cancers. *Nature* 501, 232-236 (2013).

23. Kornfeld, K., Hom, D. B. & Horvitz, H. R. The ksr-1 gene encodes a novel protein kinase involved in Ras-mediated signaling in *C. elegans*. *Cell* 83, 903-913 (1995).

24. Robers, M. B. et al. Quantitative, Real-Time Measurements of Intracellular Target Engagement Using Energy Transfer. *Methods Mol. Biol.* 1888, 45-71 (2019).

25. Ishii, N. et al. Enhanced Inhibition of ERK Signaling by a Novel Allosteric MEK Inhibitor, CH5126766, That Suppresses Feedback Reactivation of RAF Activity. *Cancer Research* vol. 73 4050-4060 (2013).

26. Vauquelin, G. & Charlton, S. J. Long-lasting target binding and rebinding as mechanisms to prolong in vivo drug action. *Br. J. Pharmacol.* 161, 488-508 (2010).

27. Lavoie, H. & Therrien, M. Regulation of RAF protein kinases in ERK signalling. *Nat. Rev. Mol. Cell Biol.* 16, 281-298 (2015).

28. Brennan, D. F. et al. A Raf-induced allosteric transition of KSR stimulates phosphorylation of MEK. *Nature* 472, 366-369 (2011).

29. Dhawan, N. S., Scopton, A. P. & Dar, A. C. Small molecule stabilization of the KSR inactive state antagonizes oncogenic Ras signalling. *Nature* 537, 112-116 (2016).

30. Haling, J. R. et al. Structure of the BRAF-MEK complex reveals a kinase activity independent role for BRAF in MAPK signaling. *Cancer Cell* 26, 402-413 (2014).

31. Liau, N. P. D. et al. Negative regulation of RAF kinase activity by ATP is overcome by 14-3-3-induced dimerization. *Nat. Struct. Mol. Biol.* 27, 134-141 (2020).

32. Copeland, R. A. The drug-target residence time model: a 10-year retrospective. *Nat. Rev. Drug Discov.* 15, 87 (2015).

33. Gilmartin, A. G. et al. GSK1120212 (JTP-74057) is an inhibitor of MEK activity and activation with favorable pharmacokinetic properties for sustained in vivo pathway inhibition. *Clin. Cancer Res.* 17, 989-1000 (2011).

34. Yaeger, R. & Corcoran, R. B. Targeting Alterations in the RAF-MEK Pathway. *Cancer Discov.* 9, 329-341 (2019).

35. Sos, M. L. et al. Oncogene mimicry as a mechanism of primary resistance to BRAF inhibitors. *Cell Rep.* 8, 1037-1048 (2014).

36. Kung, J. E. & Jura, N. Prospects for pharmacological targeting of pseudokinases. *Nat. Rev. Drug Discov.* (2019) doi:10.1038/s41573-019-0018-3.

37. Kabsch, W. XDS. *Acta Crystallogr. D Biol. Crystallogr.* 66, 125-132 (2010).

38. McCoy, A. J. et al. Phaser crystallographic software. *J. Appl. Crystallogr.* 40, 658-674 (2007).

39. Emsley, P., Lohkamp, B., Scott, W. G. & Cowtan, K. Features and development of Coot. *Acta Crystallogr. D Biol. Crystallogr.* 66, 486-501 (2010).

40. Moriarty, N. W., Grosse-Kunstleve, R. W. & Adams, P. D. electronic Ligand Builder and Optimization Workbench (eLBOW): a tool for ligand coordinate and restraint generation. *Acta Crystallogr. D Biol. Crystallogr.* 65, 1074-1080 (2009).

41. Afonine, P. V. et al. Towards automated crystallographic structure refinement with phenix.refine. *Acta Crystallogr. D Biol. Crystallogr.* 68, 352-367 (2012).

42. Vasta, J. D. et al. Quantitative, Wide-Spectrum Kinase Profiling in Live Cells for Assessing the Effect of Cellular ATP on Target Engagement. *Cell Chem Biol* 25, 206-214.e11 (2018).

43. Viswanatha, R., Li, Z., Hu, Y. & Perrimon, N. Pooled genome-wide CRISPR screening for basal and context-specific fitness gene essentiality in *Drosophila* cells. *Elife* 7, (2018).

44. Strub, T. et al. SIRT6 haploinsufficiency induces BRAFV600E melanoma cell resistance to MAPK inhibitors via IGF signalling. *Nature Communications* vol. 9 (2018).

45. Rajakulendran, T., Sahmi, M., Lefrançois, M., Sicheri, F. & Therrien, M. A dimerization-dependent mechanism drives RAF catalytic activation. *Nature* 461, 542-545 (2009).

46. Lavoie, H. et al. MEK drives BRAF activation through allosteric control of KSR proteins. *Nature* 554, 549-553 (2018).

What is claimed is:

1. An ATP non-competitive inhibitor of mitogen-activated protein kinase, having the following structure:

2. Pharmaceutically acceptable salts of the ATP non-competitive inhibitor of mitogen-activated protein kinase of claim 1.

3. Enantiomers of the ATP non-competitive inhibitor of mitogen-activated protein kinase of claim 1.

* * * * *

SEQUENCE LISTING

<160> NUMBER OF SEQ ID NOS: 44

<210> SEQ ID NO 1
<211> LENGTH: 62
<212> TYPE: PRT
<213> ORGANISM: Artificial Sequence
<220> FEATURE:
<223> OTHER INFORMATION: Amino acid sequence of human KSR1

<400> SEQUENCE: 1

Pro Ile Ser Arg Lys Ala Ser Gln Thr Ser Val Tyr Leu Gln Glu Trp
1               5                   10                  15

Asp Ile Pro Phe Glu Gln Val Glu Leu Gly Glu Pro Ile Gly Gln Gly
            20                  25                  30

Arg Trp Gly Arg Val His Arg Gly Arg Trp His Gly Glu Val Ala Ile
        35                  40                  45

Arg Leu Leu Glu Met Asp Gly His Asn Gln Asp His Leu Lys
    50                  55                  60

<210> SEQ ID NO 2
<211> LENGTH: 62
<212> TYPE: PRT
<213> ORGANISM: Artificial Sequence
<220> FEATURE:
<223> OTHER INFORMATION: Amino acid sequence of human KSR2

<400> SEQUENCE: 2

Ser Phe Pro Arg Lys Ala Ser Gln Thr Ser Ile Phe Leu Gln Glu Trp
1               5                   10                  15

Asp Ile Pro Phe Glu Gln Leu Glu Ile Gly Glu Leu Ile Gly Lys Gly
            20                  25                  30

Arg Phe Gly Gln Val Tyr His Gly Arg Trp His Gly Glu Val Ala Ile
        35                  40                  45

Arg Leu Ile Asp Ile Glu Arg Asp Asn Glu Asp Gln Leu Lys
    50                  55                  60

<210> SEQ ID NO 3
<211> LENGTH: 62
<212> TYPE: PRT
<213> ORGANISM: Artificial Sequence
<220> FEATURE:
<223> OTHER INFORMATION: Amino acid sequence of human KSR1

<400> SEQUENCE: 3

Leu Phe Lys Lys Glu Val Met Asn Tyr Arg Gln Thr Arg His Glu Asn
1               5                   10                  15

Val Val Leu Phe Met Gly Ala Cys Met Asn Pro Pro His Leu Ala Ile
            20                  25                  30

Ile Thr Ser Phe Cys Lys Gly Arg Thr Leu His Ser Phe Val Arg Asp
        35                  40                  45

Pro Lys Thr Ser Leu Asp Ile Asn Lys Thr Arg Gln Ile Ala
    50                  55                  60

<210> SEQ ID NO 4
<211> LENGTH: 62
<212> TYPE: PRT
<213> ORGANISM: Artificial Sequence
<220> FEATURE:
<223> OTHER INFORMATION: Amino acid sequence of human KSR2

<400> SEQUENCE: 4

Ala Phe Lys Arg Glu Val Met Ala Tyr Arg Gln Thr Arg His Glu Asn

-continued

_____

```
1               5                    10                   15

Val Val Leu Phe Met Gly Ala Cys Met Ser Pro Pro His Leu Ala Ile
            20                   25                   30

Ile Thr Ser Leu Cys Lys Gly Arg Thr Leu Tyr Ser Val Val Arg Asp
        35                   40                   45

Ala Lys Ile Val Leu Asp Val Asn Lys Thr Arg Gln Ile Ala
    50                   55                   60
```

<210> SEQ ID NO 5
<211> LENGTH: 62
<212> TYPE: PRT
<213> ORGANISM: Artificial Sequence
<220> FEATURE:
<223> OTHER INFORMATION: Amino acid sequence of human KSR1

<400> SEQUENCE: 5

```
Gln Glu Ile Ile Lys Gly Met Gly Tyr Leu His Ala Lys Gly Ile Val
1               5                    10                   15

His Lys Asp Leu Lys Ser Lys Asn Val Phe Tyr Asp Asn Gly Lys Val
            20                   25                   30

Val Ile Thr Asp Phe Gly Leu Phe Gly Ile Ser Gly Val Val Arg Glu
        35                   40                   45

Gly Arg Arg Glu Asn Gln Leu Lys Leu Ser His Asp Trp Leu
    50                   55                   60
```

<210> SEQ ID NO 6
<211> LENGTH: 62
<212> TYPE: PRT
<213> ORGANISM: Artificial Sequence
<220> FEATURE:
<223> OTHER INFORMATION: Amino acid sequence of human KSR2

<400> SEQUENCE: 6

```
Gln Glu Ile Val Lys Gly Met Gly Tyr Leu His Ala Lys Gly Ile Leu
1               5                    10                   15

His Lys Asp Leu Lys Ser Lys Asn Val Phe Tyr Asp Asn Gly Lys Val
            20                   25                   30

Val Ile Thr Asp Phe Gly Leu Phe Ser Ile Ser Gly Val Leu Gln Ala
        35                   40                   45

Gly Arg Arg Glu Asp Lys Leu Arg Ile Gln Asn Gly Trp Leu
    50                   55                   60
```

<210> SEQ ID NO 7
<211> LENGTH: 62
<212> TYPE: PRT
<213> ORGANISM: Artificial Sequence
<220> FEATURE:
<223> OTHER INFORMATION: Amino acid sequence of human KSR1

<400> SEQUENCE: 7

```
Cys Tyr Leu Ala Pro Glu Ile Val Arg Glu Met Thr Pro Gly Lys Asp
1               5                    10                   15

Glu Asp Gln Leu Pro Phe Ser Lys Ala Ala Asp Val Tyr Ala Phe Gly
            20                   25                   30

Thr Val Trp Tyr Glu Leu Gln Ala Arg Asp Trp Pro Leu Lys Asn Gln
        35                   40                   45

Ala Ala Glu Ala Ser Ile Trp Gln Ile Gly Ser Gly Glu Gly
    50                   55                   60
```

<210> SEQ ID NO 8

```
<211> LENGTH: 60
<212> TYPE: PRT
<213> ORGANISM: Artificial Sequence
<220> FEATURE:
<223> OTHER INFORMATION: Amino acid sequence of human KSR2

<400> SEQUENCE: 8

Cys His Leu Ala Pro Glu Ile Ile Arg Gln Leu Ser Pro Asp Thr Glu
1               5                   10                  15

Glu Asp Lys Leu Pro Phe Ser Lys His Ser Asp Val Phe Ala Leu Gly
            20                  25                  30

Thr Ile Trp Tyr Glu Leu His Ala Arg Glu Trp Pro Phe Lys Thr Gln
        35                  40                  45

Pro Ala Glu Ala Ile Ile Trp Gln Met Gly Thr Gly
    50                  55                  60

<210> SEQ ID NO 9
<211> LENGTH: 61
<212> TYPE: PRT
<213> ORGANISM: Artificial Sequence
<220> FEATURE:
<223> OTHER INFORMATION: Amino acid sequence of human KSR1

<400> SEQUENCE: 9

Met Lys Arg Val Leu Thr Ser Val Ser Leu Gly Lys Glu Val Ser Glu
1               5                   10                  15

Ile Leu Ser Ala Cys Trp Ala Phe Asp Leu Gln Glu Arg Pro Ser Phe
            20                  25                  30

Ser Leu Leu Met Asp Met Leu Glu Lys Leu Pro Lys Leu Asn Arg Arg
        35                  40                  45

Leu Ser His Pro Gly His Phe Trp Lys Ser Ala Glu Ile
    50                  55                  60

<210> SEQ ID NO 10
<211> LENGTH: 61
<212> TYPE: PRT
<213> ORGANISM: Artificial Sequence
<220> FEATURE:
<223> OTHER INFORMATION: Amino acid sequence of human KSR2

<400> SEQUENCE: 10

Met Lys Pro Asn Leu Ser Gln Ile Gly Met Gly Lys Glu Ile Ser Asp
1               5                   10                  15

Ile Leu Leu Phe Cys Trp Ala Phe Glu Gln Glu Glu Arg Pro Thr Phe
            20                  25                  30

Thr Lys Leu Met Asp Met Leu Glu Lys Leu Pro Lys Arg Asn Arg Arg
        35                  40                  45

Leu Ser His Pro Gly His Phe Trp Lys Ser Ala Glu Leu
    50                  55                  60

<210> SEQ ID NO 11
<211> LENGTH: 17
<212> TYPE: PRT
<213> ORGANISM: Artificial Sequence
<220> FEATURE:
<223> OTHER INFORMATION: Amino acid sequence of human KSR1

<400> SEQUENCE: 11

Pro Leu Lys Asn Gln Ala Ala Glu Ala Ser Ile Trp Gln Ile Gly Ser
1               5                   10                  15

Gly
```

-continued

<210> SEQ ID NO 12
<211> LENGTH: 17
<212> TYPE: PRT
<213> ORGANISM: Artificial Sequence
<220> FEATURE:
<223> OTHER INFORMATION: Amino acid sequence of human KSR2

<400> SEQUENCE: 12

Pro Phe Lys Thr Gln Pro Ala Glu Ala Ile Ile Trp Gln Met Gly Thr
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Amino acid sequence of mouse KSR2

<400> SEQUENCE: 13

Pro Phe Lys His Gln Pro Ala Glu Ala Leu Ile Trp Gln Ile Gly Ser
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Amino acid sequence of mouse KSR2

<400> SEQUENCE: 14

Pro Phe Lys Thr Gln Pro Ala Glu Ala Ile Ile Trp Gln Met Gly Thr
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Amino acid sequence of human KSR drom

<400> SEQUENCE: 15

Thr Phe Lys Asp Gln Pro Ala Glu Ser Ile Ile Trp Gln Val Gly Arg
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Amino acid sequence of caeel KSRA

<400> SEQUENCE: 16

Pro Tyr Ala Gly Glu Leu Pro His Gln Ile Leu Phe Ala Lys Thr Gln
1               5                   10                  15

Gly

<210> SEQ ID NO 17
<211> LENGTH: 18
<212> TYPE: PRT

-continued

```
<213> ORGANISM: Artificial Sequence
<220> FEATURE:
<223> OTHER INFORMATION: Amino acid sequence of human RAF1

<400> SEQUENCE: 17

Pro Tyr Ser His Ile Asn Asn Arg Asp Gln Ile Ile Phe Met Val Gly
1               5                   10                  15

Arg Gly

<210> SEQ ID NO 18
<211> LENGTH: 18
<212> TYPE: PRT
<213> ORGANISM: Artificial Sequence
<220> FEATURE:
<223> OTHER INFORMATION: Amino acid sequence of human RAF1

<400> SEQUENCE: 18

Pro Tyr Ala His Ile Asn Asn Arg Asp Gln Ile Ile Phe Met Val Gly
1               5                   10                  15

Arg Gly

<210> SEQ ID NO 19
<211> LENGTH: 18
<212> TYPE: PRT
<213> ORGANISM: Artificial Sequence
<220> FEATURE:
<223> OTHER INFORMATION: Amino acid sequence of human ARAF

<400> SEQUENCE: 19

Pro Tyr Ser His Ile Gly Cys Arg Asp Gln Ile Ile Phe Met Val Gly
1               5                   10                  15

Arg Gly

<210> SEQ ID NO 20
<211> LENGTH: 18
<212> TYPE: PRT
<213> ORGANISM: Artificial Sequence
<220> FEATURE:
<223> OTHER INFORMATION: Amino acid sequence of drom RAF

<400> SEQUENCE: 20

Pro Tyr Gly His Ile Ser Asn Lys Asp Gln Ile Leu Phe Met Val Gly
1               5                   10                  15

Arg Gly

<210> SEQ ID NO 21
<211> LENGTH: 18
<212> TYPE: PRT
<213> ORGANISM: Artificial Sequence
<220> FEATURE:
<223> OTHER INFORMATION: Amino acid sequence of caee KRAF1

<400> SEQUENCE: 21

Pro Tyr Ser Asn Ile Asn Asn Arg Asp Gln Ile Leu Phe Met Val Gly
1               5                   10                  15

Arg Gly

<210> SEQ ID NO 22
<211> LENGTH: 18
<212> TYPE: PRT
<213> ORGANISM: Artificial Sequence
<220> FEATURE:
<223> OTHER INFORMATION: Amino acid sequence of mouse BRAF
```

-continued

<400> SEQUENCE: 22

Pro Tyr Ser Asn Ile Asn Asn Arg Asp Gln Ile Ile Phe Met Val Gly
1               5                   10                  15

Arg Gly

<210> SEQ ID NO 23
<211> LENGTH: 18
<212> TYPE: PRT
<213> ORGANISM: Artificial Sequence
<220> FEATURE:
<223> OTHER INFORMATION: Amino acid sequence of human BRAF

<400> SEQUENCE: 23

Pro Tyr Ser Asn Ile Asn Asn Arg Asp Gln Ile Ile Phe Met Val Gly
1               5                   10                  15

Arg Gly

<210> SEQ ID NO 24
<211> LENGTH: 17
<212> TYPE: PRT
<213> ORGANISM: Artificial Sequence
<220> FEATURE:
<223> OTHER INFORMATION: Amino acid sequence of human KSR1

<400> SEQUENCE: 24

Pro Leu Lys Asn Gln Ala Ala Glu Ala Ser Ile Trp Gln Ile Gly Ser
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Amino acid sequence of human KSR2

<400> SEQUENCE: 25

Pro Phe Lys Thr Gln Pro Ala Glu Ala Ile Ile Trp Gln Met Gly Thr
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Amino acid sequence of mouse KSR1

<400> SEQUENCE: 26

Pro Phe Lys His Gln Pro Ala Glu Ala Leu Ile Trp Gln Ile Gly Ser
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Amino acid sequence of mutant K1

<400> SEQUENCE: 27

Pro Phe Lys His Gln Asn Ala Glu Ala Leu Ile Trp Gln Ile Gly Ser
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Amino acid sequence of mutant K2

<400> SEQUENCE: 28

Pro Phe Lys His Gln Pro Arg Glu Ala Leu Ile Trp Gln Ile Gly Ser
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: Amino acid sequence of mutant K3

<400> SEQUENCE: 29

Pro Phe Lys His Gln Asn Arg Glu Ala Leu Ile Trp Gln Ile Gly Ser
1               5                   10                  15

Gly

<210> SEQ ID NO 30
<211> LENGTH: 18
<212> TYPE: PRT
<213> ORGANISM: Artificial Sequence
<220> FEATURE:
<223> OTHER INFORMATION: Amino acid sequence of mutant K4

<400> SEQUENCE: 30

Pro Phe Lys His Gln Asn Asn Arg Glu Ala Leu Ile Trp Gln Ile Gly
1               5                   10                  15

Ser Gly

<210> SEQ ID NO 31
<211> LENGTH: 18
<212> TYPE: PRT
<213> ORGANISM: Artificial Sequence
<220> FEATURE:
<223> OTHER INFORMATION: Amino acid sequence of human ARAF

<400> SEQUENCE: 31

Pro Tyr Ser His Ile Gly Cys Arg Asp Gln Ile Ile Phe Met Val Gly
1               5                   10                  15

Arg Gly

<210> SEQ ID NO 32
<211> LENGTH: 18
<212> TYPE: PRT
<213> ORGANISM: Artificial Sequence
<220> FEATURE:
<223> OTHER INFORMATION: Amino acid sequence of mouse RAF1

<400> SEQUENCE: 32

Pro Tyr Ala His Ile Asn Asn Arg Asp Gln Ile Ile Phe Met Val Gly
1               5                   10                  15

Arg Gly

-continued

```
<210> SEQ ID NO 33
<211> LENGTH: 18
<212> TYPE: PRT
<213> ORGANISM: Artificial Sequence
<220> FEATURE:
<223> OTHER INFORMATION: Amino acid sequence of human BRAF

<400> SEQUENCE: 33

Pro Tyr Ser Asn Ile Asn Asn Arg Asp Gln Ile Ile Phe Met Val Gly
1               5                   10                  15

Arg Gly

<210> SEQ ID NO 34
<211> LENGTH: 18
<212> TYPE: PRT
<213> ORGANISM: Artificial Sequence
<220> FEATURE:
<223> OTHER INFORMATION: Amino acid sequence of mutant B1

<400> SEQUENCE: 34

Pro Tyr Ser Asn Ile Asn Ala Arg Asp Gln Ile Ile Phe Met Val Gly
1               5                   10                  15

Arg Gly

<210> SEQ ID NO 35
<211> LENGTH: 18
<212> TYPE: PRT
<213> ORGANISM: Artificial Sequence
<220> FEATURE:
<223> OTHER INFORMATION: Amino acid sequence of mutant B2

<400> SEQUENCE: 35

Pro Tyr Ser Asn Ile Asn Asn Ala Asp Gln Ile Ile Phe Met Val Gly
1               5                   10                  15

Arg Gly

<210> SEQ ID NO 36
<211> LENGTH: 18
<212> TYPE: PRT
<213> ORGANISM: Artificial Sequence
<220> FEATURE:
<223> OTHER INFORMATION: Amino acid sequence of mutant B3

<400> SEQUENCE: 36

Pro Tyr Ser Asn Ile Asn Ala Ala Asp Gln Ile Ile Phe Met Val Gly
1               5                   10                  15

Arg Gly

<210> SEQ ID NO 37
<211> LENGTH: 17
<212> TYPE: PRT
<213> ORGANISM: Artificial Sequence
<220> FEATURE:
<223> OTHER INFORMATION: Amino acid sequence of mutant B4

<400> SEQUENCE: 37

Pro Tyr Ser Asn Ile Ala Ala Asp Gln Ile Ile Phe Met Val Gly Arg
1               5                   10                  15

Gly

<210> SEQ ID NO 38
<211> LENGTH: 393
<212> TYPE: PRT
<213> ORGANISM: Artificial Sequence
```

<220> FEATURE:
<223> OTHER INFORMATION: Amino acid sequence of human MEK1 (uniprot ID
      Q02750)

<400> SEQUENCE: 38

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
                20                  25                  30

Leu Gln Lys Lys Leu Glu Glu Leu Glu Leu Asp Glu Gln Gln Arg Lys
            35                  40                  45

Arg Leu Glu Ala Phe Leu Thr Gln Lys Gln Lys Val Gly Glu Leu Lys
        50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
        130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
        210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
                260                 265                 270

Leu Met Phe Gly Cys Gln Val Glu Gly Asp Ala Ala Glu Thr Pro Pro
            275                 280                 285

Arg Pro Arg Thr Pro Gly Arg Pro Leu Ser Ser Tyr Gly Met Asp Ser
        290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
            355                 360                 365

Val Asp Phe Ala Gly Trp Leu Cys Ser Thr Ile Gly Leu Asn Gln Pro
        370                 375                 380

Ser Thr Pro Thr His Ala Ala Gly Val

-continued 385                 390

<210> SEQ ID NO 39
<211> LENGTH: 400
<212> TYPE: PRT
<213> ORGANISM: Artificial Sequence
<220> FEATURE:
<223> OTHER INFORMATION: Amino acid sequence of human MEK2 (uniprot ID
      P36507)

<400> SEQUENCE: 39

Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
            20                  25                  30

Asn Leu Val Asp Leu Gln Lys Lys Leu Glu Glu Leu Glu Leu Asp Glu
        35                  40                  45

Gln Gln Lys Lys Arg Leu Glu Ala Phe Leu Thr Gln Lys Ala Lys Val
    50                  55                  60

Gly Glu Leu Lys Asp Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
            100                 105                 110

Asn Gln Ile Ile Arg Glu Leu Gln Val Leu His Glu Cys Asn Ser Pro
        115                 120                 125

Tyr Ile Val Gly Phe Tyr Gly Ala Phe Tyr Ser Asp Gly Glu Ile Ser
    130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
            180                 185                 190

Arg Asp Val Lys Pro Ser Asn Ile Leu Val Asn Ser Arg Gly Glu Ile
        195                 200                 205

Lys Leu Cys Asp Phe Gly Val Ser Gly Gln Leu Ile Asp Ser Met Ala
    210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
                245                 250                 255

Leu Val Glu Leu Ala Val Gly Arg Tyr Pro Ile Pro Pro Asp Ala
            260                 265                 270

Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Pro Gly Arg Pro
    290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Pro Lys Leu Pro Asn Gly
                325                 330                 335

Val Phe Thr Pro Asp Phe Gln Glu Phe Val Asn Lys Cys Leu Ile Lys
            340                 345                 350

-continued

Asn Pro Ala Glu Arg Ala Asp Leu Lys Met Leu Thr Asn His Thr Phe
    355                 360                 365

Ile Lys Arg Ser Glu Val Glu Glu Val Asp Phe Ala Gly Trp Leu Cys
    370                 375                 380

Lys Thr Leu Arg Leu Asn Gln Pro Gly Thr Pro Thr Arg Thr Ala Val
385                 390                 395                 400

<210> SEQ ID NO 40
<211> LENGTH: 393
<212> TYPE: PRT
<213> ORGANISM: Artificial Sequence
<220> FEATURE:
<223> OTHER INFORMATION: Amino acid sequence of rabbit MEK1 (uniprot ID
    P29678)

<400> SEQUENCE: 40

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
            115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
            165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
            195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
            245                 250                 255

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
            275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Ala Val Phe Ser Leu Glu Phe Gln Asp
            325             330             335

Phe Val Asn Lys Cys Leu Ile Lys Asn Pro Ala Glu Arg Ala Asp Leu
            340             345             350

Lys Gln Leu Met Val His Ala Phe Ile Lys Arg Ser Asp Ala Glu Glu
        355             360             365

Val Asp Phe Ala Gly Trp Leu Cys Ser Thr Ile Gly Leu Asn Gln Pro
    370             375             380

Ser Thr Pro Thr His Ala Ala Gly Val
385                 390

<210> SEQ ID NO 41
<211> LENGTH: 923
<212> TYPE: PRT
<213> ORGANISM: Artificial Sequence
<220> FEATURE:
<223> OTHER INFORMATION: Amino acid sequence of human KSR1 (uniprot ID
      Q8IVT5)

<400> SEQUENCE: 41

Met Asp Arg Ala Ala Leu Arg Ala Ala Ala Met Gly Glu Lys Lys Glu
1               5               10              15

Gly Gly Gly Gly Gly Asp Ala Ala Ala Glu Gly Gly Ala Gly Ala
            20              25              30

Ala Ala Ser Arg Ala Leu Gln Gln Cys Gly Gln Leu Gln Lys Leu Ile
        35              40              45

Asp Ile Ser Ile Gly Ser Leu Arg Gly Leu Arg Thr Lys Cys Ala Val
    50              55              60

Ser Asn Asp Leu Thr Gln Gln Glu Ile Arg Thr Leu Glu Ala Lys Leu
65              70              75              80

Val Arg Tyr Ile Cys Lys Gln Arg Gln Cys Lys Leu Ser Val Ala Pro
            85              90              95

Gly Glu Arg Thr Pro Glu Leu Asn Ser Tyr Pro Arg Phe Ser Asp Trp
            100             105             110

Leu Tyr Thr Phe Asn Val Arg Pro Glu Val Val Gln Glu Ile Pro Arg
        115             120             125

Asp Leu Thr Leu Asp Ala Leu Leu Glu Met Asn Glu Ala Lys Val Lys
    130             135             140

Glu Thr Leu Arg Arg Cys Gly Ala Ser Gly Asp Glu Cys Gly Arg Leu
145             150             155             160

Gln Tyr Ala Leu Thr Cys Leu Arg Lys Val Thr Gly Leu Gly Gly Glu
            165             170             175

His Lys Glu Asp Ser Ser Trp Ser Ser Leu Asp Ala Arg Arg Glu Ser
            180             185             190

Gly Ser Gly Pro Ser Thr Asp Thr Leu Ser Ala Ala Ser Leu Pro Trp
        195             200             205

Pro Pro Gly Ser Ser Gln Leu Gly Arg Ala Gly Asn Ser Ala Gln Gly
    210             215             220

Pro Arg Ser Ile Ser Val Ser Ala Leu Pro Ala Ser Asp Ser Pro Thr
225             230             235             240

Pro Ser Phe Ser Glu Gly Leu Ser Asp Thr Cys Ile Pro Leu His Ala
            245             250             255

Ser Gly Arg Leu Thr Pro Arg Ala Leu His Ser Phe Ile Thr Pro Pro
            260             265             270

Thr Thr Pro Gln Leu Arg Arg His Thr Lys Leu Lys Pro Pro Arg Thr

-continued

```
                275                 280                 285

Pro Pro Pro Pro Ser Arg Lys Val Phe Gln Leu Leu Pro Ser Phe Pro
    290                 295                 300

Thr Leu Thr Arg Ser Lys Ser His Glu Ser Gln Leu Gly Asn Arg Ile
305                 310                 315                 320

Asp Asp Val Ser Ser Met Arg Phe Asp Leu Ser His Gly Ser Pro Gln
                325                 330                 335

Met Val Arg Arg Asp Ile Gly Leu Ser Val Thr His Arg Phe Ser Thr
                340                 345                 350

Lys Ser Trp Leu Ser Gln Val Cys His Val Cys Gln Lys Ser Met Ile
                355                 360                 365

Phe Gly Val Lys Cys Lys His Cys Arg Leu Lys Cys His Asn Lys Cys
    370                 375                 380

Thr Lys Glu Ala Pro Ala Cys Arg Ile Ser Phe Leu Pro Leu Thr Arg
385                 390                 395                 400

Leu Arg Arg Thr Glu Ser Val Pro Ser Asp Ile Asn Asn Pro Val Asp
                405                 410                 415

Arg Ala Ala Glu Pro His Phe Gly Thr Leu Pro Lys Ala Leu Thr Lys
                420                 425                 430

Lys Glu His Pro Pro Ala Met Asn His Leu Asp Ser Ser Ser Asn Pro
                435                 440                 445

Ser Ser Thr Thr Ser Ser Thr Pro Ser Ser Pro Ala Pro Phe Pro Thr
    450                 455                 460

Ser Ser Asn Pro Ser Ser Ala Thr Thr Pro Pro Asn Pro Ser Pro Gly
465                 470                 475                 480

Gln Arg Asp Ser Arg Phe Asn Phe Pro Ala Ala Tyr Phe Ile His His
                485                 490                 495

Arg Gln Gln Phe Ile Phe Pro Val Pro Ser Ala Gly His Cys Trp Lys
                500                 505                 510

Cys Leu Leu Ile Ala Glu Ser Leu Lys Glu Asn Ala Phe Asn Ile Ser
                515                 520                 525

Ala Phe Ala His Ala Ala Pro Leu Pro Glu Ala Ala Asp Gly Thr Arg
    530                 535                 540

Leu Asp Asp Gln Pro Lys Ala Asp Val Leu Glu Ala His Glu Ala Glu
545                 550                 555                 560

Ala Glu Glu Pro Glu Ala Gly Lys Ser Glu Ala Glu Asp Asp Glu Asp
                565                 570                 575

Glu Val Asp Asp Leu Pro Ser Ser Arg Arg Pro Trp Arg Gly Pro Ile
                580                 585                 590

Ser Arg Lys Ala Ser Gln Thr Ser Val Tyr Leu Gln Glu Trp Asp Ile
                595                 600                 605

Pro Phe Glu Gln Val Glu Leu Gly Glu Pro Ile Gly Gln Gly Arg Trp
    610                 615                 620

Gly Arg Val His Arg Gly Arg Trp His Gly Glu Val Ala Ile Arg Leu
625                 630                 635                 640

Leu Glu Met Asp Gly His Asn Gln Asp His Leu Lys Leu Phe Lys Lys
                645                 650                 655

Glu Val Met Asn Tyr Arg Gln Thr Arg His Glu Asn Val Val Leu Phe
                660                 665                 670

Met Gly Ala Cys Met Asn Pro Pro His Leu Ala Ile Ile Thr Ser Phe
                675                 680                 685

Cys Lys Gly Arg Thr Leu His Ser Phe Val Arg Asp Pro Lys Thr Ser
    690                 695                 700
```

-continued

```
Leu Asp Ile Asn Lys Thr Arg Gln Ile Ala Gln Glu Ile Ile Lys Gly
705                 710                 715                 720

Met Gly Tyr Leu His Ala Lys Gly Ile Val His Lys Asp Leu Lys Ser
                725                 730                 735

Lys Asn Val Phe Tyr Asp Asn Gly Lys Val Val Ile Thr Asp Phe Gly
                740                 745                 750

Leu Phe Gly Ile Ser Gly Val Val Arg Glu Gly Arg Arg Glu Asn Gln
            755                 760                 765

Leu Lys Leu Ser His Asp Trp Leu Cys Tyr Leu Ala Pro Glu Ile Val
        770                 775                 780

Arg Glu Met Thr Pro Gly Lys Asp Glu Asp Gln Leu Pro Phe Ser Lys
785                 790                 795                 800

Ala Ala Asp Val Tyr Ala Phe Gly Thr Val Trp Tyr Glu Leu Gln Ala
                805                 810                 815

Arg Asp Trp Pro Leu Lys Asn Gln Ala Ala Glu Ala Ser Ile Trp Gln
                820                 825                 830

Ile Gly Ser Gly Glu Gly Met Lys Arg Val Leu Thr Ser Val Ser Leu
            835                 840                 845

Gly Lys Glu Val Ser Glu Ile Leu Ser Ala Cys Trp Ala Phe Asp Leu
        850                 855                 860

Gln Glu Arg Pro Ser Phe Ser Leu Leu Met Asp Met Leu Glu Lys Leu
865                 870                 875                 880

Pro Lys Leu Asn Arg Arg Leu Ser His Pro Gly His Phe Trp Lys Ser
                885                 890                 895

Ala Asp Ile Asn Ser Ser Lys Val Val Pro Arg Phe Glu Arg Phe Gly
                900                 905                 910

Leu Gly Val Leu Glu Ser Ser Asn Pro Lys Met
        915                 920
```

```
<210> SEQ ID NO 42
<211> LENGTH: 950
<212> TYPE: PRT
<213> ORGANISM: Artificial Sequence
<220> FEATURE:
<223> OTHER INFORMATION: Amino acid sequence of human KSR2 (uniprot ID
      Q6VAB6)

<400> SEQUENCE: 42
```

```
Met Asp Glu Glu Asn Met Thr Lys Ser Glu Glu Gln Gln Pro Leu Ser
1                   5                   10                  15

Leu Gln Lys Ala Leu Gln Gln Cys Glu Leu Val Gln Asn Met Ile Asp
                20                  25                  30

Leu Ser Ile Ser Asn Leu Glu Gly Leu Arg Thr Lys Cys Ala Thr Ser
            35                  40                  45

Asn Asp Leu Thr Gln Lys Glu Ile Arg Thr Leu Glu Ser Lys Leu Val
        50                  55                  60

Lys Tyr Phe Ser Arg Gln Leu Ser Cys Lys Lys Lys Val Ala Leu Gln
65                  70                  75                  80

Glu Arg Asn Ala Glu Leu Asp Gly Phe Pro Gln Leu Arg His Trp Phe
                85                  90                  95

Arg Ile Val Asp Val Arg Lys Glu Val Leu Glu Glu Ile Ser Pro Gly
                100                 105                 110

Gln Leu Ser Leu Glu Asp Leu Leu Glu Met Thr Asp Glu Gln Val Cys
            115                 120                 125

Glu Thr Val Glu Lys Tyr Gly Ala Asn Arg Glu Glu Cys Ala Arg Leu
```

-continued

```
     130              135              140
Asn Ala Ser Leu Ser Cys Leu Arg Asn Val His Met Ser Gly Gly Asn
145              150              155              160

Leu Ser Lys Gln Asp Trp Thr Ile Gln Trp Pro Thr Thr Glu Thr Gly
              165              170              175

Lys Glu Asn Asn Pro Val Cys Pro Pro Glu Pro Thr Pro Trp Ile Arg
              180              185              190

Thr His Leu Ser Gln Ser Pro Arg Val Pro Ser Lys Cys Val Gln His
              195              200              205

Tyr Cys His Thr Ser Pro Thr Pro Gly Ala Pro Val Tyr Thr His Val
              210              215              220

Asp Arg Leu Thr Val Asp Ala Tyr Pro Gly Leu Cys Pro Pro Pro
225              230              235              240

Leu Glu Ser Gly His Arg Ser Leu Pro Pro Ser Pro Arg Gln Arg His
              245              250              255

Ala Val Arg Thr Pro Pro Arg Thr Pro Asn Ile Val Thr Thr Val Thr
              260              265              270

Pro Pro Gly Thr Pro Pro Met Arg Lys Lys Asn Lys Leu Lys Pro Pro
              275              280              285

Gly Thr Pro Pro Pro Ser Ser Arg Lys Leu Ile His Leu Ile Pro Gly
              290              295              300

Phe Thr Ala Leu His Arg Ser Lys Ser His Glu Phe Gln Leu Gly His
305              310              315              320

Arg Val Asp Glu Ala His Thr Pro Lys Ala Lys Lys Lys Ser Lys Pro
              325              330              335

Leu Asn Leu Lys Ile His Ser Ser Val Gly Ser Cys Glu Asn Ile Pro
              340              345              350

Ser Gln Gln Arg Ser Pro Leu Leu Ser Glu Arg Ser Leu Arg Ser Phe
              355              360              365

Phe Val Gly His Ala Pro Phe Leu Pro Ser Thr Pro Pro Val His Thr
              370              375              380

Glu Ala Asn Phe Ser Ala Asn Thr Leu Ser Val Pro Arg Trp Ser Pro
385              390              395              400

Gln Ile Pro Arg Arg Asp Leu Gly Asn Ser Ile Lys His Arg Phe Ser
              405              410              415

Thr Lys Tyr Trp Met Ser Gln Thr Cys Thr Val Cys Gly Lys Gly Met
              420              425              430

Leu Phe Gly Leu Lys Cys Lys Asn Cys Lys Leu Lys Cys His Asn Lys
              435              440              445

Cys Thr Lys Glu Ala Pro Pro Cys His Leu Leu Ile Ile His Arg Gly
              450              455              460

Asp Pro Ala Arg Leu Val Arg Thr Glu Ser Val Pro Cys Asp Ile Asn
465              470              475              480

Asn Pro Leu Arg Lys Pro Pro Arg Tyr Ser Asp Leu His Ile Ser Gln
              485              490              495

Thr Leu Pro Lys Thr Asn Lys Ile Asn Lys Asp His Ile Pro Val Pro
              500              505              510

Tyr Gln Pro Asp Ser Ser Ser Asn Pro Ser Ser Thr Thr Ser Ser Thr
              515              520              525

Pro Ser Ser Pro Ala Pro Pro Leu Pro Pro Ser Ala Thr Pro Pro Ser
              530              535              540

Pro Leu His Pro Ser Pro Gln Cys Thr Arg Gln Gln Lys Asn Phe Asn
545              550              555              560
```

-continued

```
Leu Pro Ala Ser His Tyr Tyr Lys Tyr Lys Gln Gln Phe Ile Phe Pro
            565             570             575

Asp Val Val Pro Val Pro Glu Thr Pro Thr Arg Ala Pro Gln Val Ile
            580             585             590

Leu His Pro Val Thr Ser Asn Pro Ile Leu Glu Gly Asn Pro Leu Leu
            595             600             605

Gln Ile Glu Val Glu Pro Thr Ser Glu Asn Glu Glu Val His Asp Glu
        610             615             620

Ala Glu Glu Ser Glu Asp Asp Phe Glu Glu Met Asn Leu Ser Leu Leu
625             630             635             640

Ser Ala Arg Ser Phe Pro Arg Lys Ala Ser Gln Thr Ser Ile Phe Leu
            645             650             655

Gln Glu Trp Asp Ile Pro Phe Glu Gln Leu Glu Ile Gly Glu Leu Ile
            660             665             670

Gly Lys Gly Arg Phe Gly Gln Val Tyr His Gly Arg Trp His Gly Glu
            675             680             685

Val Ala Ile Arg Leu Ile Asp Ile Glu Arg Asp Asn Glu Asp Gln Leu
        690             695             700

Lys Ala Phe Lys Arg Glu Val Met Ala Tyr Arg Gln Thr Arg His Glu
705             710             715             720

Asn Val Val Leu Phe Met Gly Ala Cys Met Ser Pro Pro His Leu Ala
            725             730             735

Ile Ile Thr Ser Leu Cys Lys Gly Arg Thr Leu Tyr Ser Val Val Arg
            740             745             750

Asp Ala Lys Ile Val Leu Asp Val Asn Lys Thr Arg Gln Ile Ala Gln
            755             760             765

Glu Ile Val Lys Gly Met Gly Tyr Leu His Ala Lys Gly Ile Leu His
        770             775             780

Lys Asp Leu Lys Ser Lys Asn Val Phe Tyr Asp Asn Gly Lys Val Val
785             790             795             800

Ile Thr Asp Phe Gly Leu Phe Ser Ile Ser Gly Val Leu Gln Ala Gly
            805             810             815

Arg Arg Glu Asp Lys Leu Arg Ile Gln Asn Gly Trp Leu Cys His Leu
            820             825             830

Ala Pro Glu Ile Ile Arg Gln Leu Ser Pro Asp Thr Glu Glu Asp Lys
            835             840             845

Leu Pro Phe Ser Lys His Ser Asp Val Phe Ala Leu Gly Thr Ile Trp
        850             855             860

Tyr Glu Leu His Ala Arg Glu Trp Pro Phe Lys Thr Gln Pro Ala Glu
865             870             875             880

Ala Ile Ile Trp Gln Met Gly Thr Gly Met Lys Pro Asn Leu Ser Gln
            885             890             895

Ile Gly Met Gly Lys Glu Ile Ser Asp Ile Leu Leu Phe Cys Trp Ala
            900             905             910

Phe Glu Gln Glu Glu Arg Pro Thr Phe Thr Lys Leu Met Asp Met Leu
            915             920             925

Glu Lys Leu Pro Lys Arg Asn Arg Arg Leu Ser His Pro Gly His Phe
        930             935             940

Trp Lys Ser Ala Glu Leu
945             950
```

<210> SEQ ID NO 43
<211> LENGTH: 873

<212> TYPE: PRT
<213> ORGANISM: Artificial Sequence
<220> FEATURE:
<223> OTHER INFORMATION: Amino acid sequence of mouse KSR1 (uniprot ID
      Q61097)

<400> SEQUENCE: 43

Met Asp Arg Ala Ala Leu Arg Ala Ala Ala Met Gly Glu Lys Lys Glu
1               5                   10                  15

Gly Gly Gly Gly Gly Ala Ala Ala Asp Gly Gly Ala Gly Ala Ala Val
                20                  25                  30

Ser Arg Ala Leu Gln Gln Cys Gly Gln Leu Gln Lys Leu Ile Asp Ile
        35                  40                  45

Ser Ile Gly Ser Leu Arg Gly Leu Arg Thr Lys Cys Ser Val Ser Asn
    50                  55                  60

Asp Leu Thr Gln Gln Glu Ile Arg Thr Leu Glu Ala Lys Leu Val Lys
65                  70                  75                  80

Tyr Ile Cys Lys Gln Gln Gln Ser Lys Leu Ser Val Thr Pro Ser Asp
                85                  90                  95

Arg Thr Ala Glu Leu Asn Ser Tyr Pro Arg Phe Ser Asp Trp Leu Tyr
                100                 105                 110

Ile Phe Asn Val Arg Pro Glu Val Val Gln Glu Ile Pro Gln Glu Leu
            115                 120                 125

Thr Leu Asp Ala Leu Leu Glu Met Asp Glu Ala Lys Ala Lys Glu Met
        130                 135                 140

Leu Arg Arg Trp Gly Ala Ser Thr Glu Glu Cys Ser Arg Leu Gln Gln
145                 150                 155                 160

Ala Leu Thr Cys Leu Arg Lys Val Thr Gly Leu Gly Gly Glu His Lys
                165                 170                 175

Met Asp Ser Gly Trp Ser Ser Thr Asp Ala Arg Asp Ser Ser Leu Gly
            180                 185                 190

Pro Pro Met Asp Met Leu Ser Ser Leu Gly Arg Ala Gly Ala Ser Thr
            195                 200                 205

Gln Gly Pro Arg Ser Ile Ser Val Ser Ala Leu Pro Ala Ser Asp Ser
    210                 215                 220

Pro Val Pro Gly Leu Ser Glu Gly Leu Ser Asp Ser Cys Ile Pro Leu
225                 230                 235                 240

His Thr Ser Gly Arg Leu Thr Pro Arg Ala Leu His Ser Phe Ile Thr
                245                 250                 255

Pro Pro Thr Thr Pro Gln Leu Arg Arg His Ala Lys Leu Lys Pro Pro
            260                 265                 270

Arg Thr Pro Pro Pro Ser Arg Lys Val Phe Gln Leu Leu Pro Ser
        275                 280                 285

Phe Pro Thr Leu Thr Arg Ser Lys Ser His Glu Ser Gln Leu Gly Asn
    290                 295                 300

Arg Ile Asp Asp Val Thr Pro Met Lys Phe Glu Leu Pro His Gly Ser
305                 310                 315                 320

Pro Gln Leu Val Arg Arg Asp Ile Gly Leu Ser Val Thr His Arg Phe
            325                 330                 335

Ser Thr Lys Ser Trp Leu Ser Gln Val Cys Asn Val Cys Gln Lys Ser
            340                 345                 350

Met Ile Phe Gly Val Lys Cys Lys His Cys Arg Leu Lys Cys His Asn
        355                 360                 365

Lys Cys Thr Lys Glu Ala Pro Ala Cys Arg Ile Thr Phe Leu Pro Leu
    370                 375                 380

-continued

```
Ala Arg Leu Arg Arg Thr Glu Ser Val Pro Ser Asp Ile Asn Asn Pro
385             390             395             400

Val Asp Arg Ala Ala Glu Pro His Phe Gly Thr Leu Pro Lys Ala Leu
            405             410             415

Thr Lys Lys Glu His Pro Pro Ala Met Asn Leu Asp Ser Ser Ser Asn
            420             425             430

Pro Ser Ser Thr Thr Ser Ser Thr Pro Ser Ser Pro Ala Pro Phe Leu
            435             440             445

Thr Ser Ser Asn Pro Ser Ser Ala Thr Thr Pro Pro Asn Pro Ser Pro
            450             455             460

Gly Gln Arg Asp Ser Arg Phe Ser Phe Pro Asp Ile Ser Ala Cys Ser
465             470             475             480

Gln Ala Ala Pro Leu Ser Ser Thr Ala Asp Ser Thr Arg Leu Asp Asp
            485             490             495

Gln Pro Lys Thr Asp Val Leu Gly Val His Glu Ala Glu Ala Glu Glu
            500             505             510

Pro Glu Ala Gly Lys Ser Glu Ala Glu Asp Asp Glu Glu Asp Glu Val
            515             520             525

Asp Asp Leu Pro Ser Ser Arg Arg Pro Trp Arg Gly Pro Ile Ser Arg
            530             535             540

Lys Ala Ser Gln Thr Ser Val Tyr Leu Gln Glu Trp Asp Ile Pro Phe
545             550             555             560

Glu Gln Val Glu Leu Gly Glu Pro Ile Gly Gln Gly Arg Trp Gly Arg
            565             570             575

Val His Arg Gly Arg Trp His Gly Glu Val Ala Ile Arg Leu Leu Glu
            580             585             590

Met Asp Gly His Asn Gln Asp His Leu Lys Leu Phe Lys Lys Glu Val
            595             600             605

Met Asn Tyr Arg Gln Thr Arg His Glu Asn Val Val Leu Phe Met Gly
            610             615             620

Ala Cys Met Asn Pro Pro His Leu Ala Ile Ile Thr Ser Phe Cys Lys
625             630             635             640

Gly Arg Thr Leu His Ser Phe Val Arg Asp Pro Lys Thr Ser Leu Asp
            645             650             655

Ile Asn Lys Thr Arg Gln Ile Ala Gln Glu Ile Ile Lys Gly Met Gly
            660             665             670

Tyr Leu His Ala Lys Gly Ile Val His Lys Asp Leu Lys Ser Lys Asn
            675             680             685

Val Phe Tyr Asp Asn Gly Lys Val Val Ile Thr Asp Phe Gly Leu Phe
            690             695             700

Gly Ile Ser Gly Val Val Arg Glu Glu Arg Arg Glu Asn Gln Leu Lys
705             710             715             720

Leu Ser His Asp Trp Leu Cys Tyr Leu Ala Pro Glu Ile Val Arg Glu
            725             730             735

Met Ile Pro Gly Arg Asp Glu Asp Gln Leu Pro Phe Ser Lys Ala Ala
            740             745             750

Asp Val Tyr Ala Phe Gly Thr Val Trp Tyr Glu Leu Gln Ala Arg Asp
            755             760             765

Trp Pro Phe Lys His Gln Pro Ala Glu Ala Leu Ile Trp Gln Ile Gly
            770             775             780

Ser Gly Glu Gly Val Arg Arg Val Leu Ala Ser Val Ser Leu Gly Lys
785             790             795             800
```

-continued

Glu Val Gly Glu Ile Leu Ser Ala Cys Trp Ala Phe Asp Leu Gln Glu
              805                    810                    815

Arg Pro Ser Phe Ser Leu Leu Met Asp Met Leu Glu Arg Leu Pro Lys
              820                    825                    830

Leu Asn Arg Arg Leu Ser His Pro Gly His Phe Trp Lys Ser Ala Asp
              835                    840                    845

Ile Asn Ser Ser Lys Val Met Pro Arg Phe Glu Arg Phe Gly Leu Gly
        850                    855                    860

Thr Leu Glu Ser Gly Asn Pro Lys Met
865                    870

<210> SEQ ID NO 44
<211> LENGTH: 766
<212> TYPE: PRT
<213> ORGANISM: Artificial Sequence
<220> FEATURE:
<223> OTHER INFORMATION: Amino acid sequence of human BRAF (uniprot ID
      P15056)

<400> SEQUENCE: 44

Met Ala Ala Leu Ser Gly Gly Gly Gly Gly Gly Ala Glu Pro Gly Gln
1               5                    10                    15

Ala Leu Phe Asn Gly Asp Met Glu Pro Glu Ala Gly Ala Gly Ala Gly
              20                    25                    30

Ala Ala Ala Ser Ser Ala Ala Asp Pro Ala Ile Pro Glu Glu Val Trp
        35                    40                    45

Asn Ile Lys Gln Met Ile Lys Leu Thr Gln Glu His Ile Glu Ala Leu
        50                    55                    60

Leu Asp Lys Phe Gly Gly Glu His Asn Pro Pro Ser Ile Tyr Leu Glu
65                    70                    75                    80

Ala Tyr Glu Glu Tyr Thr Ser Lys Leu Asp Ala Leu Gln Gln Arg Glu
              85                    90                    95

Gln Gln Leu Leu Glu Ser Leu Gly Asn Gly Thr Asp Phe Ser Val Ser
              100                    105                    110

Ser Ser Ala Ser Met Asp Thr Val Thr Ser Ser Ser Ser Ser Ser Leu
              115                    120                    125

Ser Val Leu Pro Ser Ser Leu Ser Val Phe Gln Asn Pro Thr Asp Val
        130                    135                    140

Ala Arg Ser Asn Pro Lys Ser Pro Gln Lys Pro Ile Val Arg Val Phe
145                    150                    155                    160

Leu Pro Asn Lys Gln Arg Thr Val Val Pro Ala Arg Cys Gly Val Thr
              165                    170                    175

Val Arg Asp Ser Leu Lys Lys Ala Leu Met Met Arg Gly Leu Ile Pro
              180                    185                    190

Glu Cys Cys Ala Val Tyr Arg Ile Gln Asp Gly Glu Lys Lys Pro Ile
              195                    200                    205

Gly Trp Asp Thr Asp Ile Ser Trp Leu Thr Gly Glu Glu Leu His Val
        210                    215                    220

Glu Val Leu Glu Asn Val Pro Leu Thr Thr His Asn Phe Val Arg Lys
225                    230                    235                    240

Thr Phe Phe Thr Leu Ala Phe Cys Asp Phe Cys Arg Lys Leu Leu Phe
              245                    250                    255

Gln Gly Phe Arg Cys Gln Thr Cys Gly Tyr Lys Phe His Gln Arg Cys
              260                    265                    270

Ser Thr Glu Val Pro Leu Met Cys Val Asn Tyr Asp Gln Leu Asp Leu
              275                    280                    285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
                355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
                435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
                515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
                580                 585                 590

Gly Asp Phe Gly Leu Ala Thr Val Lys Ser Arg Trp Ser Gly Ser His
                595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
                675                 680                 685

Met Lys Arg Leu Met Ala Glu Cys Leu Lys Lys Lys Arg Asp Glu Arg
    690                 695                 700

-continued

| Pro | Leu | Phe | Pro | Gln | Ile | Leu | Ala | Ser | Ile | Glu | Leu | Leu | Ala | Arg | Ser |
| 705 | | | | | 710 | | | | | 715 | | | | | 720 |

| Leu | Pro | Lys | Ile | His | Arg | Ser | Ala | Ser | Glu | Pro | Ser | Leu | Asn | Arg | Ala |
| | | | | 725 | | | | | 730 | | | | | 735 | |

| Gly | Phe | Gln | Thr | Glu | Asp | Phe | Ser | Leu | Tyr | Ala | Cys | Ala | Ser | Pro | Lys |
| | | | 740 | | | | | 745 | | | | | 750 | | |

| Thr | Pro | Ile | Gln | Ala | Gly | Gly | Tyr | Gly | Ala | Phe | Pro | Val | His | | |
| | | 755 | | | | | 760 | | | | | 765 | | | |